(12) United States Patent
Sano et al.

(10) Patent No.: US 11,787,809 B2
(45) Date of Patent: *Oct. 17, 2023

(54) OXIME GROUP-CONTAINING CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

(71) Applicant: NIHON NOHYAKU CO., LTD., Tokyo (JP)

(72) Inventors: Yusuke Sano, Osaka (JP); Ikki Yonemura, Osaka (JP); Soichiro Matsuo, Osaka (JP); Akiyuki Suwa, Osaka (JP); Shunpei Fujie, Osaka (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 953 days.

This patent is subject to a terminal disclaimer.

(21) Appl. No.: 16/967,199

(22) PCT Filed: Oct. 12, 2016

(86) PCT No.: PCT/JP2016/080274
§ 371 (c)(1),
(2) Date: Aug. 4, 2020

(87) PCT Pub. No.: WO2017/065183
PCT Pub. Date: Apr. 20, 2017

(65) Prior Publication Data
US 2021/0371424 A1    Dec. 2, 2021

(30) Foreign Application Priority Data

Oct. 13, 2015  (JP) ................. 2015-201937
Feb. 19, 2016  (JP) ................. 2016-030466
Jul. 15, 2016  (JP) ................. 2016-140926

(51) Int. Cl.
| | |
|---|---|
| *C07D 487/04* | (2006.01) |
| *A01N 43/40* | (2006.01) |
| *A01N 43/76* | (2006.01) |
| *A01N 43/90* | (2006.01) |
| *C07D 213/81* | (2006.01) |
| *C07D 405/04* | (2006.01) |
| *C07D 413/04* | (2006.01) |
| *C07D 413/14* | (2006.01) |
| *C07D 471/04* | (2006.01) |

(52) U.S. Cl.
CPC .......... *C07D 487/04* (2013.01); *A01N 43/40* (2013.01); *A01N 43/76* (2013.01); *A01N 43/90* (2013.01); *C07D 213/81* (2013.01); *C07D 405/04* (2013.01); *C07D 413/04* (2013.01); *C07D 413/14* (2013.01); *C07D 471/04* (2013.01)

(58) Field of Classification Search
CPC ........ A01N 43/40; A01N 43/76; A01N 43/90; C07D 487/04; C07D 213/81; C07D 405/04; C07D 413/04; C07D 413/14; C07D 471/04

See application file for complete search history.

(56) References Cited

U.S. PATENT DOCUMENTS

| | | | |
|---|---|---|---|
| 5,847,005 A | 12/1998 | Kasahara et al. | |
| 5,942,538 A | 8/1999 | Kasahara et al. | |
| 10,435,411 B2 * | 10/2019 | Shimizu | ............... C07D 471/04 |
| 10,856,548 B2 * | 12/2020 | Yonemura | ............ C07D 413/14 |
| 2006/0211737 A1 | 9/2006 | Huang et al. | |
| 2008/0096887 A1 | 4/2008 | Huang et al. | |
| 2011/0034529 A1 | 2/2011 | Huang et al. | |
| 2011/0039843 A1 | 2/2011 | Iwakoshi et al. | |
| 2011/0183977 A1 | 7/2011 | Huang et al. | |
| 2012/0015975 A1 | 1/2012 | Takahashi et al. | |

(Continued)

FOREIGN PATENT DOCUMENTS

| | | |
|---|---|---|
| EP | 0 805 148 | 9/2004 |
| EP | 2 865 266 | 4/2015 |

(Continued)

OTHER PUBLICATIONS

International Search Report (ISR) dated Jan. 10, 2017 in International (PCT) Application No. PCT/JP2016/080274.

(Continued)

*Primary Examiner* — Sean M Basquill
(74) *Attorney, Agent, or Firm* — Wenderoth, Lind & Ponack, L.L.P.

(57) ABSTRACT

Provided are an oxime group-containing condensed heterocyclic compound or a salt thereof, preferably a condensed heterocyclic compound represented by general formula (1):

[Chem. 1]

(wherein the symbols are defined in the specification); an agricultural and horticultural insecticide comprising the compound or a salt thereof as an active ingredient; and a method for using the insecticide.

16 Claims, No Drawings

(56) References Cited

U.S. PATENT DOCUMENTS

| | | |
|---|---|---|
| 2012/0108586 A1 | 5/2012 | Iwakoshi et al. |
| 2012/0178779 A1 | 7/2012 | Takahashi et al. |
| 2012/0196891 A1 | 8/2012 | Iwakoshi |
| 2012/0245167 A1 | 9/2012 | Iwakoshi et al. |
| 2013/0137686 A1 | 5/2013 | Huang et al. |
| 2013/0190271 A1 | 7/2013 | Iwakoshi et al. |
| 2013/0252981 A1 | 9/2013 | Takahashi et al. |
| 2014/0018373 A1 | 1/2014 | Takyo et al. |
| 2014/0194290 A1 | 7/2014 | Takahashi et al. |
| 2014/0343037 A1 | 11/2014 | Huang et al. |
| 2014/0364444 A1 | 12/2014 | Takyo et al. |
| 2015/0148308 A1 | 5/2015 | Suzuki et al. |
| 2015/0197532 A1 | 7/2015 | Takahashi et al. |
| 2015/0313234 A1 | 11/2015 | Takahashi et al. |
| 2016/0009715 A1 | 1/2016 | Takahashi et al. |
| 2016/0021886 A1 | 1/2016 | Yonemura et al. |
| 2016/0159743 A1 | 6/2016 | Takahashi et al. |
| 2016/0255837 A1 | 9/2016 | Edmunds et al. |
| 2016/0368915 A1 | 12/2016 | Tanabe et al. |
| 2017/0073342 A1* | 3/2017 | Fischer ............... C07D 473/40 |
| 2017/0260174 A1 | 9/2017 | Huang et al. |
| 2017/0362224 A1 | 12/2017 | Edmunds et al. |
| 2018/0002347 A1 | 1/2018 | Yonemura et al. |
| 2019/0144445 A1 | 5/2019 | Edmunds et al. |
| 2019/0241564 A1 | 8/2019 | Fischer et al. |
| 2020/0071308 A1 | 3/2020 | Huang et al. |

FOREIGN PATENT DOCUMENTS

| | | |
|---|---|---|
| JP | 2008-531599 | 8/2008 |
| JP | 2009-280574 | 12/2009 |
| JP | 2010-275301 | 12/2010 |
| JP | 2011-79774 | 4/2011 |
| JP | 2012-131780 | 7/2012 |
| JP | 2013-136519 | 7/2013 |
| JP | 2014-5263 | 1/2014 |
| WO | 2012/086848 | 6/2012 |
| WO | 2013/018928 | 2/2013 |
| WO | 2014/104407 | 7/2014 |
| WO | 2014/132972 | 9/2014 |
| WO | 2014/142292 | 9/2014 |
| WO | 2015/000715 | 1/2015 |
| WO | 2015/002211 | 1/2015 |
| WO | 2015/121136 | 8/2015 |
| WO | 2016/116338 | 7/2016 |
| WO | 2016/121997 | 8/2016 |

OTHER PUBLICATIONS

International Preliminary Report on Patentability dated Apr. 17, 2018 International (PCT) Application No. PCT/JP2016/080274.

* cited by examiner

OXIME GROUP-CONTAINING CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

TECHNICAL FIELD

The present invention relates to an oxime group-containing condensed heterocyclic compound or a salt thereof, an agricultural and horticultural insecticide comprising the compound as an active ingredient, and a method for using the insecticide.

BACKGROUND ART

Various compounds have been examined for their potential as agricultural and horticultural insecticides, and among them, certain kinds of condensed heterocyclic compounds have been reported to be useful as insecticides (for example, see Patent Literature 1 to 7). None of these references specifically disclose any compound having an oxime group bound to a condensed heterocyclic ring.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2013/018928
Patent Literature 7: WO 2015/121136

SUMMARY OF INVENTION

Technical Problem

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired.

Solution to Problem

The present inventor conducted extensive research to solve the above-described problems. As a result, the present inventor found that an oxime group-containing condensed heterocyclic compound represented by the general formula (1) or a salt thereof is highly effective for the control of agricultural and horticultural pests, and reached the completion of the present invention.

That is, the present invention relates to the following.

[1] A condensed heterocyclic compound represented by general formula (1):

[Chem. 1]

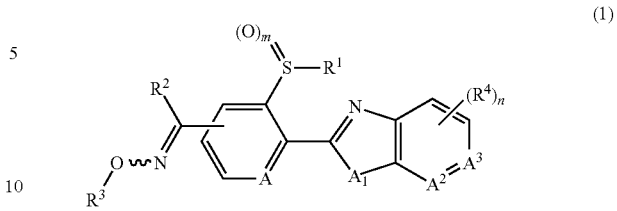

(1)

{wherein
R$^1$ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
R$^2$ represents
(b1) a hydrogen atom;
(b2) a ($C_1$-$C_6$) alkyl group;
(b3) a ($C_3$-$C_6$) cycloalkyl group;
(b4) a halo ($C_1$-$C_6$) alkyl group;
(b5) an amino group;
(b6) a cyano group;
(b7) a ($C_1$-$C_6$) alkoxycarbonyl group;
(b8) an aminocarbonyl group;
(b9) a mono-($C_1$-$C_6$) alkylaminocarbonyl group; or
(b10) a di-($C_1$-$C_6$) alkylaminocarbonyl group,
R$^3$ represents
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group;
(c14) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c15) a ($C_1$-$C_6$) alkylcarbonyl group;
(c16) a ($C_3$-$C_6$) cycloalkylcarbonyl group;
(c17) a cyanoalkyl group;
(c18) a ($C_1$-$C_6$) alkylthio ($C_1$-$C_6$) alkyl group;

(c19) a $(C_1-C_6)$ alkylsulfinyl $(C_1-C_6)$ alkyl group;
(c20) a $(C_1-C_6)$ alkylsulfonyl $(C_1-C_6)$ alkyl group;
(c21) a halo $(C_1-C_6)$ alkylthio $(C_1-C_6)$ alkyl group;
(c22) a halo $(C_1-C_6)$ alkylsulfinyl $(C_1-C_6)$ alkyl group; or
(c23) a halo $(C_1-C_6)$ alkylsulfonyl $(C_1-C_6)$ alkyl group,
$R^4$ represents
(d1) a halogen atom;
(d2) a cyano group;
(d3) a nitro group;
(d4) a $(C_1-C_6)$ alkyl group;
(d5) a $(C_1-C_6)$ alkoxy group;
(d6) a $(C_2-C_6)$ alkenyloxy group;
(d7) a $(C_2-C_6)$ alkynyloxy group;
(d8) a halo $(C_1-C_6)$ alkyl group;
(d9) a halo $(C_1-C_6)$ alkoxy group;
(d10) a halo $(C_2-C_6)$ alkenyloxy group;
(d11) a halo $(C_2-C_6)$ alkynyloxy group;
(d12) a $(C_1-C_6)$ alkylthio group;
(d13) a $(C_1-C_6)$ alkylsulfinyl group;
(d14) a $(C_1-C_6)$ alkylsulfonyl group;
(d15) a halo $(C_1-C_6)$ alkylthio group;
(d16) a halo $(C_1-C_6)$ alkylsulfinyl group; or
(d17) a halo $(C_1-C_6)$ alkylsulfonyl group,
    A, $A^2$ and $A^3$ each represent CH or a nitrogen atom,
    $A^1$ represents O, S or N—$R^5$ (wherein $R^5$ represents (e1) a $(C_1-C_6)$ alkyl group; (e2) a $(C_3-C_6)$ cycloalkyl group; (e3) a $(C_2-C_6)$ alkenyl group; or (e4) a $(C_2-C_6)$ alkynyl group),
    m represents 0, 1 or 2, and
    n represents 0, 1 or 2}, or
a salt thereof.

[2] The condensed heterocyclic compound according to the above [1] or a salt thereof, wherein the condensed heterocyclic compound is represented by general formula (1A):

[Chem. 2]

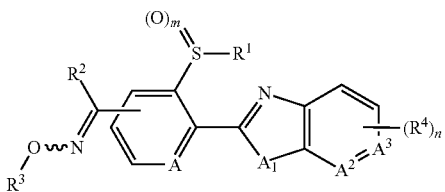

(1A)

{wherein
    $R^1$ represents (a1) a $(C_1-C_6)$ alkyl group,
    $R^2$ represents
(b1) a hydrogen atom; or
(b2) a $(C_1-C_6)$ alkyl group,
    $R^3$ represents
(c1) a hydrogen atom; or
(c8) a halo $(C_1-C_6)$ alkyl group,
    $R^4$ represents
(d8) a halo $(C_1-C_6)$ alkyl group;
(d9) a halo $(C_1-C_6)$ alkoxy group;
(d15) a halo $(C_1-C_6)$ alkylthio group;
(d16) a halo $(C_1-C_6)$ alkylsulfinyl group; or
(d17) a halo $(C_1-C_6)$ alkylsulfonyl group,
    A represents a nitrogen atom,
    $A^2$ and $A^3$ each represent CH or a nitrogen atom,
    $A^1$ represents O or N—$R^5$ (wherein $R^5$ represents (e1) a $(C_1-C_6)$ alkyl group),
    m represents 0 or 2, and
    n represents 1}.

[3] The condensed heterocyclic compound according to the above [2] or a salt thereof, wherein $A^1$ is O.

[4] An agricultural and horticultural insecticide comprising the condensed heterocyclic compound according to any one of the above [1] to [3] or a salt thereof as an active ingredient.

[5] A method for using an agricultural and horticultural insecticide, the method comprising applying an effective amount of the condensed heterocyclic compound according to any one of the above [1] to [3] or a salt thereof to plants or soil.

[6] An animal ectoparasite control agent comprising an effective amount of the condensed heterocyclic compound according to any one of the above [1] to [3] or a salt thereof as an active ingredient.

[7] The condensed heterocyclic compound according to the above [1] or a salt thereof, wherein the condensed heterocyclic compound is represented by general formula (1):

[Chem. 3]

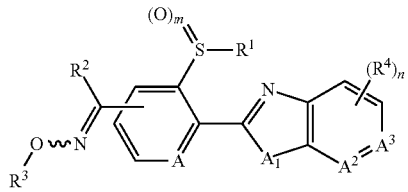

(1)

{wherein
    $R^1$ represents
(a1) a $(C_1-C_6)$ alkyl group;
(a2) a $(C_3-C_6)$ cycloalkyl group;
(a3) a $(C_2-C_6)$ alkenyl group; or
(a4) a $(C_2-C_6)$ alkynyl group,
    $R^2$ represents
(b1) a hydrogen atom;
(b2) a $(C_1-C_6)$ alkyl group;
(b3) a $(C_3-C_6)$ cycloalkyl group;
(b4) a halo $(C_1-C_6)$ alkyl group; or
(b5) an amino group,
    $R^3$ represents
(c1) a hydrogen atom;
(c2) a $(C_1-C_6)$ alkyl group;
(c3) a $(C_2-C_6)$ alkenyl group;
(c4) a $(C_2-C_6)$ alkynyl group;
(c5) a $(C_3-C_6)$ cycloalkyl group;
(c6) a $(C_3-C_6)$ cycloalkyl $(C_1-C_6)$ alkyl group;
(c7) a $(C_1-C_6)$ alkoxy $(C_1-C_6)$ alkyl group;
(c8) a halo $(C_1-C_6)$ alkyl group;
(c9) a halo $(C_2-C_6)$ alkenyl group;
(c10) a halo $(C_2-C_6)$ alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c13) a phenyl $(C_1-C_6)$ alkyl group;

(c14) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c15) a ($C_1$-$C_6$) alkylcarbonyl group; or
(c16) a ($C_3$-$C_6$) cycloalkylcarbonyl group,
$R^4$ represents
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
A, $A^2$ and $A^3$ each represent CH or a nitrogen atom,
$A^1$ represents O, S or N—$R^5$ (wherein $R^5$ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
m represents 0, 1 or 2, and
n represents 0, 1 or 2}.
[8] The condensed heterocyclic compound according to the above [7] or a salt thereof, wherein the condensed heterocyclic compound is represented by general formula (1A):

[Chem. 4]

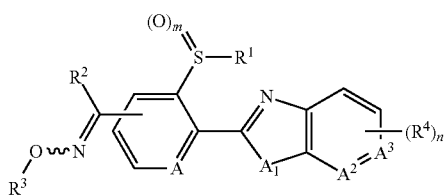

(1A)

{wherein
$R^1$ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
$R^2$ represents
(b1) a hydrogen atom;
(b2) a ($C_1$-$C_6$) alkyl group;
(b3) a ($C_3$-$C_6$) cycloalkyl group; or
(b5) an amino group,
$R^3$ represents
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group; or
(c14) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group,
$R^4$ represents
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
A, $A^2$ and $A^3$ each represent CH or a nitrogen atom,
$A^1$ represents O, S or N—$R^5$ (wherein $R^5$ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
m represents 0, 1 or 2, and
n represents 0, 1 or 2}.
[9] The condensed heterocyclic compound according to the above [8] or a salt thereof, wherein
$R^1$ represents (a1) a ($C_1$-$C_6$) alkyl group,
$R^2$ represents
(b1) a hydrogen atom; or
(b2) a ($C_1$-$C_6$) alkyl group,
$R^3$ represents
(c1) a hydrogen atom;
(c2) a ($C_1$-$C_6$) alkyl group;
(c3) a ($C_2$-$C_6$) alkenyl group;
(c7) a ($C_1$-$C_6$) alkoxy ($C_1$-$C_6$) alkyl group;

(c11) a phenyl group; or
(c13) a phenyl ($C_1$-$C_6$) alkyl group,
R⁴ represents
(d8) a halo ($C_1$-$C_6$) alkyl group; or
(d15) a halo ($C_1$-$C_6$) alkylthio group,
A, A² and A³ each represent a nitrogen atom,
A¹ represents N—R⁵ (wherein R⁵ represents (e1) a ($C_1$-$C_6$) alkyl group),
m represents 0, 1 or 2, and
n represents 1.
[10] The condensed heterocyclic compound according to the above [8] or [9] or a salt thereof, wherein
R¹ represents (a1) a ($C_1$-$C_6$) alkyl group,
R² represents
(b1) a hydrogen atom; or
(b2) a ($C_1$-$C_6$) alkyl group,
R³ represents
(c1) a hydrogen atom;
(c2) a ($C_1$-$C_6$) alkyl group;
(c3) a ($C_2$-$C_6$) alkenyl group;
(c7) a ($C_1$-$C_6$) alkoxy ($C_1$-$C_6$) alkyl group;
(c11) a phenyl group; or
(c13) a phenyl ($C_1$-$C_6$) alkyl group,
R⁴ represents (d8) a halo ($C_1$-$C_6$) alkyl group,
A, A² and A³ each represent a nitrogen atom,
A¹ represents N—R⁵ (wherein R⁵ represents (e1) a ($C_1$-$C_6$) alkyl group),
m represents 2, and
n represents 1.
[11] The condensed heterocyclic compound according to the above [7] or a salt thereof, wherein the condensed heterocyclic compound is represented by general formula (1B):

[Chem. 5]

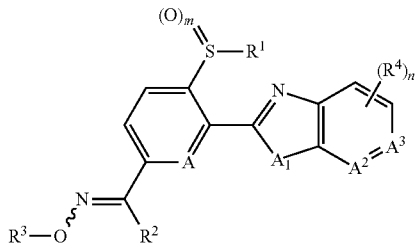

(1B)

{wherein
R¹ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
R² represents
(b1) a hydrogen atom;
(b2) a ($C_1$-$C_6$) alkyl group;
(b3) a ($C_3$-$C_6$) cycloalkyl group; or
(b5) an amino group,
R³ represents
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group; or
(c14) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group,
R⁴ represents
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
A, A² and A³ each represent CH or a nitrogen atom,
A¹ represents O, S or N—R⁵ (wherein R⁵ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
m represents 0, 1 or 2, and
n represents 0, 1 or 2}.
[12] The condensed heterocyclic compound according to the above [11] or a salt thereof, wherein
R¹ represents (a1) a ($C_1$-$C_6$) alkyl group,
R² represents
(b1) a hydrogen atom; or
(b2) a ($C_1$-$C_6$) alkyl group,
R³ represents
(c1) a hydrogen atom;
(c2) a ($C_1$-$C_6$) alkyl group;
(c3) a ($C_2$-$C_6$) alkenyl group;
(c7) a ($C_1$-$C_6$) alkoxy ($C_1$-$C_6$) alkyl group;
(c11) a phenyl group; or
(c13) a phenyl ($C_1$-$C_6$) alkyl group, R⁴ represents
(d8) a halo $(C_1-C_6)$ alkyl group; or
(d15) a halo $(C_1-C_6)$ alkylthio group,
A, $A^2$ and $A^3$ each represent a nitrogen atom,
$A^1$ represents N—$R^5$ (wherein $R^5$ represents (e1) a $(C_1-C_6)$ alkyl group),
m represents 0, 1 or 2, and
n represents 1.

[13] The condensed heterocyclic compound according to the above [11] or [12] or a salt thereof, wherein
$R^1$ represents (a1) a $(C_1-C_6)$ alkyl group,
$R^2$ represents
(b1) a hydrogen atom; or
(b2) a $(C_1-C_6)$ alkyl group,
$R^3$ represents
(c1) a hydrogen atom;
(c2) a $(C_1-C_6)$ alkyl group;
(c3) a $(C_2-C_6)$ alkenyl group;
(c7) a $(C_1-C_6)$ alkoxy $(C_1-C_6)$ alkyl group;
(c11) a phenyl group; or
(c13) a phenyl $(C_1-C_6)$ alkyl group,
$R^4$ represents (d8) a halo $(C_1-C_6)$ alkyl group,
A, $A^2$ and $A^3$ each represent a nitrogen atom,
$A^1$ represents N—$R^5$ (wherein $R^5$ represents (e1) a $(C_1-C_6)$ alkyl group),
m represents 2, and
n represents 1.

[14] An agricultural and horticultural insecticide comprising the condensed heterocyclic compound according to any one of the above [7] to [13] or a salt thereof as an active ingredient.

[15] A method for using an agricultural and horticultural insecticide, the method comprising applying an effective amount of the condensed heterocyclic compound according to any one of the above [7] to [13] or a salt thereof to plants or soil.

[16] An animal ectoparasite control agent comprising an effective amount of the condensed heterocyclic compound according to any one of the above [7] to [13] or a salt thereof as an active ingredient.

Effect of the Invention

The oxime group-containing condensed heterocyclic compound of the present invention or a salt thereof is not only highly effective as an agricultural and horticultural insecticide but also effective against pests which live on the exterior of pets such as dogs and cats and domestic animals such as cattle and sheep and against other harmful pests such as termites.

DESCRIPTION OF EMBODIMENTS

In the definitions in connection with the general formula (1) representing the oxime group-containing condensed heterocyclic compound of the present invention or a salt thereof, "halo" refers to a "halogen atom" and represents a chlorine atom, a bromine atom, an iodine atom or a fluorine atom.

The "$(C_1-C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethylpropyl group, a 3,3-dimethylbutyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, a 1-ethylpropyloxy group, a 1-methylbutyloxy group, a n-hexyloxy group, an isohexyloxy group, a 1,1,2-trimethylpropyloxy group or the like. The "$(C_2-C_6)$ alkenyloxy group" refers to a straight-chain or branched-chain alkenyloxy group of 2 to 6 carbon atoms, for example, a propenyloxy group, a butenyloxy group, a pentenyloxy group, a hexenyloxy group or the like. The "$(C_2-C_6)$ alkynyloxy group" refers to a straight-chain or branched-chain alkynyloxy group of 2 to 6 carbon atoms, for example, a propynyloxy group, a butynyloxy group, a pentynyloxy group, a hexynyloxy group or the like.

The "$(C_1-C_6)$ alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, a 1-ethylpropylthio group, a 1-methylbutylthio group, a n-hexylthio group, an isohexylthio group, a 1,1,2-trimethylpropylthio group or the like. The "$(C_1-C_6)$ alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, a 1-ethylpropylsulfinyl group, a 1-methylbutylsulfinyl group, a n-hexylsulfinyl group, an isohexylsulfinyl group, a 1,1,2-trimethylpropylsulfinyl group or the like. The "$(C_1-C_6)$ alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, a 1-ethylpropylsulfonyl group, a 1-methylbutylsulfonyl group, a n-hexylsulfonyl group, an isohexylsulfonyl group, a 1,1,2-trimethylpropylsulfonyl group or the like.

The above-mentioned "$(C_1-C_6)$ alkyl group",
"$(C_2-C_6)$ alkenyl group",
"$(C_2-C_6)$ alkynyl group",
"$(C_3-C_6)$ cycloalkyl group",
"$(C_3-C_6)$ cycloalkyloxy group",
"$(C_1-C_6)$ alkoxy group",
"$(C_2-C_6)$ alkenyloxy group",
"$(C_2-C_6)$ alkynyloxy group",
"$(C_1-C_6)$ alkylthio group",
"$(C_1-C_6)$ alkylsulfinyl group",
"$(C_1-C_6)$ alkylsulfonyl group", "($C_2$-$C_6$) alkenylthio group",
"($C_2$-$C_6$) alkynylthio group",
"($C_2$-$C_6$) alkenylsulfinyl group",
"($C_2$-$C_6$) alkynylsulfinyl group",
"($C_2$-$C_6$) alkenylsulfonyl group",
"($C_2$-$C_6$) alkynylsulfonyl group",
"($C_3$-$C_6$) cycloalkylthio group",
"($C_3$-$C_6$) cycloalkylsulfinyl group" and
"($C_3$-$C_6$) cycloalkylsulfonyl group"
may be substituted with one or more halogen atoms at a substitutable position(s), and in the case where any of the above-listed groups is substituted with two or more halogen atoms, the halogen atoms may be the same or different.

The above-mentioned "group substituted with one or more halogen atoms" is expressed as
a "halo ($C_1$-$C_6$) alkyl group",
a "halo ($C_2$-$C_6$) alkenyl group",
a "halo ($C_2$-$C_6$) alkynyl group",
a "halo ($C_3$-$C_6$) cycloalkyl group",
a "halo ($C_3$-$C_6$) cycloalkyloxy group",
a "halo ($C_1$-$C_6$) alkoxy group",
a "halo ($C_2$-$C_6$) alkenyloxy group",
a "halo ($C_2$-$C_6$) alkynyloxy group",
a "halo ($C_1$-$C_6$) alkylthio group",
a "halo ($C_1$-$C_6$) alkylsulfinyl group",
a "halo ($C_1$-$C_6$) alkylsulfonyl group",
a "halo ($C_2$-$C_6$) alkenylthio group",
a "halo ($C_2$-$C_6$) alkynylthio group",
a "halo ($C_2$-$C_6$) alkenylsulfinyl group",
a "halo ($C_2$-$C_6$) alkynylsulfinyl group",
a "halo ($C_2$-$C_6$) alkenylsulfonyl group",
a "halo ($C_2$-$C_6$) alkynylsulfonyl group",
a "halo ($C_3$-$C_6$) cycloalkylthio group",
a "halo ($C_3$-$C_6$) cycloalkylsulfinyl group" or
a "halo ($C_3$-$C_6$) cycloalkylsulfonyl group".

The above definitions and examples of each group in the present invention are all obvious to those skilled in the art.

The expressions "($C_1$-$C_6$)", "($C_2$-$C_6$)", "($C_3$-$C_6$)", etc. each refer to the range of the number of carbon atoms in each group. The same definition holds true for groups in which two or more of the above-mentioned groups are coupled together, and for example, the "($C_1$-$C_6$) alkoxy ($C_1$-$C_6$) alkyl group" means that a straight-chain or branched-chain alkoxy group of 1 to 6 carbon atoms is bound to a straight-chain or branched-chain alkyl group of 1 to 6 carbon atoms.

Examples of the salt of the oxime group-containing condensed heterocyclic compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The oxime group-containing condensed heterocyclic compound represented by the general formula (1) of the present invention and a salt thereof can have one or more chiral centers in the structural formula, and can exist as two or more kinds of optical isomers or diastereomers. All the optical isomers and mixtures of the isomers at any ratio are also included in the present invention. Further, the compound represented by the general formula (1) of the present invention and a salt thereof can exist as two kinds of geometric isomers due to a carbon-carbon double bond in the structural formula. All the geometric isomers and mixtures of the isomers at any ratio are also included in the present invention. In the case of the compound of the present invention, a syn isomer (Z isomer) and an anti isomer (E isomer) are formed due to the presence of the oxime group. The compound of the present invention may be either of the two isomers, or a mixture of them at any ratio.

As the oxime group-containing condensed heterocyclic compound represented by the general formula (1) of the present invention or a salt thereof, preferred is a compound of the general formula (1) in which
$R^1$ represents (a1) a ($C_1$-$C_6$) alkyl group,
$R^2$ represents
(b1) a hydrogen atom;
(b2) a ($C_1$-$C_6$) alkyl group; or
(b5) an amino group,
$R^3$ represents
(c1) a hydrogen atom;
(c2) a ($C_1$-$C_6$) alkyl group;
(c4) a ($C_2$-$C_6$) alkynyl group;
(c6) a ($C_3$-$C_6$) cycloalkyl ($C_1$-$C_6$) alkyl group;
(c8) a halo ($C_1$-$C_6$) alkyl group;
(c15) a ($C_1$-$C_6$) alkylcarbonyl group; or
(c16) a ($C_3$-$C_6$) cycloalkylcarbonyl group,
$R^4$ represents
(d8) a halo ($C_1$-$C_6$) alkyl group; or
(d15) a halo ($C_1$-$C_6$) alkylthio group,
A, $A^2$ and $A^3$ each represent CH or a nitrogen atom,
$A^1$ represents O or N—$R^5$ (wherein $R^5$ represents (e1) a ($C_1$-$C_6$) alkyl group),
m represents 1 or 2, and
n represents 1.

As the oxime group-containing condensed heterocyclic compound represented by the general formula (1A) of the present invention or a salt thereof, preferred is a compound of the general formula (1A) in which
$R^1$ represents (a1) a ($C_1$-$C_6$) alkyl group,
$R^2$ represents
(b1) a hydrogen atom; or
(b5) an amino group,
$R^3$ represents
(c1) a hydrogen atom;
(c2) a ($C_1$-$C_6$) alkyl group;
(c4) a ($C_2$-$C_6$) alkynyl group;
(c6) a ($C_3$-$C_6$) cycloalkyl ($C_1$-$C_6$) alkyl group; or
(c8) a halo ($C_1$-$C_6$) alkyl group,
$R^4$ represents
(d8) a halo ($C_1$-$C_6$) alkyl group; or
(d15) a halo ($C_1$-$C_6$) alkylthio group,
A, $A^2$ and $A^3$ each represent CH or a nitrogen atom,
$A^1$ represents O or N—$R^5$ (wherein $R^5$ represents (e1) a ($C_1$-$C_6$) alkyl group),
m represents 1 or 2, and
n represents 1.

As the oxime group-containing condensed heterocyclic compound represented by the general formula (1B) of the present invention or a salt thereof, preferred is a compound of the general formula (1B) in which
$R^1$ represents (a1) a ($C_1$-$C_6$) alkyl group,
$R^2$ represents
(b1) a hydrogen atom;
(b2) a ($C_1$-$C_6$) alkyl group; or
(b5) an amino group,
$R^3$ represents
(c1) a hydrogen atom;
(c2) a ($C_1$-$C_6$) alkyl group;
(c4) a ($C_2$-$C_6$) alkynyl group;
(c6) a ($C_3$-$C_6$) cycloalkyl ($C_1$-$C_6$) alkyl group; or
(c8) a halo ($C_1$-$C_6$) alkyl group, R⁴ represents (d8) a halo ($C_1$-$C_6$) alkyl group; or (d15) a halo ($C_1$-$C_6$) alkylthio group, A, $A^2$ and $A^3$ each represent CH or a nitrogen atom, $A^1$ represents O or N—$R^5$ (wherein $R^5$ represents (e1) a ($C_1$-$C_6$) alkyl group), m represents 1 or 2, and n represents 1.

The condensed heterocyclic compound of the present invention or a salt thereof can be produced according to, for example, the production methods described below, which are non-limiting examples in the present invention. The compounds used in the present invention are produced by known methods or methods known per se.

Production Method 1

[Chem. 6]

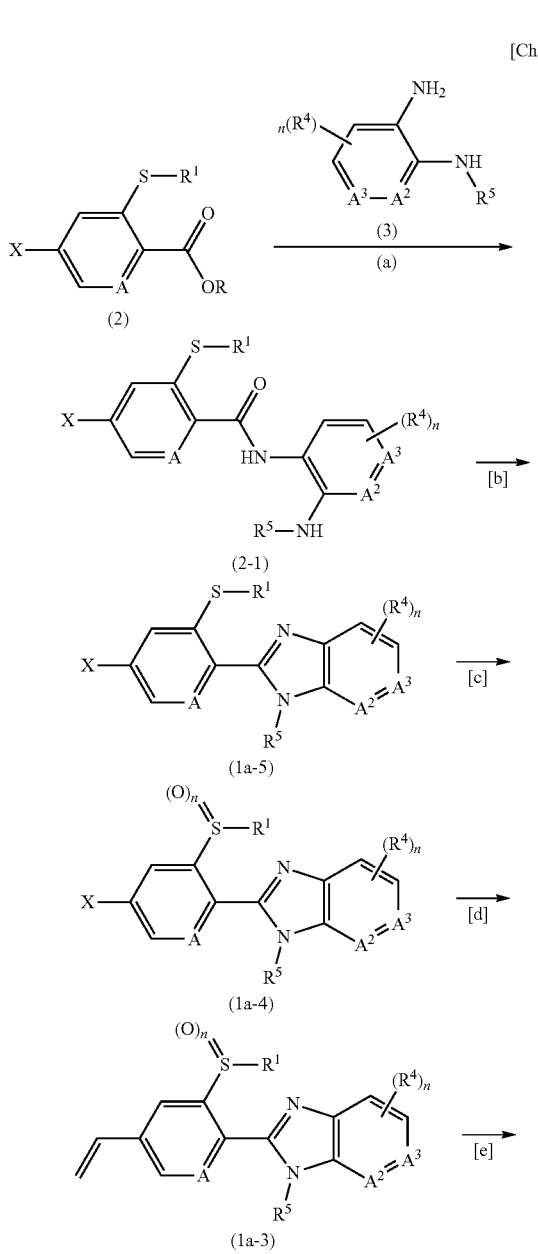

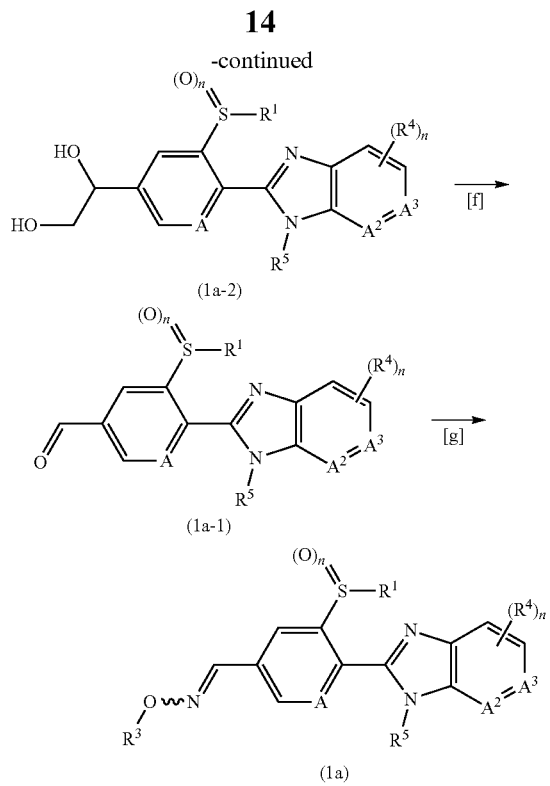

{In the formula, $R^1$, $R^3$, $R^4$, $R^5$, A, $A^2$, $A^3$, m and n are as defined above, X represents a halogen atom such as fluorine, chlorine, bromine and iodine (these definitions shall apply throughout the entirety of the present specification), and R represents a $C_1$-$C_3$ alkyl group such as a methyl group and an ethyl group.}

Production Method at Step [a]

The carboxylic acid ester represented by the general formula (2) is reacted with the compound represented by the general formula (3) in the presence of a base and an inert solvent for the production of the amide compound represented by the general formula (2-1).

Examples of the base that can be used in this reaction include inorganic bases such as sodium hydroxide, potassium hydroxide, sodium carbonate, potassium carbonate, sodium hydrogen carbonate and potassium hydrogen carbonate; alkali metal hydrides such as sodium hydride and potassium hydride; acetates such as potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (3).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, or two or more of them may be used as a mixture.

Since this reaction is an equimolar reaction of the reactants, they are basically used in equimolar amounts, but either of them may be used in an excess amount. The reaction temperature is in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by a usual method. As needed, recrystallization, column chromatography, etc. can be employed for the purification of the compound of interest.

Production Method at Step [b]

The condensed heterocyclic compound represented by the general formula (1a-5) can be produced by reacting the amide compound represented by the general formula (2-1) with an acid in the presence of an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; and phosphoric acid. The amount of the acid used is appropriately selected from the range of a 0.01- to 10-fold molar amount relative to the amide compound represented by the general formula (2-1).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, or two or more of them may be used as a mixture.

The reaction temperature is in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by a usual method. As needed, recrystallization, column chromatography, etc. can be employed for the purification of the compound of interest.

Production Method at Step [c]

The condensed heterocyclic compound represented by the general formula (1a-4) can be produced by reacting the condensed heterocyclic compound represented by the general formula (1a-5) with an oxidizing agent in an inert solvent.

Examples of the oxidizing agent used in this reaction include peroxides such as a hydrogen peroxide solution, perbenzoic acid and m-chloroperoxybenzoic acid. The amount of the oxidizing agent used is appropriately selected from the range of a 1- to 5-fold molar amount relative to the condensed heterocyclic compound represented by the general formula (1a-5).

The inert solvent used in this reaction may be any solvent that does not markedly inhibit the reaction, and the examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. One of these inert solvents may be used alone, or two or more of them may be used as a mixture.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by a usual method. As needed, recrystallization, column chromatography, etc. can be employed for the purification of the compound of interest.

Production Method at Step [d]

The condensed heterocyclic compound represented by the general formula (1a-3) can be produced by cross-coupling the condensed heterocyclic compound represented by the general formula (1a-4) with a vinylboronic acid compound in the presence of a metal catalyst and a base in an inert solvent.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of "a metal", "a supported metal", "a metal salt such as a metal chloride, a metal bromide, a metal iodide, a metal nitrate, a metal sulfate, a metal carbonate, a metal oxalate, a metal acetate and a metal oxide", or "a complex compound such as an olefin complex, a phosphine complex, an amine complex, an ammine complex and an acetylacetonate complex". Preferred is a palladium catalyst.

Examples of the palladium catalyst include palladium metals such as palladium black and palladium sponge; and supported palladium metals such as palladium/alumina, palladium/carbon, palladium/silica and palladium/type Y zeolite. Examples of the palladium metal salt include palladium chloride, palladium bromide, palladium iodide and palladium acetate. Examples of the complex compound of palladium include π-allylpalladium chloride dimer, palladium acetylacetonate, dichlorobis(acetonitrile)palladium, dichlorobis(benzonitrile)palladium, bis(dibenzylideneacetone)palladium, tris(dibenzylideneacetone)dipalladium, tris(dibenzylideneacetone)dipalladium (chloroform adduct), dichlorodiamine palladium, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium, dichloro[1,1'-bis(diphenylphosphino)ferrocene]palladium and a [(diphenylphosphino)ferrocene]dichloropalladium-dichloromethane complex.

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl) phosphine, tricyclohexylphosphine, tri-o-tolylphosphine, trioctylphosphine, 9,9-dimethyl-4,5-bis(diphenylphosphino) xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis (diphenylphosphino)butane, 1,1'-bis(diphenylphosphino) ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl.

Examples of the vinylboronic acid compound that can be used in this reaction include vinylmagnesium bromide, vinylmagnesium chloride, vinylzinc chloride, tributylvinyltin, potassium vinyltrifluoroborate, vinylboronic acid, vinylboronic anhydride, vinylboronic acid 2-methyl-2,4-pentanediol ester, vinylboronic acid pinacol ester and triethoxyvinylsilane.

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of an about 1- to 5-fold molar amount relative to the condensed heterocyclic compound represented by the general formula (1a-4).

The inert solvent used in this reaction may be any solvent that does not markedly inhibit the reaction, and the examples include alcohols such as methanol, ethanol, propanol, butanol and 2-propanol; straight-chain or cyclic ethers such as diethyl ether, tetrahydrofuran, dioxane and 1,2-dimethoxyethane (DME); aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; polar solvents such as N,N-dimethylformamide, N,N-dimethylacetamide, dimethyl sulfoxide and 1,3-dimethyl-2-imidazolidinone; and water. One of these inert solvents may be used alone, or two or more of them may be used as a mixture.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. This reaction may be conducted under the atmosphere of an inert gas such as nitrogen gas and argon gas. After the reaction is completed, the compound of interest is isolated from the post-reaction mixture by a usual method. As needed, recrystallization, column chromatography, etc. can be employed for the purification of the compound of interest.

Production Method at Step [e]

The diol-containing condensed heterocyclic compound represented by the general formula (1a-2) can be produced by the reaction of the vinyl-containing condensed heterocyclic compound represented by the general formula (1a-3) in the presence of osmium tetroxide and an oxidizing agent according to the method described in the Lecture of Experimental Chemistry (Jikken Kagaku Kouza), 4th edition, vol. 23, Organic Chemistry V, Oxidation Reaction (published by Maruzen Co., Ltd.). After the reaction is completed, the compound of interest is isolated from the post-reaction mixture by a usual method. As needed, recrystallization, column chromatography, etc. can be employed for the purification of the compound of interest.

Production Method at Step [f]

The formyl-containing condensed heterocyclic compound represented by the general formula (1a-1) can be produced by reacting the diol-containing condensed heterocyclic compound represented by the general formula (1a-2) with a periodic acid compound in the presence of an inert solvent according to the method described in the New Lecture of Experimental Chemistry (Shin Jikken Kagaku Kouza), vol. 15, Oxidation and Reduction I-1 (published by Maruzen Co., Ltd). After the reaction is completed, the compound of interest is isolated from the post-reaction mixture by a usual method. As needed, recrystallization, column chromatography, etc. can be employed for the purification of the compound of interest.

Production Method at Step [g]

The oxime-containing condensed heterocyclic compound represented by the general formula (1a) can be produced from the formyl imidazopyridazine compound represented by the general formula (1a-1) by converting the formyl group into an oxime group according to the method described in ORGANIC FUNCTIONAL GROUP PREPARATIONS III, 2nd edition, ACADEMIC PRESS, INC. After the reaction is completed, the compound of interest is isolated from the post-reaction mixture by a usual method. As needed, recrystallization, column chromatography, etc. can be employed for the purification of the compound of interest.

Production Method 2

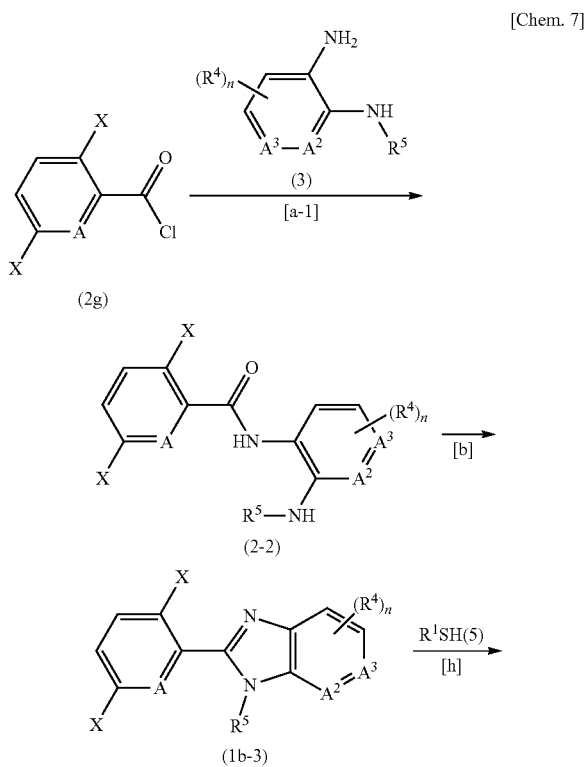

[Chem. 7]

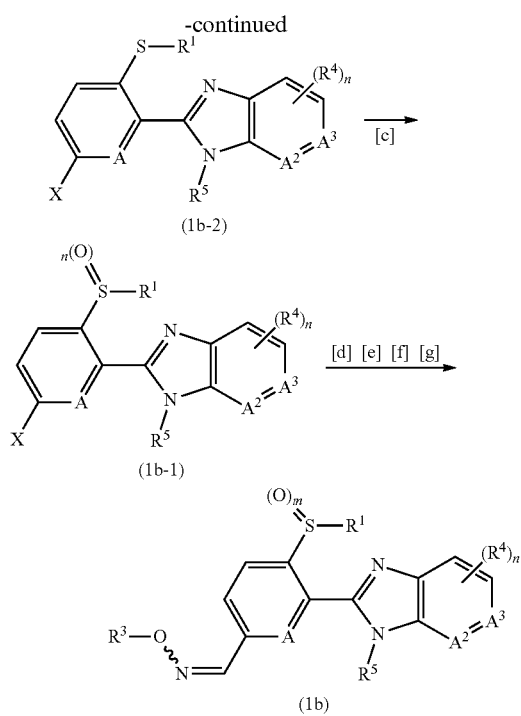

(In the formula, $R^1$, $R^3$, $R^4$, $R^5$, A, $A^2$, $A^3$, m and n are as defined above, and X represents a halogen atom.)

Production Method at Step [a-1]

The amide compound represented by the general formula (2-2) can be produced by reacting the carboxylic chloride represented by the general formula (2g) with the compound represented by the general formula (3) in the presence of a base and an inert solvent. The carboxylic chloride used is derived from the corresponding carboxylic acid by the usual method used in organic synthesis.

Examples of the base that can be used in this reaction include inorganic bases such as sodium hydroxide, potassium hydroxide, sodium carbonate, potassium carbonate, sodium hydrogen carbonate and potassium hydrogen carbonate; alkali metal hydrides such as sodium hydride and potassium hydride; acetates such as potassium acetate; alkali metal alkoxides such as potassium t-butoxide, sodium methoxide and sodium ethoxide; tertiary amines such as triethylamine, diisopropylethylamine and 1,8-diazabicyclo [5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (2g).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, or two or more of them may be used as a mixture.

Since this reaction is an equimolar reaction of the reactants, they are basically used in equimolar amounts, but either of them may be used in an excess amount. The reaction temperature is in the range of room temperature to the boiling point of the inert solvent used. The reaction time varies with the reaction scale and the reaction temperature, but is basically in the range of a few minutes to 48 hours. After the reaction is completed, the compound of interest is isolated from the post-reaction mixture by a usual method. As needed, recrystallization, column chromatography, etc. can be employed for the purification of the compound of interest.

Production Method at Step [b]

The compound represented by the general formula (1b-3) can be produced from the amide compound represented by the general formula (2-2) in the same manner as described in the step [b] of the Production Method 1 above.

Production Method at Step [h]

The compound represented by the general formula (1b-2) can be produced by reacting the compound represented by the general formula (1b-3) with $R^1SH$ (for more details, see the Production Method of Intermediate (2) shown below).

Production Method at Step [c]

The compound represented by the general formula (1b-1) can be produced from the compound represented by the general formula (1b-2) in the same manner as described in the step [c] of the Production Method 1 above.

Production Methods at Steps [d], [e], [f] and [g]

The compound represented by the general formula (1b) can be produced from the compound represented by the general formula (1b-1) in the same manner as described in the steps [d], [e], [f], [g] of the Production Method 1 above.

Production Method 3

[Chem. 8]

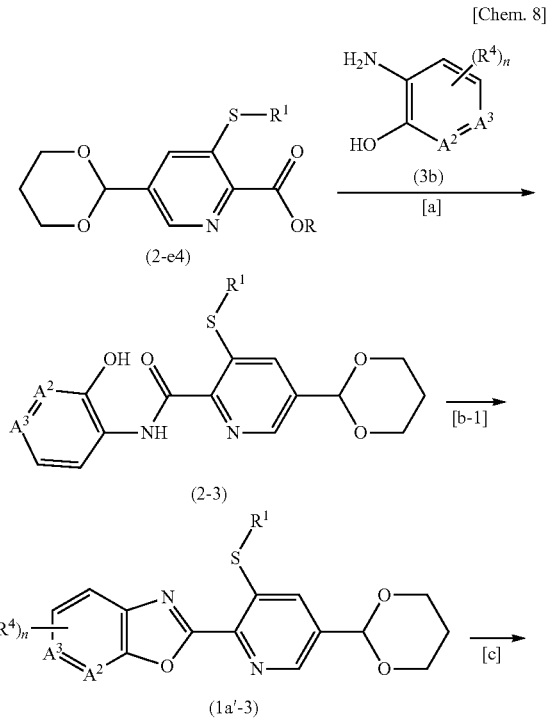

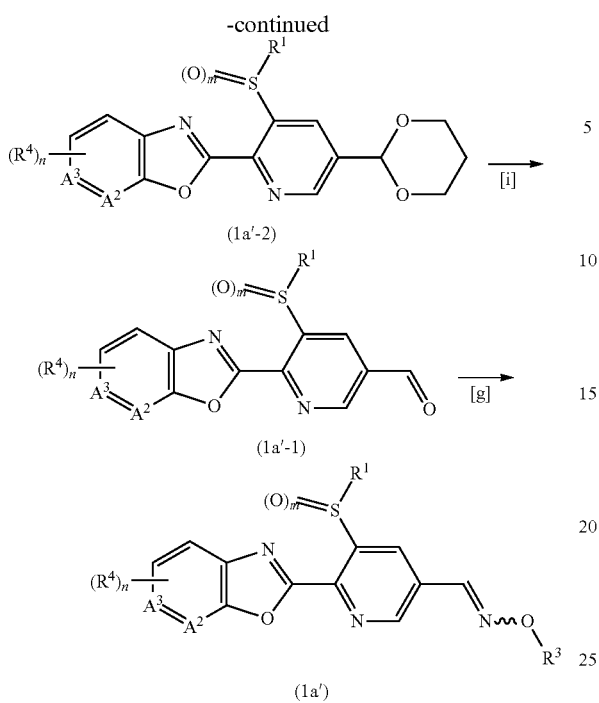

(In the formula, $R^1$, $R^3$, $R^4$, R, $A^2$, $A^3$, m and n are as defined above.)

Production Method at Step [a]

The compound represented by the general formula (2-3) can be produced from the compound represented by the general formula (2-e4) and the compound represented by the general formula (3b) in the same manner as described in the step [a] of the Production Method 1 above.

Production Method at Step [b-1]

The compound represented by the general formula (1a'-3) can be produced from the compound represented by the general formula (2-3) in the same manner as described in the step [b] of the Production Method 1 above. Alternatively, the compound represented by the general formula (1a'-3) can be produced by the reaction of the compound represented by the general formula (2-3) in the presence of an inert solvent according to the method described in Synthesis 1981, 1 (preferably, using azodicarboxylic acid diester and triphenylphosphine).

Production Method at Step [c]

The compound represented by the general formula (1a'-2) can be produced from the compound represented by the general formula (1a'-3) in the same manner as described in the step [c] of the Production Method 1 above.

Production Method at Step [i]

The compound represented by the general formula (1a'-1) can be produced by deprotection of the compound represented by the general formula (1a'-2) according to the method described in Greene's Protective GROUPS in Organic SYNTHESIS (4th Edition).

Production Method at Step [g]

The compound represented by the general formula (1a') can be produced from the compound represented by the general formula (1a'-1) in the same manner as described in the step [g] of the Production Method 1 above.

Production Method 4

[Chem. 9]

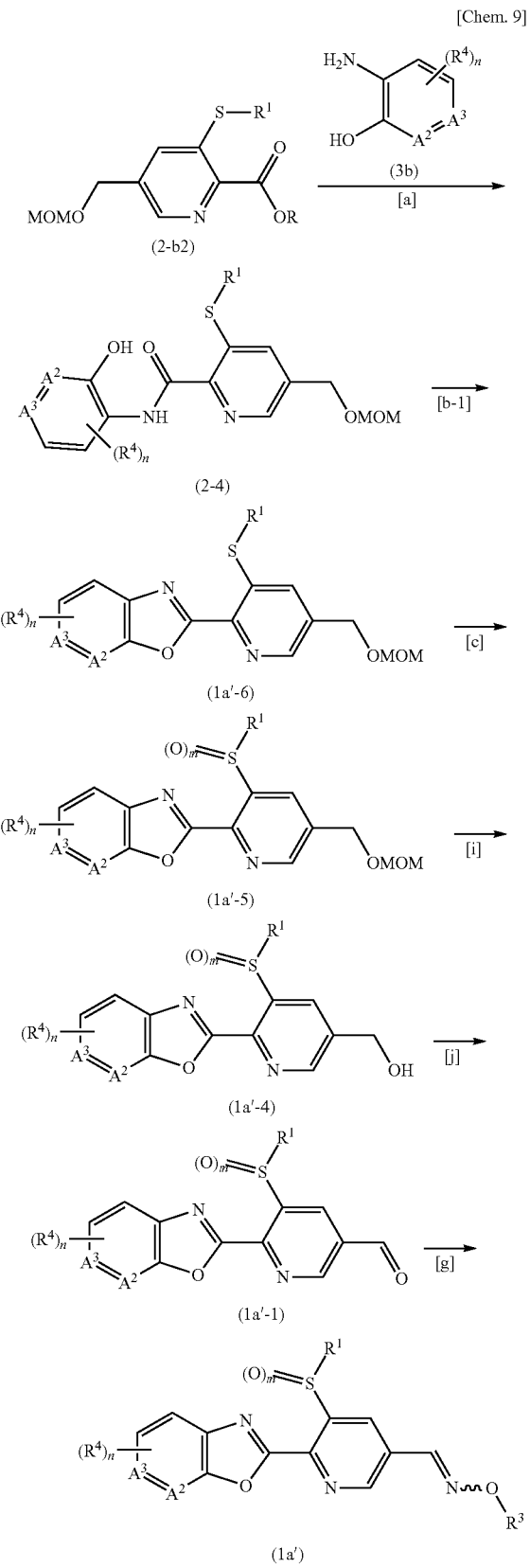

(In the formula, $R^1$, $R^3$, $R^4$, R, $A^2$, $A^3$, m and n are as defined above, and MOM stands for methoxymethyl.)

Production Method at Step [a]

The compound represented by the general formula (2-4) can be produced from the compound represented by the general formula (2-b2) and the compound represented by the general formula (3b) in the same manner as described in the step [a] of the Production Method 1 above.

Production Method at Step [b-1]

The compound represented by the general formula (1a'-6) can be produced from the compound represented by the general formula (2-4) in the same manner as described in the step [b] of the Production Method 1 above. Alternatively, the compound represented by the general formula (1a'-6) can be produced by the reaction of the compound represented by the general formula (2-4) in the presence of an inert solvent according to the method described in Synthesis 1981, 1 (preferably, using azodicarboxylic acid diester and triphenylphosphine).

Production Method at Step [c]

The compound represented by the general formula (1a'-5) can be produced from the compound represented by the general formula (1a'-6) in the same manner as described in the step [c] of the Production Method 1 above.

Production Method at Step [i]

The compound represented by the general formula (1a'-4) can be produced by deprotection of the compound represented by the general formula (1a'-5) according to the method described in Greene's Protective GROUPS in Organic SYNTHESIS (4th Edition).

Production Method at Step [j]

The compound represented by the general formula (1a'-1) can be produced from the compound represented by the general formula (1a'-4) by converting the hydroxymethyl group to a formyl group according to the method described in Synthesis 1996, 1153.

Production Method at Step [g]

The compound represented by the general formula (1a') can be produced from the compound represented by the general formula (1a'-1) by converting the formyl group to an oxime group in the same manner as described in the step [g] of Production Method 1 above.

Production Method of Intermediate (2)

[Chem. 10]

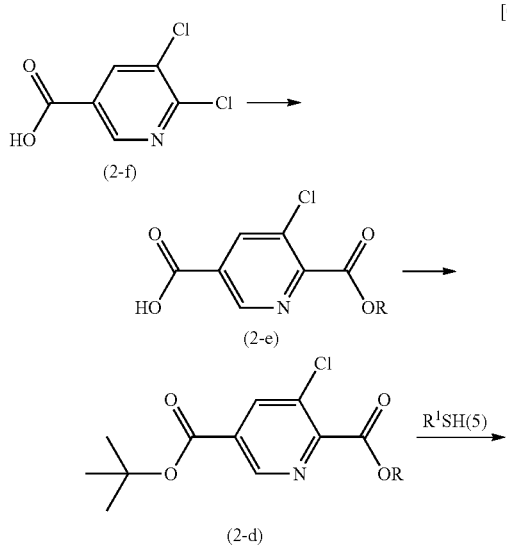

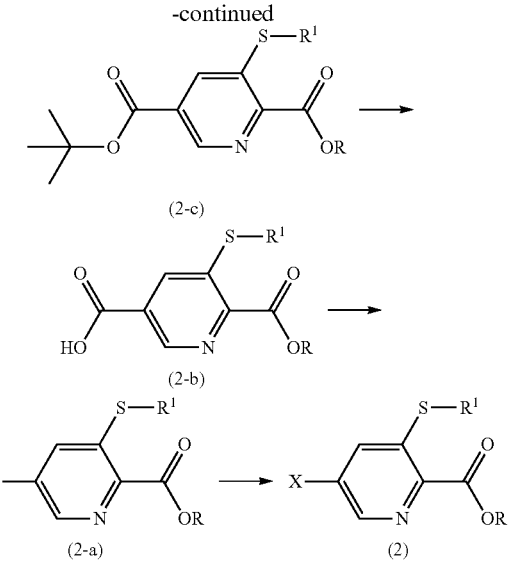

(In the formula, $R^1$ is as defined above, R represents an ester-forming group, for example, a $C_1$-$C_3$ alkyl group or the like, and X represents a halogen atom.)

The compound represented by the general formula (2), which is an intermediate in the course of the production of the compound of the present invention, can be produced by the following method.

The dichloropyridine-3-carboxylic acid (2-f), which is commonly available, is subjected to the reaction (Heck reaction) according to the method described in JP-A 2005-272338 to give the pyridine-3-carboxylic acid (2-e), which has an ester group introduced at the 6th position. After the reaction is completed, the compound of interest is isolated from the post-reaction mixture by a usual method. As needed, recrystallization, column chromatography, etc. can be employed for the purification of the compound of interest.

The pyridine-2,6-dicarboxylic acid ester (2-d) can be produced as follows. First, the pyridine-3-carboxylic acid (2-e), which has an ester group introduced, is reacted with a chlorinating agent in an inert solvent according to the common synthesis method to give a pyridinecarboxylic chloride compound. Next, the pyridinecarboxylic chloride compound is reacted with a tert-butyl alcohol to give the desired compound.

The pyridine dicarboxylic acid ester (2-c) can be produced by reacting the pyridine dicarboxylic acid ester compound represented by the general formula (2-d) with the thiol compound represented by the general formula (5) in the presence of a base and an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the pyridine dicarboxylic acid ester compound represented by the general formula (2-d). In the case where an alkali salt of the compound represented by the general formula (5) is used, it is not always necessary to use a base.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, or two or more of them may be used as a mixture.

Since this reaction is an equimolar reaction of the reactants, the compound represented by the general formula (5) and the pyridine dicarboxylic acid ester compound represented by the general formula (2-d) are used basically in equimolar amounts, but either of them may be used in an excess amount. The reaction temperature is in the range of −10° C. to the boiling point of the inert solvent used. The reaction time varies with the reaction scale and the reaction temperature, but is basically in the range of a few minutes to 48 hours. After the reaction is completed, the compound of interest is isolated from the post-reaction mixture by a usual method. As needed, recrystallization, column chromatography, etc. can be employed for the purification of the compound of interest.

The pyridine dicarboxylic acid (2-b) can be produced by hydrolyzing the pyridine dicarboxylic acid ester compound represented by the general formula (2-c) in the presence of an acid and/or an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is appropriately selected from the range of a 1- to 10-fold molar amount relative to the pyridine dicarboxylic acid ester compound represented by the general formula (2-c). In some cases, the acid can be used as the solvent as well.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, or two or more of them may be used as a mixture. In the case where the acid is used as the solvent, it is not always necessary to use another solvent.

The reaction temperature is in the range of room temperature to the boiling point of the inert solvent used. The reaction time varies with the reaction scale and the reaction temperature, but is basically in the range of a few minutes to 48 hours.

After the reaction is completed, the compound of interest is isolated from the post-reaction mixture by a usual method. As needed, recrystallization, column chromatography, etc. can be employed for the purification of the compound of interest.

The aminopyridine carboxylic acid ester (2-a) can be produced by reacting the pyridine carboxylic acid represented by the general formula (2-b) with DPPA (diphenylphosphoryl azide) in the presence of a base and tert-butyl alcohol according to the method described in J. A. Chem. Soc. 1972, 94, 6203-6205, followed by hydrolysis under acid conditions. After the reaction is completed, the compound of interest is isolated from the post-reaction mixture by a usual method. As needed, recrystallization, column chromatography, etc. can be employed for the purification of the compound of interest.

The halo pyridine carboxylic acid ester (2) can be produced by subjecting the aminopyridine carboxylic acid ester represented by the general formula (2-a) to Sandmeyer reaction, i.e., according to the method described in Chem. Rev. 1988, 88, 765. After the reaction is completed, the compound of interest is isolated from the post-reaction mixture by a usual method. As needed, recrystallization, column chromatography, etc. can be employed for the purification of the compound of interest.

Production Method of Intermediate (2-b2)

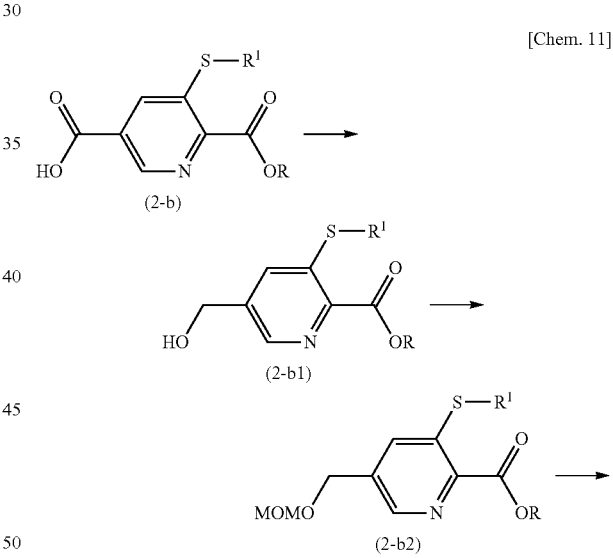

[Chem. 11]

(In the formula, $R^1$ and R are as defined above.)

The compound of the general formula (2-b) produced according to the Production Method of Intermediate shown above is subjected to the reducing reaction according to the method described in WO 2014/068988 to give the compound of the general formula (2-b1). The obtained compound is subjected to the reaction according to the method described in Greene's Protective GROUPS in Organic SYNTHESIS (4th Edition) to give the compound of the general formula (2-b2).

Production Method of Intermediate (2-e4)

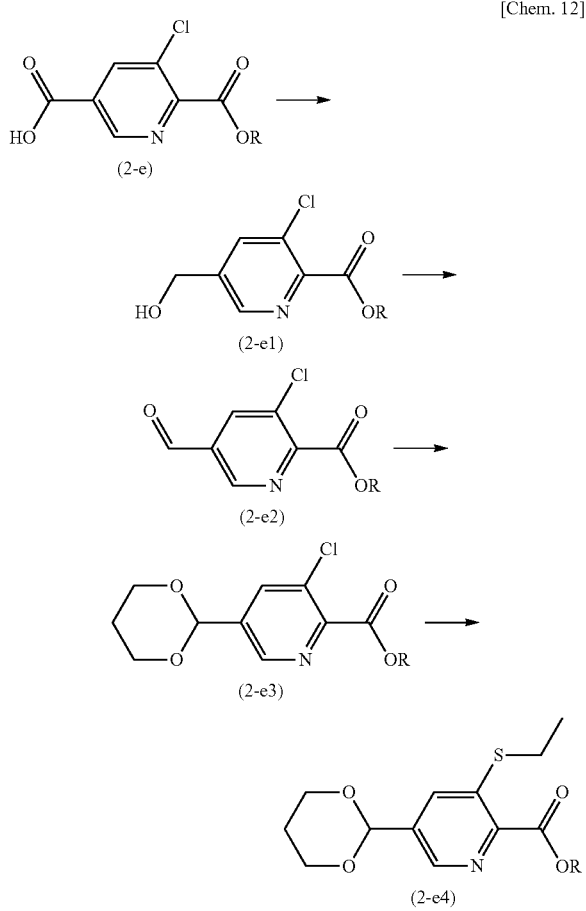

R represents a $C_1$-$C_3$ alkyl group.

The carboxylic compound of the general formula (2-e) produced according to the Production Method of Intermediate shown above is converted to the corresponding carboxylic chloride by the usual method used in organic synthesis, and the carboxylic chloride is then reduced with sodium borohydride ($NaBH_4$) to give the alcohol compound represented by the general formula (2-e1). The compound (2-e1) is converted to the aldehyde compound represented by the general formula (2-e2) by what is called Swern oxidation (using DMSO (dimethyl sulfoxide) and oxalyl chloride), and the aldehyde compound is then subjected to the reaction according to the method described in Greene's Protective GROUPS in Organic SYNTHESIS (4th Edition) to give the cyclic acetal compound represented by the general formula (2-e3).

This acetal compound is subjected to the reaction according to the method described for the production of the compound of the general formula (2-c) in the Production Method of Intermediate above, to give the compound represented by the general formula (2-e4).

Production Method of Intermediate (3)

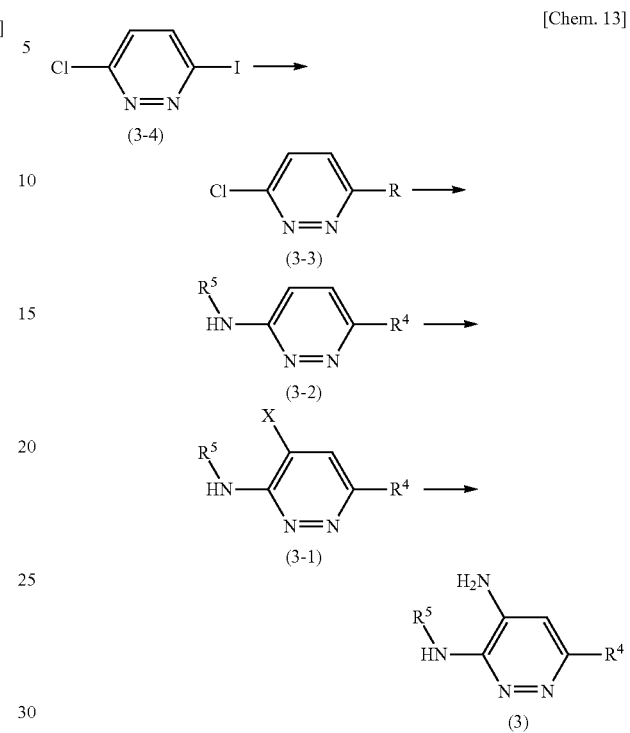

(In the formula, $R^4$ and $R^5$ are as defined above, and X represents a halogen atom.)

The compound of the general formula (3), which is an intermediate in the course of the production of the compound of the present invention, can be produced by the following method.

First, the iodopyridazine compound of the general formula (3-4) produced by the method described in the literature (Tetrahedron, 1999, 55, 15067) is cross-coupled with an iodine compound such as an alkyl iodide in the presence of a metal catalyst, a base and an inert solvent according to any of the methods described in the literature (Journal of Synthetic Organic Chemistry, Japan, vol. 69, No. 7, 2011; Chem. Rev. 2011, 4475; and WO 2013/018928) for the production of the pyridazine compound represented by the general formula (3-3).

The catalyst used in this reaction may be a palladium compound, including usually available zerovalent or divalent palladium metals and their salts (including their complexes). Such a palladium compound may be supported on activated carbon etc. Preferable examples of the palladium compound include palladium(0)/carbon, palladium(II) acetate, palladium(II) chloride, bis(triphenylphosphine)palladium(II) chloride and tetrakis(triphenylphosphine)palladium(0).

For the reaction at this step, the above-mentioned catalyst can be used with a ligand. Examples of the ligand include phosphine ligands such as triphenylphosphine ($PPh_3$), methyldiphenylphosphine ($Ph_2PCH_3$), trifurylphosphine (P(2-furyl)$_3$), tri(o-tolyl)phosphine (P(o-tol)$_3$), tri(cyclohexyl)phosphine ($PCy_3$), dicyclohexylphenylphosphine ($PhPCy_2$), tri(t-butyl) phosphine ($PtBu_3$), 2,2'-bis(diphenylphosphino)-1,1'-binaphthyl (BINAP), diphenylphosphinoferrocene (DPPF), 1,1'-bis(di-t-butylphosphino)ferrocene (DtBPF), N,N-dimethyl-1-[2-(diphenylphosphino)ferrocenyl]ethylamine, 1-[2-(diphenylphosphino)ferrocenyl]ethyl methyl ether and Xantphos; and phosphine mimic ligands such as imidazol-2-ylidene carbene (see Angewandte Chemie International Edition in English, vol. 36, p. 2163 (1997)).

Examples of the base that can be used in the present invention include hydroxides such as lithium hydroxide, sodium hydroxide and potassium hydroxide; carbonates such as lithium carbonate, lithium hydrogen carbonate, sodium carbonate, sodium hydrogen carbonate, potassium carbonate, potassium hydrogen carbonate and cesium carbonate; acetates such as lithium acetate, sodium acetate and potassium acetate; alkoxides such as sodium methoxide, sodium ethoxide and potassium tert-butoxide; metal hydrides such as sodium hydride and potassium hydride; and organic bases such as pyridine, picoline, lutidine, triethylamine, tributylamine and diisopropylethylamine. The amount of the base used is appropriately selected from the range of a 1- to 5.0-fold molar amount relative to the compound represented by the general formula (3-4).

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours.

The amino pyridazine compound represented by the general formula (3-2) can be produced by reacting the pyridazine compound represented by the general formula (3-3) with an amino compound ($R^5NH_2$).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and other solvents such as dimethyl sulfoxide and 1,3-dimethyl-2-imidazolidinone. One of these inert solvents may be used alone, or two or more of them may be used as a mixture.

If needed, a base may be used, and examples of the base used include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (3-3).

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. The amount of the amino compound ($R^5NH_2$) used is appropriately selected from the range of a 1- to 5-fold molar amount relative to the pyridazine compound represented by the general formula (3-3).

After the reaction is completed, the compound of interest is isolated from the post-reaction mixture by a usual method. As needed, recrystallization, column chromatography, etc. can be employed for the purification of the compound of interest.

The halo pyridazine compound represented by the general formula (3-1) can be produced by reacting the amino pyridazine compound represented by the general formula (3-2) with a halogenating agent.

The inert solvent used in this reaction may be any solvent that does not markedly inhibit the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; esters such as ethyl acetate; and polar solvents such as N,N-dimethylformamide, N,N-dimethylacetamide, 1,3-dimethyl-2-imidazolidinone, water and acetic acid. One of these inert solvents may be used alone, or two or more of them may be used as a mixture.

Examples of the halogenating agent used in the reaction include halogen molecules such as a chlorine, bromine or iodine molecule; halosuccinimides such as NCS and NBS; halogenated hydantoins such as DIH; and thionyl chloride.

The reaction temperature in this reaction is appropriately selected from the range of −30° C. to the reflux temperature of the inert solvent used. The reaction time varies with the reaction scale, the reaction temperature and the like and is not the same in every case, but is basically selected as appropriate from the range of a few minutes to 48 hours.

After the reaction is completed, the compound of interest is isolated from the post-reaction mixture by a usual method. As needed, recrystallization, column chromatography, etc. can be employed for the purification of the compound of interest.

The amino pyridazine compound (3) can be produced by reacting the halo pyridazine compound represented by the general formula (3-1) with ammonia in the presence of a copper catalyst and a solvent.

The inert solvent used in this reaction may be any solvent that does not markedly inhibit the progress of the reaction, and the examples include alcohols such as methanol, ethanol, propanol, butanol and 2-propanol; aromatic hydrocarbons such as benzene, toluene and xylene; halogenated aromatic hydrocarbons such as chlorobenzene and dichlorobenzene; straight-chain or cyclic ethers such as diethyl ether, methyl tert-butyl ether, dioxane and tetrahydrofuran; amides such as dimethylformamide, dimethylacetamide and N-methylpyrrolidone; and other solvents such as dimethyl sulfoxide and 1,3-dimethyl-2-imidazolidinone. One of these inert solvents may be used alone, or two or more of them may be used as a mixture. The copper catalyst used in this reaction can be copper oxide, copper bromide, copper chloride or the like. The amount of the copper catalyst used is appropriately selected from the range of a 1- to 5-fold molar amount relative to the halo pyridazine compound represented by the general formula (3-1).

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. The amount of the ammonia used is appropriately selected from the range of a 1- to 5-fold molar amount relative to the halo pyridazine compound represented by the general formula (3-1). For efficient progress of the reaction, autoclave can be used. After the reaction is completed, the compound of interest is isolated from the post-reaction mixture by a usual method. As needed, recrystallization, column chromatography, etc. can be employed for the purification of the compound of interest.

Specific examples of the compound of the present invention are shown below. In the following tables, Me stands for a methyl group, Et stands for an ethyl group, n-Pr stands for a n-propyl group, i-Pr stands for an isopropyl group, c-Pr stands for a cyclopropyl group, Allyl stands for an allyl group, t-Bu stands for a tertiary-butyl group, Ph stands for a phenyl group, Bn stands for a benzyl group, and Ac stands for an acetyl group. The "E" or "Z" in the column of "Isomerism" means geometric isomerism due to the oxime group. Shown in the column of "Physical property" is a melting point (° C.) or "NMR". NMR data are shown in Table 7.

[Chem. 14]

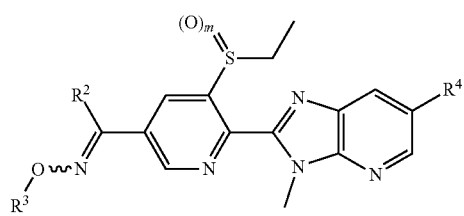

(1A-1)

TABLE 1

| Compound No. | $R^2$ | $R^3$ | $R^4$ | Isomerism | m | Physical property |
|---|---|---|---|---|---|---|
| 1-1 | H | H | $CF_3$ | E | 0 | |
| 1-2 | H | H | $CF_3$ | E | 1 | |
| 1-3 | H | H | $CF_3$ | E | 2 | 240-241 |
| 1-4 | H | Me | $CF_3$ | E | 0 | |
| 1-5 | H | Me | $CF_3$ | E | 1 | |
| 1-6 | H | Me | $CF_3$ | E | 2 | |
| 1-7 | H | Et | $CF_3$ | E | 0 | |
| 1-8 | H | Et | $CF_3$ | E | 1 | |
| 1-9 | H | Et | $CF_3$ | E | 2 | |
| 1-10 | H | Et | $CF_3$ | Z | 0 | |
| 1-11 | H | Et | $CF_3$ | Z | 1 | |
| 1-12 | H | Et | $CF_3$ | Z | 2 | |
| 1-13 | H | Allyl | $CF_3$ | E | 0 | |
| 1-14 | H | Allyl | $CF_3$ | E | 1 | |
| 1-15 | H | Allyl | $CF_3$ | E | 2 | |
| 1-16 | H | Allyl | $CF_3$ | Z | 0 | |
| 1-17 | H | Allyl | $CF_3$ | Z | 1 | |
| 1-18 | H | Allyl | $CF_3$ | Z | 2 | |
| 1-19 | H | Bn | $CF_3$ | E | 0 | |
| 1-20 | H | Bn | $CF_3$ | E | 1 | |
| 1-21 | H | Bn | $CF_3$ | E | 2 | |
| 1-22 | Me | Me | $CF_3$ | E | 0 | |
| 1-23 | Me | Me | $CF_3$ | E | 1 | |
| 1-24 | Me | Me | $CF_3$ | E | 2 | |
| 1-25 | Me | Me | $CF_3$ | Z | 0 | |
| 1-26 | Me | Me | $CF_3$ | Z | 1 | |
| 1-27 | Me | Me | $CF_3$ | Z | 2 | |
| 1-28 | Me | Et | $CF_3$ | E | 0 | |
| 1-29 | Me | Et | $CF_3$ | E | 1 | |
| 1-30 | Me | Et | $CF_3$ | E | 2 | |

TABLE 2

Table 1 (continued)

| Compound No. | $R^2$ | $R^3$ | $R^4$ | Isomerism | m | Physical property |
|---|---|---|---|---|---|---|
| 1-31 | Me | Et | $CF_3$ | Z | 0 | |
| 1-32 | Me | Et | $CF_3$ | Z | 1 | |
| 1-33 | Me | Et | $CF_3$ | Z | 2 | |
| 1-34 | Me | Allyl | $CF_3$ | E | 0 | |
| 1-35 | Me | Allyl | $CF_3$ | E | 1 | |
| 1-36 | Me | Allyl | $CF_3$ | E | 2 | |
| 1-37 | Me | Allyl | $CF_3$ | Z | 0 | |
| 1-38 | Me | Allyl | $CF_3$ | Z | 1 | |
| 1-39 | Me | Allyl | $CF_3$ | Z | 2 | |
| 1-40 | Me | Bn | $CF_3$ | E | 0 | |
| 1-41 | Me | Bn | $CF_3$ | E | 1 | |
| 1-42 | Me | Bn | $CF_3$ | E | 2 | |
| 1-43 | Me | Bn | $CF_3$ | Z | 0 | |
| 1-44 | Me | Bn | $CF_3$ | Z | 1 | |
| 1-45 | Me | Bn | $CF_3$ | Z | 2 | |
| 1-46 | H | t-Bu | $CF_3$ | E | 0 | |
| 1-47 | H | t-Bu | $CF_3$ | E | 1 | |
| 1-48 | H | t-Bu | $CF_3$ | E | 2 | |
| 1-49 | H | t-Bu | $CF_3$ | Z | 0 | |
| 1-50 | H | t-Bu | $CF_3$ | Z | 1 | |
| 1-51 | H | t-Bu | $CF_3$ | Z | 2 | |
| 1-52 | H | Ph | $CF_3$ | E | 0 | |
| 1-53 | H | Ph | $CF_3$ | E | 1 | |
| 1-54 | H | Ph | $CF_3$ | E | 2 | |
| 1-55 | H | $C(CH_3)_2(OMe)$ | $CF_3$ | E | 0 | |
| 1-56 | H | $C(CH_3)_2(OMe)$ | $CF_3$ | E | 1 | |
| 1-57 | H | $C(CH_3)_2(OMe)$ | $CF_3$ | E | 2 | |
| 1-58 | H | $CH_2CF_3$ | $CF_3$ | E | 0 | |
| 1-59 | H | $CH_2CF_3$ | $CF_3$ | E | 1 | |
| 1-60 | H | $CH_2CF_3$ | $CF_3$ | E | 2 | 202-203 |

TABLE 3

Table 1 (continued)

| Compound No. | $R^2$ | $R^3$ | $R^4$ | Isomerism | m | Physical property |
|---|---|---|---|---|---|---|
| 1-61 | H | $CH_2CF_3$ | $CF_3$ | Z | 0 | |
| 1-62 | H | $CH_2CF_3$ | $CF_3$ | Z | 1 | |
| 1-63 | H | $CH_2CF_3$ | $CF_3$ | Z | 2 | |
| 1-64 | Me | $CH_2CF_3$ | $CF_3$ | E | 0 | |
| 1-65 | Me | $CH_2CF_3$ | $CF_3$ | E | 1 | |
| 1-66 | Me | $CH_2CF_3$ | $CF_3$ | E | 2 | |
| 1-67 | Me | $CH_2CF_3$ | $CF_3$ | Z | 0 | |
| 1-68 | Me | $CH_2CF_3$ | $CF_3$ | Z | 1 | |
| 1-69 | Me | $CH_2CF_3$ | $CF_3$ | Z | 2 | |
| 1-70 | H | $CH_2CHF_2$ | $CF_3$ | E | 0 | |
| 1-71 | H | $CH_2CHF_2$ | $CF_3$ | E | 1 | |
| 1-72 | H | $CH_2CHF_2$ | $CF_3$ | E | 2 | 188-189 |
| 1-73 | H | $CH_2CHF_2$ | $CF_3$ | Z | 0 | |
| 1-74 | H | $CH_2CHF_2$ | $CF_3$ | Z | 1 | |
| 1-75 | H | $CH_2CHF_2$ | $CF_3$ | Z | 2 | |
| 1-76 | Me | $CH_2CHF_2$ | $CF_3$ | E | 0 | |
| 1-77 | Me | $CH_2CHF_2$ | $CF_3$ | E | 1 | |
| 1-78 | Me | $CH_2CHF_2$ | $CF_3$ | E | 2 | |
| 1-79 | Me | $CH_2CHF_2$ | $CF_3$ | Z | 0 | |
| 1-80 | Me | $CH_2CHF_2$ | $CF_3$ | Z | 1 | |
| 1-81 | Me | $CH_2CHF_2$ | $CF_3$ | Z | 2 | |
| 1-82 | H | $CHF_2$ | $CF_3$ | E | 0 | |
| 1-83 | H | $CHF_2$ | $CF_3$ | E | 1 | |
| 1-84 | H | $CHF_2$ | $CF_3$ | E | 2 | |
| 1-85 | H | $CHF_2$ | $CF_3$ | Z | 0 | |
| 1-86 | H | $CHF_2$ | $CF_3$ | Z | 1 | |
| 1-87 | H | $CHF_2$ | $CF_3$ | Z | 2 | |
| 1-88 | Me | $CHF_2$ | $CF_3$ | E | 0 | |
| 1-89 | Me | $CHF_2$ | $CF_3$ | E | 1 | |
| 1-90 | Me | $CHF_2$ | $CF_3$ | E | 2 | |

TABLE 4

Table 1 (continued)

| Compound No. | $R^2$ | $R^3$ | $R^4$ | Isomerism | m | Physical property |
|---|---|---|---|---|---|---|
| 1-91 | Me | $CHF_2$ | $CF_3$ | Z | 0 | |
| 1-92 | Me | $CHF_2$ | $CF_3$ | Z | 1 | |
| 1-93 | Me | $CHF_2$ | $CF_3$ | Z | 2 | |
| 1-94 | H | H | $SCF_3$ | E | 0 | |
| 1-95 | H | H | $SCF_3$ | E | 1 | |
| 1-96 | H | H | $SCF_3$ | E | 2 | |
| 1-97 | H | Me | $SCF_3$ | E | 0 | |
| 1-98 | H | Me | $SCF_3$ | E | 1 | |
| 1-99 | H | Me | $SCF_3$ | E | 2 | |
| 1-100 | H | Et | $SCF_3$ | E | 0 | |
| 1-101 | H | Et | $SCF_3$ | E | 1 | |
| 1-102 | H | Et | $SCF_3$ | E | 2 | |
| 1-103 | H | Et | $SCF_3$ | Z | 0 | |
| 1-104 | H | Et | $SCF_3$ | Z | 1 | |
| 1-105 | H | Et | $SCF_3$ | Z | 2 | |
| 1-106 | H | Allyl | $SCF_3$ | E | 0 | |
| 1-107 | H | Allyl | $SCF_3$ | E | 1 | |
| 1-108 | H | Allyl | $SCF_3$ | E | 2 | |
| 1-109 | H | Allyl | $SCF_3$ | Z | 0 | |
| 1-110 | H | Allyl | $SCF_3$ | Z | 1 | |
| 1-111 | H | Allyl | $SCF_3$ | Z | 2 | |
| 1-112 | H | Bn | $SCF_3$ | E | 0 | |
| 1-113 | H | Bn | $SCF_3$ | E | 1 | |
| 1-114 | H | Bn | $SCF_3$ | E | 2 | |
| 1-115 | Me | Me | $SCF_3$ | E | 0 | |
| 1-116 | Me | Me | $SCF_3$ | E | 1 | |
| 1-117 | Me | Me | $SCF_3$ | E | 2 | |
| 1-118 | Me | Me | $SCF_3$ | Z | 0 | |
| 1-119 | Me | Me | $SCF_3$ | Z | 1 | |
| 1-120 | Me | Me | $SCF_3$ | Z | 2 | |

TABLE 5

Table 1 (continued)

| Compound No. | $R^2$ | $R^3$ | $R^4$ | Isomerism | m | Physical property |
|---|---|---|---|---|---|---|
| 1-121 | Me | Et | $SCF_3$ | E | 0 | |
| 1-122 | Me | Et | $SCF_3$ | E | 1 | |
| 1-123 | Me | Et | $SCF_3$ | E | 2 | |
| 1-124 | Me | Et | $SCF_3$ | Z | 0 | |
| 1-125 | Me | Et | $SCF_3$ | Z | 1 | |
| 1-126 | Me | Et | $SCF_3$ | Z | 2 | |
| 1-127 | Me | Allyl | $SCF_3$ | E | 0 | |
| 1-128 | Me | Allyl | $SCF_3$ | E | 1 | |
| 1-129 | Me | Allyl | $SCF_3$ | E | 2 | |
| 1-130 | Me | Allyl | $SCF_3$ | Z | 0 | |
| 1-131 | Me | Allyl | $SCF_3$ | Z | 1 | |
| 1-132 | Me | Allyl | $SCF_3$ | Z | 2 | |
| 1-133 | Me | Bn | $SCF_3$ | E | 0 | |
| 1-134 | Me | Bn | $SCF_3$ | E | 1 | |
| 1-135 | Me | Bn | $SCF_3$ | E | 2 | |
| 1-136 | Me | Bn | $SCF_3$ | Z | 0 | |
| 1-137 | Me | Bn | $SCF_3$ | Z | 1 | |
| 1-138 | Me | Bn | $SCF_3$ | Z | 2 | |
| 1-139 | H | t-Bu | $SCF_3$ | E | 0 | |
| 1-140 | H | t-Bu | $SCF_3$ | E | 1 | |
| 1-141 | H | t-Bu | $SCF_3$ | E | 2 | |
| 1-142 | H | t-Bu | $SCF_3$ | Z | 0 | |
| 1-143 | H | t-Bu | $SCF_3$ | Z | 1 | |
| 1-144 | H | t-Bu | $SCF_3$ | Z | 2 | |
| 1-145 | H | Ph | $SCF_3$ | E | 0 | |
| 1-146 | H | Ph | $SCF_3$ | E | 1 | |
| 1-147 | H | Ph | $SCF_3$ | E | 2 | |
| 1-148 | H | $C(CH_3)_2(OMe)$ | $SCF_3$ | E | 0 | |
| 1-149 | H | $C(CH_3)_2(OMe)$ | $SCF_3$ | E | 1 | |
| 1-150 | H | $C(CH_3)_2(OMe)$ | $SCF_3$ | E | 2 | |

TABLE 6

Table 1 (continued)

| Compound No. | $R^2$ | $R^3$ | $R^4$ | Isomerism | m | Physical property |
|---|---|---|---|---|---|---|
| 1-151 | H | $CH_2CF_3$ | $SCF_3$ | E | 0 | |
| 1-152 | H | $CH_2CF_3$ | $SCF_3$ | E | 1 | |
| 1-153 | H | $CH_2CF_3$ | $SCF_3$ | E | 2 | |
| 1-154 | H | $CH_2CF_3$ | $SCF_3$ | Z | 0 | |
| 1-155 | H | $CH_2CF_3$ | $SCF_3$ | Z | 1 | |
| 1-156 | H | $CH_2CF_3$ | $SCF_3$ | Z | 2 | |
| 1-157 | Me | $CH_2CF_3$ | $SCF_3$ | E | 0 | |
| 1-158 | Me | $CH_2CF_3$ | $SCF_3$ | E | 1 | |
| 1-159 | Me | $CH_2CF_3$ | $SCF_3$ | E | 2 | |
| 1-160 | Me | $CH_2CF_3$ | $SCF_3$ | Z | 0 | |
| 1-161 | Me | $CH_2CF_3$ | $SCF_3$ | Z | 1 | |
| 1-162 | Me | $CH_2CF_3$ | $SCF_3$ | Z | 2 | |
| 1-163 | H | $CH_2CHF_2$ | $SCF_3$ | E | 0 | |
| 1-164 | H | $CH_2CHF_2$ | $SCF_3$ | E | 1 | |
| 1-165 | H | $CH_2CHF_2$ | $SCF_3$ | E | 2 | |
| 1-166 | H | $CH_2CHF_2$ | $SCF_3$ | Z | 0 | |
| 1-167 | H | $CH_2CHF_2$ | $SCF_3$ | Z | 1 | |
| 1-168 | H | $CH_2CHF_2$ | $SCF_3$ | Z | 2 | |
| 1-169 | Me | $CH_2CHF_2$ | $SCF_3$ | E | 0 | |
| 1-170 | Me | $CH_2CHF_2$ | $SCF_3$ | E | 1 | |
| 1-171 | Me | $CH_2CHF_2$ | $SCF_3$ | E | 2 | |
| 1-172 | Me | $CH_2CHF_2$ | $SCF_3$ | Z | 0 | |
| 1-173 | Me | $CH_2CHF_2$ | $SCF_3$ | Z | 1 | |
| 1-174 | Me | $CH_2CHF_2$ | $SCF_3$ | Z | 2 | |
| 1-175 | H | $CHF_2$ | $SCF_3$ | E | 0 | |
| 1-176 | H | $CHF_2$ | $SCF_3$ | E | 1 | |
| 1-177 | H | $CHF_2$ | $SCF_3$ | E | 2 | |
| 1-178 | H | $CHF_2$ | $SCF_3$ | Z | 0 | |
| 1-179 | H | $CHF_2$ | $SCF_3$ | Z | 1 | |
| 1-180 | H | $CHF_2$ | $SCF_3$ | Z | 2 | |

TABLE 7

Table 1 (continued)

| Compound No. | $R^2$ | $R^3$ | $R^4$ | Isomerism | m | Physical property |
|---|---|---|---|---|---|---|
| 1-181 | Me | $CHF_2$ | $SCF_3$ | E | 0 | |
| 1-182 | Me | $CHF_2$ | $SCF_3$ | E | 1 | |
| 1-183 | Me | $CHF_2$ | $SCF_3$ | E | 2 | |
| 1-184 | Me | $CHF_2$ | $SCF_3$ | Z | 0 | |
| 1-185 | Me | $CHF_2$ | $SCF_3$ | Z | 1 | |
| 1-186 | Me | $CHF_2$ | $SCF_3$ | Z | 2 | |
| 1-187 | H | H | $CF_2CF_3$ | E | 0 | |
| 1-188 | H | H | $CF_2CF_3$ | E | 1 | |
| 1-189 | H | H | $CF_2CF_3$ | E | 2 | 240-242 |
| 1-190 | H | Me | $CF_2CF_3$ | E | 0 | |
| 1-191 | H | Me | $CF_2CF_3$ | E | 1 | |
| 1-192 | H | Me | $CF_2CF_3$ | E | 2 | 193-194 |
| 1-193 | H | Et | $CF_2CF_3$ | E | 0 | |
| 1-194 | H | Et | $CF_2CF_3$ | E | 1 | |
| 1-195 | H | Et | $CF_2CF_3$ | E | 2 | 162-164 |
| 1-196 | H | Et | $CF_2CF_3$ | Z | 0 | |
| 1-197 | H | Et | $CF_2CF_3$ | Z | 1 | |
| 1-198 | H | Et | $CF_2CF_3$ | Z | 2 | 179-180 |
| 1-199 | H | Allyl | $CF_2CF_3$ | E | 0 | |
| 1-200 | H | Allyl | $CF_2CF_3$ | E | 1 | |
| 1-201 | H | Allyl | $CF_2CF_3$ | E | 2 | 155-160 |
| 1-202 | H | Allyl | $CF_2CF_3$ | Z | 0 | |
| 1-203 | H | Allyl | $CF_2CF_3$ | Z | 1 | |
| 1-204 | H | Allyl | $CF_2CF_3$ | Z | 2 | 141-142 |
| 1-205 | H | Bn | $CF_2CF_3$ | E | 0 | |
| 1-206 | H | Bn | $CF_2CF_3$ | E | 1 | |
| 1-207 | H | Bn | $CF_2CF_3$ | E | 2 | NMR |
| 1-208 | Me | Me | $CF_2CF_3$ | E | 0 | |
| 1-209 | Me | Me | $CF_2CF_3$ | E | 1 | |
| 1-210 | Me | Me | $CF_2CF_3$ | E | 2 | 175-176 |

TABLE 8

Table 1 (continued)

| Compound No. | $R^2$ | $R^3$ | $R^4$ | Isomerism | m | Physical property |
|---|---|---|---|---|---|---|
| 1-211 | Me | Me | $CF_2CF_3$ | Z | 0 | |
| 1-212 | Me | Me | $CF_2CF_3$ | Z | 1 | |
| 1-213 | Me | Me | $CF_2CF_3$ | Z | 2 | NMR |
| 1-214 | Me | Et | $CF_2CF_3$ | E | 0 | |
| 1-215 | Me | Et | $CF_2CF_3$ | E | 1 | |
| 1-216 | Me | Et | $CF_2CF_3$ | E | 2 | 163-164 |
| 1-217 | Me | Et | $CF_2CF_3$ | Z | 0 | |
| 1-218 | Me | Et | $CF_2CF_3$ | Z | 1 | |
| 1-219 | Me | Et | $CF_2CF_3$ | Z | 2 | NMR |
| 1-220 | Me | Allyl | $CF_2CF_3$ | E | 0 | |
| 1-221 | Me | Allyl | $CF_2CF_3$ | E | 1 | |
| 1-222 | Me | Allyl | $CF_2CF_3$ | E | 2 | 173-174 |
| 1-223 | Me | Allyl | $CF_2CF_3$ | Z | 0 | |
| 1-224 | Me | Allyl | $CF_2CF_3$ | Z | 1 | |
| 1-225 | Me | Allyl | $CF_2CF_3$ | Z | 2 | NMR |
| 1-226 | Me | Bn | $CF_2CF_3$ | E | 0 | |
| 1-227 | Me | Bn | $CF_2CF_3$ | E | 1 | |
| 1-228 | Me | Bn | $CF_2CF_3$ | E | 2 | 213-214 |
| 1-229 | Me | Bn | $CF_2CF_3$ | Z | 0 | |
| 1-230 | Me | Bn | $CF_2CF_3$ | Z | 1 | |
| 1-231 | Me | Bn | $CF_2CF_3$ | Z | 2 | 117-119 |
| 1-232 | H | t-Bu | $CF_2CF_3$ | E | 0 | |
| 1-233 | H | t-Bu | $CF_2CF_3$ | E | 1 | |
| 1-234 | H | t-Bu | $CF_2CF_3$ | E | 2 | NMR |
| 1-235 | H | t-Bu | $CF_2CF_3$ | Z | 0 | |
| 1-236 | H | t-Bu | $CF_2CF_3$ | Z | 1 | |
| 1-237 | H | t-Bu | $CF_2CF_3$ | Z | 2 | NMR |
| 1-238 | H | Ph | $CF_2CF_3$ | E | 0 | |
| 1-239 | H | Ph | $CF_2CF_3$ | E | 1 | |
| 1-240 | H | Ph | $CF_2CF_3$ | E | 2 | 168-169 |

TABLE 9

Table 1 (continued)

| Compound No. | $R^2$ | $R^3$ | $R^4$ | Isomerism | m | Physical property |
|---|---|---|---|---|---|---|
| 1-241 | H | $C(CH_3)_2(OMe)$ | $CF_2CF_3$ | E | 0 | |
| 1-242 | H | $C(CH_3)_2(OMe)$ | $CF_2CF_3$ | E | 1 | |
| 1-243 | H | $C(CH_3)_2(OMe)$ | $CF_2CF_3$ | E | 2 | NMR |
| 1-244 | H | $CH_2CF_3$ | $CF_2CF_3$ | E | 0 | |
| 1-245 | H | $CH_2CF_3$ | $CF_2CF_3$ | E | 1 | |
| 1-246 | H | $CH_2CF_3$ | $CF_2CF_3$ | E | 2 | 207-208 |
| 1-247 | H | $CH_2CF_3$ | $CF_2CF_3$ | Z | 0 | |
| 1-248 | H | $CH_2CF_3$ | $CF_2CF_3$ | Z | 1 | |
| 1-249 | H | $CH_2CF_3$ | $CF_2CF_3$ | Z | 2 | |
| 1-250 | Me | $CH_2CF_3$ | $CF_2CF_3$ | E | 0 | |
| 1-251 | Me | $CH_2CF_3$ | $CF_2CF_3$ | E | 1 | |
| 1-252 | Me | $CH_2CF_3$ | $CF_2CF_3$ | E | 2 | 207-208 |
| 1-253 | Me | $CH_2CF_3$ | $CF_2CF_3$ | Z | 0 | |
| 1-254 | Me | $CH_2CF_3$ | $CF_2CF_3$ | Z | 1 | |
| 1-255 | Me | $CH_2CF_3$ | $CF_2CF_3$ | Z | 2 | |
| 1-256 | H | $CH_2CHF_2$ | $CF_2CF_3$ | E | 0 | |
| 1-257 | H | $CH_2CHF_2$ | $CF_2CF_3$ | E | 1 | |
| 1-258 | H | $CH_2CHF_2$ | $CF_2CF_3$ | E | 2 | 207-208 |
| 1-259 | H | $CH_2CHF_2$ | $CF_2CF_3$ | Z | 0 | |
| 1-260 | H | $CH_2CHF_2$ | $CF_2CF_3$ | Z | 1 | |
| 1-261 | H | $CH_2CHF_2$ | $CF_2CF_3$ | Z | 2 | |
| 1-262 | Me | $CH_2CHF_2$ | $CF_2CF_3$ | E | 0 | |
| 1-263 | Me | $CH_2CHF_2$ | $CF_2CF_3$ | E | 1 | |
| 1-264 | Me | $CH_2CHF_2$ | $CF_2CF_3$ | E | 2 | |
| 1-265 | Me | $CH_2CHF_2$ | $CF_2CF_3$ | Z | 0 | |
| 1-266 | Me | $CH_2CHF_2$ | $CF_2CF_3$ | Z | 1 | |
| 1-267 | Me | $CH_2CHF_2$ | $CF_2CF_3$ | Z | 2 | |
| 1-268 | H | $CHF_2$ | $CF_2CF_3$ | E | 0 | |
| 1-269 | H | $CHF_2$ | $CF_2CF_3$ | E | 1 | |
| 1-270 | H | $CHF_2$ | $CF_2CF_3$ | E | 2 | |

TABLE 10

Table 1 (continued)

| Compound No. | $R^2$ | $R^3$ | $R^4$ | Isomerism | m | Physical property |
|---|---|---|---|---|---|---|
| 1-271 | H | $CHF_2$ | $CF_2CF_3$ | Z | 0 | |
| 1-272 | H | $CHF_2$ | $CF_2CF_3$ | Z | 1 | |
| 1-273 | H | $CHF_2$ | $CF_2CF_3$ | Z | 2 | |
| 1-274 | Me | $CHF_2$ | $CF_2CF_3$ | E | 0 | |
| 1-275 | Me | $CHF_2$ | $CF_2CF_3$ | E | 1 | |
| 1-276 | Me | $CHF_2$ | $CF_2CF_3$ | E | 2 | |
| 1-277 | Me | $CHF_2$ | $CF_2CF_3$ | Z | 0 | |
| 1-278 | Me | $CHF_2$ | $CF_2CF_3$ | Z | 1 | |
| 1-279 | Me | $CHF_2$ | $CF_2CF_3$ | Z | 2 | |
| 1-280 | H | n-Pr | $CF_2CF_3$ | E | 0 | |
| 1-281 | H | n-Pr | $CF_2CF_3$ | E | 1 | |
| 1-282 | H | n-Pr | $CF_2CF_3$ | E | 2 | |
| 1-283 | H | n-Pr | $CF_2CF_3$ | Z | 0 | |
| 1-284 | H | n-Pr | $CF_2CF_3$ | Z | 1 | |
| 1-285 | H | n-Pr | $CF_2CF_3$ | Z | 2 | |
| 1-286 | Me | n-Pr | $CF_2CF_3$ | E | 0 | |
| 1-287 | Me | n-Pr | $CF_2CF_3$ | E | 1 | |
| 1-288 | Me | n-Pr | $CF_2CF_3$ | E | 2 | |
| 1-289 | Me | n-Pr | $CF_2CF_3$ | Z | 0 | |
| 1-290 | Me | n-Pr | $CF_2CF_3$ | Z | 1 | |
| 1-291 | Me | n-Pr | $CF_2CF_3$ | Z | 2 | |
| 1-292 | H | i-Pr | $CF_2CF_3$ | E | 0 | |
| 1-293 | H | i-Pr | $CF_2CF_3$ | E | 1 | |
| 1-294 | H | i-Pr | $CF_2CF_3$ | E | 2 | |
| 1-295 | H | i-Pr | $CF_2CF_3$ | Z | 0 | |
| 1-296 | H | i-Pr | $CF_2CF_3$ | Z | 1 | |
| 1-297 | H | i-Pr | $CF_2CF_3$ | Z | 2 | |
| 1-298 | Me | i-Pr | $CF_2CF_3$ | E | 0 | |
| 1-299 | Me | i-Pr | $CF_2CF_3$ | E | 1 | |
| 1-300 | Me | i-Pr | $CF_2CF_3$ | E | 2 | |

TABLE 11

Table 1 (continued)

| Compound No. | $R^2$ | $R^3$ | $R^4$ | Isomerism | m | Physical property |
|---|---|---|---|---|---|---|
| 1-301 | Me | i-Pr | $CF_2CF_3$ | Z | 0 | |
| 1-302 | Me | i-Pr | $CF_2CF_3$ | Z | 1 | |
| 1-303 | Me | i-Pr | $CF_2CF_3$ | Z | 2 | |
| 1-304 | H | $CH_2CF_2CF_3$ | $CF_2CF_3$ | E | 0 | |
| 1-305 | H | $CH_2CF_2CF_3$ | $CF_2CF_3$ | E | 1 | |
| 1-306 | H | $CH_2CF_2CF_3$ | $CF_2CF_3$ | E | 2 | 136-137 |
| 1-307 | H | $CH_2CF_2CF_3$ | $CF_2CF_3$ | Z | 0 | |
| 1-308 | H | $CH_2CF_2CF_3$ | $CF_2CF_3$ | Z | 1 | |
| 1-309 | H | $CH_2CF_2CF_3$ | $CF_2CF_3$ | Z | 2 | |
| 1-310 | Me | $CH_2CF_2CF_3$ | $CF_2CF_3$ | E | 0 | |
| 1-311 | Me | $CH_2CF_2CF_3$ | $CF_2CF_3$ | E | 1 | |
| 1-312 | Me | $CH_2CF_2CF_3$ | $CF_2CF_3$ | E | 2 | |
| 1-313 | Me | $CH_2CF_2CF_3$ | $CF_2CF_3$ | Z | 0 | |
| 1-314 | Me | $CH_2CF_2CF_3$ | $CF_2CF_3$ | Z | 1 | |
| 1-315 | Me | $CH_2CF_2CF_3$ | $CF_2CF_3$ | Z | 2 | |
| 1-316 | $CF_3$ | H | $CF_3$ | E | 0 | |
| 1-317 | $CF_3$ | H | $CF_3$ | E | 1 | |
| 1-318 | $CF_3$ | H | $CF_3$ | E | 2 | |
| 1-319 | $CF_3$ | Me | $CF_3$ | E | 0 | |
| 1-320 | $CF_3$ | Me | $CF_3$ | E | 1 | |
| 1-321 | $CF_3$ | Me | $CF_3$ | E | 2 | |
| 1-322 | $CF_3$ | Et | $CF_3$ | E | 0 | |
| 1-323 | $CF_3$ | Et | $CF_3$ | E | 1 | |
| 1-324 | $CF_3$ | Et | $CF_3$ | E | 2 | |
| 1-325 | $CF_3$ | Et | $CF_3$ | Z | 0 | |
| 1-326 | $CF_3$ | Et | $CF_3$ | Z | 1 | |
| 1-327 | $CF_3$ | Et | $CF_3$ | Z | 2 | |
| 1-328 | $CF_3$ | H | $C_2F_5$ | E | 0 | |
| 1-329 | $CF_3$ | H | $C_2F_5$ | E | 1 | |
| 1-330 | $CF_3$ | H | $C_2F_5$ | E | 2 | |

TABLE 12

Table 1 (continued)

| Compound No. | R² | R³ | R⁴ | Isomerism | m | Physical property |
|---|---|---|---|---|---|---|
| 1-331 | CF₃ | Me | C₂F₅ | E | 0 | |
| 1-332 | CF₃ | Me | C₂F₅ | E | 1 | |
| 1-333 | CF₃ | Me | C₂F₅ | E | 2 | |
| 1-334 | CF₃ | Et | C₂F₅ | E | 0 | |
| 1-335 | CF₃ | Et | C₂F₅ | E | 1 | |
| 1-336 | CF₃ | Et | C₂F₅ | E | 2 | |
| 1-337 | CF₃ | Et | C₂F₅ | Z | 0 | |
| 1-338 | CF₃ | Et | C₂F₅ | Z | 1 | |
| 1-339 | CF₃ | Et | C₂F₅ | Z | 2 | |
| 1-340 | CF₃ | CH₂CHF₂ | CF₃ | E | 0 | |
| 1-341 | CF₃ | CH₂CHF₂ | CF₃ | E | 1 | |
| 1-342 | CF₃ | CH₂CHF₂ | CF₃ | E | 2 | |
| 1-343 | CF₃ | CH₂CHF₂ | CF₃ | Z | 0 | |
| 1-344 | CF₃ | CH₂CHF₂ | CF₃ | Z | 1 | |
| 1-345 | CF₃ | CH₂CHF₂ | CF₃ | Z | 2 | |
| 1-346 | CF₃ | CH₂CHF₂ | C₂F₅ | E | 0 | |
| 1-347 | CF₃ | CH₂CHF₂ | C₂F₅ | E | 1 | |
| 1-348 | CF₃ | CH₂CHF₂ | C₂F₅ | E | 2 | |
| 1-349 | CF₃ | CH₂CHF₂ | C₂F₅ | Z | 0 | |
| 1-350 | CF₃ | CH₂CHF₂ | C₂F₅ | Z | 1 | |
| 1-351 | CF₃ | CH₂CHF₂ | C₂F₅ | Z | 2 | |
| 1-352 | H | CH₂C₂F₅ | C₂F₅ | E | 2 | 136-137 |
| 1-353 | NH₂ | H | C₂F₅ | E | 2 | 241-242 |
| 1-354 | H | CH₂CF₂CHF₂ | CF₃ | E | 2 | 88-89 |
| 1-355 | NH₂ | CH₂CHF₂ | C₂F₅ | E | 2 | 85-86 |
| 1-356 | NH₂ | CH₂CF₃ | CF₃ | E | 2 | NMR |
| 1-357 | H | CH₂SCH₃ | CF₃ | E | 2 | |
| 1-358 | Me | CH₂SCH₃ | CF₃ | E | 2 | |
| 1-359 | H | CH₂SOCH₃ | CF₃ | E | 2 | |
| 1-360 | Me | CH₂SOCH₃ | CF₃ | E | 2 | |

TABLE 13

Table 1 (continued)

| Compound No. | R² | R³ | R⁴ | Isomerism | m | Physical property |
|---|---|---|---|---|---|---|
| 1-361 | H | CH₂SO₂CH₃ | CF₃ | E | 2 | |
| 1-362 | Me | CH₂SO₂CH₃ | CF₃ | E | 2 | |
| 1-363 | H | CH₂SCH₂CH₃ | CF₃ | E | 2 | |
| 1-364 | Me | CH₂SCH₂CH₃ | CF₃ | E | 2 | |
| 1-365 | H | CH₂SOCH₂CH₃ | CF₃ | E | 2 | |
| 1-366 | Me | CH₂SOCH₂CH₃ | CF₃ | E | 2 | |
| 1-367 | H | CH₂SO₂CH₂CH₃ | CF₃ | E | 2 | |
| 1-368 | Me | CH₂SO₂CH₂CH₃ | CF₃ | E | 2 | |
| 1-369 | H | CH₂CH₂SCH₃ | CF₃ | E | 2 | |
| 1-370 | Me | CH₂CH₂SCH₃ | CF₃ | E | 2 | |
| 1-371 | H | CH₂CH₂SOCH₃ | CF₃ | E | 2 | |
| 1-372 | Me | CH₂CH₂SOCH₃ | CF₃ | E | 2 | |
| 1-373 | H | CH₂CH₂SO₂CH₃ | CF₃ | E | 2 | |
| 1-374 | Me | CH₂CH₂SO₂CH₃ | CF₃ | E | 2 | |
| 1-375 | H | CH₂CH₂SCH₂CH₃ | CF₃ | E | 2 | |
| 1-376 | Me | CH₂CH₂SCH₂CH₃ | CF₃ | E | 2 | |
| 1-377 | H | CH₂CH₂SOCH₂CH₃ | CF₃ | E | 2 | |
| 1-378 | Me | CH₂CH₂SOCH₂CH₃ | CF₃ | E | 2 | |
| 1-379 | H | CH₂CH₂SO₂CH₂CH₃ | CF₃ | E | 2 | |
| 1-380 | Me | CH₂CH₂SO₂CH₂CH₃ | CF₃ | E | 2 | |
| 1-381 | H | CH₂CH₂SCF₃ | CF₃ | E | 2 | |
| 1-382 | Me | CH₂CH₂SCF₃ | CF₃ | E | 2 | |
| 1-383 | H | CH₂CH₂SOCF₃ | CF₃ | E | 2 | |
| 1-384 | Me | CH₂CH₂SOCF₃ | CF₃ | E | 2 | |
| 1-385 | H | CH₂CH₂SO₂CF₃ | CF₃ | E | 2 | |
| 1-386 | Me | CH₂CH₂SO₂CF₃ | CF₃ | E | 2 | |
| 1-387 | CN | Me | CF₃ | E | 2 | |
| 1-388 | CN | Et | CF₃ | E | 2 | |
| 1-389 | CN | n-Pr | CF₃ | E | 2 | |
| 1-390 | CN | i-Pr | CF₃ | E | 2 | |

TABLE 14

Table 1 (continued)

| Compound No. | R² | R³ | R⁴ | Isomerism | m | Physical property |
|---|---|---|---|---|---|---|
| 1-391 | CN | H | CF₃ | E | 2 | |
| 1-392 | CN | CH₂CF₃ | CF₃ | E | 2 | |
| 1-393 | CN | CH₂C₂F₅ | CF₃ | E | 2 | |
| 1-394 | CN | CH₂CHF₂ | CF₃ | E | 2 | |
| 1-395 | CN | CH₂CF₂CHF₂ | CF₃ | E | 2 | |
| 1-396 | CN | CH₂SCH₃ | CF₃ | E | 2 | |
| 1-397 | CN | CH₂SOCH₃ | CF₃ | E | 2 | |
| 1-398 | CN | CH₂SO₂CH₃ | CF₃ | E | 2 | |
| 1-399 | CN | CH₂SCH₂CH₃ | CF₃ | E | 2 | |
| 1-400 | CN | CH₂SOCH₂CH₃ | CF₃ | E | 2 | |
| 1-401 | CN | CH₂SO₂CH₂CH₃ | CF₃ | E | 2 | |
| 1-402 | CN | CH₂CH₂SCH₃ | CF₃ | E | 2 | |
| 1-403 | CN | CH₂CH₂SOCH₃ | CF₃ | E | 2 | |
| 1-404 | CN | CH₂CH₂SO₂CH₃ | CF₃ | E | 2 | |
| 1-405 | CN | CH₂CH₂SCH₂CH₃ | CF₃ | E | 2 | |
| 1-406 | CN | CH₂CH₂SOCH₂CH₃ | CF₃ | E | 2 | |
| 1-407 | CN | CH₂CH₂SO₂CH₂CH₃ | CF₃ | E | 2 | |
| 1-408 | CN | CH₂CH₂SCF₃ | CF₃ | E | 2 | |
| 1-409 | CN | CH₂CH₂SOCF₃ | CF₃ | E | 2 | |
| 1-410 | CN | CH₂CH₂SO₂CF₃ | CF₃ | E | 2 | |
| 1-411 | COOMe | Me | CF₃ | E | 2 | |
| 1-412 | COOMe | Et | CF₃ | E | 2 | |
| 1-413 | COOMe | n-Pr | CF₃ | E | 2 | |
| 1-414 | COOMe | i-Pr | CF₃ | E | 2 | |
| 1-415 | COOMe | H | CF₃ | E | 2 | |
| 1-416 | COOMe | CH₂CF₃ | CF₃ | E | 2 | |
| 1-417 | COOMe | CH₂C2F₅ | CF₃ | E | 2 | |
| 1-418 | COOMe | CH₂CHF₂ | CF₃ | E | 2 | |
| 1-419 | COOMe | CH₂CF₂CHF₂ | CF₃ | E | 2 | |
| 1-420 | COOMe | CH₂SCH₃ | CF₃ | E | 2 | |

TABLE 15

Table 1 (continued)

| Compound No. | R² | R³ | R⁴ | Isomerism | m | Physical property |
|---|---|---|---|---|---|---|
| 1-421 | COOMe | CH₂SOCH₃ | CF₃ | E | 2 | |
| 1-422 | COOMe | CH₂SO₂CH₃ | CF₃ | E | 2 | |
| 1-423 | COOMe | CH₂SCH₂CH₃ | CF₃ | E | 2 | |
| 1-424 | COOMe | CH₂SOCH₂CH₃ | CF₃ | E | 2 | |
| 1-425 | COOMe | CH₂SO₂CH₂CH₃ | CF₃ | E | 2 | |
| 1-426 | COOMe | CH₂CH₂SCH₃ | CF₃ | E | 2 | |
| 1-427 | COOMe | CH₂CH₂SOCH₃ | CF₃ | E | 2 | |
| 1-428 | COOMe | CH₂CH₂SO₂CH₃ | CF₃ | E | 2 | |
| 1-429 | COOMe | CH₂CH₂SCH₂CH₃ | CF₃ | E | 2 | |
| 1-430 | COOMe | CH₂CH₂SOCH₂CH₃ | CF₃ | E | 2 | |
| 1-431 | COOMe | CH₂CH₂SO₂CH₂CH₃ | CF₃ | E | 2 | |
| 1-432 | COOMe | CH₂CH₂SCF₃ | CF₃ | E | 2 | |
| 1-433 | COOMe | CH₂CH₂SOCF₃ | CF₃ | E | 2 | |
| 1-434 | COOMe | CH₂CH₂SO₂CF₃ | CF₃ | E | 2 | |
| 1-435 | COOEt | Me | CF₃ | E | 2 | |
| 1-436 | COOEt | Et | CF₃ | E | 2 | |
| 1-437 | COOEt | n-Pr | CF₃ | E | 2 | |
| 1-438 | COOEt | i-Pr | CF₃ | E | 2 | |
| 1-439 | COOEt | H | CF₃ | E | 2 | |
| 1-440 | COOEt | CH₂CF₃ | CF₃ | E | 2 | |
| 1-441 | COOEt | CH₂C₂F₅ | CF₃ | E | 2 | |
| 1-442 | COOEt | CH₂CHF₂ | CF₃ | E | 2 | |
| 1-443 | COOEt | CH₂CF₂CHF₂ | CF₃ | E | 2 | |
| 1-444 | COOEt | CH₂SCH₃ | CF₃ | E | 2 | |
| 1-445 | COOEt | CH₂SOCH₃ | CF₃ | E | 2 | |
| 1-446 | COOEt | CH₂SO₂CH₃ | CF₃ | E | 2 | |
| 1-447 | COOEt | CH₂SCH₂CH₃ | CF₃ | E | 2 | |
| 1-448 | COOEt | CH₂SOCH₂CH3 | CF₃ | E | 2 | |
| 1-449 | COOEt | CH₂SO₂CH₂CH₃ | CF₃ | E | 2 | |
| 1-450 | COOEt | CH₂CH₂SCH₃ | CF₃ | E | 2 | |

TABLE 16

Table 1 (continued)

| Compound No. | R² | R³ | R⁴ | Isomerism | m | Physical property |
|---|---|---|---|---|---|---|
| 1-451 | COOEt | CH₂CH₂SOCH₃ | CF₃ | E | 2 | |
| 1-452 | COOEt | CH₂CH₂SO₂CH₃ | CF₃ | E | 2 | |
| 1-453 | COOEt | CH₂CH₂SCH₂CH₃ | CF₃ | E | 2 | |
| 1-454 | COOEt | CH₂CH₂SOCH₂CH₃ | CF₃ | E | 2 | |
| 1-455 | COOEt | CH₂CH₂SO₂CH₂CH₃ | CF₃ | E | 2 | |
| 1-456 | COOEt | CH₂CH₂SCF₃ | CF₃ | E | 2 | |
| 1-457 | COOEt | CH₂CH₂SOCF₃ | CF₃ | E | 2 | |
| 1-458 | COOEt | CH₂CH₂SO₂CF₃ | CF₃ | E | 2 | |
| 1-459 | CONH₂ | Me | CF₃ | E | 2 | |
| 1-460 | CONH₂ | Et | CF₃ | E | 2 | |
| 1-461 | CONH₂ | n-Pr | CF₃ | E | 2 | |
| 1-462 | CONH₂ | i-Pr | CF₃ | E | 2 | |
| 1-463 | CONH₂ | H | CF₃ | E | 2 | |
| 1-464 | CONH₂ | CH₂CF₃ | CF₃ | E | 2 | |
| 1-465 | CONH₂ | CH₂C₂F₅ | CF₃ | E | 2 | |
| 1-466 | CONH₂ | CH₂CHF₂ | CF₃ | E | 2 | |
| 1-467 | CONH₂ | CH₂CF₂CHF₂ | CF₃ | E | 2 | |
| 1-468 | CONH₂ | CH₂SCH₃ | CF₃ | E | 2 | |
| 1-469 | CONH₂ | CH₂SOCH₃ | CF₃ | E | 2 | |
| 1-470 | CONH₂ | CH₂SO₂CH₃ | CF₃ | E | 2 | |
| 1-471 | CONH₂ | CH₂SCH₂CH₃ | CF₃ | E | 2 | |
| 1-472 | CONH₂ | CH₂SOCH₂CH₃ | CF₃ | E | 2 | |
| 1-473 | CONH₂ | CH₂SO₂CH₂CH₃ | CF₃ | E | 2 | |
| 1-474 | CONH₂ | CH₂CH₂SCH₃ | CF₃ | E | 2 | |
| 1-475 | CONH₂ | CH₂CH₂SOCH₃ | CF₃ | E | 2 | |
| 1-476 | CONH₂ | CH₂CH₂SO₂CH₃ | CF₃ | E | 2 | |
| 1-477 | CONH₂ | CH₂CH₂SCH₂CH₃ | CF₃ | E | 2 | |
| 1-478 | CONH₂ | CH₂CH₂SOCH₂CH₃ | CF₃ | E | 2 | |
| 1-479 | CONH₂ | CH₂CH₂SO₂CH₂CH₃ | CF₃ | E | 2 | |
| 1-480 | CONH₂ | CH₂CH₂SCF₃ | CF₃ | E | 2 | |

TABLE 17

Table 1 (continued)

| Compound No. | R² | R³ | R⁴ | Isomerism | m | Physical property |
|---|---|---|---|---|---|---|
| 1-481 | CONH₂ | CH₂CH₂SOCF₃ | CF₃ | E | 2 | |
| 1-482 | CONH₂ | CH₂CH₂SO₂CF₃ | CF₃ | E | 2 | |
| 1-483 | CONHMe | Me | CF₃ | E | 2 | |
| 1-484 | CONHMe | Et | CF₃ | E | 2 | |
| 1-485 | CONHMe | n-Pr | CF₃ | E | 2 | |
| 1-486 | CONHMe | i-Pr | CF₃ | E | 2 | |
| 1-487 | CONHMe | H | CF₃ | E | 2 | |
| 1-488 | CONHMe | CH₂CF₃ | CF₃ | E | 2 | |
| 1-489 | CONHMe | CH₂C2F₅ | CF₃ | E | 2 | |
| 1-490 | CONHMe | CH₂CHF₂ | CF₃ | E | 2 | |
| 1-491 | CONHMe | CH₂CF₂CHF₂ | CF₃ | E | 2 | |
| 1-492 | CONHMe | CH₂SCH₃ | CF₃ | E | 2 | |
| 1-493 | CONHMe | CH₂SOCH₃ | CF₃ | E | 2 | |
| 1-494 | CONHMe | CH₂SO₂CH₃ | CF₃ | E | 2 | |
| 1-495 | CONHMe | CH₂SCH₂CH₃ | CF₃ | E | 2 | |
| 1-496 | CONHMe | CH₂SOCH₂CH₃ | CF₃ | E | 2 | |
| 1-497 | CONHMe | CH₂SO₂CH₂CH₃ | CF₃ | E | 2 | |
| 1-498 | CONHMe | CH₂CH₂SCH₃ | CF₃ | E | 2 | |
| 1-499 | CONHMe | CH₂CH₂SOCH₃ | CF₃ | E | 2 | |
| 1-500 | CONHMe | CH₂CH₂SO₂CH₃ | CF₃ | E | 2 | |
| 1-501 | CONHMe | CH₂CH₂SCH₂CH₃ | CF₃ | E | 2 | |
| 1-502 | CONHMe | CH₂CH₂SOCH₂CH₃ | CF₃ | E | 2 | |
| 1-503 | CONHMe | CH₂CH₂SO₂CH₂CH₃ | CF₃ | E | 2 | |
| 1-504 | CONHMe | CH₂CH₂SCF₃ | CF₃ | E | 2 | |
| 1-505 | CONHMe | CH₂CH₂SOCF₃ | CF₃ | E | 2 | |
| 1-506 | CONHMe | CH₂CH₂SO₂CF₃ | CF₃ | E | 2 | |
| 1-507 | CONHMe | Me | CF₃ | E | 2 | |
| 1-508 | CONMe₂ | Me | CF₃ | E | 2 | |
| 1-509 | CONMe₂ | Et | CF₃ | E | 2 | |
| 1-510 | CONMe₂ | n-Pr | CF₃ | E | 2 | |

TABLE 18

Table 1 (continued)

| Compound No. | R² | R³ | R⁴ | Isomerism | m | Physical property |
|---|---|---|---|---|---|---|
| 1-511 | CONMe₂ | i-Pr | CF₃ | E | 2 | |
| 1-512 | CONMe₂ | H | CF₃ | E | 2 | |
| 1-513 | CONMe₂ | CH₂CF₃ | CF₃ | E | 2 | |
| 1-514 | CONMe₂ | CH₂C₂F₅ | CF₃ | E | 2 | |
| 1-515 | CONMe₂ | CH₂CHF₂ | CF₃ | E | 2 | |
| 1-516 | CONMe₂ | CH₂CF₂CHF₂ | CF₃ | E | 2 | |
| 1-517 | CONMe₂ | CH₂SCH₃ | CF₃ | E | 2 | |
| 1-518 | CONMe₂ | CH₂SOCH₃ | CF₃ | E | 2 | |
| 1-519 | CONMe₂ | CH₂SO₂CH₃ | CF₃ | E | 2 | |
| 1-520 | CONMe₂ | CH₂SCH₂CH₃ | CF₃ | E | 2 | |
| 1-521 | CONMe₂ | CH₂SOCH₂CH₃ | CF₃ | E | 2 | |
| 1-522 | CONMe₂ | CH₂SO₂CH₂CH₃ | CF₃ | E | 2 | |
| 1-523 | CONMe₂ | CH₂CH₂SCH₃ | CF₃ | E | 2 | |
| 1-524 | CONMe₂ | CH₂CH₂SOCH₃ | CF₃ | E | 2 | |
| 1-525 | CONMe₂ | CH₂CH₂SO₂CH₃ | CF₃ | E | 2 | |
| 1-526 | CONMe₂ | CH₂CH₂SCH₂CH₃ | CF₃ | E | 2 | |
| 1-527 | CONMe₂ | CH₂CH₂SOCH₂CH₃ | CF₃ | E | 2 | |
| 1-528 | CONMe₂ | CH₂CH₂SO₂CH₂CH₃ | CF₃ | E | 2 | |
| 1-529 | CONMe₂ | CH₂CH₂SCF₃ | CF₃ | E | 2 | |
| 1-530 | CONMe₂ | CH₂CH₂SOCF₃ | CF₃ | E | 2 | |
| 1-531 | CONMe₂ | CH₂CH₂SO₂CF₃ | CF₃ | E | 2 | |

[Chem. 15]

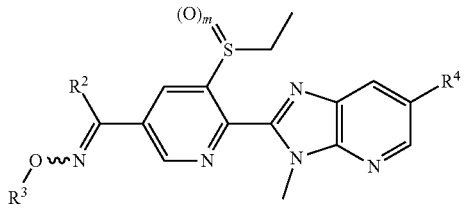

(1A-2)

TABLE 19

Table 2

| Compound No. | R² | R³ | R⁴ | Isomerism | m | Physical property |
|---|---|---|---|---|---|---|
| 2-1 | H | H | CF₃ | E | 0 | |
| 2-2 | H | H | CF₃ | E | 1 | |
| 2-3 | H | H | CF₃ | E | 2 | 256-257 |
| 2-4 | H | Me | CF₃ | E | 0 | |
| 2-5 | H | Me | CF₃ | E | 1 | |
| 2-6 | H | Me | CF₃ | E | 2 | 245-246 |
| 2-7 | H | Et | CF₃ | E | 0 | |
| 2-8 | H | Et | CF₃ | E | 1 | |
| 2-9 | H | Et | CF₃ | E | 2 | 190-191 |
| 2-10 | H | Et | CF₃ | Z | 0 | |
| 2-11 | H | Et | CF₃ | Z | 1 | |
| 2-12 | H | Et | CF₃ | Z | 2 | 143-144 |
| 2-13 | Me | Me | CF₃ | E | 0 | |
| 2-14 | Me | Me | CF₃ | E | 1 | |
| 2-15 | Me | Me | CF₃ | E | 2 | 204-205 |
| 2-16 | Me | Me | CF₃ | Z | 0 | |
| 2-17 | Me | Me | CF₃ | Z | 1 | |
| 2-18 | Me | Me | CF₃ | Z | 2 | |
| 2-19 | Me | Et | CF₃ | E | 0 | |
| 2-20 | Me | Et | CF₃ | E | 1 | |
| 2-21 | Me | Et | CF₃ | E | 2 | |
| 2-22 | Me | Et | CF₃ | Z | 0 | |
| 2-23 | Me | Et | CF₃ | Z | 1 | |
| 2-24 | Me | Et | CF₃ | Z | 2 | |
| 2-25 | H | t-Bu | CF₃ | E | 0 | |
| 2-26 | H | t-Bu | CF₃ | E | 1 | |

TABLE 19-continued

Table 2

| Compound No. | R² | R³ | R⁴ | Isomerism | m | Physical property |
|---|---|---|---|---|---|---|
| 2-27 | H | t-Bu | CF₃ | E | 2 | |
| 2-28 | H | t-Bu | CF₃ | Z | 0 | |
| 2-29 | H | t-Bu | CF₃ | Z | 1 | |
| 2-30 | H | t-Bu | CF₃ | Z | 2 | |

TABLE 20

Table 2 (continued)

| Compound No. | R² | R³ | R⁴ | Isomerism | m | Physical property |
|---|---|---|---|---|---|---|
| 2-31 | H | CH₂CF₃ | CF₃ | E | 0 | |
| 2-32 | H | CH₂CF₃ | CF₃ | E | 1 | |
| 2-33 | H | CH₂CF₃ | CF₃ | E | 2 | 125-126 |
| 2-34 | H | CH₂CF₃ | CF₃ | Z | 0 | |
| 2-35 | H | CH₂CF₃ | CF₃ | Z | 1 | |
| 2-36 | H | CH₂CF₃ | CF₃ | Z | 2 | |
| 2-37 | Me | CH₂CF₃ | CF₃ | E | 0 | |
| 2-38 | Me | CH₂CF₃ | CF₃ | E | 1 | |
| 2-39 | Me | CH₂CF₃ | CF₃ | E | 2 | 127-128 |
| 2-40 | Me | CH₂CF₃ | CF₃ | Z | 0 | |
| 2-41 | Me | CH₂CF₃ | CF₃ | Z | 1 | |
| 2-42 | Me | CH₂CF₃ | CF₃ | Z | 2 | |
| 2-43 | H | CH₂CHF₂ | CF₃ | E | 0 | |
| 2-44 | H | CH₂CHF₂ | CF₃ | E | 1 | |
| 2-45 | H | CH₂CHF₂ | CF₃ | E | 2 | 158-159 |
| 2-46 | H | CH₂CHF₂ | CF₃ | Z | 0 | |
| 2-47 | H | CH₂CHF₂ | CF₃ | Z | 1 | |
| 2-48 | H | CH₂CHF₂ | CF₃ | Z | 2 | |
| 2-49 | Me | CH₂CHF₂ | CF₃ | E | 0 | |
| 2-50 | Me | CH₂CHF₂ | CF₃ | E | 1 | |
| 2-51 | Me | CH₂CHF₂ | CF₃ | E | 2 | |
| 2-52 | Me | CH₂CHF₂ | CF₃ | Z | 0 | |
| 2-53 | Me | CH₂CHF₂ | CF₃ | Z | 1 | |
| 2-54 | Me | CH₂CHF₂ | CF₃ | Z | 2 | |
| 2-55 | H | CHF₂ | CF₃ | E | 0 | |
| 2-56 | H | CHF₂ | CF₃ | E | 1 | |
| 2-57 | H | CHF₂ | CF₃ | E | 2 | |
| 2-58 | H | CHF₂ | CF₃ | Z | 0 | |
| 2-59 | H | CHF₂ | CF₃ | Z | 1 | |
| 2-60 | H | CHF₂ | CF₃ | Z | 2 | |

TABLE 21

Table 2 (continued)

| Compound No. | R² | R³ | R⁴ | Isomerism | m | Physical property |
|---|---|---|---|---|---|---|
| 2-61 | Me | CHF₂ | CF₃ | E | 0 | |
| 2-62 | Me | CHF₂ | CF₃ | E | 1 | |
| 2-63 | Me | CHF₂ | CF₃ | E | 2 | |
| 2-64 | Me | CHF₂ | CF₃ | Z | 0 | |
| 2-65 | Me | CHF₂ | CF₃ | Z | 1 | |
| 2-66 | Me | CHF₂ | CF₃ | Z | 2 | |
| 2-67 | H | H | SCF₃ | E | 0 | |
| 2-68 | H | H | SCF₃ | E | 1 | |
| 2-69 | H | H | SCF₃ | E | 2 | |
| 2-70 | H | Me | SCF₃ | E | 0 | |
| 2-71 | H | Me | SCF₃ | E | 1 | |
| 2-72 | H | Me | SCF₃ | E | 2 | |
| 2-73 | H | Et | SCF₃ | E | 0 | |
| 2-74 | H | Et | SCF₃ | E | 1 | |
| 2-75 | H | Et | SCF₃ | E | 2 | |
| 2-76 | H | Et | SCF₃ | Z | 0 | |
| 2-77 | H | Et | SCF₃ | Z | 1 | |
| 2-78 | H | Et | SCF₃ | Z | 2 | |
| 2-79 | Me | Me | SCF₃ | E | 0 | |
| 2-80 | Me | Me | SCF₃ | E | 1 | |

TABLE 21-continued

Table 2 (continued)

| Compound No. | R² | R³ | R⁴ | Isomerism | m | Physical property |
|---|---|---|---|---|---|---|
| 2-81 | Me | Me | SCF₃ | E | 2 | |
| 2-82 | Me | Me | SCF₃ | Z | 0 | |
| 2-83 | Me | Me | SCF₃ | Z | 1 | |
| 2-84 | Me | Me | SCF₃ | Z | 2 | |
| 2-85 | Me | Et | SCF₃ | E | 0 | |
| 2-86 | Me | Et | SCF₃ | E | 1 | |
| 2-87 | Me | Et | SCF₃ | E | 2 | |
| 2-88 | Me | Et | SCF₃ | Z | 0 | |
| 2-89 | Me | Et | SCF₃ | Z | 1 | |
| 2-90 | Me | Et | SCF₃ | Z | 2 | |

TABLE 22

Table 2 (continued)

| Compound No. | R² | R³ | R⁴ | Isomerism | m | Physical property |
|---|---|---|---|---|---|---|
| 2-91 | H | t-Bu | SCF₃ | E | 0 | |
| 2-92 | H | t-Bu | SCF₃ | E | 1 | |
| 2-93 | H | t-Bu | SCF₃ | E | 2 | |
| 2-94 | H | t-Bu | SCF₃ | Z | 0 | |
| 2-95 | H | t-Bu | SCF₃ | Z | 1 | |
| 2-96 | H | t-Bu | SCF₃ | Z | 2 | |
| 2-97 | H | CH₂CF₃ | SCF₃ | E | 0 | |
| 2-98 | H | CH₂CF₃ | SCF₃ | E | 1 | |
| 2-99 | H | CH₂CF₃ | SCF₃ | E | 2 | |
| 2-100 | H | CH₂CF₃ | SCF₃ | Z | 0 | |
| 2-101 | H | CH₂CF₃ | SCF₃ | Z | 1 | |
| 2-102 | H | CH₂CF₃ | SCF₃ | Z | 2 | |
| 2-103 | Me | CH₂CF₃ | SCF₃ | E | 0 | |
| 2-104 | Me | CH₂CF₃ | SCF₃ | E | 1 | |
| 2-105 | Me | CH₂CF₃ | SCF₃ | E | 2 | |
| 2-106 | Me | CH₂CF₃ | SCF₃ | Z | 0 | |
| 2-107 | Me | CH₂CF₃ | SCF₃ | Z | 1 | |
| 2-108 | Me | CH₂CF₃ | SCF₃ | Z | 2 | |
| 2-109 | H | CH₂CHF₂ | SCF₃ | E | 0 | |
| 2-110 | H | CH₂CHF₂ | SCF₃ | E | 1 | |
| 2-111 | H | CH₂CHF₂ | SCF₃ | E | 2 | |
| 2-112 | H | CH₂CHF₂ | SCF₃ | Z | 0 | |
| 2-113 | H | CH₂CHF₂ | SCF₃ | Z | 1 | |
| 2-114 | H | CH₂CHF₂ | SCF₃ | Z | 2 | |
| 2-115 | Me | CH₂CHF₂ | SCF₃ | E | 0 | |
| 2-116 | Me | CH₂CHF₂ | SCF₃ | E | 1 | |
| 2-117 | Me | CH₂CHF₂ | SCF₃ | E | 2 | |
| 2-118 | Me | CH₂CHF₂ | SCF₃ | Z | 0 | |
| 2-119 | Me | CH₂CHF₂ | SCF₃ | Z | 1 | |
| 2-120 | Me | CH₂CHF₂ | SCF₃ | Z | 2 | |

TABLE 23

Table 2 (continued)

| Compound No. | R² | R³ | R⁴ | Isomerism | m | Physical property |
|---|---|---|---|---|---|---|
| 2-121 | H | CHF₂ | SCF₃ | E | 0 | |
| 2-122 | H | CHF₂ | SCF₃ | E | 1 | |
| 2-123 | H | CHF₂ | SCF₃ | E | 2 | |
| 2-124 | H | CHF₂ | SCF₃ | Z | 0 | |
| 2-125 | H | CHF₂ | SCF₃ | Z | 1 | |
| 2-126 | H | CHF₂ | SCF₃ | Z | 2 | |
| 2-127 | Me | CHF₂ | SCF₃ | E | 0 | |
| 2-128 | Me | CHF₂ | SCF₃ | E | 1 | |
| 2-129 | Me | CHF₂ | SCF₃ | E | 2 | |
| 2-130 | Me | CHF₂ | SCF₃ | Z | 0 | |
| 2-131 | Me | CHF₂ | SCF₃ | Z | 1 | |
| 2-132 | Me | CHF₂ | SCF₃ | Z | 2 | |
| 2-133 | H | H | CF₂CF₃ | E | 0 | |
| 2-134 | H | H | CF₂CF₃ | E | 1 | |

TABLE 23-continued

Table 2 (continued)

| Compound No. | R² | R³ | R⁴ | Isomerism | m | Physical property |
|---|---|---|---|---|---|---|
| 2-135 | H | H | $CF_2CF_3$ | E | 2 | |
| 2-136 | H | Me | $CF_2CF_3$ | E | 0 | |
| 2-137 | H | Me | $CF_2CF_3$ | E | 1 | |
| 2-138 | H | Me | $CF_2CF_3$ | E | 2 | |
| 2-139 | H | Et | $CF_2CF_3$ | E | 0 | |
| 2-140 | H | Et | $CF_2CF_3$ | E | 1 | |
| 2-141 | H | Et | $CF_2CF_3$ | E | 2 | |
| 2-142 | H | Et | $CF_2CF_3$ | Z | 0 | |
| 2-143 | H | Et | $CF_2CF_3$ | Z | 1 | |
| 2-144 | H | Et | $CF_2CF_3$ | Z | 2 | |
| 2-145 | Me | Me | $CF_2CF_3$ | E | 0 | |
| 2-146 | Me | Me | $CF_2CF_3$ | E | 1 | |
| 2-147 | Me | Me | $CF_2CF_3$ | E | 2 | |
| 2-148 | Me | Me | $CF_2CF_3$ | Z | 0 | |
| 2-149 | Me | Me | $CF_2CF_3$ | Z | 1 | |
| 2-150 | Me | Me | $CF_2CF_3$ | Z | 2 | |

TABLE 24

| Compound No. | R² | R³ | R⁴ | Isomerism | m | Physical property |
|---|---|---|---|---|---|---|
| 2-151 | Me | Et | $CF_2CF_3$ | E | 0 | |
| 2-152 | Me | Et | $CF_2CF_3$ | E | 1 | |
| 2-153 | Me | Et | $CF_2CF_3$ | E | 2 | |
| 2-154 | Me | Et | $CF_2CF_3$ | Z | 0 | |
| 2-155 | Me | Et | $CF_2CF_3$ | Z | 1 | |
| 2-156 | Me | Et | $CF_2CF_3$ | Z | 2 | |
| 2-157 | H | t-Bu | $CF_2CF_3$ | E | 0 | |
| 2-158 | H | t-Bu | $CF_2CF_3$ | E | 1 | |
| 2-159 | H | t-Bu | $CF_2CF_3$ | E | 2 | |
| 2-160 | H | t-Bu | $CF_2CF_3$ | Z | 0 | |
| 2-161 | H | t-Bu | $CF_2CF_3$ | Z | 1 | |
| 2-162 | H | t-Bu | $CF_2CF_3$ | Z | 2 | |
| 2-163 | H | $CH_2CF_3$ | $CF_2CF_3$ | E | 0 | |
| 2-164 | H | $CH_2CF_3$ | $CF_2CF_3$ | E | 1 | |
| 2-165 | H | $CH_2CF_3$ | $CF_2CF_3$ | E | 2 | |
| 2-166 | H | $CH_2CF_3$ | $CF_2CF_3$ | Z | 0 | |
| 2-167 | H | $CH_2CF_3$ | $CF_2CF_3$ | Z | 1 | |
| 2-168 | H | $CH_2CF_3$ | $CF_2CF_3$ | Z | 2 | |
| 2-169 | Me | $CH_2CF_3$ | $CF_2CF_3$ | E | 0 | |
| 2-170 | Me | $CH_2CF_3$ | $CF_2CF_3$ | E | 1 | |
| 2-171 | Me | $CH_2CF_3$ | $CF_2CF_3$ | E | 2 | |
| 2-172 | Me | $CH_2CF_3$ | $CF_2CF_3$ | Z | 0 | |
| 2-173 | Me | $CH_2CF_3$ | $CF_2CF_3$ | Z | 1 | |
| 2-174 | Me | $CH_2CF_3$ | $CF_2CF_3$ | Z | 2 | |
| 2-175 | H | $CH_2CHF_2$ | $CF_2CF_3$ | E | 0 | |
| 2-176 | H | $CH_2CHF_2$ | $CF_2CF_3$ | E | 1 | |
| 2-177 | H | $CH_2CHF_2$ | $CF_2CF_3$ | E | 2 | |
| 2-178 | H | $CH_2CHF_2$ | $CF_2CF_3$ | Z | 0 | |
| 2-179 | H | $CH_2CHF_2$ | $CF_2CF_3$ | Z | 1 | |
| 2-180 | H | $CH_2CHF_2$ | $CF_2CF_3$ | Z | 2 | |

TABLE 25

| Compound No. | R² | R³ | R⁴ | Isomerism | m | Physical property |
|---|---|---|---|---|---|---|
| 2-181 | Me | $CH_2CHF_2$ | $CF_2CF_3$ | E | 0 | |
| 2-182 | Me | $CH_2CHF_2$ | $CF_2CF_3$ | E | 1 | |
| 2-183 | Me | $CH_2CHF_2$ | $CF_2CF_3$ | E | 2 | |
| 2-184 | Me | $CH_2CHF_2$ | $CF_2CF_3$ | Z | 0 | |
| 2-185 | Me | $CH_2CHF_2$ | $CF_2CF_3$ | Z | 1 | |
| 2-186 | Me | $CH_2CHF_2$ | $CF_2CF_3$ | Z | 2 | |
| 2-187 | H | $CHF_2$ | $CF_2CF_3$ | E | 0 | |
| 2-188 | H | $CHF_2$ | $CF_2CF_3$ | E | 1 | |
| 2-189 | H | $CHF_2$ | $CF_2CF_3$ | E | 2 | |
| 2-190 | H | $CHF_2$ | $CF_2CF_3$ | Z | 0 | |
| 2-191 | H | $CHF_2$ | $CF_2CF_3$ | Z | 1 | |
| 2-192 | H | $CHF_2$ | $CF_2CF_3$ | Z | 2 | |

TABLE 25-continued

| Compound No. | R² | R³ | R⁴ | Isomerism | m | Physical property |
|---|---|---|---|---|---|---|
| 2-193 | Me | $CHF_2$ | $CF_2CF_3$ | E | 0 | |
| 2-194 | Me | $CHF_2$ | $CF_2CF_3$ | E | 1 | |
| 2-195 | Me | $CHF_2$ | $CF_2CF_3$ | E | 2 | |
| 2-196 | Me | $CHF_2$ | $CF_2CF_3$ | Z | 0 | |
| 2-197 | Me | $CHF_2$ | $CF_2CF_3$ | Z | 1 | |
| 2-198 | Me | $CHF_2$ | $CF_2CF_3$ | Z | 2 | |
| 2-199 | H | n-Pr | $CF_2CF_3$ | E | 0 | |
| 2-200 | H | n-Pr | $CF_2CF_3$ | E | 1 | |
| 2-201 | H | n-Pr | $CF_2CF_3$ | E | 2 | |
| 2-202 | H | n-Pr | $CF_2CF_3$ | Z | 0 | |
| 2-203 | H | n-Pr | $CF_2CF_3$ | Z | 1 | |
| 2-204 | H | n-Pr | $CF_2CF_3$ | Z | 2 | |
| 2-205 | Me | n-Pr | $CF_2CF_3$ | E | 0 | |
| 2-206 | Me | n-Pr | $CF_2CF_3$ | E | 1 | |
| 2-207 | Me | n-Pr | $CF_2CF_3$ | E | 2 | |
| 2-208 | Me | n-Pr | $CF_2CF_3$ | Z | 0 | |
| 2-209 | Me | n-Pr | $CF_2CF_3$ | Z | 1 | |
| 2-210 | Me | n-Pr | $CF_2CF_3$ | Z | 2 | |

TABLE 26

| Compound No. | R² | R³ | R⁴ | Isomerism | m | Physical property |
|---|---|---|---|---|---|---|
| 2-211 | H | i-Pr | $CF_2CF_3$ | E | 0 | |
| 2-212 | H | i-Pr | $CF_2CF_3$ | E | 1 | |
| 2-213 | H | i-Pr | $CF_2CF_3$ | E | 2 | |
| 2-214 | H | i-Pr | $CF_2CF_3$ | Z | 0 | |
| 2-215 | H | i-Pr | $CF_2CF_3$ | Z | 1 | |
| 2-216 | H | i-Pr | $CF_2CF_3$ | Z | 2 | |
| 2-217 | Me | i-Pr | $CF_2CF_3$ | E | 0 | |
| 2-218 | Me | i-Pr | $CF_2CF_3$ | E | 1 | |
| 2-219 | Me | i-Pr | $CF_2CF_3$ | E | 2 | |
| 2-220 | Me | i-Pr | $CF_2CF_3$ | Z | 0 | |
| 2-221 | Me | i-Pr | $CF_2CF_3$ | Z | 1 | |
| 2-222 | Me | i-Pr | $CF_2CF_3$ | Z | 2 | |
| 2-223 | H | $CH_2CF_2CF_3$ | $CF_2CF_3$ | E | 0 | |
| 2-224 | H | $CH_2CF_2CF_3$ | $CF_2CF_3$ | E | 1 | |
| 2-225 | H | $CH_2CF_2CF_3$ | $CF_2CF_3$ | E | 2 | |
| 2-226 | H | $CH_2CF_2CF_3$ | $CF_2CF_3$ | Z | 0 | |
| 2-227 | H | $CH_2CF_2CF_3$ | $CF_2CF_3$ | Z | 1 | |
| 2-228 | H | $CH_2CF_2CF_3$ | $CF_2CF_3$ | Z | 2 | |
| 2-229 | Me | $CH_2CF_2CF_3$ | $CF_2CF_3$ | E | 0 | |
| 2-230 | Me | $CH_2CF_2CF_3$ | $CF_2CF_3$ | E | 1 | |

TABLE 27

| Compound No. | R² | R³ | R⁴ | Isomerism | m | Physical property |
|---|---|---|---|---|---|---|
| 2-231 | Me | $CH_2CF_2CF_3$ | $CF_2CF_3$ | E | 2 | |
| 2-232 | Me | $CH_2CF_2CF_3$ | $CF_2CF_3$ | Z | 0 | |
| 2-233 | Me | $CH_2CF_2CF_3$ | $CF_2CF_3$ | Z | 1 | |
| 2-234 | Me | $CH_2CF_2CF_3$ | $CF_2CF_3$ | Z | 2 | |
| 2-235 | H | Ac | $CF_3$ | E | 2 | 217-218 |
| 2-236 | H | CO-c-Pr | $CF_3$ | E | 2 | 194-195 |
| 2-237 | H | $CH_2$-c-Pr | $CF_3$ | E | 2 | 140-142 |
| 2-238 | H | $CH_2C\equiv CH$ | $CF_3$ | E | 2 | 204-205 |
| 2-239 | Me | H | $CF_3$ | E | 2 | 194-195 |
| 2-240 | Me | $CH_2CF_2CF_3$ | $CF_3$ | E | 2 | 114-115 |
| 2-241 | H | Me | $CF_3$ | Z | 2 | 204-205 |
| 2-242 | H | n-Pr | $CF_3$ | E | 2 | 134-135 |
| 2-243 | Me | n-Pr | $CF_3$ | E | 2 | |
| 2-244 | H | n-Pr | $CF_3$ | E | 2 | 156-157 |
| 2-245 | Me | n-Pr | $CF_3$ | E | 2 | |
| 2-246 | H | $CH_2SCH_3$ | $CF_3$ | E | 2 | NMR |
| 2-247 | Me | $CH_2SCH_3$ | $CF_3$ | E | 2 | |
| 2-248 | H | $CH_2SOCH_3$ | $CF_3$ | E | 2 | NMR |
| 2-249 | Me | $CH_2SOCH_3$ | $CF_3$ | E | 2 | |
| 2-250 | H | $CH_2SO_2CH_3$ | $CF_3$ | E | 2 | 205-206 |
| 2-251 | Me | $CH_2SO_2CH_3$ | $CF_3$ | E | 2 | |
| 2-252 | H | $CH_2SCH_2CH_3$ | $CF_3$ | E | 2 | |

TABLE 27-continued

| Compound No. | R² | R³ | R⁴ | Isomerism | m | Physical property |
|---|---|---|---|---|---|---|
| 2-253 | Me | CH₂SCH₂CH₃ | CF₃ | E | 2 | |
| 2-254 | H | CH₂SOCH₂CH₃ | CF₃ | E | 2 | |
| 2-255 | Me | CH₂SOCH₂CH₃ | CF₃ | E | 2 | |
| 2-256 | H | CH₂SO₂CH₂CH₃ | CF₃ | E | 2 | |
| 2-257 | Me | CH₂SO₂CH₂CH₃ | CF₃ | E | 2 | |
| 2-258 | H | CH₂CH₂SCH₃ | CF₃ | E | 2 | 97-98 |
| 2-259 | Me | CH₂CH₂SCH₃ | CF₃ | E | 2 | |
| 2-260 | H | CH₂CH₂SOCH₃ | CF₃ | E | 2 | |

TABLE 28

| Compound No. | R² | R³ | R⁴ | Isomerism | m | Physical property |
|---|---|---|---|---|---|---|
| 2-261 | Me | CH₂CH₂SOCH₃ | CF₃ | E | 2 | |
| 2-262 | H | CH₂CH₂SO₂CH₃ | CF₃ | E | 2 | 107-108 |
| 2-263 | Me | CH₂CH₂SO₂CH₃ | CF₃ | E | 2 | |
| 2-264 | H | CH₂CH₂SCH₂CH₃ | CF₃ | E | 2 | 115-116 |
| 2-265 | Me | CH₂CH₂SCH₂CH₃ | CF₃ | E | 2 | |
| 2-266 | H | CH₂CH₂SOCH₂CH₃ | CF₃ | E | 2 | |
| 2-267 | Me | CH₂CH₂SOCH₂CH₃ | CF₃ | E | 2 | |
| 2-268 | H | CH₂CH₂SO₂CH₂CH₃ | CF₃ | E | 2 | |
| 2-269 | Me | CH₂CH₂SO₂CH₂CH₃ | CF₃ | E | 2 | |
| 2-270 | H | CH₂CH₂SCF₃ | CF₃ | E | 2 | |
| 2-271 | Me | CH₂CH₂SCF₃ | CF₃ | E | 2 | |
| 2-272 | H | CH₂CH₂SOCF₃ | CF₃ | E | 2 | |
| 2-273 | Me | CH₂CH₂SOCF₃ | CF₃ | E | 2 | |
| 2-274 | H | CH₂CH₂SO₂CF₃ | CF₃ | E | 2 | |
| 2-275 | Me | CH₂CH₂SO₂CF₃ | CF₃ | E | 2 | |
| 2-276 | H | CH₂C≡N | CF₃ | E | 2 | 204-205 |
| 2-277 | Me | CH₂C≡N | CF₃ | E | 2 | |
| 2-278 | H | c-Pen | CF₃ | E | 2 | 124-125 |
| 2-279 | Me | c-Pen | CF₃ | E | 2 | |
| 2-280 | H | CH₂CH=CHCl | CF₃ | E | 2 | 159-160 |
| 2-281 | Me | CH₂CH=CHCl | CF₃ | E | 2 | |
| 2-282 | H | n-Bu | CF₃ | E | 2 | 119-120 |
| 2-283 | Me | n-Bu | CF₃ | E | 2 | |
| 2-284 | H | n-Pen | CF₃ | E | 2 | 133-134 |
| 2-285 | Me | n-Pen | CF₃ | E | 2 | |
| 2-286 | H | CH₂CH=C(CH₃)₂ | CF₃ | E | 2 | 132-133 |
| 2-287 | Me | CH₂CH=C(CH₃)₂ | CF₃ | E | 2 | |
| 2-288 | CN | Me | CF₃ | E | 2 | |
| 2-289 | CN | Et | CF₃ | E | 2 | |
| 2-290 | CN | n-Pr | CF₃ | E | 2 | 148-151 |

TABLE 29

| Compound No. | R² | R³ | R⁴ | Isomerism | m | Physical property |
|---|---|---|---|---|---|---|
| 2-291 | CN | i-Pr | CF₃ | E | 2 | |
| 2-292 | CN | H | CF₃ | E | 2 | |
| 2-293 | CN | CH₂CF₃ | CF₃ | E | 2 | 163-166 |
| 2-294 | CN | CH₂C₂F₅ | CF₃ | E | 2 | |
| 2-295 | CN | CH₂CHF₂ | CF₃ | E | 2 | |
| 2-296 | CN | CH₂CF₂CHF₂ | CF₃ | E | 2 | |
| 2-297 | CN | CH₂SCH₃ | CF₃ | E | 2 | |
| 2-298 | CN | CH₂SOCH₃ | CF₃ | E | 2 | |
| 2-299 | CN | CH₂SO₂CH₃ | CF₃ | E | 2 | |
| 2-300 | CN | CH₂SCH₂CH₃ | CF₃ | E | 2 | |
| 2-301 | CN | CH₂SOCH₂CH₃ | CF₃ | E | 2 | |
| 2-302 | CN | CH₂SO₂CH₂CH₃ | CF₃ | E | 2 | |
| 2-303 | CN | CH₂CH₂SCH₃ | CF₃ | E | 2 | |
| 2-304 | CN | CH₂CH₂SOCH₃ | CF₃ | E | 2 | |
| 2-305 | CN | CH₂CH₂SO₂CH₃ | CF₃ | E | 2 | |
| 2-306 | CN | CH₂CH₂SCH₂CH₃ | CF₃ | E | 2 | |
| 2-307 | CN | CH₂CH₂SOCH₂CH₃ | CF₃ | E | 2 | |
| 2-308 | CN | CH₂CH₂SO₂CH₂CH₃ | CF₃ | E | 2 | |
| 2-309 | CN | CH₂CH₂SCF₃ | CF₃ | E | 2 | |
| 2-310 | CN | CH₂CH₂SOCF₃ | CF₃ | E | 2 | |
| 2-311 | CN | CH₂CH₂SO₂CF₃ | CF₃ | E | 2 | |
| 2-312 | COOMe | Me | CF₃ | E | 2 | |
| 2-313 | COOMe | Et | CF₃ | E | 2 | |
| 2-314 | COOMe | n-Pr | CF₃ | E | 2 | |
| 2-315 | COOMe | i-Pr | CF₃ | E | 2 | |
| 2-316 | COOMe | H | CF₃ | E | 2 | |
| 2-317 | COOMe | CH₂CF₃ | CF₃ | E | 2 | |
| 2-318 | COOMe | CH₂C₂F₅ | CF₃ | E | 2 | |
| 2-319 | COOMe | CH₂CHF₂ | CF₃ | E | 2 | |
| 2-320 | COOMe | CH₂CF₂CHF₂ | CF₃ | E | 2 | |

TABLE 30

| Compound No. | R² | R³ | R⁴ | Isomerism | m | Physical property |
|---|---|---|---|---|---|---|
| 2-321 | COOMe | CH₂SCH₃ | CF₃ | E | 2 | |
| 2-322 | COOMe | CH₂SOCH₃ | CF₃ | E | 2 | |
| 2-323 | COOMe | CH₂SO₂CH₃ | CF₃ | E | 2 | |
| 2-324 | COOMe | CH₂SCH₂CH₃ | CF₃ | E | 2 | |
| 2-325 | COOMe | CH₂SOCH₂CH₃ | CF₃ | E | 2 | |
| 2-326 | COOMe | CH₂SO₂CH₂CH₃ | CF₃ | E | 2 | |
| 2-327 | COOMe | CH₂CH₂SCH₃ | CF₃ | E | 2 | |
| 2-328 | COOMe | CH₂CH₂SOCH₃ | CF₃ | E | 2 | |
| 2-329 | COOMe | CH₂CH₂SO₂CH₃ | CF₃ | E | 2 | |
| 2-330 | COOMe | CH₂CH₂SCH₂CH₃ | CF₃ | E | 2 | |
| 2-331 | COOMe | CH₂CH₂SOCH₂CH₃ | CF₃ | E | 2 | |
| 2-332 | COOMe | CH₂CH₂SO₂CH₂CH₃ | CF₃ | E | 2 | |
| 2-333 | COOMe | CH₂CH₂SCF₃ | CF₃ | E | 2 | |
| 2-334 | COOMe | CH₂CH₂SOCF₃ | CF₃ | E | 2 | |
| 2-335 | COOMe | CH₂CH₂SO₂CF₃ | CF₃ | E | 2 | |
| 2-336 | COOEt | Me | CF₃ | E | 2 | |
| 2-337 | COOEt | Et | CF₃ | E | 2 | |
| 2-338 | COOEt | n-Pr | CF₃ | E | 2 | |
| 2-339 | COOEt | i-Pr | CF₃ | E | 2 | |
| 2-340 | COOEt | H | CF₃ | E | 2 | |
| 2-341 | COOEt | CH₂CF₃ | CF₃ | E | 2 | |
| 2-342 | COOEt | CH₂C₂F₅ | CF₃ | E | 2 | |
| 2-343 | COOEt | CH₂CHF₂ | CF₃ | E | 2 | |
| 2-344 | COOEt | CH₂CF₂CHF₂ | CF₃ | E | 2 | |
| 2-345 | COOEt | CH₂SCH₃ | CF₃ | E | 2 | |
| 2-346 | COOEt | CH₂SOCH₃ | CF₃ | E | 2 | |
| 2-347 | COOEt | CH₂SO₂CH₃ | CF₃ | E | 2 | |
| 2-348 | COOEt | CH₂SCH₂CH₃ | CF₃ | E | 2 | |
| 2-349 | COOEt | CH₂SOCH₂CH₃ | CF₃ | E | 2 | |
| 2-350 | COOEt | CH₂SO₂CH₂CH₃ | CF₃ | E | 2 | |

TABLE 31

| Compound No. | R² | R³ | R⁴ | Isomerism | m | Physical property |
|---|---|---|---|---|---|---|
| 2-351 | COOEt | CH₂CH₂SCH₃ | CF₃ | E | 2 | |
| 2-352 | COOEt | CH₂CH₂SOCH₃ | CF₃ | E | 2 | |
| 2-353 | COOEt | CH₂CH₂SO₂CH₃ | CF₃ | E | 2 | |
| 2-354 | COOEt | CH₂CH₂SCH₂CH₃ | CF₃ | E | 2 | |
| 2-355 | COOEt | CH₂CH₂SOCH₂CH₃ | CF₃ | E | 2 | |
| 2-356 | COOEt | CH₂CH₂SO₂CH₂CH₃ | CF₃ | E | 2 | |
| 2-357 | COOEt | CH₂CH₂SCF₃ | CF₃ | E | 2 | |
| 2-358 | COOEt | CH₂CH₂SOCF₃ | CF₃ | E | 2 | |
| 2-359 | COOEt | CH₂CH₂SO₂CF₃ | CF₃ | E | 2 | |
| 2-360 | CONH₂ | Me | CF₃ | E | 2 | |
| 2-361 | CONH₂ | Et | CF₃ | E | 2 | |
| 2-362 | CONH₂ | n-Pr | CF₃ | E | 2 | |
| 2-363 | CONH₂ | i-Pr | CF₃ | E | 2 | |
| 2-364 | CONH₂ | H | CF₃ | E | 2 | |
| 2-365 | CONH₂ | CH₂CF₃ | CF₃ | E | 2 | |
| 2-366 | CONH₂ | CH₂C₂F₅ | CF₃ | E | 2 | |
| 2-367 | CONH₂ | CH₂CHF₂ | CF₃ | E | 2 | |
| 2-368 | CONH₂ | CH₂CF₂CHF₂ | CF₃ | E | 2 | |

TABLE 31-continued

| Compound No. | R² | R³ | R⁴ | Isomerism | m | Physical property |
|---|---|---|---|---|---|---|
| 2-369 | CONH₂ | CH₂SCH₃ | CF₃ | E | 2 | |
| 2-370 | CONH₂ | CH₂SOCH₃ | CF₃ | E | 2 | |
| 2-371 | CONH₂ | CH₂SO₂CH₃ | CF₃ | E | 2 | |
| 2-372 | CONH₂ | CH₂SCH₂CH₃ | CF₃ | E | 2 | |
| 2-373 | CONH₂ | CH₂SOCH₂CH₃ | CF₃ | E | 2 | |
| 2-374 | CONH₂ | CH₂SO₂CH₂CH₃ | CF₃ | E | 2 | |
| 2-375 | CONH₂ | CH₂CH₂SCH₃ | CF₃ | E | 2 | |
| 2-376 | CONH₂ | CH₂CH₂SOCH₃ | CF₃ | E | 2 | |
| 2-377 | CONH₂ | CH₂CH₂SO₂CH₃ | CF₃ | E | 2 | |
| 2-378 | CONH₂ | CH₂CH₂SCH₂CH₃ | CF₃ | E | 2 | |
| 2-379 | CONH₂ | CH₂CH₂SOCH₂CH₃ | CF₃ | E | 2 | |
| 2-380 | CONH₂ | CH₂CH₂SO₂CH₂CH₃ | CF₃ | E | 2 | |

TABLE 32

| Compound No. | R² | R³ | R⁴ | Isomerism | m | Physical property |
|---|---|---|---|---|---|---|
| 2-381 | CONH₂ | CH₂CH₂SCF₃ | CF₃ | E | 2 | |
| 2-382 | CONH₂ | CH₂CH₂SOCF₃ | CF₃ | E | 2 | |
| 2-383 | CONH₂ | CH₂CH₂SO₂CF₃ | CF₃ | E | 2 | |
| 2-384 | CONHMe | Me | CF₃ | E | 2 | |
| 2-385 | CONHMe | Et | CF₃ | E | 2 | |
| 2-386 | CONHMe | n-Pr | CF₃ | E | 2 | |
| 2-387 | CONHMe | i-Pr | CF₃ | E | 2 | |
| 2-388 | CONHMe | H | CF₃ | E | 2 | |
| 2-389 | CONHMe | CH₂CF₃ | CF₃ | E | 2 | |
| 2-390 | CONHMe | CH₂C₂F₅ | CF₃ | E | 2 | |
| 2-391 | CONHMe | CH₂CHF₂ | CF₃ | E | 2 | |
| 2-392 | CONHMe | CH₂CF₂CHF₂ | CF₃ | E | 2 | |
| 2-393 | CONHMe | CH₂SCH₃ | CF₃ | E | 2 | |
| 2-394 | CONHMe | CH₂SOCH₃ | CF₃ | E | 2 | |
| 2-395 | CONHMe | CH₂SO₂CH₃ | CF₃ | E | 2 | |
| 2-396 | CONHMe | CH₂SCH₂CH₃ | CF₃ | E | 2 | |
| 2-397 | CONHMe | CH₂SOCH₂CH₃ | CF₃ | E | 2 | |
| 2-398 | CONHMe | CH₂SO₂CH₂CH₃ | CF₃ | E | 2 | |
| 2-399 | CONHMe | CH₂CH₂SCH₃ | CF₃ | E | 2 | |
| 2-400 | CONHMe | CH₂CH₂SOCH₃ | CF₃ | E | 2 | |
| 2-401 | CONHMe | CH₂CH₂SO₂CH₃ | CF₃ | E | 2 | |
| 2-402 | CONHMe | CH₂CH₂SCH₂CH₃ | CF₃ | E | 2 | |
| 2-403 | CONHMe | CH₂CH₂SOCH₂CH₃ | CF₃ | E | 2 | |
| 2-404 | CONHMe | CH₂CH₂SO₂CH₂CH₃ | CF₃ | E | 2 | |
| 2-405 | CONHMe | CH₂CH₂SCF₃ | CF₃ | E | 2 | |
| 2-406 | CONHMe | CH₂CH₂SOCF₃ | CF₃ | E | 2 | |
| 2-407 | CONHMe | CH₂CH₂SO₂CF₃ | CF₃ | E | 2 | |
| 2-408 | CONHMe | Me | CF₃ | E | 2 | |
| 2-409 | CONMe₂ | Me | CF₃ | E | 2 | |
| 2-410 | CONMe₂ | Et | CF₃ | E | 2 | |

TABLE 33

| Compound No. | R² | R³ | R⁴ | Isomerism | m | Physical property |
|---|---|---|---|---|---|---|
| 2-411 | CONMe₂ | n-Pr | CF₃ | E | 2 | |
| 2-412 | CONMe₂ | i-Pr | CF₃ | E | 2 | |
| 2-413 | CONMe₂ | H | CF₃ | E | 2 | |
| 2-414 | CONMe₂ | CHCF₃ | CF₃ | E | 2 | |
| 2-415 | CONMe₂ | CH₂C₂F₅ | CF₃ | E | 2 | |
| 2-416 | CONMe₂ | CH₂CHF₂ | CF₃ | E | 2 | |
| 2-417 | CONMe₂ | CH₂CF₂CHF₂ | CF₃ | E | 2 | |
| 2-418 | CONMe₂ | CH₂SCH₃ | CF₃ | E | 2 | |
| 2-419 | CONMe₂ | CH₂SOCH₃ | CF₃ | E | 2 | |
| 2-420 | CONMe₂ | CH₂SO₂CH₃ | CF₃ | E | 2 | |
| 2-421 | CONMe₂ | CH₂SCH₂CH₃ | CF₃ | E | 2 | |
| 2-422 | CONMe₂ | CH₂SOCH₂CH₃ | CF₃ | E | 2 | |
| 2-423 | CONMe₂ | CH₂SO₂CH₂CH₃ | CF₃ | E | 2 | |
| 2-424 | CONMe₂ | CH₂CH₂SCH₃ | CF₃ | E | 2 | |
| 2-425 | CONMe₂ | CH₂CH₂SOCH₃ | CF₃ | E | 2 | |
| 2-426 | CONMe₂ | CH₂CH₂SO₂CH₃ | CF₃ | E | 2 | |
| 2-427 | CONMe₂ | CH₂CH₂SCH₂CH₃ | CF₃ | E | 2 | |
| 2-428 | CONMe₂ | CH₂CH₂SOCH₂CH₃ | CF₃ | E | 2 | |
| 2-429 | CONMe₂ | CH₂CH₂SO₂CH₂CH₃ | CF₃ | E | 2 | |
| 2-430 | CONMe₂ | CH₂CH₂SCF₃ | CF₃ | E | 2 | |
| 2-431 | CONMe₂ | CH₂CH₂SOCF₃ | CF₃ | E | 2 | |
| 2-432 | CONMe₂ | CH₂CH₂SO₂CF₃ | CF₃ | E | 2 | |

[Chem. 16]

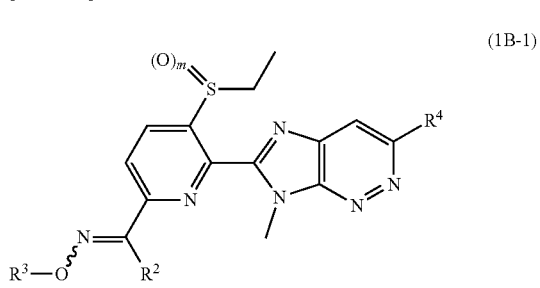

(1B-1)

TABLE 34

| Compound No. | R² | R³ | R⁴ | Isomerism | m | Physical property |
|---|---|---|---|---|---|---|
| 3-1 | H | H | CF₃ | E | 2 | 157-158 |
| 3-2 | H | CH₂CF₃ | CF₃ | E | 2 | 84-85 |
| 3-3 | H | CH₂CHF₂ | CF₃ | E | 2 | NMR |
| 3-4 | H | CH₂C₂F₅ | CF₃ | E | 2 | NMR |
| 3-5 | H | CH₂CF₂CHF₂ | CF₃ | E | 2 | NMR |
| 3-6 | Me | H | CF₃ | E | 2 | |
| 3-7 | Me | CH₂CF₃ | CF₃ | E | 2 | |
| 3-8 | Me | CH₂CHF₂ | CF₃ | E | 2 | |
| 3-9 | Me | CH₂C₂F₅ | CF₃ | E | 2 | |
| 3-10 | Me | CH₂CF₂CHF₂ | CF₃ | E | 2 | |
| 3-11 | H | H | CF₂CF₃ | E | 2 | 219-220 |
| 3-12 | H | CH₂CF₃ | CF₂CF₃ | E | 2 | NMR |
| 3-13 | H | CH₂CHF₂ | CF₂CF₃ | E | 2 | NMR |
| 3-14 | Me | H | CF₂CF₃ | E | 2 | |
| 3-15 | Me | CH₂CF₃ | CF₂CF₃ | E | 2 | |
| 3-16 | Me | CH₂CHF₂ | CF₂CF₃ | E | 2 | |
| 3-17 | H | n-Pr | CF₃ | E | 2 | |
| 3-18 | Me | n-Pr | CF₃ | E | 2 | |
| 3-19 | H | i-Pr | CF₃ | E | 2 | |
| 3-20 | Me | i-Pr | CF₃ | E | 2 | |
| 3-21 | H | CH₂SCH₃ | CF₃ | E | 2 | |
| 3-22 | Me | CH₂SCH₃ | CF₃ | E | 2 | |
| 3-23 | H | CH₂SOCH₃ | CF₃ | E | 2 | |
| 3-24 | Me | CH₂SOCH₃ | CF₃ | E | 2 | |
| 3-25 | H | CH₂SO₂CH₃ | CF₃ | E | 2 | |
| 3-26 | Me | CH₂SO₂CH₃ | CF₃ | E | 2 | |
| 3-27 | H | CH₂SCH₂CH₃ | CF₃ | E | 2 | |
| 3-28 | Me | CH₂SCH₂CH₃ | CF₃ | E | 2 | |
| 3-29 | H | CH₂SOCH₂CH₃ | CF₃ | E | 2 | |
| 3-30 | Me | CH₂SOCH₂CH₃ | CF₃ | E | 2 | |
| 3-31 | H | CH₂SO₂CH₂CH₃ | CF₃ | E | 2 | |

TABLE 35

| Compound No. | $R^2$ | $R^3$ | $R^4$ | Isomerism | m | Physical property |
|---|---|---|---|---|---|---|
| 3-32 | Me | $CH_2SO_2CH_2CH_3$ | $CF_3$ | E | 2 | |
| 3-33 | H | $CH_2CH_2SCH_3$ | $CF_3$ | E | 2 | |
| 3-34 | Me | $CH_2CH_2SCH_3$ | $CF_3$ | E | 2 | |
| 3-35 | H | $CH_2CH_2SOCH_3$ | $CF_3$ | E | 2 | |
| 3-36 | Me | $CH_2CH_2SOCH_3$ | $CF_3$ | E | 2 | |
| 3-37 | H | $CH_2CH_2SO_2CH_3$ | $CF_3$ | E | 2 | |
| 3-38 | Me | $CH_2CH_2SO_2CH_3$ | $CF_3$ | E | 2 | |
| 3-39 | H | $CH_2CH_2SCH_2CH_3$ | $CF_3$ | E | 2 | |
| 3-40 | Me | $CH_2CH_2SCH_2CH_3$ | $CF_3$ | E | 2 | |
| 3-41 | H | $CH_2CH_2SOCH_2CH_3$ | $CF_3$ | E | 2 | |
| 3-42 | Me | $CH_2CH_2SOCH_2CH_3$ | $CF_3$ | E | 2 | |
| 3-43 | H | $CH_2CH_2SO_2CH_2CH_3$ | $CF_3$ | E | 2 | |
| 3-44 | Me | $CH_2CH_2SO_2CH_2CH_3$ | $CF_3$ | E | 2 | |
| 3-45 | H | $CH_2CH_2SCF_3$ | $CF_3$ | E | 2 | |
| 3-46 | Me | $CH_2CH_2SCF_3$ | $CF_3$ | E | 2 | |
| 3-47 | H | $CH_2CH_2SOCF_3$ | $CF_3$ | E | 2 | |
| 3-48 | Me | $CH_2CH_2SOCF_3$ | $CF_3$ | E | 2 | |
| 3-49 | H | $CH_2CH_2SO_2CF_3$ | $CF_3$ | E | 2 | |
| 3-50 | Me | $CH_2CH_2SO_2CF_3$ | $CF_3$ | E | 2 | |
| 3-51 | H | $CH_2C\equiv N$ | $CF_3$ | E | 2 | |
| 3-52 | Me | $CH_2C\equiv N$ | $CF_3$ | E | 2 | |
| 3-53 | H | c-Pen | $CF_3$ | E | 2 | |
| 3-54 | Me | c-Pen | $CF_3$ | E | 2 | |
| 3-55 | H | $CH_2CH=CHCl$ | $CF_3$ | E | 2 | |
| 3-56 | Me | $CH_2CH=CHCl$ | $CF_3$ | E | 2 | |
| 3-57 | H | n-Bu | $CF_3$ | E | 2 | |
| 3-58 | Me | n-Bu | $CF_3$ | E | 2 | |
| 3-59 | H | n-Pen | $CF_3$ | E | 2 | |
| 3-60 | Me | n-Pen | $CF_3$ | E | 2 | |
| 3-61 | H | $CH_2CH=C(CH_3)_2$ | $CF_3$ | E | 2 | |
| 3-62 | Me | $CH_2CH=C(CH_3)_2$ | $CF_3$ | E | 2 | |

TABLE 36

| Compound No. | $R^2$ | $R^3$ | $R^4$ | Isomerism | m | Physical property |
|---|---|---|---|---|---|---|
| 3-63 | CN | Me | $CF_3$ | E | 2 | |
| 3-64 | CN | Et | $CF_3$ | E | 2 | |
| 3-65 | CN | n-Pr | $CF_3$ | E | 2 | |
| 3-66 | CN | i-Pr | $CF_3$ | E | 2 | |
| 3-67 | CN | H | $CF_3$ | E | 2 | |
| 3-68 | CN | $CHCF_3$ | $CF_3$ | E | 2 | |
| 3-69 | CN | $CH_2C_2F_5$ | $CF_3$ | E | 2 | |
| 3-70 | CN | $CH_2CHF_2$ | $CF_3$ | E | 2 | |
| 3-71 | CN | $CH_2CF_2CHF_2$ | $CF_3$ | E | 2 | |
| 3-72 | CN | $CH_2SCH_3$ | $CF_3$ | E | 2 | |
| 3-73 | CN | $CH_2SOCH_3$ | $CF_3$ | E | 2 | |
| 3-74 | CN | $CH_2SO_2CH_3$ | $CF_3$ | E | 2 | |
| 3-75 | CN | $CH_2SCH_2CH_3$ | $CF_3$ | E | 2 | |
| 3-76 | CN | $CH_2SOCH_2CH_3$ | $CF_3$ | E | 2 | |
| 3-77 | CN | $CH_2SO_2CH_2CH_3$ | $CF_3$ | E | 2 | |
| 3-78 | CN | $CH_2CH_2SCH_3$ | $CF_3$ | E | 2 | |
| 3-79 | CN | $CH_2CH_2SOCH_3$ | $CF_3$ | E | 2 | |
| 3-80 | CN | $CH_2CH_2SO_2CH_3$ | $CF_3$ | E | 2 | |
| 3-81 | CN | $CH_2CH_2SCH_2CH_3$ | $CF_3$ | E | 2 | |
| 3-82 | CN | $CH_2CH_2SOCH_2CH_3$ | $CF_3$ | E | 2 | |
| 3-83 | CN | $CH_2CH_2SO_2CH_2CH_3$ | $CF_3$ | E | 2 | |
| 3-84 | CN | $CH_2CH_2SCF_3$ | $CF_3$ | E | 2 | |
| 3-85 | CN | $CH_2CH_2SOCF_3$ | $CF_3$ | E | 2 | |
| 3-86 | CN | $CH_2CH_2SO_2CF_3$ | $CF_3$ | E | 2 | |
| 3-87 | COOMe | Me | $CF_3$ | E | 2 | |
| 3-88 | COOMe | Et | $CF_3$ | E | 2 | |
| 3-89 | COOMe | n-Pr | $CF_3$ | E | 2 | |
| 3-90 | COOMe | i-Pr | $CF_3$ | E | 2 | |
| 3-91 | COOMe | H | $CF_3$ | E | 2 | |
| 3-92 | COOMe | $CH_2CF_3$ | $CF_3$ | E | 2 | |

TABLE 37

| Compound No. | $R^2$ | $R^3$ | $R^4$ | Isomerism | m | Physical property |
|---|---|---|---|---|---|---|
| 3-93 | COOMe | $CH_2C_2F_5$ | $CF_3$ | E | 2 | |
| 3-94 | COOMe | $CH_2CHF_2$ | $CF_3$ | E | 2 | |
| 3-95 | COOMe | $CH_2CF_2CHF_2$ | $CF_3$ | E | 2 | |
| 3-96 | COOMe | $CH_2SCH_3$ | $CF_3$ | E | 2 | |
| 3-97 | COOMe | $CH_2SOCH_3$ | $CF_3$ | E | 2 | |
| 3-98 | COOMe | $CH_2SO_2CH_3$ | $CF_3$ | E | 2 | |
| 3-99 | COOMe | $CH_2SCH_2CH_3$ | $CF_3$ | E | 2 | |
| 3-100 | COOMe | $CH_2SOCH_2CH_3$ | $CF_3$ | E | 2 | |
| 3-101 | COOMe | $CH_2SO_2CH_2CH_3$ | $CF_3$ | E | 2 | |
| 3-102 | COOMe | $CH_2CH_2SCH_3$ | $CF_3$ | E | 2 | |
| 3-103 | COOMe | $CH_2CH_2SOCH_3$ | $CF_3$ | E | 2 | |
| 3-104 | COOMe | $CH_2CH_2SO_2CH_3$ | $CF_3$ | E | 2 | |
| 3-105 | COOMe | $CH_2CH_2SCH_2CH_3$ | $CF_3$ | E | 2 | |
| 3-106 | COOMe | $CH_2CH_2SOCH_2CH_3$ | $CF_3$ | E | 2 | |
| 3-107 | COOMe | $CH_2CH_2SO_2CH_2CH_3$ | $CF_3$ | E | 2 | |
| 3-108 | COOMe | $CH_2CH_2SCF_3$ | $CF_3$ | E | 2 | |
| 3-109 | COOMe | $CH_2CH_2SOCF_3$ | $CF_3$ | E | 2 | |
| 3-110 | COOMe | $CH_2CH_2SO_2CF_3$ | $CF_3$ | E | 2 | |
| 3-111 | COOEt | Me | $CF_3$ | E | 2 | |
| 3-112 | COOEt | Et | $CF_3$ | E | 2 | |
| 3-113 | COOEt | n-Pr | $CF_3$ | E | 2 | |
| 3-114 | COOEt | i-Pr | $CF_3$ | E | 2 | |
| 3-115 | COOEt | H | $CF_3$ | E | 2 | |
| 3-116 | COOEt | $CH_2CF_3$ | $CF_3$ | E | 2 | |
| 3-117 | COOEt | $CH_2C_2F_5$ | $CF_3$ | E | 2 | |
| 3-118 | COOEt | $CH_2CHF_2$ | $CF_3$ | E | 2 | |
| 3-119 | COOEt | $CH_2CF_2CHF_2$ | $CF_3$ | E | 2 | |
| 3-120 | COOEt | $CH_2SCH_3$ | $CF_3$ | E | 2 | |
| 3-121 | COOEt | $CH_2SOCH_3$ | $CF_3$ | E | 2 | |
| 3-122 | COOEt | $CH_2SO_2CH_3$ | $CF_3$ | E | 2 | |

TABLE 38

| Compound No. | $R^2$ | $R^3$ | $R^4$ | Isomerism | m | Physical property |
|---|---|---|---|---|---|---|
| 3-123 | COOEt | $CH_2SCH_2CH_3$ | $CF_3$ | E | 2 | |
| 3-124 | COOEt | $CH_2SOCH_2CH_3$ | $CF_3$ | E | 2 | |
| 3-125 | COOEt | $CH_2SO_2CH_2CH_3$ | $CF_3$ | E | 2 | |
| 3-126 | COOEt | $CH_2CH_2SCH_3$ | $CF_3$ | E | 2 | |
| 3-127 | COOEt | $CH_2CH_2SOCH_3$ | $CF_3$ | E | 2 | |
| 3-128 | COOEt | $CH_2CH_2SO_2CH_3$ | $CF_3$ | E | 2 | |
| 3-129 | COOEt | $CH_2CH_2SCH_2CH_3$ | $CF_3$ | E | 2 | |
| 3-130 | COOEt | $CH_2CH_2SOCH_2CH_3$ | $CF_3$ | E | 2 | |
| 3-131 | COOEt | $CH_2CH_2SO_2CH_2CH_3$ | $CF_3$ | E | 2 | |
| 3-132 | COOEt | $CH_2CH_2SCF_3$ | $CF_3$ | E | 2 | |
| 3-133 | COOEt | $CH_2CH_2SOCF_3$ | $CF_3$ | E | 2 | |
| 3-134 | COOEt | $CH_2CH_2SO_2CF_3$ | $CF_3$ | E | 2 | |
| 3-135 | $CONH_2$ | Me | $CF_3$ | E | 2 | |
| 3-136 | $CONH_2$ | Et | $CF_3$ | E | 2 | |
| 3-137 | $CONH_2$ | n-Pr | $CF_3$ | E | 2 | |
| 3-138 | $CONH_2$ | i-Pr | $CF_3$ | E | 2 | |
| 3-139 | $CONH_2$ | H | $CF_3$ | E | 2 | |
| 3-140 | $CONH_2$ | $CH_2CF_3$ | $CF_3$ | E | 2 | |
| 3-141 | $CONH_2$ | $CH_2C_2F_5$ | $CF_3$ | E | 2 | |
| 3-142 | $CONH_2$ | $CH_2CHF_2$ | $CF_3$ | E | 2 | |
| 3-143 | $CONH_2$ | $CH_2CF_2CHF_2$ | $CF_3$ | E | 2 | |
| 3-144 | $CONH_2$ | $CH_2SCH_3$ | $CF_3$ | E | 2 | |
| 3-145 | $CONH_2$ | $CH_2SOCH_3$ | $CF_3$ | E | 2 | |
| 3-146 | $CONH_2$ | $CH_2SO_2CH_3$ | $CF_3$ | E | 2 | |
| 3-147 | $CONH_2$ | $CH_2SCH_2CH_3$ | $CF_3$ | E | 2 | |
| 3-148 | $CONH_2$ | $CH_2SOCH_2CH_3$ | $CF_3$ | E | 2 | |
| 3-149 | $CONH_2$ | $CH_2SO_2CH_2CH_3$ | $CF_3$ | E | 2 | |
| 3-150 | $CONH_2$ | $CH_2SCH_3$ | $CF_3$ | E | 2 | |
| 3-151 | $CONH_2$ | $CH_2CH_2SOCH_3$ | $CF_3$ | E | 2 | |
| 3-152 | $CONH_2$ | $CH_2CH_2SO_2CH_3$ | $CF_3$ | E | 2 | |

TABLE 39

Table 3 (continued)

| Compound No. | $R^2$ | $R^3$ | $R^4$ | Isomerism | m | Physical property |
|---|---|---|---|---|---|---|
| 3-153 | CONH$_2$ | CH$_2$CH$_2$SCH$_2$CH$_3$ | CF$_3$ | E | 2 | |
| 3-154 | CONH$_2$ | CH$_2$CH$_2$SOCH$_2$CH$_3$ | CF$_3$ | E | 2 | |
| 3-155 | CONH$_2$ | CH$_2$CH$_2$SO$_2$CH$_2$CH$_3$ | CF$_3$ | E | 2 | |
| 3-156 | CONH$_2$ | CH$_2$CH$_2$SCF$_3$ | CF$_3$ | E | 2 | |
| 3-157 | CONH$_2$ | CH$_2$CH$_2$SOCF$_3$ | CF$_3$ | E | 2 | |
| 3-158 | CONH$_2$ | CH$_2$CH$_2$SO$_2$CF$_3$ | CF$_3$ | E | 2 | |
| 3-159 | CONHMe | Me | CF$_3$ | E | 2 | |
| 3-160 | CONHMe | Et | CF$_3$ | E | 2 | |
| 3-161 | CONHMe | n-Pr | CF$_3$ | E | 2 | |
| 3-162 | CONHMe | i-Pr | CF$_3$ | E | 2 | |
| 3-163 | CONHMe | H | CF$_3$ | E | 2 | |
| 3-164 | CONHMe | CH$_2$CF$_3$ | CF$_3$ | E | 2 | |
| 3-165 | CONHMe | CH$_2$C$_2$F$_5$ | CF$_3$ | E | 2 | |
| 3-166 | CONHMe | CH$_2$CHF$_2$ | CF$_3$ | E | 2 | |
| 3-167 | CONHMe | CH$_2$CF$_2$CHF$_2$ | CF$_3$ | E | 2 | |
| 3-168 | CONHMe | CH$_2$SCH$_3$ | CF$_3$ | E | 2 | |
| 3-169 | CONHMe | CH$_2$SOCH$_3$ | CF$_3$ | E | 2 | |
| 3-170 | CONHMe | CH$_2$SO$_2$CH$_3$ | CF$_3$ | E | 2 | |
| 3-171 | CONHMe | CH$_2$SCH$_2$CH$_3$ | CF$_3$ | E | 2 | |
| 3-172 | CONHMe | CH$_2$SOCH$_2$CH$_3$ | CF$_3$ | E | 2 | |
| 3-173 | CONHMe | CH$_2$SO$_2$CH$_2$CH$_3$ | CF$_3$ | E | 2 | |
| 3-174 | CONHMe | CH$_2$CH$_2$SCH$_3$ | CF$_3$ | E | 2 | |
| 3-175 | CONHMe | CH$_2$CH$_2$SOCH$_3$ | CF$_3$ | E | 2 | |
| 3-176 | CONHMe | CH$_2$CH$_2$SO$_2$CH$_3$ | CF$_3$ | E | 2 | |
| 3-177 | CONHMe | CH$_2$CH$_2$SCH$_2$CH$_3$ | CF$_3$ | E | 2 | |
| 3-178 | CONHMe | CH$_2$CH$_2$SOCH$_2$CH$_3$ | CF$_3$ | E | 2 | |
| 3-179 | CONHMe | CH$_2$CH$_2$SO$_2$CH$_2$CH$_3$ | CF$_3$ | E | 2 | |
| 3-180 | CONHMe | CH$_2$CH$_2$SCF$_3$ | CF$_3$ | E | 2 | |
| 3-181 | CONHMe | CH$_2$CH$_2$SOCF$_3$ | CF$_3$ | E | 2 | |
| 3-182 | CONHMe | CH$_2$CH$_2$SO$_2$CF$_3$ | CF$_3$ | E | 2 | |

TABLE 40

Table 3 (continued)

| Compound No. | $R^2$ | $R^3$ | $R^4$ | Isomerism | m | Physical property |
|---|---|---|---|---|---|---|
| 3-183 | CONHMe | Me | CF$_3$ | E | 2 | |
| 3-184 | CONMe$_2$ | Me | CF$_3$ | E | 2 | |
| 3-185 | CONMe$_2$ | Et | CF$_3$ | E | 2 | |
| 3-186 | CONMe$_2$ | n-Pr | CF$_3$ | E | 2 | |
| 3-187 | CONMe$_2$ | i-Pr | CF$_3$ | E | 2 | |
| 3-188 | CONMe$_2$ | H | CF$_3$ | E | 2 | |
| 3-189 | CONMe$_2$ | CH$_2$CF$_3$ | CF$_3$ | E | 2 | |
| 3-190 | CONMe$_2$ | CH$_2$C$_2$F$_5$ | CF$_3$ | E | 2 | |
| 3-191 | CONMe$_2$ | CH$_2$CHF$_2$ | CF$_3$ | E | 2 | |
| 3-192 | CONMe$_2$ | CH$_2$CF$_2$CHF$_2$ | CF$_3$ | E | 2 | |
| 3-193 | CONMe$_2$ | CH$_2$SCH$_3$ | CF$_3$ | E | 2 | |
| 3-194 | CONMe$_2$ | CH$_2$SOCH$_3$ | CF$_3$ | E | 2 | |
| 3-195 | CONMe$_2$ | CH$_2$SO$_2$CH$_3$ | CF$_3$ | E | 2 | |
| 3-196 | CONMe$_2$ | CH$_2$SCH$_2$CH$_3$ | CF$_3$ | E | 2 | |
| 3-197 | CONMe$_2$ | CH$_2$SOCH$_2$CH$_3$ | CF$_3$ | E | 2 | |
| 3-198 | CONMe$_2$ | CH$_2$SO$_2$CH$_2$CH$_3$ | CF$_3$ | E | 2 | |
| 3-199 | CONMe$_2$ | CH$_2$CH$_2$SCH$_3$ | CF$_3$ | E | 2 | |
| 3-200 | CONMe$_2$ | CH$_2$CH$_2$SOCH$_3$ | CF$_3$ | E | 2 | |
| 3-201 | CONMe$_2$ | CH$_2$CH$_2$SO$_2$CH$_3$ | CF$_3$ | E | 2 | |
| 3-202 | CONMe$_2$ | CH$_2$CH$_2$SCH$_2$CH$_3$ | CF$_3$ | E | 2 | |
| 3-203 | CONMe$_2$ | CH$_2$CH$_2$SOCH$_2$CH$_3$ | CF$_3$ | E | 2 | |
| 3-204 | CONMe$_2$ | CH$_2$CH$_2$SO$_2$CH$_2$CH$_3$ | CF$_3$ | E | 2 | |
| 3-205 | CONMe$_2$ | CH$_2$CH$_2$SCF$_3$ | CF$_3$ | E | 2 | |
| 3-206 | CONMe$_2$ | CH$_2$CH$_2$SOCF$_3$ | CF$_3$ | E | 2 | |
| 3-207 | CONMe$_2$ | CH$_2$CH$_2$SO$_2$CF$_3$ | CF$_3$ | E | 2 | |

[Chem. 17]

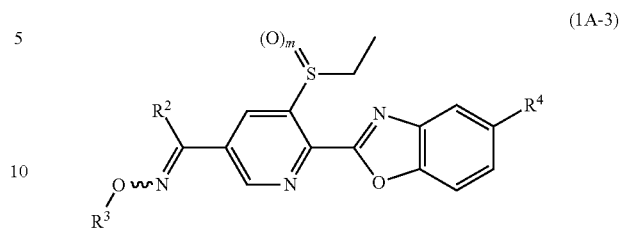

(1A-3)

TABLE 41

Table 4

| Compound No. | $R^2$ | $R^3$ | $R^4$ | Isomerism | m | Physical property |
|---|---|---|---|---|---|---|
| 4-1 | H | H | CF$_3$ | E | 2 | 243-244 |
| 4-2 | H | CH$_2$CF$_3$ | CF$_3$ | E | 2 | 187-188 |
| 4-3 | H | CH$_2$C$_2$F$_5$ | CF$_3$ | E | 2 | 180-181 |
| 4-4 | H | CH$_2$CF$_3$ | CF$_3$ | E | 1 | |
| 4-5 | H | CH$_2$C$_2$F$_5$ | CF$_3$ | E | 1 | |
| 4-6 | Me | H | CF$_3$ | E | 2 | |
| 4-7 | Me | CH$_2$CF$_3$ | CF$_3$ | E | 2 | |
| 4-8 | Me | CH$_2$C$_2$F$_5$ | CF$_3$ | E | 2 | |
| 4-9 | Me | CH$_2$CF$_3$ | CF$_3$ | Z | 2 | |
| 4-10 | Me | CH$_2$C$_2$F$_5$ | CF$_3$ | Z | 2 | |
| 4-11 | H | H | SCF$_3$ | E | 2 | 213-214 |
| 4-12 | H | CH$_2$CF$_3$ | SCF$_3$ | E | 2 | 157-158 |
| 4-13 | H | CH$_2$C$_2$F$_5$ | SCF$_3$ | E | 2 | 135-138 |
| 4-14 | H | CH$_2$CF$_3$ | SCF$_3$ | E | 1 | 200-202 |
| 4-15 | H | CH$_2$C$_2$F$_5$ | SCF$_3$ | E | 1 | 196-197 |
| 4-16 | Me | H | SCF$_3$ | E | 2 | |
| 4-17 | Me | CH$_2$CF$_3$ | SCF$_3$ | E | 2 | |
| 4-18 | Me | CH$_2$C$_2$F$_5$ | SCF$_3$ | E | 2 | |
| 4-19 | Me | CH$_2$CF$_3$ | SCF$_3$ | Z | 2 | |
| 4-20 | Me | CH$_2$C$_2$F$_5$ | SCF$_3$ | Z | 2 | |

TABLE 42

Table 4 (continued)

| Compound No. | $R^2$ | $R^3$ | $R^4$ | Isomerism | m | Physical property |
|---|---|---|---|---|---|---|
| 4-21 | H | CH$_2$CHF$_2$ | CF$_3$ | E | 2 | |
| 4-22 | H | CH$_2$CF$_2$CHF$_2$ | CF$_3$ | E | 2 | |
| 4-23 | Me | CH$_2$CHF$_2$ | CF$_3$ | E | 2 | |
| 4-24 | Me | CH$_2$CF$_2$CHF$_2$ | CF$_3$ | E | 2 | |
| 4-25 | H | CH$_2$CHF$_2$ | SCF$_3$ | E | 2 | 154-155 |
| 4-26 | H | CH$_2$CF$_2$CHF$_2$ | SCF$_3$ | E | 2 | |
| 4-27 | Me | CH$_2$CHF$_2$ | SCF$_3$ | E | 2 | |
| 4-28 | Me | CH$_2$CF$_2$CHF$_2$ | SCF$_3$ | E | 2 | |
| 4-29 | H | H | OCF$_3$ | E | 2 | 169-170 |
| 4-30 | H | CH$_2$CHF$_2$ | OCF$_3$ | E | 2 | 153-154 |
| 4-31 | H | CH$_2$CHF$_2$ | OCF$_3$ | Z | 2 | 150-151 |
| 4-32 | H | CH$_2$CF$_3$ | OCF$_3$ | E | 2 | 153-154 |
| 4-33 | H | CH$_2$CF$_2$CHF$_2$ | OCF$_3$ | E | 2 | 127-128 |
| 4-34 | H | CH$_2$C$_2$F$_5$ | OCF$_3$ | E | 2 | 143-144 |
| 4-35 | H | CH$_2$CF$_3$ | OCF$_3$ | E | 1 | |
| 4-36 | H | CH$_2$C$_2$F$_5$ | OCF$_3$ | E | 1 | |
| 4-37 | Me | H | OCF$_3$ | E | 2 | |
| 4-38 | Me | CH$_2$CHF$_2$ | OCF$_3$ | E | 2 | |
| 4-39 | Me | CH$_2$CF$_3$ | OCF$_3$ | E | 2 | |
| 4-40 | Me | CH$_2$CF$_2$CHF$_2$ | OCF$_3$ | E | 2 | |
| 4-41 | Me | CH$_2$C$_2$F$_5$ | OCF$_3$ | E | 2 | |
| 4-42 | Me | CH$_2$CF$_3$ | OCF$_3$ | E | 1 | |
| 4-43 | Me | CH$_2$C$_2$F$_5$ | OCF$_3$ | E | 1 | |

TABLE 43

Table 4 (continued)

| Compound No. | $R^2$ | $R^3$ | $R^4$ | Isomerism | m | Physical property |
|---|---|---|---|---|---|---|
| 4-44 | H | n-Pr | $SCF_3$ | E | 2 | 143-144 |
| 4-45 | Me | n-Pr | $SCF_3$ | E | 2 | |
| 4-46 | H | i-Pr | $SCF_3$ | E | 2 | 153-154 |
| 4-47 | Me | i-Pr | $SCF_3$ | E | 2 | |
| 4-48 | H | $CH_2SCH_3$ | $SCF_3$ | E | 2 | 150-151 |
| 4-49 | Me | $CH_2SCH_3$ | $SCF_3$ | E | 2 | |
| 4-50 | H | $CH_2SOCH_3$ | $SCF_3$ | E | 2 | |
| 4-51 | Me | $CH_2SOCH_3$ | $SCF_3$ | E | 2 | |
| 4-52 | H | $CH_2SO_2CH_3$ | $SCF_3$ | E | 2 | |
| 4-53 | Me | $CH_2SO_2CH_3$ | $SCF_3$ | E | 2 | |
| 4-54 | H | $CH_2SCH_2CH_3$ | $SCF_3$ | E | 2 | |
| 4-55 | Me | $CH_2SCH_2CH_3$ | $SCF_3$ | E | 2 | |
| 4-56 | H | $CH_2SOCH_2CH_3$ | $SCF_3$ | E | 2 | |
| 4-57 | Me | $CH_2SOCH_2CH_3$ | $SCF_3$ | E | 2 | |
| 4-58 | H | $CH_2SO_2CH_2CH_3$ | $SCF_3$ | E | 2 | |
| 4-59 | Me | $CH_2SO_2CH_2CH_3$ | $SCF_3$ | E | 2 | |
| 4-60 | H | $CH_2CH_2SCH_3$ | $SCF_3$ | E | 2 | 141-142 |
| 4-61 | Me | $CH_2CH_2SCH_3$ | $SCF_3$ | E | 2 | |
| 4-62 | H | $CH_2CH_2SOCH_3$ | $SCF_3$ | E | 2 | |
| 4-63 | Me | $CH_2CH_2SOCH_3$ | $SCF_3$ | E | 2 | |
| 4-64 | H | $CH_2CH_2SO_2CH_3$ | $SCF_3$ | E | 2 | |
| 4-65 | Me | $CH_2CH_2SO_2CH_3$ | $SCF_3$ | E | 2 | |
| 4-66 | H | $CH_2CH_2SCH_2CH_3$ | $SCF_3$ | E | 2 | |
| 4-67 | Me | $CH_2CH_2SCH_2CH_3$ | $SCF_3$ | E | 2 | |
| 4-68 | H | $CH_2CH_2SOCH_2CH_3$ | $SCF_3$ | E | 2 | |
| 4-69 | Me | $CH_2CH_2SOCH_2CH_3$ | $SCF_3$ | E | 2 | |
| 4-70 | H | $CH_2CH_2SO_2CH_2CH_3$ | $SCF_3$ | E | 2 | |
| 4-71 | Me | $CH_2CH_2SO_2CH_2CH_3$ | $SCF_3$ | E | 2 | |
| 4-72 | H | $CH_2CH_2SCF_3$ | $SCF_3$ | E | 2 | |
| 4-73 | Me | $CH_2CH_2SCF_3$ | $SCF_3$ | E | 2 | |

TABLE 44

Table 4 (continued)

| Compound No. | $R^2$ | $R^3$ | $R^4$ | Isomerism | m | Physical property |
|---|---|---|---|---|---|---|
| 4-74 | H | $CH_2CH_2SOCF_3$ | $SCF_3$ | E | 2 | |
| 4-75 | Me | $CH_2CH_2SOCF_3$ | $SCF_3$ | E | 2 | |
| 4-76 | H | $CH_2CH_2SO_2CF_3$ | $SCF_3$ | E | 2 | |
| 4-77 | Me | $CH_2CH_2SO_2CF_3$ | $SCF_3$ | E | 2 | |
| 4-78 | H | $CH_2C\equiv N$ | $SCF_3$ | E | 2 | |
| 4-79 | Me | $CH_2C\equiv N$ | $SCF_3$ | E | 2 | |
| 4-80 | H | c-Pen | $SCF_3$ | E | 2 | |
| 4-81 | Me | c-Pen | $SCF_3$ | E | 2 | |
| 4-82 | H | $CH_2CH=CHCl$ | $SCF_3$ | E | 2 | 139-140 |
| 4-83 | Me | $CH_2CH=CHCl$ | $SCF_3$ | E | 2 | |
| 4-84 | H | n-Bu | $SCF_3$ | E | 2 | 126-127 |
| 4-85 | Me | n-Bu | $SCF_3$ | E | 2 | |
| 4-86 | H | n-Pen | $SCF_3$ | E | 2 | 128-129 |
| 4-87 | Me | n-Pen | $SCF_3$ | E | 2 | |
| 4-88 | H | $CH_2CH=C(CH_3)_2$ | $SCF_3$ | E | 2 | 81-82 |
| 4-89 | Me | $CH_2CH=C(CH_3)_2$ | $SCF_3$ | E | 2 | |
| 4-90 | H | H | $SO_2CF_3$ | E | 2 | |
| 4-91 | H | $CH_2CF_3$ | $SO_2CF_3$ | E | 2 | 164-165 |
| 4-92 | H | $CH_2C_2F_5$ | $SO_2CF_3$ | E | 2 | |
| 4-93 | H | $CH_2CHF_2$ | $SO_2CF_3$ | E | 2 | 161-162 |
| 4-94 | H | $CH_2CF_2CHF_2$ | $SO_2CF_3$ | E | 2 | |
| 4-95 | Me | H | $SO_2CF_3$ | E | 2 | |
| 4-96 | Me | $CH_2CF_3$ | $SO_2CF_3$ | E | 2 | 140-141 |
| 4-97 | Me | $CH_2C_2F_5$ | $SO_2CF_3$ | E | 2 | |
| 4-98 | Me | $CH_2CHF_2$ | $SO_2CF_3$ | E | 2 | 118-119 |
| 4-99 | Me | $CH_2CF_2CHF_2$ | $SO_2CF_3$ | E | 2 | |
| 4-100 | H | H | $OCHF_2$ | E | 2 | |
| 4-101 | H | $CH_2CF_3$ | $OCHF_2$ | E | 0 | 144-145 |
| 4-102 | H | $CH_2CF_3$ | $OCHF_2$ | E | 2 | 146-147 |
| 4-103 | H | $CH_2C_2F_5$ | $OCHF_2$ | E | 2 | |

TABLE 45

Table 4 (continued)

| Compound No. | $R^2$ | $R^3$ | $R^4$ | Isomerism | m | Physical property |
|---|---|---|---|---|---|---|
| 4-104 | H | $CH_2CHF_2$ | $OCHF_2$ | E | 2 | |
| 4-105 | H | $CH_2CF_2CHF_2$ | $OCHF_2$ | E | 2 | |
| 4-106 | Me | H | $OCHF_2$ | E | 2 | |
| 4-107 | Me | $CH_2CF_3$ | $OCHF_2$ | E | 2 | |
| 4-108 | Me | $CH_2C_2F_5$ | $OCHF_2$ | E | 2 | |
| 4-109 | Me | $CH_2CHF_2$ | $OCHF_2$ | E | 2 | |
| 4-110 | Me | $CH_2CF_2CHF_2$ | $OCHF_2$ | E | 2 | |
| 4-111 | H | H | $SOCF_3$ | E | 2 | |
| 4-112 | H | $CH_2CF_3$ | $SOCF_3$ | E | 2 | |
| 4-113 | H | $CH_2C_2F_5$ | $SOCF_3$ | E | 2 | |
| 4-114 | H | $CH_2CHF_2$ | $SOCF_3$ | E | 2 | 138-139 |
| 4-115 | H | $CH_2CF_2CHF_2$ | $SOCF_3$ | E | 2 | |
| 4-116 | Me | H | $SOCF_3$ | E | 2 | |
| 4-117 | Me | $CH_2CF_3$ | $SOCF_3$ | E | 2 | |
| 4-118 | Me | $CH_2C_2F_5$ | $SOCF_3$ | E | 2 | |
| 4-119 | Me | $CH_2CHF_2$ | $SOCF_3$ | E | 2 | |
| 4-120 | Me | $CH_2CF_2CHF_2$ | $SOCF_3$ | E | 2 | |
| 4-121 | H | n-Pr | $SOCF_3$ | E | 2 | |
| 4-122 | Me | n-Pr | $SOCF_3$ | E | 2 | |
| 4-123 | H | i-Pr | $SOCF_3$ | E | 2 | |
| 4-124 | Me | i-Pr | $SOCF_3$ | E | 2 | |
| 4-125 | H | $CH_2SCH_3$ | $SOCF_3$ | E | 2 | |
| 4-126 | Me | $CH_2SCH_3$ | $SOCF_3$ | E | 2 | |
| 4-127 | H | $CH_2SOCH_3$ | $SOCF_3$ | E | 2 | |
| 4-128 | Me | $CH_2SOCH_3$ | $SOCF_3$ | E | 2 | |
| 4-129 | H | $CH_2SO_2CH_3$ | $SOCF_3$ | E | 2 | |
| 4-130 | Me | $CH_2SO_2CH_3$ | $SOCF_3$ | E | 2 | |
| 4-131 | H | $CH_2SCH_2CH_3$ | $SOCF_3$ | E | 2 | |
| 4-132 | Me | $CH_2SCH_2CH_3$ | $SOCF_3$ | E | 2 | |
| 4-133 | H | $CH_2SOCH_2CH_3$ | $SOCF_3$ | E | 2 | |

TABLE 46

Table 4 (continued)

| Compound No. | $R^2$ | $R^3$ | $R^4$ | Isomerism | m | Physical property |
|---|---|---|---|---|---|---|
| 4-134 | Me | $CH_2SOCH_2CH_3$ | $SOCF_3$ | E | 2 | |
| 4-135 | H | $CH_2SO_2CH_2CH_3$ | $SOCF_3$ | E | 2 | |
| 4-136 | Me | $CH_2SO_2CH_2CH_3$ | $SOCF_3$ | E | 2 | |
| 4-137 | H | $CH_2CH_2SCH_3$ | $SOCF_3$ | E | 2 | |
| 4-138 | Me | $CH_2CH_2SCH_3$ | $SOCF_3$ | E | 2 | |
| 4-139 | H | $CH_2CH_2SOCH_3$ | $SOCF_3$ | E | 2 | |
| 4-140 | Me | $CH_2CH_2SOCH_3$ | $SOCF_3$ | E | 2 | |
| 4-141 | H | $CH_2CH_2SO_2CH_3$ | $SOCF_3$ | E | 2 | |
| 4-142 | Me | $CH_2CH_2SO_2CH_3$ | $SOCF_3$ | E | 2 | |
| 4-143 | H | $CH_2CH_2SCH_2CH_3$ | $SOCF_3$ | E | 2 | |
| 4-144 | Me | $CH_2CH_2SCH_2CH_3$ | $SOCF_3$ | E | 2 | |
| 4-145 | H | $CH_2CH_2SOCH_2CH_3$ | $SOCF_3$ | E | 2 | |
| 4-146 | Me | $CH_2CH_2SOCH_2CH_3$ | $SOCF_3$ | E | 2 | |
| 4-147 | H | $CH_2CH_2SO_2CH_2CH_3$ | $SOCF_3$ | E | 2 | |
| 4-148 | Me | $CH_2CH_2SO_2CH_2CH_3$ | $SOCF_3$ | E | 2 | |
| 4-149 | H | $CH_2CH_2SCF_3$ | $SOCF_3$ | E | 2 | |
| 4-150 | Me | $CH_2CH_2SCF_3$ | $SOCF_3$ | E | 2 | |
| 4-151 | H | $CH_2CH_2SOCF_3$ | $SOCF_3$ | E | 2 | |
| 4-152 | Me | $CH_2CH_2SOCF_3$ | $SOCF_3$ | E | 2 | |
| 4-153 | H | $CH_2CH_2SO_2CF_3$ | $SOCF_3$ | E | 2 | |
| 4-154 | Me | $CH_2CH_2SO_2CF_3$ | $SOCF_3$ | E | 2 | |
| 4-155 | H | $CH_2C\equiv N$ | $SOCF_3$ | E | 2 | |
| 4-156 | Me | $CH_2C\equiv N$ | $SOCF_3$ | E | 2 | |
| 4-157 | H | c-Pen | $SOCF_3$ | E | 2 | |
| 4-158 | Me | c-Pen | $SOCF_3$ | E | 2 | |
| 4-159 | H | $CH_2CH=CHCl$ | $SOCF_3$ | E | 2 | |
| 4-160 | Me | $CH_2CH=CHCl$ | $SOCF_3$ | E | 2 | |
| 4-161 | H | n-Bu | $SOCF_3$ | E | 2 | |
| 4-162 | Me | n-Bu | $SOCF_3$ | E | 2 | |
| 4-163 | H | n-Pen | $SOCF_3$ | E | 2 | |

TABLE 47

Table 4 (continued)

| Compound No. | $R^2$ | $R^3$ | $R^4$ | Isomerism | m | Physical property |
|---|---|---|---|---|---|---|
| 4-164 | Me | n-Pen | $SOCF_3$ | E | 2 | |
| 4-165 | H | $CH_2CH=C(CH_3)_2$ | $SOCF_3$ | E | 2 | |
| 4-166 | Me | $CH_2CH=C(CH_3)_2$ | $SOCF_3$ | E | 2 | |
| 4-167 | H | n-Pr | $SO_2CF_3$ | E | 2 | |
| 4-168 | Me | n-Pr | $SO_2CF_3$ | E | 2 | |
| 4-169 | H | i-Pr | $SO_2CF_3$ | E | 2 | |
| 4-170 | Me | i-Pr | $SO_2CF_3$ | E | 2 | |
| 4-171 | H | $CH_2SCH_3$ | $SO_2CF_3$ | E | 2 | |
| 4-172 | Me | $CH_2SCH_3$ | $SO_2CF_3$ | E | 2 | |
| 4-173 | H | $CH_2SOCH_3$ | $SO_2CF_3$ | E | 2 | |
| 4-174 | Me | $CH_2SOCH_3$ | $SO_2CF_3$ | E | 2 | |
| 4-175 | H | $CH_2SO_2CH_3$ | $SO_2CF_3$ | E | 2 | |
| 4-176 | Me | $CH_2SO_2CH_3$ | $SO_2CF_3$ | E | 2 | |
| 4-177 | H | $CH_2SCH_2CH_3$ | $SO_2CF_3$ | E | 2 | |
| 4-178 | Me | $CH_2SCH_2CH_3$ | $SO_2CF_3$ | E | 2 | |
| 4-179 | H | $CH_2SOCH_2CH_3$ | $SO_2CF_3$ | E | 2 | |
| 4-180 | Me | $CH_2SOCH_2CH_3$ | $SO_2CF_3$ | E | 2 | |
| 4-181 | H | $CH_2SO_2CH_2CH_3$ | $SO_2CF_3$ | E | 2 | |
| 4-182 | Me | $CH_2SO_2CH_2CH_3$ | $SO_2CF_3$ | E | 2 | |
| 4-183 | H | $CH_2CH_2SCH_3$ | $SO_2CF_3$ | E | 2 | |
| 4-184 | Me | $CH_2CH_2SCH_3$ | $SO_2CF_3$ | E | 2 | |
| 4-185 | H | $CH_2CH_2SOCH_3$ | $SO_2CF_3$ | E | 2 | |
| 4-186 | Me | $CH_2CH_2SOCH_3$ | $SO_2CF_3$ | E | 2 | |
| 4-187 | H | $CH_2CH_2SO_2CH_3$ | $SO_2CF_3$ | E | 2 | |
| 4-188 | Me | $CH_2CH_2SO_2CH_3$ | $SO_2CF_3$ | E | 2 | |
| 4-189 | H | $CH_2CH_2SCH_2CH_3$ | $SO_2CF_3$ | E | 2 | |
| 4-190 | Me | $CH_2CH_2SCH_2CH_3$ | $SO_2CF_3$ | E | 2 | |
| 4-191 | H | $CH_2CH_2SOCH_2CH_3$ | $SO_2CF_3$ | E | 2 | |
| 4-192 | Me | $CH_2CH_2SOCH_2CH_3$ | $SO_2CF_3$ | E | 2 | |
| 4-193 | H | $CH_2CH_2SO_2CH_2CH_3$ | $SO_2CF_3$ | E | 2 | |

TABLE 48

Table 4 (continued)

| Compound No. | $R^2$ | $R^3$ | $R^4$ | Isomerism | m | Physical property |
|---|---|---|---|---|---|---|
| 4-194 | Me | $CH_2CH_2SO_2CH_2CH_3$ | $SO_2CF_3$ | E | 2 | |
| 4-195 | H | $CH_2CH_2SCF_3$ | $SO_2CF_3$ | E | 2 | |
| 4-196 | Me | $CH_2CH_2SCF_3$ | $SO_2CF_3$ | E | 2 | |
| 4-197 | H | $CH_2CH_2SOCF_3$ | $SO_2CF_3$ | E | 2 | |
| 4-198 | Me | $CH_2CH_2SOCF_3$ | $SO_2CF_3$ | E | 2 | |
| 4-199 | H | $CH_2CH_2SO_2CF_3$ | $SO_2CF_3$ | E | 2 | |
| 4-200 | Me | $CH_2CH_2SO_2CF_3$ | $SO_2CF_3$ | E | 2 | |
| 4-201 | H | $CH_2C\equiv N$ | $SO_2CF_3$ | E | 2 | |
| 4-202 | Me | $CH_2C\equiv N$ | $SO_2CF_3$ | E | 2 | |
| 4-203 | H | c-Pen | $SO_2CF_3$ | E | 2 | |
| 4-204 | Me | c-Pen | $SO_2CF_3$ | E | 2 | |
| 4-205 | H | $CH_2CH=CHCl$ | $SO_2CF_3$ | E | 2 | |
| 4-206 | Me | $CH_2CH=CHCl$ | $SO_2CF_3$ | E | 2 | |
| 4-207 | H | n-Bu | $SO_2CF_3$ | E | 2 | |
| 4-208 | Me | n-Bu | $SO_2CF_3$ | E | 2 | |
| 4-209 | H | n-Pen | $SO_2CF_3$ | E | 2 | |
| 4-210 | Me | n-Pen | $SO_2CF_3$ | E | 2 | |
| 4-211 | H | $CH_2CH=C(CH_3)_2$ | $SO_2CF_3$ | E | 2 | |
| 4-212 | Me | $CH_2CH=C(CH_3)_2$ | $SO_2CF_3$ | E | 2 | |
| 4-213 | H | Me | $SOCF_3$ | E | 2 | |
| 4-214 | Me | Me | $SOCF_3$ | E | 2 | |
| 4-215 | H | Et | $SOCF_3$ | E | 2 | |
| 4-216 | Me | Et | $SOCF_3$ | E | 2 | |
| 4-217 | H | Me | $SO_2CF_3$ | E | 2 | |
| 4-218 | Me | Me | $SO_2CF_3$ | E | 2 | |
| 4-219 | H | Et | $SO_2CF_3$ | E | 2 | |
| 4-220 | Me | Et | $SO_2CF_3$ | E | 2 | |
| 4-221 | CN | Me | $SO_2CF_3$ | E | 2 | |
| 4-222 | CN | Et | $SO_2CF_3$ | E | 2 | |
| 4-223 | CN | n-Pr | $SO_2CF_3$ | E | 2 | |

TABLE 49

Table 4 (continued)

| Compound No. | $R^2$ | $R^3$ | $R^4$ | Isomerism | m | Physical property |
|---|---|---|---|---|---|---|
| 4-224 | CN | i-Pr | $SO_2CF_3$ | E | 2 | |
| 4-225 | CN | H | $SOCF_3$ | E | 2 | |
| 4-226 | CN | $CH_2CF_3$ | $SOCF_3$ | E | 2 | |
| 4-227 | CN | $CH_2C_2F_5$ | $SOCF_3$ | E | 2 | |
| 4-228 | CN | $CH_2CHF_2$ | $SOCF_3$ | E | 2 | |
| 4-229 | CN | $CH_2CF_2CHF_2$ | $SOCF_3$ | E | 2 | |
| 4-230 | CN | $CH_2SCH_3$ | $SO_2CF_3$ | E | 2 | |
| 4-231 | CN | $CH_2SOCH_3$ | $SO_2CF_3$ | E | 2 | |
| 4-232 | CN | $CH_2SO_2CH_3$ | $SO_2CF_3$ | E | 2 | |
| 4-233 | CN | $CH_2SCH_2CH_3$ | $SO_2CF_3$ | E | 2 | |
| 4-234 | CN | $CH_2SOCH_2CH_3$ | $SO_2CF_3$ | E | 2 | |
| 4-235 | CN | $CH_2SO_2CH_2CH_3$ | $SO_2CF_3$ | E | 2 | |
| 4-236 | CN | $CH_2CH_2SCH_3$ | $SO_2CF_3$ | E | 2 | |
| 4-237 | CN | $CH_2CH_2SOCH_3$ | $SO_2CF_3$ | E | 2 | |
| 4-238 | CN | $CH_2CH_2SO_2CH_3$ | $SO_2CF_3$ | E | 2 | |
| 4-239 | CN | $CH_2CH_2SCH_2CH_3$ | $SO_2CF_3$ | E | 2 | |
| 4-240 | CN | $CH_2CH_2SOCH_2CH_3$ | $SO_2CF_3$ | E | 2 | |
| 4-241 | CN | $CH_2CH_2SO_2CH_2CH_3$ | $SO_2CF_3$ | E | 2 | |
| 4-242 | CN | $CH_2CH_2SCF_3$ | $SO_2CF_3$ | E | 2 | |
| 4-243 | CN | $CH_2CH_2SOCF_3$ | $SO_2CF_3$ | E | 2 | |
| 4-244 | CN | $CH_2CH_2SO_2CF_3$ | $SO_2CF_3$ | E | 2 | |
| 4-245 | CN | Me | $SCF_3$ | E | 2 | |
| 4-246 | CN | Et | $SCF_3$ | E | 2 | |
| 4-247 | CN | n-Pr | $SCF_3$ | E | 2 | 127-129 |
| 4-248 | CN | i-Pr | $SCF_3$ | E | 2 | |
| 4-249 | CN | H | $SCF_3$ | E | 2 | |
| 4-250 | CN | $CH_2CF_3$ | $SCF_3$ | E | 2 | 148-153 |
| 4-251 | CN | $CH_2C_2F_5$ | $SCF_3$ | E | 2 | |
| 4-252 | CN | $CH_2CHF_2$ | $SCF_3$ | E | 2 | |
| 4-253 | CN | $CH_2CF_2CHF_2$ | $SCF_3$ | E | 2 | |

TABLE 50

Table 4 (continued)

| Compound No. | $R^2$ | $R^3$ | $R^4$ | Isomerism | m | Physical property |
|---|---|---|---|---|---|---|
| 4-254 | CN | $CH_2SCH_3$ | $SCF_3$ | E | 2 | |
| 4-255 | CN | $CH_2SOCH_3$ | $SCF_3$ | E | 2 | |
| 4-256 | CN | $CH_2SO_2CH_3$ | $SCF_3$ | E | 2 | |
| 4-257 | CN | $CH_2SCH_2CH_3$ | $SCF_3$ | E | 2 | |
| 4-258 | CN | $CH_2SOCH_2CH_3$ | $SCF_3$ | E | 2 | |
| 4-259 | CN | $CH_2SO_2CH_2CH_3$ | $SCF_3$ | E | 2 | |
| 4-260 | CN | $CH_2CH_2SCH_3$ | $SCF_3$ | E | 2 | |
| 4-261 | CN | $CH_2CH_2SOCH_3$ | $SCF_3$ | E | 2 | |
| 4-262 | CN | $CH_2CH_2SO_2CH_3$ | $SCF_3$ | E | 2 | |
| 4-263 | CN | $CH_2CH_2SCH_2CH_3$ | $SCF_3$ | E | 2 | |
| 4-264 | CN | $CH_2CH_2SOCH_2CH_3$ | $SCF_3$ | E | 2 | |
| 4-265 | CN | $CH_2CH_2SO_2CH_2CH_3$ | $SCF_3$ | E | 2 | |
| 4-266 | CN | $CH_2CH_2SCF_3$ | $SCF_3$ | E | 2 | |
| 4-267 | CN | $CH_2CH_2SOCF_3$ | $SCF_3$ | E | 2 | |
| 4-268 | CN | $CH_2CH_2SO_2CF_3$ | $SCF_3$ | E | 2 | |
| 4-269 | COOMe | Me | $SO_2CF_3$ | E | 2 | |
| 4-270 | COOMe | Et | $SO_2CF_3$ | E | 2 | |
| 4-271 | COOMe | n-Pr | $SO_2CF_3$ | E | 2 | |
| 4-272 | COOMe | i-Pr | $SO_2CF_3$ | E | 2 | |
| 4-273 | COOMe | H | $SOCF_3$ | E | 2 | |
| 4-274 | COOMe | $CH_2CF_3$ | $SOCF_3$ | E | 2 | |
| 4-275 | COOMe | $CH_2C_2F_5$ | $SOCF_3$ | E | 2 | |
| 4-276 | COOMe | $CH_2CHF_2$ | $SOCF_3$ | E | 2 | |
| 4-277 | COOMe | $CH_2CF_2CHF_2$ | $SOCF_3$ | E | 2 | |
| 4-278 | COOMe | $CH_2SCH_3$ | $SO_2CF_3$ | E | 2 | |
| 4-279 | COOMe | $CH_2SOCH_3$ | $SO_2CF_3$ | E | 2 | |
| 4-280 | COOMe | $CH_2SO_2CH_3$ | $SO_2CF_3$ | E | 2 | |
| 4-281 | COOMe | $CH_2SCH_2CH_3$ | $SO_2CF_3$ | E | 2 | |
| 4-282 | COOMe | $CH_2SOCH_2CH_3$ | $SO_2CF_3$ | E | 2 | |
| 4-283 | COOMe | $CH_2SO_2CH_2CH_3$ | $SO_2CF_3$ | E | 2 | |

TABLE 51

Table 4 (continued)

| Compound No. | R² | R³ | R⁴ | Isomerism | m | Physical property |
|---|---|---|---|---|---|---|
| 4-284 | COOMe | CH₂CH₂SCH₃ | SO₂CF₃ | E | 2 | |
| 4-285 | COOMe | CH₂CH₂SOCH₃ | SO₂CF₃ | E | 2 | |
| 4-286 | COOMe | CH₂CH₂SO₂CH₃ | SO₂CF₃ | E | 2 | |
| 4-287 | COOMe | CH₂CH₂SCH₂CH₃ | SO₂CF₃ | E | 2 | |
| 4-288 | COOMe | CH₂CH₂SOCH₂CH₃ | SO₂CF₃ | E | 2 | |
| 4-289 | COOMe | CH₂CH₂SO₂CH₂CH₃ | SO₂CF₃ | E | 2 | |
| 4-290 | COOMe | CH₂CH₂SCF₃ | SO₂CF₃ | E | 2 | |
| 4-291 | COOMe | CH₂CH₂SOCF₃ | SO₂CF₃ | E | 2 | |
| 4-292 | COOMe | CH₂CH₂SO₂CF₃ | SO₂CF₃ | E | 2 | |
| 4-293 | COOMe | Me | SCF₃ | E | 2 | |
| 4-294 | COOMe | Et | SCF₃ | E | 2 | |
| 4-295 | COOMe | n-Pr | SCF₃ | E | 2 | |
| 4-296 | COOMe | i-Pr | SCF₃ | E | 2 | |
| 4-297 | COOMe | H | SCF₃ | E | 2 | |
| 4-298 | COOMe | CH₂CF₃ | SCF₃ | E | 2 | |
| 4-299 | COOMe | CH₂C₂F₅ | SCF₃ | E | 2 | |
| 4-300 | COOMe | CH₂CHF₂ | SCF₃ | E | 2 | |
| 4-301 | COOMe | CH₂CF₂CHF₂ | SCF₃ | E | 2 | |
| 4-302 | COOMe | CH₂SCH₃ | SCF₃ | E | 2 | |
| 4-303 | COOMe | CH₂SOCH₃ | SCF₃ | E | 2 | |
| 4-304 | COOMe | CH₂SO₂CH₃ | SCF₃ | E | 2 | |
| 4-305 | COOMe | CH₂SCH₂CH₃ | SCF₃ | E | 2 | |
| 4-306 | COOMe | CH₂SOCH₂CH₃ | SCF₃ | E | 2 | |
| 4-307 | COOMe | CH₂SO₂CH₂CH₃ | SCF₃ | E | 2 | |
| 4-308 | COOMe | CH₂CH₂SCH₃ | SCF₃ | E | 2 | |
| 4-309 | COOMe | CH₂CH₂SOCH₃ | SCF₃ | E | 2 | |
| 4-310 | COOMe | CH₂CH₂SO₂CH₃ | SCF₃ | E | 2 | |
| 4-311 | COOMe | CH₂CH₂SCH₂CH₃ | SCF₃ | E | 2 | |
| 4-312 | COOMe | CH₂CH₂SOCH₂CH₃ | SCF₃ | E | 2 | |
| 4-313 | COOMe | CH₂CH₂SO₂CH₂CH₃ | SCF₃ | E | 2 | |

TABLE 52

Table 4 (continued)

| Compound No. | R² | R³ | R⁴ | Isomerism | m | Physical property |
|---|---|---|---|---|---|---|
| 4-314 | COOMe | CH₂CH₂SCF₃ | SCF₃ | E | 2 | |
| 4-315 | COOMe | CH₂CH₂SOCF₃ | SCF₃ | E | 2 | |
| 4-316 | COOMe | CH₂CH₂SO₂CF₃ | SCF₃ | E | 2 | |
| 4-317 | COOEt | Me | SO₂CF₃ | E | 2 | |
| 4-318 | COOEt | Et | SO₂CF₃ | E | 2 | |
| 4-319 | COOEt | n-Pr | SO₂CF₃ | E | 2 | |
| 4-320 | COOEt | i-Pr | SO₂CF₃ | E | 2 | |
| 4-321 | COOEt | H | SOCF₃ | E | 2 | |
| 4-322 | COOEt | CH₂CF₃ | SOCF₃ | E | 2 | |
| 4-323 | COOEt | CH₂C₂F₅ | SOCF₃ | E | 2 | |
| 4-324 | COOEt | CH₂CHF₂ | SOCF₃ | E | 2 | |
| 4-325 | COOEt | CH₂CF₂CHF₂ | SOCF₃ | E | 2 | |
| 4-326 | COOEt | CH₂SCH₃ | SO₂CF₃ | E | 2 | |
| 4-327 | COOEt | CH₂SOCH₃ | SO₂CF₃ | E | 2 | |
| 4-328 | COOEt | CH₂SO₂CH₃ | SO₂CF₃ | E | 2 | |
| 4-329 | COOEt | CH₂SCH₂CH₃ | SO₂CF₃ | E | 2 | |
| 4-330 | COOEt | CH₂SOCH₂CH₃ | SO₂CF₃ | E | 2 | |
| 4-331 | COOEt | CH₂SO₂CH₂CH₃ | SO₂CF₃ | E | 2 | |
| 4-332 | COOEt | CH₂CH₂SCH₃ | SO₂CF₃ | E | 2 | |
| 4-333 | COOEt | CH₂CH₂SOCH₃ | SO₂CF₃ | E | 2 | |
| 4-334 | COOEt | CH₂CH₂SO₂CH₃ | SO₂CF₃ | E | 2 | |
| 4-335 | COOEt | CH₂CH₂SCH₂CH₃ | SO₂CF₃ | E | 2 | |
| 4-336 | COOEt | CH₂CH₂SOCH₂CH₃ | SO₂CF₃ | E | 2 | |
| 4-337 | COOEt | CH₂CH₂SO₂CH₂CH₃ | SO₂CF₃ | E | 2 | |
| 4-338 | COOEt | CH₂CH₂SCF₃ | SO₂CF₃ | E | 2 | |
| 4-339 | COOEt | CH₂CH₂SOCF₃ | SO₂CF₃ | E | 2 | |
| 4-340 | COOEt | CH₂CH₂SO₂CF₃ | SO₂CF₃ | E | 2 | |
| 4-341 | COOEt | Me | SCF₃ | E | 2 | |
| 4-342 | COOEt | Et | SCF₃ | E | 2 | |
| 4-343 | COOEt | n-Pr | SCF₃ | E | 2 | |

TABLE 53

Table 4 (continued)

| Compound No. | R² | R³ | R⁴ | Isomerism | m | Physical property |
|---|---|---|---|---|---|---|
| 4-344 | COOEt | i-Pr | SCF₃ | E | 2 | |
| 4-345 | COOEt | H | SCF₃ | E | 2 | |
| 4-346 | COOEt | CH₂CF₃ | SCF₃ | E | 2 | |
| 4-347 | COOEt | CH₂C₂F₅ | SCF₃ | E | 2 | |
| 4-348 | COOEt | CH₂CHF₂ | SCF₃ | E | 2 | |
| 4-349 | COOEt | CH₂CF₂CHF₂ | SCF₃ | E | 2 | |
| 4-350 | COOEt | CH₂SCH₃ | SCF₃ | E | 2 | |
| 4-351 | COOEt | CH₂SOCH₃ | SCF₃ | E | 2 | |
| 4-352 | COOEt | CH₂SO₂CH₃ | SCF₃ | E | 2 | |
| 4-353 | COOEt | CH₂SCH₂CH₃ | SCF₃ | E | 2 | |
| 4-354 | COOEt | CH₂SOCH₂CH₃ | SCF₃ | E | 2 | |
| 4-355 | COOEt | CH₂SO₂CH₂CH₃ | SCF₃ | E | 2 | |
| 4-356 | COOEt | CH₂CH₂SCH₃ | SCF₃ | E | 2 | |
| 4-357 | COOEt | CH₂CH₂SOCH₃ | SCF₃ | E | 2 | |
| 4-358 | COOEt | CH₂CH₂SO₂CH₃ | SCF₃ | E | 2 | |
| 4-359 | COOEt | CH₂CH₂SCH₂CH₃ | SCF₃ | E | 2 | |
| 4-360 | COOEt | CH₂CH₂SOCH₂CH₃ | SCF₃ | E | 2 | |
| 4-361 | COOEt | CH₂CH₂SO₂CH₂CH₃ | SCF₃ | E | 2 | |
| 4-362 | COOEt | CH₂CH₂SCF₃ | SCF₃ | E | 2 | |
| 4-363 | COOEt | CH₂CH₂SOCF₃ | SCF₃ | E | 2 | |
| 4-364 | COOEt | CH₂CH₂SO₂CF₃ | SCF₃ | E | 2 | |
| 4-365 | CONH₂ | Me | SO₂CF₃ | E | 2 | |
| 4-366 | CONH₂ | Et | SO₂CF₃ | E | 2 | |
| 4-367 | CONH₂ | n-Pr | SO₂CF₃ | E | 2 | |
| 4-368 | CONH₂ | i-Pr | SO₂CF₃ | E | 2 | |
| 4-369 | CONH₂ | H | SOCF₃ | E | 2 | |
| 4-370 | CONH₂ | CH₂CF₃ | SOCF₃ | E | 2 | |
| 4-371 | CONH₂ | CH₂C₂F₅ | SOCF₃ | E | 2 | |
| 4-372 | CONH₂ | CH₂CHF₂ | SOCF₃ | E | 2 | |
| 4-373 | CONH₂ | CH₂CF₂CHF₂ | SOCF₃ | E | 2 | |

TABLE 54

Table 4 (continued)

| Compound No. | R² | R³ | R⁴ | Isomerism | m | Physical property |
|---|---|---|---|---|---|---|
| 4-374 | CONH₂ | CH₂SCH₃ | SO₂CF₃ | E | 2 | |
| 4-375 | CONH₂ | CH₂SOCH₃ | SO₂CF₃ | E | 2 | |
| 4-376 | CONH₂ | CH₂SO₂CH₃ | SO₂CF₃ | E | 2 | |
| 4-377 | CONH₂ | CH₂SCH₂CH₃ | SO₂CF₃ | E | 2 | |
| 4-378 | CONH₂ | CH₂SOCH₂CH₃ | SO₂CF₃ | E | 2 | |
| 4-379 | CONH₂ | CH₂SO₂CH₂CH₃ | SO₂CF₃ | E | 2 | |
| 4-380 | CONH₂ | CH₂CH₂SCH₃ | SO₂CF₃ | E | 2 | |
| 4-381 | CONH₂ | CH₂CH₂SOCH₃ | SO₂CF₃ | E | 2 | |
| 4-382 | CONH₂ | CH₂CH₂SO₂CH₃ | SO₂CF₃ | E | 2 | |
| 4-383 | CONH₂ | CH₂CH₂SCH₂CH₃ | SO₂CF₃ | E | 2 | |
| 4-384 | CONH₂ | CH₂CH₂SOCH₂CH₃ | SO₂CF₃ | E | 2 | |
| 4-385 | CONH₂ | CH₂CH₂SO₂CH₂CH₃ | SO₂CF₃ | E | 2 | |
| 4-386 | CONH₂ | CH₂CH₂SCF₃ | SO₂CF₃ | E | 2 | |
| 4-387 | CONH₂ | CH₂CH₂SOCF₃ | SO₂CF₃ | E | 2 | |
| 4-388 | CONH₂ | CH₂CH₂SO₂CF₃ | SO₂CF₃ | E | 2 | |
| 4-389 | CONH₂ | Me | SCF₃ | E | 2 | |
| 4-390 | CONH₂ | Et | SCF₃ | E | 2 | |
| 4-391 | CONH₂ | n-Pr | SCF₃ | E | 2 | |
| 4-392 | CONH₂ | i-Pr | SCF₃ | E | 2 | |
| 4-393 | CONH₂ | H | SCF₃ | E | 2 | |
| 4-394 | CONH₂ | CH₂CF₃ | SCF₃ | E | 2 | |
| 4-395 | CONH₂ | CH₂C₂F₅ | SCF₃ | E | 2 | |
| 4-396 | CONH₂ | CH₂CHF₂ | SCF₃ | E | 2 | |
| 4-397 | CONH₂ | CH₂CF₂CHF₂ | SCF₃ | E | 2 | |
| 4-398 | CONH₂ | CH₂SCH₃ | SCF₃ | E | 2 | |
| 4-399 | CONH₂ | CH₂SOCH₃ | SCF₃ | E | 2 | |
| 4-400 | CONH₂ | CH₂SO₂CH₃ | SCF₃ | E | 2 | |
| 4-401 | CONH₂ | CH₂SCH₂CH₃ | SCF₃ | E | 2 | |
| 4-402 | CONH₂ | CH₂SOCH₂CH₃ | SCF₃ | E | 2 | |
| 4-403 | CONH₂ | CH₂SO₂CH₂CH₃ | SCF₃ | E | 2 | |

TABLE 55

Table 4 (continued)

| Compound No. | R² | R³ | R⁴ | Isomerism | m | Physical property |
|---|---|---|---|---|---|---|
| 4-404 | CONH₂ | CH₂CH₂SCH₃ | SCF₃ | E | 2 | |
| 4-405 | CONH₂ | CH₂CH₂SOCH₃ | SCF₃ | E | 2 | |
| 4-406 | CONH₂ | CH₂CH₂SO₂CH₃ | SCF₃ | E | 2 | |
| 4-407 | CONH₂ | CH₂CH₂SCH₂CH₃ | SCF₃ | E | 2 | |
| 4-408 | CONH₂ | CH₂CH₂SOCH₂CH₃ | SCF₃ | E | 2 | |
| 4-409 | CONH₂ | CH₂CH₂SO₂CH₂CH₃ | SCF₃ | E | 2 | |
| 4-410 | CONH₂ | CH₂CH₂SCF₃ | SCF₃ | E | 2 | |
| 4-411 | CONH₂ | CH₂CH₂SOCF₃ | SCF₃ | E | 2 | |
| 4-412 | CONH₂ | CH₂CH₂SO₂CF₃ | SCF₃ | E | 2 | |
| 4-413 | CONHMe | Me | SO₂CF₃ | E | 2 | |
| 4-414 | CONHMe | Et | SO₂CF₃ | E | 2 | |
| 4-415 | CONHMe | n-Pr | SO₂CF₃ | E | 2 | |
| 4-416 | CONHMe | i-Pr | SO₂CF₃ | E | 2 | |
| 4-417 | CONHMe | H | SOCF₃ | E | 2 | |
| 4-418 | CONHMe | CH₂CF₃ | SOCF₃ | E | 2 | |
| 4-419 | CONHMe | CH₂C₂F₅ | SOCF₃ | E | 2 | |
| 4-420 | CONHMe | CH₂CHF₂ | SOCF₃ | E | 2 | |
| 4-421 | CONHMe | CH₂CF₂CHF₂ | SOCF₃ | E | 2 | |
| 4-422 | CONHMe | CH₂SCH₃ | SO₂CF₃ | E | 2 | |
| 4-423 | CONHMe | CH₂SOCH₃ | SO₂CF₃ | E | 2 | |
| 4-424 | CONHMe | CH₂SO₂CH₃ | SO₂CF₃ | E | 2 | |
| 4-425 | CONHMe | CH₂SCH₂CH₃ | SO₂CF₃ | E | 2 | |
| 4-426 | CONHMe | CH₂SOCH₂CH₃ | SO₂CF₃ | E | 2 | |
| 4-427 | CONHMe | CH₂SO₂CH₂CH₃ | SO₂CF₃ | E | 2 | |
| 4-428 | CONHMe | CH₂CH₂SCH₃ | SO₂CF₃ | E | 2 | |
| 4-429 | CONHMe | CH₂CH₂SOCH₃ | SO₂CF₃ | E | 2 | |
| 4-430 | CONHMe | CH₂CH₂SO₂CH₃ | SO₂CF₃ | E | 2 | |
| 4-431 | CONHMe | CH₂CH₂SCH₂CH₃ | SO₂CF₃ | E | 2 | |
| 4-432 | CONHMe | CH₂CH₂SOCH₂CH₃ | SO₂CF₃ | E | 2 | |
| 4-433 | CONHMe | CH₂CH₂SO₂CH₂CH₃ | SO₂CF₃ | E | 2 | |

TABLE 56

Table 4 (continued)

| Compound No. | R² | R³ | R⁴ | Isomerism | m | Physical property |
|---|---|---|---|---|---|---|
| 4-434 | CONHMe | CH₂CH₂SCF₃ | SO₂CF₃ | E | 2 | |
| 4-435 | CONHMe | CH₂CH₂SOCF₃ | SO₂CF₃ | E | 2 | |
| 4-436 | CONHMe | CH₂CH₂SO₂CF₃ | SO₂CF₃ | E | 2 | |
| 4-437 | CONHMe | Me | SCF₃ | E | 2 | |
| 4-438 | CONHMe | Et | SCF₃ | E | 2 | |
| 4-439 | CONHMe | n-Pr | SCF₃ | E | 2 | |
| 4-440 | CONHMe | i-Pr | SCF₃ | E | 2 | |
| 4-441 | CONHMe | H | SCF₃ | E | 2 | |
| 4-442 | CONHMe | CH₂CF₃ | SCF₃ | E | 2 | |
| 4-443 | CONHMe | CH₂C₂F₅ | SCF₃ | E | 2 | |
| 4-444 | CONHMe | CH₂CHF₂ | SCF₃ | E | 2 | |
| 4-445 | CONHMe | CH₂CF₂CHF₂ | SCF₃ | E | 2 | |
| 4-446 | CONHMe | CH₂SCH₃ | SCF₃ | E | 2 | |
| 4-447 | CONHMe | CH₂SOCH₃ | SCF₃ | E | 2 | |
| 4-448 | CONHMe | CH₂SO₂CH₃ | SCF₃ | E | 2 | |
| 4-449 | CONHMe | CH₂SCH₂CH₃ | SCF₃ | E | 2 | |
| 4-450 | CONHMe | CH₂SOCH₂CH₃ | SCF₃ | E | 2 | |
| 4-451 | CONHMe | CH₂SO₂CH₂CH₃ | SCF₃ | E | 2 | |
| 4-452 | CONHMe | CH₂CH₂SCH₃ | SCF₃ | E | 2 | |
| 4-453 | CONHMe | CH₂CH₂SOCH₃ | SCF₃ | E | 2 | |
| 4-454 | CONHMe | CH₂CH₂SO₂CH₃ | SCF₃ | E | 2 | |
| 4-455 | CONHMe | CH₂CH₂SCH₂CH₃ | SCF₃ | E | 2 | |
| 4-456 | CONHMe | CH₂CH₂SOCH₂CH₃ | SCF₃ | E | 2 | |
| 4-457 | CONHMe | CH₂CH₂SO₂CH₂CH₃ | SCF₃ | E | 2 | |
| 4-458 | CONHMe | CH₂CH₂SCF₃ | SCF₃ | E | 2 | |
| 4-459 | CONHMe | CH₂CH₂SOCF₃ | SCF₃ | E | 2 | |
| 4-460 | CONHMe | CH₂CH₂SO₂CF₃ | SCF₃ | E | 2 | |
| 4-461 | CONMe₂ | Me | SO₂CF₃ | E | 2 | |
| 4-462 | CONMe₂ | Et | SO₂CF₃ | E | 2 | |
| 4-463 | CONMe₂ | n-Pr | SO₂CF₃ | E | 2 | |

TABLE 57

Table 4 (continued)

| Compound No. | R² | R³ | R⁴ | Isomerism | m | Physical property |
|---|---|---|---|---|---|---|
| 4-464 | CONMe₂ | i-Pr | SO₂CF₃ | E | 2 | |
| 4-465 | CONMe₂ | H | SOCF₃ | E | 2 | |
| 4-466 | CONMe₂ | CH₂CF₃ | SOCF₃ | E | 2 | |
| 4-467 | CONMe₂ | CH₂C₂F₅ | SOCF₃ | E | 2 | |
| 4-468 | CONMe₂ | CH₂CHF₂ | SOCF₃ | E | 2 | |
| 4-469 | CONMe₂ | CH₂CF₂CHF₂ | SOCF₃ | E | 2 | |
| 4-470 | CONMe₂ | CH₂SCH₃ | SO₂CF₃ | E | 2 | |
| 4-471 | CONMe₂ | CH₂SOCH₃ | SO₂CF₃ | E | 2 | |
| 4-472 | CONMe₂ | CH₂SO₂CH₃ | SO₂CF₃ | E | 2 | |
| 4-473 | CONMe₂ | CH₂SCH₂CH₃ | SO₂CF₃ | E | 2 | |
| 4-474 | CONMe₂ | CH₂SOCH₂CH₃ | SO₂CF₃ | E | 2 | |
| 4-475 | CONMe₂ | CH₂SO₂CH₂CH₃ | SO₂CF₃ | E | 2 | |
| 4-476 | CONMe₂ | CH₂CH₂SCH₃ | SO₂CF₃ | E | 2 | |
| 4-477 | CONMe₂ | CH₂CH₂SOCH₃ | SO₂CF₃ | E | 2 | |
| 4-478 | CONMe₂ | CH₂CH₂SO₂CH₃ | SO₂CF₃ | E | 2 | |
| 4-479 | CONMe₂ | CH₂CH₂SCH₂CH₃ | SO₂CF₃ | E | 2 | |
| 4-480 | CONMe₂ | CH₂CH₂SOCH₂CH₃ | SO₂CF₃ | E | 2 | |
| 4-481 | CONMe₂ | CH₂CH₂SO₂CH₂CH₃ | SO₂CF₃ | E | 2 | |
| 4-482 | CONMe₂ | CH₂CH₂SCF₃ | SO₂CF₃ | E | 2 | |
| 4-483 | CONMe₂ | CH₂CH₂SOCF₃ | SO₂CF₃ | E | 2 | |
| 4-484 | CONMe₂ | CH₂CH₂SO₂CF₃ | SO₂CF₃ | E | 2 | |
| 4-485 | CONMe₂ | Me | SCF₃ | E | 2 | |
| 4-486 | CONMe₂ | Et | SCF₃ | E | 2 | |
| 4-487 | CONMe₂ | n-Pr | SCF₃ | E | 2 | |
| 4-488 | CONMe₂ | i-Pr | SCF₃ | E | 2 | |
| 4-489 | CONMe₂ | H | SCF₃ | E | 2 | |
| 4-490 | CONMe₂ | CH₂CF₃ | SCF₃ | E | 2 | |
| 4-491 | CONMe₂ | CH₂C₂F₅ | SCF₃ | E | 2 | |
| 4-492 | CONMe₂ | CH₂CHF₂ | SCF₃ | E | 2 | |
| 4-493 | CONMe₂ | CH₂CF₂CHF₂ | SCF₃ | E | 2 | |

TABLE 58

Table 4 (continued)

| Compound No. | R² | R³ | R⁴ | Isomerism | m | Physical property |
|---|---|---|---|---|---|---|
| 4-494 | CONMe₂ | CH₂SCH₃ | SCF₃ | E | 2 | |
| 4-495 | CONMe₂ | CH₂SOCH₃ | SCF₃ | E | 2 | |
| 4-496 | CONMe₂ | CH₂SO₂CH₃ | SCF₃ | E | 2 | |
| 4-497 | CONMe₂ | CH₂SCH₂CH₃ | SCF₃ | E | 2 | |
| 4-498 | CONMe₂ | CH₂SOCH₂CH₃ | SCF₃ | E | 2 | |
| 4-499 | CONMe₂ | CH₂SO₂CH₂CH₃ | SCF₃ | E | 2 | |
| 4-500 | CONMe₂ | CH₂CH₂SCH₃ | SCF₃ | E | 2 | |
| 4-501 | CONMe₂ | CH₂CH₂SOCH₃ | SCF₃ | E | 2 | |
| 4-502 | CONMe₂ | CH₂CH₂SO₂CH₃ | SCF₃ | E | 2 | |
| 4-503 | CONMe₂ | CH₂CH₂SCH₂CH₃ | SCF₃ | E | 2 | |
| 4-504 | CONMe₂ | CH₂CH₂SOCH₂CH₃ | SCF₃ | E | 2 | |
| 4-505 | CONMe₂ | CH₂CH₂SO₂CH₂CH₃ | SCF₃ | E | 2 | |
| 4-506 | CONMe₂ | CH₂CH₂SCF₃ | SCF₃ | E | 2 | |
| 4-507 | CONMe₂ | CH₂CH₂SOCF₃ | SCF₃ | E | 2 | |
| 4-508 | CONMe₂ | CH₂CH₂SO₂CF₃ | SCF₃ | E | 2 | |

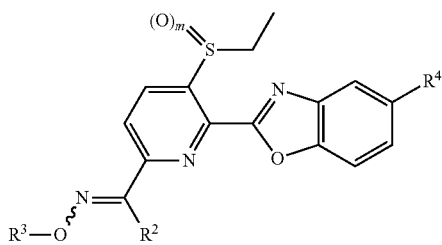

(1B-2)

TABLE 59

Table 5

| Compound No. | $R^2$ | $R^3$ | $R^4$ | Isomerism | m | Physical property |
|---|---|---|---|---|---|---|
| 5-1 | H | H | $CF_3$ | E | 2 | |
| 5-2 | H | $CH_2CHF_2$ | $CF_3$ | E | 2 | |
| 5-3 | H | $CH_2CF_3$ | $CF_3$ | E | 2 | |
| 5-4 | H | $CH_2CF_2CHF_2$ | $CF_3$ | E | 2 | |
| 5-5 | H | $CH_2C_2F_5$ | $CF_3$ | E | 2 | |
| 5-6 | H | $CH_2CF_3$ | $CF_3$ | E | 1 | |
| 5-7 | H | $CH_2C_2F_5$ | $CF_3$ | E | 1 | |
| 5-8 | Me | H | $CF_3$ | E | 2 | |
| 5-9 | Me | $CH_2CHF_2$ | $CF_3$ | E | 2 | |
| 5-10 | Me | $CH_2CF_3$ | $CF_3$ | E | 2 | |
| 5-11 | Me | $CH_2CF_2CHF_2$ | $CF_3$ | E | 2 | |
| 5-12 | Me | $CH_2C_2F_5$ | $CF_3$ | E | 2 | |
| 5-13 | Me | $CH_2CF_3$ | $CF_3$ | E | 1 | |
| 5-14 | Me | $CH_2C_2F_5$ | $CF_3$ | E | 1 | |
| 5-15 | H | H | $SCF_3$ | E | 2 | 81-82 |
| 5-16 | H | $CH_2CHF_2$ | $SCF_3$ | E | 2 | 138-139 |
| 5-17 | H | $CH_2CF_3$ | $SCF_3$ | E | 2 | 121-122 |
| 5-18 | H | $CH_2CF_2CHF_2$ | $SCF_3$ | E | 2 | 127-128 |
| 5-19 | H | $CH_2C_2F_5$ | $SCF_3$ | E | 2 | 123-124 |
| 5-20 | H | $CH_2CF_3$ | $SCF_3$ | E | 1 | |

TABLE 60

Table 5 (continued)

| Compound No. | $R^2$ | $R^3$ | $R^4$ | Isomerism | m | Physical property |
|---|---|---|---|---|---|---|
| 5-21 | H | $CH_2C_2F_5$ | $SCF_3$ | E | 1 | |
| 5-22 | Me | H | $SCF_3$ | E | 2 | |
| 5-23 | Me | $CH_2CHF_2$ | $SCF_3$ | E | 2 | |
| 5-24 | Me | $CH_2CF_3$ | $SCF_3$ | E | 2 | |
| 5-25 | Me | $CH_2CF_2CHF_2$ | $SCF_3$ | E | 2 | |
| 5-26 | Me | $CH_2C_2F_5$ | $SCF_3$ | E | 2 | |
| 5-27 | Me | $CH_2CF_3$ | $SCF_3$ | E | 1 | |
| 5-28 | Me | $CH_2C_2F_5$ | $SCF_3$ | E | 1 | |
| 5-29 | H | H | $OCF_3$ | E | 2 | |
| 5-30 | H | $CH_2CHF_2$ | $OCF_3$ | E | 2 | |
| 5-31 | H | $CH_2CHF_2$ | $OCF_3$ | Z | 2 | |
| 5-32 | H | $CH_2CF_3$ | $OCF_3$ | E | 2 | |
| 5-33 | H | $CH_2CF_2CHF_2$ | $OCF_3$ | E | 2 | |
| 5-34 | H | $CH_2C_2F_5$ | $OCF_3$ | E | 2 | |
| 5-35 | H | $CH_2CF_3$ | $OCF_3$ | E | 1 | |
| 5-36 | H | $CH_2C_2F_5$ | $OCF_3$ | E | 1 | |
| 5-37 | Me | H | $OCF_3$ | E | 2 | |
| 5-38 | Me | $CH_2CHF_2$ | $OCF_3$ | E | 2 | |
| 5-39 | Me | $CH_2CF_3$ | $OCF_3$ | E | 2 | |
| 5-40 | Me | $CH_2CF_2CHF_2$ | $OCF_3$ | E | 2 | |
| 5-41 | Me | $CH_2C_2F_5$ | $OCF_3$ | E | 2 | |
| 5-42 | Me | $CH_2CF_3$ | $OCF_3$ | E | 1 | |
| 5-43 | Me | $CH_2C_2F_5$ | $OCF_3$ | E | 1 | |

TABLE 61

Table 5 (continued)

| Compound No. | $R^2$ | $R^3$ | $R^4$ | Isomerism | m | Physical property |
|---|---|---|---|---|---|---|
| 5-44 | H | n-Pr | $OCF_3$ | E | 2 | NMR |
| 5-45 | Me | n-Pr | $OCF_3$ | E | 2 | |
| 5-46 | H | i-Pr | $OCF_3$ | E | 2 | 115-116 |
| 5-47 | Me | i-Pr | $OCF_3$ | E | 2 | |
| 5-48 | H | $CH_2SCH_3$ | $OCF_3$ | E | 2 | 96-98 |
| 5-49 | Me | $CH_2SCH_3$ | $OCF_3$ | E | 2 | |
| 5-50 | H | $CH_2SOCH_3$ | $OCF_3$ | E | 2 | |
| 5-51 | Me | $CH_2SOCH_3$ | $OCF_3$ | E | 2 | |
| 5-52 | H | $CH_2SO_2CH_3$ | $OCF_3$ | E | 2 | |
| 5-53 | Me | $CH_2SO_2CH_3$ | $OCF_3$ | E | 2 | |
| 5-54 | H | $CH_2SCH_2CH_3$ | $OCF_3$ | E | 2 | |
| 5-55 | Me | $CH_2SCH_2CH_3$ | $OCF_3$ | E | 2 | |
| 5-56 | H | $CH_2SOCH_2CH_3$ | $OCF_3$ | E | 2 | |
| 5-57 | Me | $CH_2SOCH_2CH_3$ | $OCF_3$ | E | 2 | |
| 5-58 | H | $CH_2SO_2CH_2CH_3$ | $OCF_3$ | E | 2 | |
| 5-59 | Me | $CH_2SO_2CH_2CH_3$ | $OCF_3$ | E | 2 | |
| 5-60 | H | $CH_2CH_2SCH_3$ | $OCF_3$ | E | 2 | 107-108 |
| 5-61 | Me | $CH_2CH_2SCH_3$ | $OCF_3$ | E | 2 | |
| 5-62 | H | $CH_2CH_2SOCH_3$ | $OCF_3$ | E | 2 | 169-170 |
| 5-63 | Me | $CH_2CH_2SOCH_3$ | $OCF_3$ | E | 2 | |
| 5-64 | H | $CH_2CH_2SO_2CH_3$ | $OCF_3$ | E | 2 | 187-188 |
| 5-65 | Me | $CH_2CH_2SO_2CH_3$ | $OCF_3$ | E | 2 | |
| 5-66 | H | $CH_2CH_2SCH_2CH_3$ | $OCF_3$ | E | 2 | |
| 5-67 | Me | $CH_2CH_2SCH_2CH_3$ | $OCF_3$ | E | 2 | |
| 5-68 | H | $CH_2CH_2SOCH_2CH_3$ | $OCF_3$ | E | 2 | |
| 5-69 | Me | $CH_2CH_2SOCH_2CH_3$ | $OCF_3$ | E | 2 | |
| 5-70 | H | $CH_2CH_2SO_2CH_2CH_3$ | $OCF_3$ | E | 2 | |
| 5-71 | Me | $CH_2CH_2SO_2CH_2CH_3$ | $OCF_3$ | E | 2 | |
| 5-72 | H | $CH_2CH_2SCF_3$ | $OCF_3$ | E | 2 | |
| 5-73 | Me | $CH_2CH_2SCF_3$ | $OCF_3$ | E | 2 | |

TABLE 62

Table 5 (continued)

| Compound No. | $R^2$ | $R^3$ | $R^4$ | Isomerism | m | Physical property |
|---|---|---|---|---|---|---|
| 5-74 | H | $CH_2CH_2SOCF_3$ | $OCF_3$ | E | 2 | |
| 5-75 | Me | $CH_2CH_2SOCF_3$ | $OCF_3$ | E | 2 | |
| 5-76 | H | $CH_2CH_2SO_2CF_3$ | $OCF_3$ | E | 2 | |
| 5-77 | Me | $CH_2CH_2SO_2CF_3$ | $OCF_3$ | E | 2 | |
| 5-78 | H | $CH_2C{\equiv}N$ | $OCF_3$ | E | 2 | |
| 5-79 | Me | $CH_2C{\equiv}N$ | $OCF_3$ | E | 2 | |
| 5-80 | H | c-Pen | $OCF_3$ | E | 2 | 113-114 |
| 5-81 | Me | c-Pen | $OCF_3$ | E | 2 | |
| 5-82 | H | $CH_2CH{=}CHCl$ | $OCF_3$ | E | 2 | NMR |
| 5-83 | Me | $CH_2CH{=}CHCl$ | $OCF_3$ | E | 2 | |
| 5-84 | H | n-Bu | $OCF_3$ | E | 2 | 77-78 |
| 5-85 | Me | n-Bu | $OCF_3$ | E | 2 | |
| 5-86 | H | n-Pen | $OCF_3$ | E | 2 | 69-70 |
| 5-87 | Me | n-Pen | $OCF_3$ | E | 2 | |
| 5-88 | H | $CH_2CH{=}C(CH_3)_2$ | $OCF_3$ | E | 2 | NMR |
| 5-89 | Me | $CH_2CH{=}C(CH_3)_2$ | $OCF_3$ | E | 2 | |
| 5-90 | H | H | $SO_2CF_3$ | E | 2 | |
| 5-91 | H | $CH_2CF_3$ | $SO_2CF_3$ | E | 2 | |
| 5-92 | H | $CH_2C_2F_5$ | $SO_2CF_3$ | E | 2 | |
| 5-93 | H | $CH_2CHF_2$ | $SO_2CF_3$ | E | 2 | 127-128 |
| 5-94 | H | $CH_2CF_2CHF_2$ | $SO_2CF_3$ | E | 2 | |
| 5-95 | Me | H | $SO_2CF_3$ | E | 2 | |
| 5-96 | Me | $CH_2CF_3$ | $SO_2CF_3$ | E | 2 | |
| 5-97 | Me | $CH_2C_2F_5$ | $SO_2CF_3$ | E | 2 | |
| 5-98 | Me | $CH_2CHF_2$ | $SO_2CF_3$ | E | 2 | |
| 5-99 | Me | $CH_2CF_2CHF_2$ | $SO_2CF_3$ | E | 2 | |
| 5-100 | H | H | $SOCF_3$ | E | 2 | |
| 5-101 | H | $CH_2CF_3$ | $SOCF_3$ | E | 2 | |
| 5-102 | H | $CH_2C_2F_5$ | $SOCF_3$ | E | 2 | |
| 5-103 | H | $CH_2CHF_2$ | $SOCF_3$ | E | 2 | |

TABLE 63

Table 5 (continued)

| Compound No. | $R^2$ | $R^3$ | $R^4$ | Isomerism | m | Physical property |
|---|---|---|---|---|---|---|
| 5-104 | H | $CH_2CF_2CHF_2$ | $SOCF_3$ | E | 2 | |
| 5-105 | Me | H | $SOCF_3$ | E | 2 | |
| 5-106 | Me | $CH_2CF_3$ | $SOCF_3$ | E | 2 | |
| 5-107 | Me | $CH_2C_2F_5$ | $SOCF_3$ | E | 2 | |
| 5-108 | Me | $CH_2CHF_2$ | $SOCF_3$ | E | 2 | |
| 5-109 | Me | $CH_2CF_2CHF_2$ | $SOCF_3$ | E | 2 | |
| 5-110 | H | n-Pr | $SOCF_3$ | E | 2 | |
| 5-111 | Me | n-Pr | $SOCF_3$ | E | 2 | |
| 5-112 | H | i-Pr | $SOCF_3$ | E | 2 | |
| 5-113 | Me | i-Pr | $SOCF_3$ | E | 2 | |
| 5-114 | H | $CH_2SCH_3$ | $SOCF_3$ | E | 2 | |
| 5-115 | Me | $CH_2SCH_3$ | $SOCF_3$ | E | 2 | |
| 5-116 | H | $CH_2SOCH_3$ | $SOCF_3$ | E | 2 | |
| 5-117 | Me | $CH_2SOCH_3$ | $SOCF_3$ | E | 2 | |
| 5-118 | H | $CH_2SO_2CH_3$ | $SOCF_3$ | E | 2 | |
| 5-119 | Me | $CH_2SO_2CH_3$ | $SOCF_3$ | E | 2 | |
| 5-120 | H | $CH_2SCH_2CH_3$ | $SOCF_3$ | E | 2 | |
| 5-121 | Me | $CH_2SCH_2CH_3$ | $SOCF_3$ | E | 2 | |
| 5-122 | H | $CH_2SOCH_2CH_3$ | $SOCF_3$ | E | 2 | |
| 5-123 | Me | $CH_2SOCH_2CH_3$ | $SOCF_3$ | E | 2 | |
| 5-124 | H | $CH_2SO_2CH_2CH_3$ | $SOCF_3$ | E | 2 | |
| 5-125 | Me | $CH_2SO_2CH_2CH_3$ | $SOCF_3$ | E | 2 | |
| 5-126 | H | $CH_2CH_2SCH_3$ | $SOCF_3$ | E | 2 | |
| 5-127 | Me | $CH_2CH_2SCH_3$ | $SOCF_3$ | E | 2 | |
| 5-128 | H | $CH_2CH_2SOCH_3$ | $SOCF_3$ | E | 2 | |
| 5-129 | Me | $CH_2CH_2SOCH_3$ | $SOCF_3$ | E | 2 | |
| 5-130 | H | $CH_2CH_2SO_2CH_3$ | $SOCF_3$ | E | 2 | |
| 5-131 | Me | $CH_2CH_2SO_2CH_3$ | $SOCF_3$ | E | 2 | |
| 5-132 | H | $CH_2CH_2SCH_2CH_3$ | $SOCF_3$ | E | 2 | |
| 5-133 | Me | $CH_2CH_2SCH_2CH_3$ | $SOCF_3$ | E | 2 | |

TABLE 64

Table 5 (continued)

| Compound No. | $R^2$ | $R^3$ | $R^4$ | Isomerism | m | Physical property |
|---|---|---|---|---|---|---|
| 5-134 | H | $CH_2CH_2SOCH_2CH_3$ | $SOCF_3$ | E | 2 | |
| 5-135 | Me | $CH_2CH_2SOCH_2CH_3$ | $SOCF_3$ | E | 2 | |
| 5-136 | H | $CH_2CH_2SO_2CH_2CH_3$ | $SOCF_3$ | E | 2 | |
| 5-137 | Me | $CH_2CH_2SO_2CH_2CH_3$ | $SOCF_3$ | E | 2 | |
| 5-138 | H | $CH_2CH_2SCF_3$ | $SOCF_3$ | E | 2 | |
| 5-139 | Me | $CH_2CH_2SCF_3$ | $SOCF_3$ | E | 2 | |
| 5-140 | H | $CH_2CH_2SOCF_3$ | $SOCF_3$ | E | 2 | |
| 5-141 | Me | $CH_2CH_2SOCF_3$ | $SOCF_3$ | E | 2 | |
| 5-142 | H | $CH_2CH_2SO_2CF_3$ | $SOCF_3$ | E | 2 | |
| 5-143 | Me | $CH_2CH_2SO_2CF_3$ | $SOCF_3$ | E | 2 | |
| 5-144 | H | $CH_2C{\equiv}N$ | $SOCF_3$ | E | 2 | |
| 5-145 | Me | $CH_2C{\equiv}N$ | $SOCF_3$ | E | 2 | |
| 5-146 | H | c-Pen | $SOCF_3$ | E | 2 | |
| 5-147 | Me | c-Pen | $SOCF_3$ | E | 2 | |
| 5-148 | H | $CH_2CH{=}CHCl$ | $SOCF_3$ | E | 2 | |
| 5-149 | Me | $CH_2CH{=}CHCl$ | $SOCF_3$ | E | 2 | |
| 5-150 | H | n-Bu | $SOCF_3$ | E | 2 | |
| 5-151 | Me | n-Bu | $SOCF_3$ | E | 2 | |
| 5-152 | H | n-Pen | $SOCF_3$ | E | 2 | |
| 5-153 | Me | n-Pen | $SOCF_3$ | E | 2 | |
| 5-154 | H | $CH_2CH{=}C(CH_3)_2$ | $SOCF_3$ | E | 2 | |
| 5-155 | Me | $CH_2CH{=}C(CH_3)_2$ | $SOCF_3$ | E | 2 | |
| 5-156 | H | n-Pr | $SO_2CF_3$ | E | 2 | |
| 5-157 | Me | n-Pr | $SO_2CF_3$ | E | 2 | |
| 5-158 | H | i-Pr | $SO_2CF_3$ | E | 2 | |
| 5-159 | Me | i-Pr | $SO_2CF_3$ | E | 2 | |
| 5-160 | H | $CH_2SCH_3$ | $SO_2CF_3$ | E | 2 | |
| 5-161 | Me | $CH_2SCH_3$ | $SO_2CF_3$ | E | 2 | |
| 5-162 | H | $CH_2SOCH_3$ | $SO_2CF_3$ | E | 2 | |
| 5-163 | Me | $CH_2SOCH_3$ | $SO_2CF_3$ | E | 2 | |

TABLE 65

Table 5 (continued)

| Compound No. | $R^2$ | $R^3$ | $R^4$ | Isomerism | m | Physical property |
|---|---|---|---|---|---|---|
| 5-164 | H | $CH_2SO_2CH_3$ | $SO_2CF_3$ | E | 2 | |
| 5-165 | Me | $CH_2SO_2CH_3$ | $SO_2CF_3$ | E | 2 | |
| 5-166 | H | $CH_2SCH_2CH_3$ | $SO_2CF_3$ | E | 2 | |
| 5-167 | Me | $CH_2SCH_2CH_3$ | $SO_2CF_3$ | E | 2 | |
| 5-168 | H | $CH_2SOCH_2CH_3$ | $SO_2CF_3$ | E | 2 | |
| 5-169 | Me | $CH_2SOCH_2CH_3$ | $SO_2CF_3$ | E | 2 | |
| 5-170 | H | $CH_2SO_2CH_2CH_3$ | $SO_2CF_3$ | E | 2 | |
| 5-171 | Me | $CH_2SO_2CH_2CH_3$ | $SO_2CF_3$ | E | 2 | |
| 5-172 | H | $CH_2CH_2SCH_3$ | $SO_2CF_3$ | E | 2 | |
| 5-173 | Me | $CH_2CH_2SCH_3$ | $SO_2CF_3$ | E | 2 | |
| 5-174 | H | $CH_2CH_2SOCH_3$ | $SO_2CF_3$ | E | 2 | |
| 5-175 | Me | $CH_2CH_2SOCH_3$ | $SO_2CF_3$ | E | 2 | |
| 5-176 | H | $CH_2CH_2SO_2CH_3$ | $SO_2CF_3$ | E | 2 | |
| 5-177 | Me | $CH_2CH_2SO_2CH_3$ | $SO_2CF_3$ | E | 2 | |
| 5-178 | H | $CH_2CH_2SCH_2CH_3$ | $SO_2CF_3$ | E | 2 | |
| 5-179 | Me | $CH_2CH_2SCH_2CH_3$ | $SO_2CF_3$ | E | 2 | |
| 5-180 | H | $CH_2CH_2SOCH_2CH_3$ | $SO_2CF_3$ | E | 2 | |
| 5-181 | Me | $CH_2CH_2SOCH_2CH_3$ | $SO_2CF_3$ | E | 2 | |
| 5-182 | H | $CH_2CH_2SO_2CH_2CH_3$ | $SO_2CF_3$ | E | 2 | |
| 5-183 | Me | $CH_2CH_2SO_2CH_2CH_3$ | $SO_2CF_3$ | E | 2 | |
| 5-184 | H | $CH_2CH_2SCF_3$ | $SO_2CF_3$ | E | 2 | |
| 5-185 | Me | $CH_2CH_2SCF_3$ | $SO_2CF_3$ | E | 2 | |
| 5-186 | H | $CH_2CH_2SOCF_3$ | $SO_2CF_3$ | E | 2 | |
| 5-187 | Me | $CH_2CH_2SOCF_3$ | $SO_2CF_3$ | E | 2 | |
| 5-188 | H | $CH_2CH_2SO_2CF_3$ | $SO_2CF_3$ | E | 2 | |
| 5-189 | Me | $CH_2CH_2SO_2CF_3$ | $SO_2CF_3$ | E | 2 | |
| 5-190 | H | $CH_2C{\equiv}N$ | $SO_2CF_3$ | E | 2 | |
| 5-191 | Me | $CH_2C{\equiv}N$ | $SO_2CF_3$ | E | 2 | |
| 5-192 | H | c-Pen | $SO_2CF_3$ | E | 2 | |
| 5-193 | Me | c-Pen | $SO_2CF_3$ | E | 2 | |

TABLE 66

Table 5 (continued)

| Compound No. | $R^2$ | $R^3$ | $R^4$ | Isomerism | m | Physical property |
|---|---|---|---|---|---|---|
| 5-194 | H | $CH_2CH{=}CHCl$ | $SO_2CF_3$ | E | 2 | |
| 5-195 | Me | $CH_2CH{=}CHCl$ | $SO_2CF_3$ | E | 2 | |
| 5-196 | H | n-Bu | $SO_2CF_3$ | E | 2 | |
| 5-197 | Me | n-Bu | $SO_2CF_3$ | E | 2 | |
| 5-198 | H | n-Pen | $SO_2CF_3$ | E | 2 | |
| 5-199 | Me | n-Pen | $SO_2CF_3$ | E | 2 | |
| 5-200 | H | $CH_2CH{=}C(CH_3)_2$ | $SO_2CF_3$ | E | 2 | |
| 5-201 | Me | $CH_2CH{=}C(CH_3)_2$ | $SO_2CF_3$ | E | 2 | |
| 5-202 | H | Me | $SOCF_3$ | E | 2 | |
| 5-203 | Me | Me | $SOCF_3$ | E | 2 | |
| 5-204 | H | Et | $SOCF_3$ | E | 2 | |
| 5-205 | Me | Et | $SOCF_3$ | E | 2 | |
| 5-206 | H | Me | $SO_2CF_3$ | E | 2 | |
| 5-207 | H | Me | $SO_2CF_3$ | E | 2 | |
| 5-208 | H | Et | $SO_2CF_3$ | E | 2 | |
| 5-209 | Me | Et | $SO_2CF_3$ | E | 2 | |
| 5-210 | CN | Me | $SO_2CF_3$ | E | 2 | |
| 5-211 | CN | Et | $SO_2CF_3$ | E | 2 | |
| 5-212 | CN | n-Pr | $SO_2CF_3$ | E | 2 | |
| 5-213 | CN | i-Pr | $SO_2CF_3$ | E | 2 | |
| 5-214 | CN | H | $SOCF_3$ | E | 2 | |
| 5-215 | CN | $CH_2CF_3$ | $SOCF_3$ | E | 2 | |
| 5-216 | CN | $CH_2C_2F_5$ | $SOCF_3$ | E | 2 | |
| 5-217 | CN | $CH_2CHF_2$ | $SOCF_3$ | E | 2 | |
| 5-218 | CN | $CH_2CF_2CHF_2$ | $SOCF_3$ | E | 2 | |
| 5-219 | CN | $CH_2SCH_3$ | $SO_2CF_3$ | E | 2 | |
| 5-220 | CN | $CH_2SOCH_3$ | $SO_2CF_3$ | E | 2 | |
| 5-221 | CN | $CH_2SO_2CH_3$ | $SO_2CF_3$ | E | 2 | |
| 5-222 | CN | $CH_2SCH_2CH_3$ | $SO_2CF_3$ | E | 2 | |
| 5-223 | CN | $CH_2SOCH_2CH_3$ | $SO_2CF_3$ | E | 2 | |

TABLE 67

Table 5 (continued)

| Compound No. | R² | R³ | R⁴ | Isomerism | m | Physical property |
|---|---|---|---|---|---|---|
| 5-224 | CN | CH₂SO₂CH₂CH₃ | SO₂CF₃ | E | 2 | |
| 5-225 | CN | CH₂CH₂SCH₃ | SO₂CF₃ | E | 2 | |
| 5-226 | CN | CH₂CH₂SOCH₃ | SO₂CF₃ | E | 2 | |
| 5-227 | CN | CH₂CH₂SO₂CH₃ | SO₂CF₃ | E | 2 | |
| 5-228 | CN | CH₂CH₂SCH₂CH₃ | SO₂CF₃ | E | 2 | |
| 5-229 | CN | CH₂CH₂SOCH₂CH₃ | SO₂CF₃ | E | 2 | |
| 5-230 | CN | CH₂CH₂SO₂CH₂CH₃ | SO₂CF₃ | E | 2 | |
| 5-231 | CN | CH₂CH₂SCF₃ | SO₂CF₃ | E | 2 | |
| 5-232 | CN | CH₂CH₂SOCF₃ | SO₂CF₃ | E | 2 | |
| 5-233 | CN | CH₂CH₂SO₂CF₃ | SO₂CF₃ | E | 2 | |
| 5-234 | CN | Me | SCF₃ | E | 2 | |
| 5-235 | CN | Et | SCF₃ | E | 2 | |
| 5-236 | CN | n-Pr | SCF₃ | E | 2 | |
| 5-237 | CN | i-Pr | SCF₃ | E | 2 | |
| 5-238 | CN | H | SCF₃ | E | 2 | |
| 5-239 | CN | CH₂CF₃ | SCF₃ | E | 2 | |
| 5-240 | CN | CH₂C₂F₅ | SCF₃ | E | 2 | |
| 5-241 | CN | CH₂CHF₂ | SCF₃ | E | 2 | |
| 5-242 | CN | CH₂CF₂CHF₂ | SCF₃ | E | 2 | |
| 5-243 | CN | CH₂SCH₃ | SCF₃ | E | 2 | |
| 5-244 | CN | CH₂SOCH₃ | SCF₃ | E | 2 | |
| 5-245 | CN | CH₂SO₂CH₃ | SCF₃ | E | 2 | |
| 5-246 | CN | CH₂SCH₂CH₃ | SCF₃ | E | 2 | |
| 5-247 | CN | CH₂SOCH₂CH₃ | SCF₃ | E | 2 | |
| 5-248 | CN | CH₂SO₂CH₂CH₃ | SCF₃ | E | 2 | |
| 5-249 | CN | CH₂CH₂SCH₃ | SCF₃ | E | 2 | |
| 5-250 | CN | CH₂CH₂SOCH₃ | SCF₃ | E | 2 | |
| 5-251 | CN | CH₂CH₂SO₂CH₃ | SCF₃ | E | 2 | |
| 5-252 | CN | CH₂CH₂SCH₂CH₃ | SCF₃ | E | 2 | |
| 5-253 | CN | CH₂CH₂SOCH₂CH₃ | SCF₃ | E | 2 | |

TABLE 68

Table 5 (continued)

| Compound No. | R² | R³ | R⁴ | Isomerism | m | Physical property |
|---|---|---|---|---|---|---|
| 5-255 | CN | CH₂CH₂SCF₃ | SCF₃ | E | 2 | |
| 5-256 | CN | CH₂CH₂SOCF₃ | SCF₃ | E | 2 | |
| 5-257 | CN | CH₂CH₂SO₂CF₃ | SCF₃ | E | 2 | |
| 5-258 | COOMe | Me | SO₂CF₃ | E | 2 | |
| 5-259 | COOMe | Et | SO₂CF₃ | E | 2 | |
| 5-260 | COOMe | n-Pr | SO₂CF₃ | E | 2 | |
| 5-261 | COOMe | i-Pr | SO₂CF₃ | E | 2 | |
| 5-262 | COOMe | H | SOCF₃ | E | 2 | |
| 5-263 | COOMe | CH₂CF₃ | SOCF₃ | E | 2 | |
| 5-264 | COOMe | CH₂C₂F₅ | SOCF₃ | E | 2 | |
| 5-265 | COOMe | CH₂CHF₂ | SOCF₃ | E | 2 | |
| 5-266 | COOMe | CH₂CF₂CHF₂ | SOCF₃ | E | 2 | |
| 5-267 | COOMe | CH₂SCH₃ | SO₂CF₃ | E | 2 | |
| 5-268 | COOMe | CH₂SOCH₃ | SO₂CF₃ | E | 2 | |
| 5-269 | COOMe | CH₂SO₂CH₃ | SO₂CF₃ | E | 2 | |
| 5-270 | COOMe | CH₂SCH₂CH₃ | SO₂CF₃ | E | 2 | |
| 5-271 | COOMe | CH₂SOCH₂CH₃ | SO₂CF₃ | E | 2 | |
| 5-272 | COOMe | CH₂SO₂CH₂CH₃ | SO₂CF₃ | E | 2 | |
| 5-273 | COOMe | CH₂CH₂SCH₃ | SO₂CF₃ | E | 2 | |
| 5-274 | COOMe | CH₂CH₂SOCH₃ | SO₂CF₃ | E | 2 | |
| 5-275 | COOMe | CH₂CH₂SO₂CH₃ | SO₂CF₃ | E | 2 | |
| 5-276 | COOMe | CH₂CH₂SCH₂CH₃ | SO₂CF₃ | E | 2 | |
| 5-277 | COOMe | CH₂CH₂SOCH₂CH₃ | SO₂CF₃ | E | 2 | |
| 5-278 | COOMe | CH₂CH₂SO₂CH₂CH₃ | SO₂CF₃ | E | 2 | |
| 5-279 | COOMe | CH₂CH₂SCF₃ | SO₂CF₃ | E | 2 | |
| 5-280 | COOMe | CH₂CH₂SOCF₃ | SO₂CF₃ | E | 2 | |
| 5-281 | COOMe | CH₂CH₂SO₂CF₃ | SO₂CF₃ | E | 2 | |
| 5-282 | COOMe | Me | SCF₃ | E | 2 | |
| 5-283 | COOMe | Et | SCF₃ | E | 2 | |

TABLE 69

Table 5 (continued)

| Compound No. | R² | R³ | R⁴ | Isomerism | m | Physical property |
|---|---|---|---|---|---|---|
| 5-284 | COOMe | n-Pr | SCF₃ | E | 2 | |
| 5-285 | COOMe | i-Pr | SCF₃ | E | 2 | |
| 5-286 | COOMe | H | SCF₃ | E | 2 | |
| 5-287 | COOMe | CH₂CF₃ | SCF₃ | E | 2 | |
| 5-288 | COOMe | CH₂C₂F₅ | SCF₃ | E | 2 | |
| 5-289 | COOMe | CH₂CHF₂ | SCF₃ | E | 2 | |
| 5-290 | COOMe | CH₂CF₂CHF₂ | SCF₃ | E | 2 | |
| 5-291 | COOMe | CH₂SCH₃ | SCF₃ | E | 2 | |
| 5-292 | COOMe | CH₂SOCH₃ | SCF₃ | E | 2 | |
| 5-293 | COOMe | CH₂SO₂CH₃ | SCF₃ | E | 2 | |
| 5-294 | COOMe | CH₂SCH₂CH₃ | SCF₃ | E | 2 | |
| 5-295 | COOMe | CH₂SOCH₂CH₃ | SCF₃ | E | 2 | |
| 5-296 | COOMe | CH₂SO₂CH₂CH₃ | SCF₃ | E | 2 | |
| 5-297 | COOMe | CH₂CH₂SCH₃ | SCF₃ | E | 2 | |
| 5-298 | COOMe | CH₂CH₂SOCH₃ | SCF₃ | E | 2 | |
| 5-299 | COOMe | CH₂CH₂SO₂CH₃ | SCF₃ | E | 2 | |
| 5-300 | COOMe | CH₂CH₂SCH₂CH₃ | SCF₃ | E | 2 | |
| 5-301 | COOMe | CH₂CH₂SOCH₂CH₃ | SCF₃ | E | 2 | |
| 5-302 | COOMe | CH₂CH₂SO₂CH₂CH₃ | SCF₃ | E | 2 | |
| 5-303 | COOMe | CH₂CH₂SCF₃ | SCF₃ | E | 2 | |
| 5-304 | COOMe | CH₂CH₂SOCF₃ | SCF₃ | E | 2 | |
| 5-305 | COOMe | CH₂CH₂SO₂CF₃ | SCF₃ | E | 2 | |
| 5-306 | COOEt | Me | SO₂CF₃ | E | 2 | |
| 5-307 | COOEt | Et | SO₂CF₃ | E | 2 | |
| 5-308 | COOEt | n-Pr | SO₂CF₃ | E | 2 | |
| 5-309 | COOEt | i-Pr | SO₂CF₃ | E | 2 | |
| 5-310 | COOEt | H | SOCF₃ | E | 2 | |
| 5-311 | COOEt | CH₂CF₃ | SOCF₃ | E | 2 | |
| 5-312 | COOEt | CH₂C₂F₅ | SOCF₃ | E | 2 | |
| 5-313 | COOEt | CH₂CHF₂ | SOCF₃ | E | 2 | |

TABLE 70

Table 5 (continued)

| Compound No. | R² | R³ | R⁴ | Isomerism | m | Physical property |
|---|---|---|---|---|---|---|
| 5-314 | COOEt | CH₂CF₂CHF₂ | SOCF₃ | E | 2 | |
| 5-315 | COOEt | CH₂SCH₃ | SO₂CF₃ | E | 2 | |
| 5-316 | COOEt | CH₂SOCH₃ | SO₂CF₃ | E | 2 | |
| 5-317 | COOEt | CH₂SO₂CH₃ | SO₂CF₃ | E | 2 | |
| 5-318 | COOEt | CH₂SCH₂CH₃ | SO₂CF₃ | E | 2 | |
| 5-319 | COOEt | CH₂SOCH₂CH₃ | SO₂CF₃ | E | 2 | |
| 5-320 | COOEt | CH₂SO₂CH₂CH₃ | SO₂CF₃ | E | 2 | |
| 5-321 | COOEt | CH₂CH₂SCH₃ | SO₂CF₃ | E | 2 | |
| 5-322 | COOEt | CH₂CH₂SOCH₃ | SO₂CF₃ | E | 2 | |
| 5-323 | COOEt | CH₂CH₂SO₂CH₃ | SO₂CF₃ | E | 2 | |
| 5-324 | COOEt | CH₂CH₂SCH₂CH₃ | SO₂CF₃ | E | 2 | |
| 5-325 | COOEt | CH₂CH₂SOCH₂CH₃ | SO₂CF₃ | E | 2 | |
| 5-326 | COOEt | CH₂CH₂SO₂CH₂CH₃ | SO₂CF₃ | E | 2 | |
| 5-327 | COOEt | CH₂CH₂SCF₃ | SO₂CF₃ | E | 2 | |
| 5-328 | COOEt | CH₂CH₂SOCF₃ | SO₂CF₃ | E | 2 | |
| 5-329 | COOEt | CH₂CH₂SO₂CF₃ | SO₂CF₃ | E | 2 | |
| 5-330 | COOEt | Me | SCF₃ | E | 2 | |
| 5-331 | COOEt | Et | SCF₃ | E | 2 | |
| 5-332 | COOEt | n-Pr | SCF₃ | E | 2 | |
| 5-333 | COOEt | i-Pr | SCF₃ | E | 2 | |
| 5-334 | COOEt | H | SCF₃ | E | 2 | |
| 5-335 | COOEt | CH₂CF₃ | SCF₃ | E | 2 | |
| 5-336 | COOEt | CH₂C₂F₅ | SCF₃ | E | 2 | |
| 5-337 | COOEt | CH₂CHF₂ | SCF₃ | E | 2 | |
| 5-338 | COOEt | CH₂CF₂CHF₂ | SCF₃ | E | 2 | |
| 5-339 | COOEt | CH₂SCH₃ | SCF₃ | E | 2 | |
| 5-340 | COOEt | CH₂SOCH₃ | SCF₃ | E | 2 | |
| 5-341 | COOEt | CH₂SO₂CH₃ | SCF₃ | E | 2 | |
| 5-342 | COOEt | CH₂SCH₂CH₃ | SCF₃ | E | 2 | |
| 5-343 | COOEt | CH₂SOCH₂CH₃ | SCF₃ | E | 2 | |

TABLE 71

Table 5 (continued)

| Compound No. | R² | R³ | R⁴ | Isomerism | m | Physical property |
|---|---|---|---|---|---|---|
| 5-344 | COOEt | CH₂SO₂CH₂CH₃ | SCF₃ | E | 2 | |
| 5-345 | COOEt | CH₂CH₂SCH₃ | SCF₃ | E | 2 | |
| 5-346 | COOEt | CH₂CH₂SOCH₃ | SCF₃ | E | 2 | |
| 5-347 | COOEt | CH₂CH₂SO₂CH₃ | SCF₃ | E | 2 | |
| 5-348 | COOEt | CH₂CH₂SCH₂CH₃ | SCF₃ | E | 2 | |
| 5-349 | COOEt | CH₂CH₂SOCH₂CH₃ | SCF₃ | E | 2 | |
| 5-350 | COOEt | CH₂CH₂SO₂CH₂CH₃ | SCF₃ | E | 2 | |
| 5-351 | COOEt | CH₂CH₂SCF₃ | SCF₃ | E | 2 | |
| 5-352 | COOEt | CH₂CH₂SOCF₃ | SCF₃ | E | 2 | |
| 5-353 | COOEt | CH₂CH₂SO₂CF₃ | SCF₃ | E | 2 | |
| 5-354 | CONH₂ | Me | SO₂CF₃ | E | 2 | |
| 5-355 | CONH₂ | Et | SO₂CF₃ | E | 2 | |
| 5-356 | CONH₂ | n-Pr | SO₂CF₃ | E | 2 | |
| 5-357 | CONH₂ | i-Pr | SO₂CF₃ | E | 2 | |
| 5-358 | CONH₂ | H | SOCF₃ | E | 2 | |
| 5-359 | CONH₂ | CH₂CF₃ | SOCF₃ | E | 2 | |
| 5-360 | CONH₂ | CH₂C₂F₅ | SOCF₃ | E | 2 | |
| 5-361 | CONH₂ | CH₂CHF₂ | SOCF₃ | E | 2 | |
| 5-362 | CONH₂ | CH₂CF₂CHF₂ | SOCF₃ | E | 2 | |
| 5-363 | CONH₂ | CH₂SCH₃ | SO₂CF₃ | E | 2 | |
| 5-364 | CONH₂ | CH₂SOCH₃ | SO₂CF₃ | E | 2 | |
| 5-365 | CONH₂ | CH₂SO₂CH₃ | SO₂CF₃ | E | 2 | |
| 5-366 | CONH₂ | CH₂SCH₂CH₃ | SO₂CF₃ | E | 2 | |
| 5-367 | CONH₂ | CH₂SOCH₂CH₃ | SO₂CF₃ | E | 2 | |
| 5-368 | CONH₂ | CH₂SO₂CH₂CH₃ | SO₂CF₃ | E | 2 | |
| 5-369 | CONH₂ | CH₂CH₂SCH₃ | SO₂CF₃ | E | 2 | |
| 5-370 | CONH₂ | CH₂CH₂SOCH₃ | SO₂CF₃ | E | 2 | |
| 5-371 | CONH₂ | CH₂CH₂SO₂CH₃ | SO₂CF₃ | E | 2 | |
| 5-372 | CONH₂ | CH₂CH₂SCH₂CH₃ | SO₂CF₃ | E | 2 | |
| 5-373 | CONH₂ | CH₂CH₂SOCH₂CH₃ | SO₂CF₃ | E | 2 | |

TABLE 72

Table 5 (continued)

| Compound No. | R² | R³ | R⁴ | Isomerism | m | Physical property |
|---|---|---|---|---|---|---|
| 5-374 | CONH₂ | CH₂CH₂SO₂CH₂CH₃ | SO₂CF₃ | E | 2 | |
| 5-375 | CONH₂ | CH₂CH₂SCF₃ | SO₂CF₃ | E | 2 | |
| 5-376 | CONH₂ | CH₂CH₂SOCF₃ | SO₂CF₃ | E | 2 | |
| 5-377 | CONH₂ | CH₂CH₂SO₂CF₃ | SO₂CF₃ | E | 2 | |
| 5-378 | CONH₂ | Me | SCF₃ | E | 2 | |
| 5-379 | CONH₂ | Et | SCF₃ | E | 2 | |
| 5-380 | CONH₂ | n-Pr | SCF₃ | E | 2 | |
| 5-381 | CONH₂ | i-Pr | SCF₃ | E | 2 | |
| 5-382 | CONH₂ | H | SCF₃ | E | 2 | |
| 5-383 | CONH₂ | CH₂CF₃ | SCF₃ | E | 2 | |
| 5-384 | CONH₂ | CH₂C₂F₅ | SCF₃ | E | 2 | |
| 5-385 | CONH₂ | CH₂CHF₂ | SCF₃ | E | 2 | |
| 5-386 | CONH₂ | CH₂CF₂CHF₂ | SCF₃ | E | 2 | |
| 5-387 | CONH₂ | CH₂SCH₃ | SCF₃ | E | 2 | |
| 5-388 | CONH₂ | CH₂SOCH₃ | SCF₃ | E | 2 | |
| 5-389 | CONH₂ | CH₂SO₂CH₃ | SCF₃ | E | 2 | |
| 5-390 | CONH₂ | CH₂SCH₂CH₃ | SCF₃ | E | 2 | |
| 5-391 | CONH₂ | CH₂SOCH₂CH₃ | SCF₃ | E | 2 | |
| 5-392 | CONH₂ | CH₂SO₂CH₂CH₃ | SCF₃ | E | 2 | |
| 5-393 | CONH₂ | CH₂CH₂SCH₃ | SCF₃ | E | 2 | |
| 5-394 | CONH₂ | CH₂CH₂SOCH₃ | SCF₃ | E | 2 | |
| 5-395 | CONH₂ | CH₂CH₂SO₂CH₃ | SCF₃ | E | 2 | |
| 5-396 | CONH₂ | CH₂CH₂SCH₂CH₃ | SCF₃ | E | 2 | |
| 5-397 | CONH₂ | CH₂CH₂SOCH₂CH₃ | SCF₃ | E | 2 | |
| 5-398 | CONH₂ | CH₂CH₂SO₂CH₂CH₃ | SCF₃ | E | 2 | |
| 5-399 | CONH₂ | CH₂CH₂SCF₃ | SCF₃ | E | 2 | |
| 5-400 | CONH₂ | CH₂CH₂SOCF₃ | SCF₃ | E | 2 | |
| 5-401 | CONH₂ | CH₂CH₂SO₂CF₃ | SCF₃ | E | 2 | |
| 5-402 | CONHMe | Me | SO₂CF₃ | E | 2 | |
| 5-403 | CONHMe | Et | SO₂CF₃ | E | 2 | |

TABLE 73

Table 5 (continued)

| Compound No. | R² | R³ | R⁴ | Isomerism | m | Physical property |
|---|---|---|---|---|---|---|
| 5-404 | CONHMe | n-Pr | SO₂CF₃ | E | 2 | |
| 5-405 | CONHMe | i-Pr | SO₂CF₃ | E | 2 | |
| 5-406 | CONHMe | H | SOCF₃ | E | 2 | |
| 5-407 | CONHMe | CH₂CF₃ | SOCF₃ | E | 2 | |
| 5-408 | CONHMe | CH₂C₂F₅ | SOCF₃ | E | 2 | |
| 5-409 | CONHMe | CH₂CHF₂ | SOCF₃ | E | 2 | |
| 5-410 | CONHMe | CH₂CF₂CHF₂ | SOCF₃ | E | 2 | |
| 5-411 | CONHMe | CH₂SCH₃ | SO₂CF₃ | E | 2 | |
| 5-412 | CONHMe | CH₂SOCH₃ | SO₂CF₃ | E | 2 | |
| 5-413 | CONHMe | CH₂SO₂CH₃ | SO₂CF₃ | E | 2 | |
| 5-414 | CONHMe | CH₂SCH₂CH₃ | SO₂CF₃ | E | 2 | |
| 5-415 | CONHMe | CH₂SOCH₂CH₃ | SO₂CF₃ | E | 2 | |
| 5-416 | CONHMe | CH₂SO₂CH₂CH₃ | SO₂CF₃ | E | 2 | |
| 5-417 | CONHMe | CH₂CH₂SCH₃ | SO₂CF₃ | E | 2 | |
| 5-418 | CONHMe | CH₂CH₂SOCH₃ | SO₂CF₃ | E | 2 | |
| 5-419 | CONHMe | CH₂CH₂SO₂CH₃ | SO₂CF₃ | E | 2 | |
| 5-420 | CONHMe | CH₂CH₂SCH₂CH₃ | SO₂CF₃ | E | 2 | |
| 5-421 | CONHMe | CH₂CH₂SOCH₂CH₃ | SO₂CF₃ | E | 2 | |
| 5-422 | CONHMe | CH₂CH₂SO₂CH₂CH₃ | SO₂CF₃ | E | 2 | |
| 5-423 | CONHMe | CH₂CH₂SCF₃ | SO₂CF₃ | E | 2 | |
| 5-424 | CONHMe | CH₂CH₂SOCF₃ | SO₂CF₃ | E | 2 | |
| 5-425 | CONHMe | CH₂CH₂SO₂CF₃ | SO₂CF₃ | E | 2 | |
| 5-426 | CONHMe | Me | SCF₃ | E | 2 | |
| 5-427 | CONHMe | Et | SCF₃ | E | 2 | |
| 5-428 | CONHMe | n-Pr | SCF₃ | E | 2 | |
| 5-429 | CONHMe | i-Pr | SCF₃ | E | 2 | |
| 5-430 | CONHMe | H | SCF₃ | E | 2 | |
| 5-431 | CONHMe | CH₂CF₃ | SCF₃ | E | 2 | |
| 5-432 | CONHMe | CH₂C₂F₅ | SCF₃ | E | 2 | |
| 5-433 | CONHMe | CH₂CHF₂ | SCF₃ | E | 2 | |

TABLE 74

Table 5 (continued)

| Compound No. | R² | R³ | R⁴ | Isomerism | m | Physical property |
|---|---|---|---|---|---|---|
| 5-434 | CONHMe | CH₂CF₂CHF₂ | SCF₃ | E | 2 | |
| 5-435 | CONHMe | CH₂SCH₃ | SCF₃ | E | 2 | |
| 5-436 | CONHMe | CH₂SOCH₃ | SCF₃ | E | 2 | |
| 5-437 | CONHMe | CH₂SO₂CH₃ | SCF₃ | E | 2 | |
| 5-438 | CONHMe | CH₂SCH₂CH₃ | SCF₃ | E | 2 | |
| 5-439 | CONHMe | CH₂SOCH₂CH₃ | SCF₃ | E | 2 | |
| 5-440 | CONHMe | CH₂SO₂CH₂CH₃ | SCF₃ | E | 2 | |
| 5-441 | CONHMe | CH₂CH₂SCH₃ | SCF₃ | E | 2 | |
| 5-442 | CONHMe | CH₂CH₂SOCH₃ | SCF₃ | E | 2 | |
| 5-443 | CONHMe | CH₂CH₂SO₂CH₃ | SCF₃ | E | 2 | |
| 5-444 | CONHMe | CH₂CH₂SCH₂CH₃ | SCF₃ | E | 2 | |
| 5-445 | CONHMe | CH₂CH₂SOCH₂CH₃ | SCF₃ | E | 2 | |
| 5-446 | CONHMe | CH₂CH₂SO₂CH₂CH₃ | SCF₃ | E | 2 | |
| 5-447 | CONHMe | CH₂CH₂SCF₃ | SCF₃ | E | 2 | |
| 5-448 | CONHMe | CH₂CH₂SOCF₃ | SCF₃ | E | 2 | |
| 5-449 | CONHMe | CH₂CH₂SO₂CF₃ | SCF₃ | E | 2 | |
| 5-450 | CONMe₂ | Me | SO₂CF₃ | E | 2 | |
| 5-451 | CONMe₂ | Et | SO₂CF₃ | E | 2 | |
| 5-452 | CONMe₂ | n-Pr | SO₂CF₃ | E | 2 | |
| 5-453 | CONMe₂ | i-Pr | SO₂CF₃ | E | 2 | |
| 5-454 | CONMe₂ | H | SOCF₃ | E | 2 | |
| 5-455 | CONMe₂ | CH₂CF₃ | SOCF₃ | E | 2 | |
| 5-456 | CONMe₂ | CH₂C₂F₅ | SOCF₃ | E | 2 | |
| 5-457 | CONMe₂ | CH₂CHF₂ | SOCF₃ | E | 2 | |
| 5-458 | CONMe₂ | CH₂CF₂CHF₂ | SOCF₃ | E | 2 | |
| 5-459 | CONMe₂ | CH₂SCH₃ | SO₂CF₃ | E | 2 | |
| 5-460 | CONMe₂ | CH₂SOCH₃ | SO₂CF₃ | E | 2 | |
| 5-461 | CONMe₂ | CH₂SO₂CH₃ | SO₂CF₃ | E | 2 | |
| 5-462 | CONMe₂ | CH₂SCH₂CH₃ | SO₂CF₃ | E | 2 | |
| 5-463 | CONMe₂ | CH₂SOCH₂CH₃ | SO₂CF₃ | E | 2 | |

TABLE 75

Table 5 (continued)

| Compound No. | R² | R³ | R⁴ | Isomerism | m | Physical property |
|---|---|---|---|---|---|---|
| 5-464 | CONMe₂ | CH₂SO₂CH₂CH₃ | SO₂CF₃ | E | 2 | |
| 5-465 | CONMe₂ | CH₂CH₂SCH₃ | SO₂CF₃ | E | 2 | |
| 5-466 | CONMe₂ | CH₂CH₂SOCH₃ | SO₂CF₃ | E | 2 | |
| 5-467 | CONMe₂ | CH₂CH₂SO₂CH₃ | SO₂CF₃ | E | 2 | |
| 5-468 | CONMe₂ | CH₂CH₂SCH₂CH₃ | SO₂CF₃ | E | 2 | |
| 5-469 | CONMe₂ | CH₂CH₂SOCH₂CH₃ | SO₂CF₃ | E | 2 | |
| 5-470 | CONMe₂ | CH₂CH₂SO₂CH₂CH₃ | SO₂CF₃ | E | 2 | |
| 5-471 | CONMe₂ | CH₂CH₂SCF₃ | SO₂CF₃ | E | 2 | |
| 5-472 | CONMe₂ | CH₂CH₂SOCF₃ | SO₂CF₃ | E | 2 | |
| 5-473 | CONMe₂ | CH₂CH₂SO₂CF₃ | SO₂CF₃ | E | 2 | |
| 5-474 | CONMe₂ | Me | SCF₃ | E | 2 | |
| 5-475 | CONMe₂ | Et | SCF₃ | E | 2 | |
| 5-476 | CONMe₂ | n-Pr | SCF₃ | E | 2 | |
| 5-477 | CONMe₂ | i-Pr | SCF₃ | E | 2 | |
| 5-478 | CONMe₂ | H | SCF₃ | E | 2 | |
| 5-479 | CONMe₂ | CH₂CF₃ | SCF₃ | E | 2 | |
| 5-480 | CONMe₂ | CH₂C₂F₅ | SCF₃ | E | 2 | |
| 5-481 | CONMe₂ | CH₂CHF₂ | SCF₃ | E | 2 | |
| 5-482 | CONMe₂ | CH₂CF₂CHF₂ | SCF₃ | E | 2 | |
| 5-483 | CONMe₂ | CH₂SCH₃ | SCF₃ | E | 2 | |
| 5-484 | CONMe₂ | CH₂SOCH₃ | SCF₃ | E | 2 | |
| 5-485 | CONMe₂ | CH₂SO₂CH₃ | SCF₃ | E | 2 | |
| 5-486 | CONMe₂ | CH₂SCH₂CH₃ | SCF₃ | E | 2 | |
| 5-487 | CONMe₂ | CH₂SOCH₂CH₃ | SCF₃ | E | 2 | |
| 5-488 | CONMe₂ | CH₂SO₂CH₂CH₃ | SCF₃ | E | 2 | |
| 5-489 | CONMe₂ | CH₂CH₂SCH₃ | SCF₃ | E | 2 | |
| 5-490 | CONMe₂ | CH₂CH₂SOCH₃ | SCF₃ | E | 2 | |
| 5-491 | CONMe₂ | CH₂CH₂SO₂CH₃ | SCF₃ | E | 2 | |
| 5-492 | CONMe₂ | CH₂CH₂SCH₂CH₃ | SCF₃ | E | 2 | |
| 5-493 | CONMe₂ | CH₂CH₂SOCH₂CH₃ | SCF₃ | E | 2 | |
| 5-494 | CONMe₂ | CH₂CH₂SO₂CH₂CH₃ | SCF₃ | E | 2 | |
| 5-495 | CONMe₂ | CH₂CH₂SCF₃ | SCF₃ | E | 2 | |
| 5-496 | CONMe₂ | CH₂CH₂SOCF₃ | SCF₃ | E | 2 | |
| 5-497 | CONMe₂ | CH₂CH₂SO₂CF₃ | SCF₃ | E | 2 | |

[Chem. 19]

(1B-3)

Chemical structure: pyridine ring with $_m(O)$–S–ethyl substituent, connected via C=N–O–R₃ (with R₂ on the C=N carbon), fused to imidazo[4,5-b]pyridine bearing N-methyl and R⁴ substituent.

TABLE 76

Table 6

| Compound No. | R² | R³ | R⁴ | Isomerism | m | Physical property |
|---|---|---|---|---|---|---|
| 6-1 | H | H | CF₃ | E | 2 | 201-202 |
| 6-2 | H | CH₂CF₃ | CF₃ | E | 2 | NMR |
| 6-3 | H | CH₂CHF₂ | CF₃ | E | 2 | |
| 6-4 | H | CH₂C₂F₅ | CF₃ | E | 2 | NMR |
| 6-5 | H | CH₂CF₂CHF₂ | CF₃ | E | 2 | NMR |
| 6-6 | Me | H | CF₃ | E | 2 | |
| 6-7 | Me | CH₂CF₃ | CF₃ | E | 2 | |
| 6-8 | Me | CH₂CHF₂ | CF₃ | E | 2 | |
| 6-9 | Me | CH₂C₂F₅ | CF₃ | E | 2 | |
| 6-10 | Me | CH₂CF₂CHF₂ | CF₃ | E | 2 | |

TABLE 76-continued

Table 6

| Compound No. | R² | R³ | R⁴ | Isomerism | m | Physical property |
|---|---|---|---|---|---|---|
| 6-11 | H | H | CF₂CF₃ | E | 2 | |
| 6-12 | H | CH₂CF₃ | CF₂CF₃ | E | 2 | |
| 6-13 | H | CH₂CHF₂ | CF₂CF₃ | E | 2 | |
| 6-14 | Me | H | CF₂CF₃ | E | 2 | |
| 6-15 | Me | CH₂CF₃ | CF₂CF₃ | E | 2 | |
| 6-16 | Me | CH₂CHF₂ | CF₂CF₃ | E | 2 | |
| 6-17 | H | n-Pr | CF₃ | E | 2 | NMR |
| 6-18 | Me | n-Pr | CF₃ | E | 2 | |
| 6-19 | H | i-Pr | CF₃ | E | 2 | 142-143 |
| 6-20 | Me | i-Pr | CF₃ | E | 2 | |
| 6-21 | H | CH₂SCH₃ | CF₃ | E | 2 | NMR |
| 6-22 | Me | CH₂SCH₃ | CF₃ | E | 2 | |
| 6-23 | H | CH₂SOCH₃ | CF₃ | E | 2 | |
| 6-24 | Me | CH₂SOCH₃ | CF₃ | E | 2 | |
| 6-25 | H | CH₂SO₂CH₃ | CF₃ | E | 2 | |
| 6-26 | Me | CH₂SO₂CH₃ | CF₃ | E | 2 | |
| 6-27 | H | CH₂SCH₂CH₃ | CF₃ | E | 2 | |
| 6-28 | Me | CH₂SCH₂CH₃ | CF₃ | E | 2 | |
| 6-29 | H | CH₂SOCH₂CH₃ | CF₃ | E | 2 | |
| 6-30 | Me | CH₂SOCH₂CH₃ | CF₃ | E | 2 | |
| 6-31 | H | CH₂SO₂CH₂CH₃ | CF₃ | E | 2 | |

TABLE 77

Table 6 (continued)

| Compound No. | R² | R³ | R⁴ | Isomerism | m | Physical property |
|---|---|---|---|---|---|---|
| 6-32 | Me | CH₂SO₂CH₂CH₃ | CF₃ | E | 2 | |
| 6-33 | H | CH₂CH₂SCH₃ | CF₃ | E | 2 | |
| 6-34 | Me | CH₂CH₂SCH₃ | CF₃ | E | 2 | |
| 6-35 | H | CH₂CH₂SOCH₃ | CF₃ | E | 2 | |
| 6-36 | Me | CH₂CH₂SOCH₃ | CF₃ | E | 2 | |
| 6-37 | H | CH₂CH₂SO₂CH₃ | CF₃ | E | 2 | |
| 6-38 | Me | CH₂CH₂SO₂CH₃ | CF₃ | E | 2 | |
| 6-39 | H | CH₂CH₂SCH₂CH₃ | CF₃ | E | 2 | |
| 6-40 | Me | CH₂CH₂SCH₂CH₃ | CF₃ | E | 2 | |
| 6-41 | H | CH₂CH₂SOCH₂CH₃ | CF₃ | E | 2 | |
| 6-42 | Me | CH₂CH₂SOCH₂CH₃ | CF₃ | E | 2 | |
| 6-43 | H | CH₂CH₂SO₂CH₂CH₃ | CF₃ | E | 2 | |
| 6-44 | Me | CH₂CH₂SO₂CH₂CH₃ | CF₃ | E | 2 | |
| 6-45 | H | CH₂CH₂SCF₃ | CF₃ | E | 2 | |
| 6-46 | Me | CH₂CH₂SCF₃ | CF₃ | E | 2 | |
| 6-47 | H | CH₂CH₂SOCF₃ | CF₃ | E | 2 | |
| 6-48 | Me | CH₂CH₂SOCF₃ | CF₃ | E | 2 | |
| 6-49 | H | CH₂CH₂SO₂CF₃ | CF₃ | E | 2 | |
| 6-50 | Me | CH₂CH₂SO₂CF₃ | CF₃ | E | 2 | |
| 6-51 | H | CH₂CEN | CF₃ | E | 2 | |
| 6-52 | Me | CH₂CEN | CF₃ | E | 2 | |
| 6-53 | H | c-Pen | CF₃ | E | 2 | |
| 6-54 | Me | c-Pen | CF₃ | E | 2 | |
| 6-55 | H | CH₂CH=CHCl | CF₃ | E | 2 | NMR |
| 6-56 | Me | CH₂CH=CHCl | CF₃ | E | 2 | |
| 6-57 | H | n-Bu | CF₃ | E | 2 | NMR |
| 6-58 | Me | n-Bu | CF₃ | E | 2 | |
| 6-59 | H | n-Pen | CF₃ | E | 2 | NMR |
| 6-60 | Me | n-Pen | CF₃ | E | 2 | |
| 6-61 | H | CH₂CH=C(CH₃)₂ | CF₃ | E | 2 | NMR |
| 6-62 | Me | CH₂CH=C(CH₃)₂ | CF₃ | E | 2 | |

TABLE 78

Table 6 (continued)

| Compound No. | R² | R³ | R⁴ | Isomerism | m | Physical property |
|---|---|---|---|---|---|---|
| 6-63 | CN | Me | CF₃ | E | 2 | |
| 6-64 | CN | Et | CF₃ | E | 2 | |
| 6-65 | CN | n-Pr | CF₃ | E | 2 | |
| 6-66 | CN | i-Pr | CF₃ | E | 2 | |
| 6-67 | CN | H | CF₃ | E | 2 | |
| 6-68 | CN | CH₂CF₃ | CF₃ | E | 2 | |
| 6-69 | CN | CH₂C₂F₅ | CF₃ | E | 2 | |
| 6-70 | CN | CH₂CHF₂ | CF₃ | E | 2 | |
| 6-71 | CN | CH₂CF₂CHF₂ | CF₃ | E | 2 | |
| 6-72 | CN | CH₂SCH₃ | CF₃ | E | 2 | |
| 6-73 | CN | CH₂SOCH₃ | CF₃ | E | 2 | |
| 6-74 | CN | CH₂SO₂CH₃ | CF₃ | E | 2 | |
| 6-75 | CN | CH₂SCH₂CH₃ | CF₃ | E | 2 | |
| 6-76 | CN | CH₂SOCH₂CH₃ | CF₃ | E | 2 | |
| 6-77 | CN | CH₂SO₂CH₂CH₃ | CF₃ | E | 2 | |
| 6-78 | CN | CH₂CH₂SCH₃ | CF₃ | E | 2 | |
| 6-79 | CN | CH₂CH₂SOCH₃ | CF₃ | E | 2 | |
| 6-80 | CN | CH₂CH₂SO₂CH₃ | CF₃ | E | 2 | |
| 6-81 | CN | CH₂CH₂SCH₂CH₃ | CF₃ | E | 2 | |
| 6-82 | CN | CH₂CH₂SOCH₂CH₃ | CF₃ | E | 2 | |
| 6-83 | CN | CH₂CH₂SO₂CH₂CH₃ | CF₃ | E | 2 | |
| 6-84 | CN | CH₂CH₂SCF₃ | CF₃ | E | 2 | |
| 6-85 | CN | CH₂CH₂SOCF₃ | CF₃ | E | 2 | |
| 6-86 | CN | CH₂CH₂SO₂CF₃ | CF₃ | E | 2 | |
| 6-87 | COOMe | Me | CF₃ | E | 2 | |
| 6-88 | COOMe | Et | CF₃ | E | 2 | |
| 6-89 | COOMe | n-Pr | CF₃ | E | 2 | |
| 6-90 | COOMe | i-Pr | CF₃ | E | 2 | |
| 6-91 | COOMe | H | CF₃ | E | 2 | |
| 6-92 | COOMe | CH₂CF₃ | CF₃ | E | 2 | |
| 6-93 | COOMe | CH₂C₂F₅ | CF₃ | E | 2 | |

TABLE 79

Table 6 (continued)

| Compound No. | R² | R³ | R⁴ | Isomerism | m | Physical property |
|---|---|---|---|---|---|---|
| 6-94 | COOMe | CH₂CHF₂ | CF₃ | E | 2 | |
| 6-95 | COOMe | CH₂CF₂CHF₂ | CF₃ | E | 2 | |
| 6-96 | COOMe | CH₂SCH₃ | CF₃ | E | 2 | |
| 6-97 | COOMe | CH₂SOCH₃ | CF₃ | E | 2 | |
| 6-98 | COOMe | CH₂SO₂CH₃ | CF₃ | E | 2 | |
| 6-99 | COOMe | CH₂SCH₂CH₃ | CF₃ | E | 2 | |
| 6-100 | COOMe | CH₂SOCH₂CH₃ | CF₃ | E | 2 | |
| 6-101 | COOMe | CH₂SO₂CH₂CH₃ | CF₃ | E | 2 | |
| 6-102 | COOMe | CH₂CH₂SCH₃ | CF₃ | E | 2 | |
| 6-103 | COOMe | CH₂CH₂SOCH₃ | CF₃ | E | 2 | |
| 6-104 | COOMe | CH₂CH₂SO₂CH₃ | CF₃ | E | 2 | |
| 6-105 | COOMe | CH₂CH₂SCH₂CH₃ | CF₃ | E | 2 | |
| 6-106 | COOMe | CH₂CH₂SOCH₂CH₃ | CF₃ | E | 2 | |
| 6-107 | COOMe | CH₂CF₂CHF₂ | CF₃ | E | 2 | |
| 6-108 | COOMe | CH₂CH₂SCF₃ | CF₃ | E | 2 | |
| 6-109 | COOMe | CH₂CH₂SOCF₃ | CF₃ | E | 2 | |
| 6-110 | COOMe | CH₂CH₂SO₂CF₃ | CF₃ | E | 2 | |
| 6-111 | COOEt | Me | CF₃ | E | 2 | |
| 6-112 | COOEt | Et | CF₃ | E | 2 | |
| 6-113 | COOEt | n-Pr | CF₃ | E | 2 | |
| 6-114 | COOEt | i-Pr | CF₃ | E | 2 | |
| 6-115 | COOEt | H | CF₃ | E | 2 | |
| 6-116 | COOEt | CH₂CF₃ | CF₃ | E | 2 | |
| 6-117 | COOEt | CH₂C₂F₅ | CF₃ | E | 2 | |
| 6-118 | COOEt | CH₂CHF₂ | CF₃ | E | 2 | |
| 6-119 | COOEt | CH₂CF₂CHF₂ | CF₃ | E | 2 | |
| 6-120 | COOEt | CH₂SCH₃ | CF₃ | E | 2 | |
| 6-121 | COOEt | CH₂SOCH₃ | CF₃ | E | 2 | |
| 6-122 | COOEt | CH₂SO₂CH₃ | CF₃ | E | 2 | |
| 6-123 | COOEt | CH₂SCH₂CH₃ | CF₃ | E | 2 | |

TABLE 80

Table 6 (continued)

| Compound No. | R² | R³ | R⁴ | Isomerism | m | Physical property |
|---|---|---|---|---|---|---|
| 6-124 | COOEt | CH₂SOCH₂CH₃ | CF₃ | E | 2 | |
| 6-125 | COOEt | CH₂SO₂CH₂CH₃ | CF₃ | E | 2 | |
| 6-126 | COOEt | CH₂CH₂SCH₃ | CF₃ | E | 2 | |
| 6-127 | COOEt | CH₂CH₂SOCH₃ | CF₃ | E | 2 | |
| 6-128 | COOEt | CH₂CH₂SO₂CH₃ | CF₃ | E | 2 | |
| 6-129 | COOEt | CH₂CH₂SCH₂CH₃ | CF₃ | E | 2 | |
| 6-130 | COOEt | CH₂CH₂SOCH₂CH₃ | CF₃ | E | 2 | |
| 6-131 | COOEt | CH₂CH₂SO₂CH₂CH₃ | CF₃ | E | 2 | |
| 6-132 | COOEt | CH₂CH₂SCF₃ | CF₃ | E | 2 | |
| 6-133 | COOEt | CH₂CH₂SOCF₃ | CF₃ | E | 2 | |
| 6-134 | COOEt | CH₂CH₂SO₂CF₃ | CF₃ | E | 2 | |
| 6-135 | CONH₂ | Me | CF₃ | E | 2 | |
| 6-136 | CONH₂ | Et | CF₃ | E | 2 | |
| 6-137 | CONH₂ | n-Pr | CF₃ | E | 2 | |
| 6-138 | CONH₂ | i-Pr | CF₃ | E | 2 | |
| 6-139 | CONH₂ | H | CF₃ | E | 2 | |
| 6-140 | CONH₂ | CH₂CF₃ | CF₃ | E | 2 | |
| 6-141 | CONH₂ | CH₂C₂F₅ | CF₃ | E | 2 | |
| 6-142 | CONH₂ | CH₂CHF₂ | CF₃ | E | 2 | |
| 6-143 | CONH₂ | CH₂CF₂CHF₂ | CF₃ | E | 2 | |
| 6-144 | CONH₂ | CH₂SCH₃ | CF₃ | E | 2 | |
| 6-145 | CONH₂ | CH₂SOCH₃ | CF₃ | E | 2 | |
| 6-146 | CONH₂ | CH₂SO₂CH₃ | CF₃ | E | 2 | |
| 6-147 | CONH₂ | CH₂SCH₂CH₃ | CF₃ | E | 2 | |
| 6-148 | CONH₂ | CH₂SOCH₂CH₃ | CF₃ | E | 2 | |
| 6-149 | CONH₂ | CH₂SO₂CH₂CH₃ | CF₃ | E | 2 | |
| 6-150 | CONH₂ | CH₂CH₂SCH₃ | CF₃ | E | 2 | |
| 6-151 | CONH₂ | CH₂CH₂SOCH₃ | CF₃ | E | 2 | |
| 6-152 | CONH₂ | CH₂CH₂SO₂CH₃ | CF₃ | E | 2 | |
| 6-153 | CONH₂ | CH₂CH₂SCH₂CH₃ | CF₃ | E | 2 | |

TABLE 81

Table 6 (continued)

| Compound No. | R² | R³ | R⁴ | Isomerism | m | Physical property |
|---|---|---|---|---|---|---|
| 6-154 | CONH₂ | CH₂CH₂SOCH₂CH₃ | CF₃ | E | 2 | |
| 6-155 | CONH₂ | CH₂CH₂SO₂CH₂CH₃ | CF₃ | E | 2 | |
| 6-156 | CONH₂ | CH₂CH₂SCF₃ | CF₃ | E | 2 | |
| 6-157 | CONH₂ | CH₂CH₂SOCF₃ | CF₃ | E | 2 | |
| 6-158 | CONH₂ | CH₂CH₂SO₂CF₃ | CF₃ | E | 2 | |
| 6-159 | CONHMe | Me | CF₃ | E | 2 | |
| 6-160 | CONHMe | Et | CF₃ | E | 2 | |
| 6-161 | CONHMe | n-Pr | CF₃ | E | 2 | |
| 6-162 | CONHMe | i-Pr | CF₃ | E | 2 | |
| 6-163 | CONHMe | H | CF₃ | E | 2 | |
| 6-164 | CONHMe | CH₂CF₃ | CF₃ | E | 2 | |
| 6-165 | CONHMe | CH₂C₂F₅ | CF₃ | E | 2 | |
| 6-166 | CONHMe | CH₂CHF₂ | CF₃ | E | 2 | |
| 6-167 | CONHMe | CH₂CF₂CHF₂ | CF₃ | E | 2 | |
| 6-168 | CONHMe | CH₂SCH₃ | CF₃ | E | 2 | |
| 6-169 | CONHMe | CH₂SOCH₃ | CF₃ | E | 2 | |
| 6-170 | CONHMe | CH₂SO₂CH₃ | CF₃ | E | 2 | |
| 6-171 | CONHMe | CH₂SCH₂CH₃ | CF₃ | E | 2 | |
| 6-172 | CONHMe | CH₂SOCH₂CH₃ | CF₃ | E | 2 | |
| 6-173 | CONHMe | CH₂SO₂CH₂CH₃ | CF₃ | E | 2 | |
| 6-174 | CONHMe | CH₂CH₂SCH₃ | CF₃ | E | 2 | |
| 6-175 | CONHMe | CH₂CH₂SOCH₃ | CF₃ | E | 2 | |
| 6-176 | CONHMe | CH₂CH₂SO₂CH₃ | CF₃ | E | 2 | |
| 6-177 | CONHMe | CH₂CH₂SCH₂CH₃ | CF₃ | E | 2 | |
| 6-178 | CONHMe | CH₂CH₂SOCH₂CH₃ | CF₃ | E | 2 | |
| 6-179 | CONHMe | CH₂CH₂SO₂CH₂CH₃ | CF₃ | E | 2 | |
| 6-180 | CONHMe | CH₂CH₂SCF₃ | CF₃ | E | 2 | |
| 6-181 | CONHMe | CH₂CH₂SOCF₃ | CF₃ | E | 2 | |
| 6-182 | CONHMe | CH₂CH₂SO₂CF₃ | CF₃ | E | 2 | |
| 6-183 | CONHMe | Me | CF₃ | E | 2 | |

TABLE 82

Table 6 (continued)

| Compound No. | R² | R³ | R⁴ | Isomerism | m | Physical property |
|---|---|---|---|---|---|---|
| 6-184 | CONMe₂ | Me | CF₃ | E | 2 | |
| 6-185 | CONMe₂ | Et | CF₃ | E | 2 | |
| 6-186 | CONMe₂ | n-Pr | CF₃ | E | 2 | |
| 6-187 | CONMe₂ | i-Pr | CF₃ | E | 2 | |
| 6-188 | CONMe₂ | H | CF₃ | E | 2 | |
| 6-189 | CONMe₂ | CH₂CF₃ | CF₃ | E | 2 | |
| 6-190 | CONMe₂ | CH₂C₂F₅ | CF₃ | E | 2 | |
| 6-191 | CONMe₂ | CH₂CHF₂ | CF₃ | E | 2 | |
| 6-192 | CONMe₂ | CH₂CF₂CHF₂ | CF₃ | E | 2 | |
| 6-193 | CONMe₂ | CH₂SCH₃ | CF₃ | E | 2 | |
| 6-194 | CONMe₂ | CH₂SOCH₃ | CF₃ | E | 2 | |
| 6-195 | CONMe₂ | CH₂SO₂CH₃ | CF₃ | E | 2 | |
| 6-196 | CONMe₂ | CH₂SCH₂CH₃ | CF₃ | E | 2 | |
| 6-197 | CONMe₂ | CH₂SOCH₂CH₃ | CF₃ | E | 2 | |
| 6-198 | CONMe₂ | CH₂SO₂CH₂CH₃ | CF₃ | E | 2 | |
| 6-199 | CONMe₂ | CH₂CH₂SCH₃ | CF₃ | E | 2 | |
| 6-200 | CONMe₂ | CH₂CH₂SOCH₃ | CF₃ | E | 2 | |
| 6-201 | CONMe₂ | CH₂CH₂SO₂CH₃ | CF₃ | E | 2 | |
| 6-202 | CONMe₂ | CH₂CH₂SCH₂CH₃ | CF₃ | E | 2 | |
| 6-203 | CONMe₂ | CH₂CH₂SOCH₂CH₃ | CF₃ | E | 2 | |
| 6-204 | CONMe₂ | CH₂CH₂SO₂CH₂CH₃ | CF₃ | E | 2 | |
| 6-205 | CONMe₂ | CH₂CH₂SCF₃ | CF₃ | E | 2 | |
| 6-206 | CONMe₂ | CH₂CH₂SOCF₃ | CF₃ | E | 2 | |
| 6-207 | CONMe₂ | CH₂CH₂SO₂CF₃ | CF₃ | E | 2 | |

TABLE 7

| Compound No. | ¹H-NMR data (CDCl₃) |
|---|---|
| 1-207 | 9.28 (d, 1H), 8.71 (d, 1H), 8.21 (s, 1H), 7.25-4.45 (m, 5H), 5.34 (s, 2H), 4.07 (s, 3H), 3.80 (q, 2H), 1.39 (t, 3H) |
| 1-213 | 9.16 (d, 1H), 8.64 (d, 1H), 8.21 (s, 1H), 4.10 (s, 3H), 3.96 (s, 3H), 3.81 (q, 2H), 2.90 (s, 3H), 1.39 (t, 3H) |
| 1-219 | 9.19 (d, 1H), 8.72 (d, 1H), 8.22 (s, 1H), 4.23 (q, 2H), 4.10 (s, 3H), 3.81 (q, 2H), 2.38 (s, 3H), 1.40 (t, 3H), 1.30 (t, 3H) |
| 1-225 | 9.17 (d, 1H), 8.68 (d, 1H), 8.21 (s, 1H), 6.00 (tdd, 1H), 5.31 (ddd, 1H), 5.26 (ddd, 1H), 4.66 (td, 2H), 4.10 (s, 3H), 3.79 (q, 2H), 2.39 (s, 3H), 1.38 (t, 3H) |
| 1-234 | 9.18 (d, 1H), 8.66 (d, 3H), 8.22 (s, 1H), 8.21 (s, 1H), 4.09 (s, 3H), 3.82 (q, 2H), 1.43 (t, 3H), 1.42 (s, 9H) |
| 1-237 | 9.45 (d, 1H), 9.10 (d, 3H), 8.21 (s, 1H), 7.57 (s, 1H), 4.09 (s, 3H), 3.80 (q, 2H), 1.45 (s, 9H), 1.39 (t, 3H) |
| 1-243 | 9.24 (d, 1H), 8.71 (d, 3H), 8.32 (s, 1H), 8.21 (s, 1H), 4.09 (s, 3H), 3.82 (q, 2H), 3.33 (s, 3H), 1.59 (s, 6H), 1.41 (t, 3H) |
| 1-356 | 9.39 (d, 1H), 8.84 (d, 1H), 8.21 (d, 1H), 6.01 (s, 2H), 4.53 (q, 2H), 4.07 (s, 3H), 3.79 (q, 2H), 1.38 (t, 3H) |
| 2-246 | 9.15 (d, 1H), 8.77 (d, 1H), 8.71 (d, 1H), 8.31 (d, 1H), 8.30 (s, 1H), 5.35 (s, 2H), 3.91 (s, 3H), 3.89 (q, 2H), 2.32 (s, 3H), 1.40 (t, 3H) |
| 2-248 | 9.14 (d, 1H), 8.78 (d, 1H), 8.74 (d, 1H), 8.44 (s, 1H), 8.32 (s, 1H), 5.18 (s, 2H), 3.91 (s, 3H), 3.90 (q, 2H), 2.68 (s, 3H), 1.39 (t, 3H) |
| 3-3 | 8.54 (d, 1H), 8.31 (s, 1H), 8.28 (d, 1H), 8.20 (s, 1H), 6.07 (tt, 1H), 4.49 (td, 2H), 4.07 (s, 3H), 3.74 (q, 2H), 1.38 (t, 3H) |
| 3-4 | 8.56 (d, 1H), 8.34 (s, 1H), 8.29 (d, 1H), 8.20 (s, 1H), 4.76 (q, 2H), 4.08 (s, 3H), 3.75 (q, 2H), 1.38 (t, 3H) |
| 3-5 | 8.56 (d, 1H), 8.33 (s, 1H), 8.29 (d, 1H), 8.20 (s, 1H), 5.94 (tt, 1H), 4.71 (t, 2H), 4.07 (s, 3H), 3.75 (q, 2H), 1.37 (t, 3H) |
| 3-12 | 8.56 (d, 1H), 8.34 (s, 1H), 8.29 (d, 1H), 8.22 (s, 1H), 4.66 (q, 2H), 4.07 (s, 3H), 3.76 (q, 2H), 1.38 (t, 3H) |

TABLE 7

| Compound No. | ¹H-NMR data (CDCl₃) |
|---|---|
| 3-13 | 8.56 (d, 1H), 8.31 (s, 1H), 8.28 (d, 1H), 8.22 (s, 1H), 6.07 (tt, 1H), 4.49 (td, 2H), 4.07 (s, 3H), 3.75 (q, 2H), 1.38 (t, 3H) |
| 5-44 | 8.50 (d, 1H), 8.29 (s, 1H), 8.23 (d, 1H), 7.72 (d, 1H), 7.69 (d, 1H), 7.35 (dd, 1H), 4.25 (t, 2H), 3.95 (q, 2H), 1.79 (dd, 2H), 1.42 (t, 3H), 1.00 (t, 3H) |
| 5-82 | 8.53 (d, 1H), 8.31 (s, 1H), 8.21 (d, 1H), 7.72 (d, 1H), 7.69 (d, 1H), 7.36 (dd, 1H), 6.38 (td, 1H), 6.18 (d, 1H), 4.76 (dd, 2H), 3.96 (q, 2H), 1.42 (t, 3H) |
| 5-88 | 8.50 (d, 1H), 8.28 (s, 1H), 8.21 (d, 1H), 7.71 (d, 1H), 7.68 (d, 1H), 7.34 (dd, 1H), 5.49 (t, 1H), 4.79 (d, 2H), 3.94 (q, 2H), 1.82 (s, 3H), 1.78 (s, 3H), 1.42 (t, 3H) |
| 6-2 | 8.78 (d, 1H), 8.54 (d, 1H), 8.34 (s, 1H), 8.32 (d, 1H), 8.23 (d, 1H), 4.65 (q, 2H), 3.89 (s, 3H), 3.82 (q, 2H), 1.38 (t, 3H) |
| 6-4 | 8.78 (d, 1H), 8.54 (d, 1H), 8.32 (s, 1H), 8.31 (d, 1H), 8.22 (d, 1H), 4.75 (t, 2H), 3.89 (s, 3H), 3.82 (q, 2H), 1.37 (t, 3H) |
| 6-5 | 8.78 (d, 1H), 8.54 (d, 1H), 8.32 (s, 1H), 8.31 (d, 1H), 8.22 (d, 1H), 5.91 (tt, 1H), 4.70 (t, 2H), 3.89 (s, 3H), 3.82 (q, 2H), 1.37 (t, 3H), |
| 6-17 | 8.76 (d, 1H), 8.48 (d, 1H), 8.31 (d, 1H), 8.24 (s, 1H), 8.21 (d, 1H), 4.26 (t, 2H), 3.88 (s, 3H), 3.80 (q, 2H), 1.78 (td, 2H), 1.37 (t, 3H), 1.01 (t, 3H) |
| 6-21 | 8.77 (d, 1H), 8.51 (d, 1H), 8.31 (d, 1H), 8.28 (s, 1H), 8.24 (d, 1H), 5.35 (s, 2H), 3.88 (s, 3H), 3.80 (q, 2H), 2.32 (s, 3H), 1.36 (t, 3H) |
| 6-55 | 8.76 (d, 1H), 8.50 (d, 1H), 8.31 (d, 1H), 8.23 (d, 1H), 8.20 (s, 1H), 6.39 (td, 1H), 6.18 (d, 1H), 4.77 (d, 2H), 3.88 (s, 3H), 3.80 (q, 2H), 1.37 (t, 3H) |
| 6-57 | 8.76 (d, 1H), 8.47 (d, 1H), 8.31 (d, 1H), 8.21 (d, 1H), 8.20 (s, 1H), 4.30 (t, 2H), 3.88 (s, 3H), 3.79 (q, 2H), 1.75 (dd, 2H), 1.46 (dd, 2H), 1.36 (t, 3H), 0.98 (t, 3H) |
| 6-59 | 8.76 (d, 1H), 8.47 (d, 1H), 8.31 (d, 1H), 8.21 (d, 1H), 8.20 (s, 1H), 4.29 (t, 2H), 3.88 (s, 3H), 3.80 (q, 2H), 1.77 (dd, 2H), 1.39 (dd, 2H), 1.37 (dd, 2H), 1.37 (t, 3H), 0.93 (t, 3H) |

TABLE 7

| Compound No. | $^1$H-NMR data (CDCl$_3$) |
|---|---|
| 6-61 | 8.76 (d, 1H), 8.48 (d, 1H), 8.30 (d, 1H), 8.22 (d, 1H), 8.20 (s, 1H), 5.50 (t, 1H), 4.80 (d, 2H), 3.87 (s, 3H), 3.80 (q, 2H), 1.81 (ds, 3H), 1.78 (s, 3H), 1.36 (t, 3H) |

The agricultural and horticultural insecticide comprising the oxime group-containing condensed heterocyclic compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, termites, etc.

Specific examples of the pests, nematodes, etc. include the following:

the species of the order Lepidoptera such as *Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura*, a species of the family Tortricidae (*Eucosma aporema*), *Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocupreanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis*;

the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophum rufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecaniumpersicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatella, Eurydema pulchrum, Cletus trigonus, Clovia punctata, Empoasca* sp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acan-* thocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens and Aphis gossypii;

the species of the order Coleoptera such as Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica spp., Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes spp., Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea and Anthonomus grandis;

the species of the order Diptera such as Culexpipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans, the species of the family Phoridae such as Megaselia spiracularis, Clogmia albipunctata, Tipula aino, Phormia regina, Culex tritaeniorhynchus, Anopheles sinensis, Hylemya brassicae, Asphondylia sp., Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens and Rhagoletis pomonella;

the species of the order Hymenoptera such as Pristomyrmex pungens, the species of the family Bethylidae, Monomorium pharaonis, Pheidole noda, Athalia rosae, Dryocosmus kuriphilus, Formica fusca japonica, the species of the subfamily Vespinae, Athalia infumata infumata, Arge pagana, Athalia japonica, Acromyrmex spp., Solenopsis spp., Arge mali and Ochetellus glaber;

the species of the order Orthoptera such as Homorocoryphus lineosus, Gryllotalpa sp., Oxya hyla intricata, Oxyayezoensis, Locusta migratoria, Oxya japonica, Homorocoryphus jezoensis and Teleogryllus emma;

the species of the order Thysanoptera such as Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Franklinella occidentalis, Thrips palmi, Frankliniella lilivora and Liothrips vaneeckei;

the species of the order Acari such as Leptotrombidium akamushi, Tetranychus ludeni, Dermacentor variabilis, Tetranychus truncatus, Ornithonyssus bacoti, Demodex canis, Tetranychus viennensis, Tetranychus kanzawai, the species of the family Ixodidae such as Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini and Sancassania sp.;

the species of the order Isoptera such as Reticulitermes miyatakei, Incisitermes minor, Coptotermes formosanus, Hodotermopsis japonica, Reticulitermes sp., Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei and Reticulitermes speratus;

the species of the order Blattodea such as Periplaneta fuliginosa, Blattella germanica, Blatta orientalis, Periplaneta brunnea, Blattella lituricollis, Periplaneta japonica and Periplaneta americana;

the species of the order Siphonaptera such as Pulex irritans, Ctenocephalides felis and Ceratophyllus gallinae;

the species of the phylum Nematoda such as Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus and Tylenchus semipenetrans;

the species of the phylum Mollusca such as *Pomacea canaliculata, Achatina fulica, Meghimatium bilineatum, Lehmannina valentiana, Limax flavus* and *Acusta despecta sieboldiana*.

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanesis; Dermanyssus gallinae;* the species of the genus *Ornithonyssus* such as *Ornithonyssus sylviarum* and *Ornithonyssus bursa;* the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai;* the species of the family Cheyletidae such as *Cheyletiella yasguri, Cheyletiella parasitivorax* and *Cheyletiella blakei;* the species of the superfamily Sarcoptoidea such as *Psoroptes cuniculi, Chorioptes bovis, Otodectes cynotis, Sarcoptes scabiei* and *Notoedres cati;* and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus*.

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis;* the species of the suborder Mallophaga such as *Trichodectes canis;* and hematophagous Dipteran insect pests such as *Tabanus trigonus, Culicoides schultzei* and *Simulium ornatum*. Also included are endoparasites, for example, nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis;* trematodes such as *Schistosoma japonicum* and *Fasciola hepatica;* and protozoa such as coccidia, *Plasmodium*, intestinal *Sarcocystis, Toxoplasma* and *Cryptosporidium*.

The agricultural and horticultural insecticide comprising the oxime group-containing condensed heterocyclic compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide utilizes so-called penetration and translocation. That is, nursery soil, soil in transplanting holes, plant foot, irrigation water, cultivation water in hydroponics, or the like is treated with the agricultural and horticultural insecticide to allow crops, ornamental flowering plants, etc. to absorb the compound of the present invention through the roots via soil or otherwise.

Examples of useful plants to which the agricultural and horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., chrysanthemum, rose, carnation, orchid, tulip, lily, etc.), garden trees (e.g., ginkgo trees, cherry trees, Japanese aucuba, etc.) and forest trees (e.g., *Abies sachalinensis, Picea jezoensis*, pine, yellow cedar, Japanese cedar, hinoki cypress, eucalyptus, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control target pests, the agricultural and horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer or the like, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared in the usual method for preparing agrochemical formulations.

That is, the oxime group-containing condensed heterocyclic compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, or two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers or a combination of two or more of them may be used.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethylether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, or two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, or two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticide of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticide).

The application rate of the agricultural and horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 areas depending on the purpose.

Furthermore, for the expansion of the range of target pests and the appropriate time for pest control, or for dose reduction, the agricultural and horticultural insecticide of the present invention can be used after mixed with other agricultural and horticultural insecticides, acaricides, nematicides, microbicides, biopesticides and/or the like. Further, the agricultural and horticultural insecticide can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai*, *Bacillus thuringiensis israelensis*, *Bacillus thuringiensis japonensis*, *Bacillus thuringiensis kurstaki* and *Bacillus thuringiensis tenebrionis*, BPMC, Bt toxin-derived insecticidal compounds, chlorfenson (CPCBS), dichlorodiisopropyl ether (DCIP), 1,3-dichloropropene (D-D), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Examples of the agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Further, examples of the herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Examples of the biopesticides include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor*, avirulent *Erwinia carotovora* and *Bacillus subtilis*; and biopesticides used as a herbicide, such as *Xanthomonas campestris*. A combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

Hereinafter, the production examples of representative compounds of the present invention and their intermediates will be described in more detail, but the present invention is not limited only to these examples.

EXAMPLES

Production Example 1 of Intermediate (2)

Production Method of
5-Chloro-6-ethoxycarbonylpyridine-3-carboxylic Acid

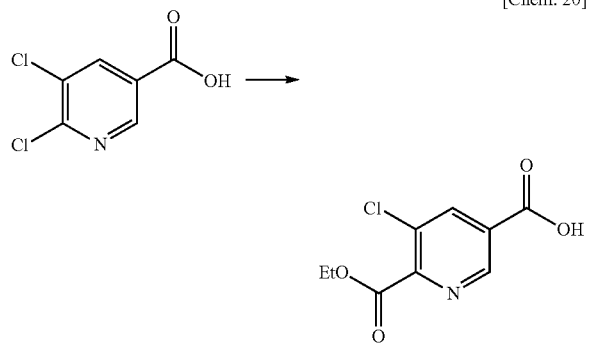

[Chem. 20]

An autoclave was charged with an ethanol (60 mL) solution of 5,6-dichloropyridine-3-carboxylic acid (10 g, 52 mmol). To this, DPPB (1,4-bis(diphenylphosphino)butane) (2.2 g, 10 mol %), triethylamine (14 g, 2.5 Eq) and PdCl$_2$(PPh$_3$)$_2$ (911 mg, 2.5 mol %) were added, the atmosphere in the reaction system was replaced with carbon monoxide (CO pressure, 4.0 MPa), and the mixture was stirred at 135° C. for 4 hours. Water and 3 N hydrochloric acid were added to the reaction mixture for the acidification of the aqueous layer, and ethyl acetate extraction was performed several times. The organic layer was dried over sodium sulfate and then concentrated, and the resulting solid was washed with a hexane-ethyl acetate (2:1 (v/v)) mixture to give the desired compound, i.e., 5-chloro-6-ethoxycarbonylpyridine-3-carboxylic acid (10.9 g, 76%).

Physical property: $^1$H-NMR (CDCl$_3$): 9.02 (d, 1H), 8.44 (d, 1H), 4.42 (dd, 2H), 1.33 (t, 3H)

Production Example 2 of Intermediate (2)

Production Method of
5-Chloro-6-ethoxycarbonylpyridine-3-carboxylic Acid t-butyl Ester

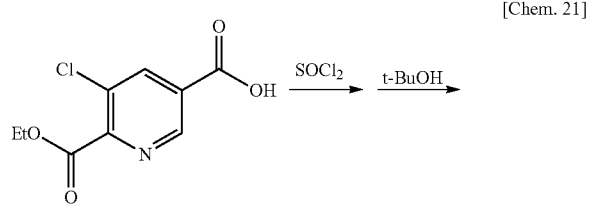

[Chem. 21]

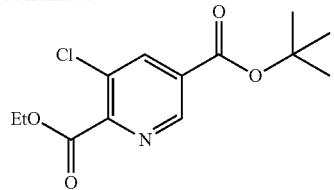

The 5-chloro-6-ethoxycarbonylpyridine-3-carboxylic acid (10.9 g, 47.6 mmol) obtained in the previous step was dissolved in toluene (30 mL), and DMF (dimethylformamide) (4 mL) was added. Subsequently, thionyl chloride (11 g, 2 Eq) was added, and the mixture was heated with stirring at 90° C. for 3 hours. The reaction mixture was allowed to come to room temperature and then concentrated. The concentrated residue was slowly added to a mixture of t-butanol (35 mL, 10 Eq), THF (tetrahydrofuran) (100 mL), diisopropylethylamine (50 mL, 7 Eq) and DMAP (N,N-dimethyl-4-aminopyridine) (6 g, 1 Eq) in another vessel under ice cooling. The reaction mixture was heated under reflux for 3 hours, and allowed to cool down to room temperature. To this, water and ethyl acetate were added, and extraction was performed several times. The organic layer was dried over sodium sulfate and then concentrated. The residue was subjected to column chromatography (hexane-AcOEt (acetic acid ethyl ester)=5:1 (v/v)) to give the desired compound, i.e., 5-chloro-6-ethoxycarbonylpyridine-3-carboxylic acid t-butyl ester (8.43 g, 62%).

Physical property: $^1$H-NMR (CDCl$_3$): 9.05 (d, 1H), 8.30 (d, 1H), 4.50 (dd, 2H), 1.61 (s, 9H), 1.44 (t, 3H)

Production Example 3 of Intermediate (2)

Production Method of
5-Ethylthio-6-ethoxycarbonylpyridine-3-carboxylic Acid t-butyl Ester

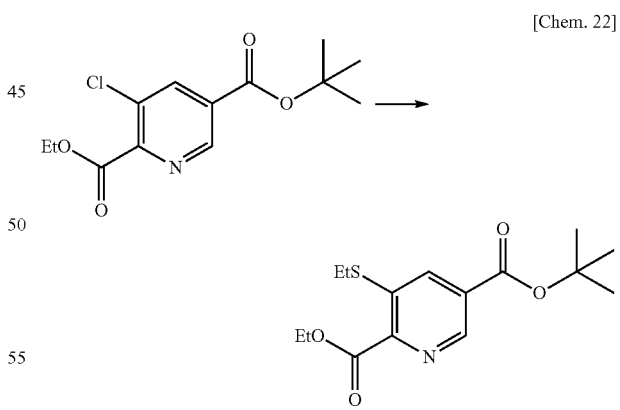

[Chem. 22]

5-Chloro-6-ethoxycarbonylpyridine-3-carboxylic acid t-butyl ester (8.43 g, 21.65 mmol) was dissolved in DMF (100 mL). Sodium ethanethiolate (2.27 g, 1 Eq) was slowly added to the solution under ice cooling, and the mixture was stirred for 5 minutes. To this, water and 0.5 N hydrochloric acid were successively added. After ethyl acetate extraction was performed several times, the organic layer was dried over sodium sulfate and then concentrated. The residue was subjected to column chromatography (hexane-AcOEt=5:1

(v/v)) to give the desired compound, i.e., 5-ethylthio-6-ethoxycarbonylpyridine-3-carboxylic acid t-butyl ester (6.17 g, 92%).

Physical property: $^1$H-NMR (CDCl$_3$): 8.91 (d, 1H), 8.22 (d, 1H), 4.49 (dd, 2H), 2.99 (dd, 2H), 1.61 (s, 9H), 1.45 (t, 3H), 1.40 (t, 3H)

Production Example 4 of Intermediate (2)

Production Method of 3-Ethylthio-5-t-butoxycarbonylaminopyridine-2-carboxylic Acid Ethyl Ester

[Chem. 23]

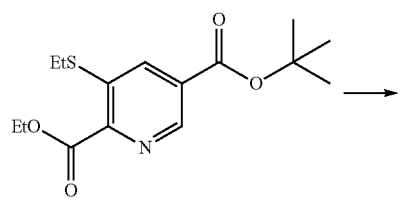

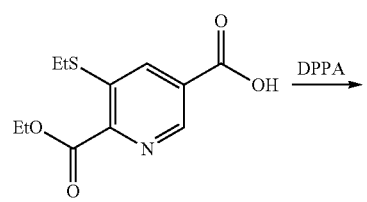

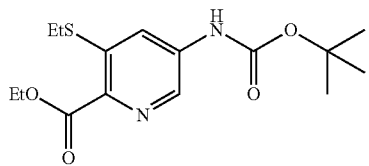

5-Ethylthio-6-ethoxycarbonylpyridine-3-carboxylic acid t-butyl ester (6.17 g, 19.9 mmol) was dissolved in trifluoroacetic acid (30 mL), and the solution was heated under reflux for 30 minutes. The reaction mixture was concentrated, toluene and ethyl acetate were added to the residue, and the mixture was concentrated again. To the residue, t-butanol (100 mL), triethylamine (6.5 g, 3 Eq) and DPPA (diphenylphosphoryl azide) (11.74 g, 2 Eq) were added, and the mixture was stirred at room temperature for 1 hour and then refluxed for 4 hours. The reaction mixture was concentrated, and the residue was subjected to column chromatography (hexane-ethyl acetate=2:1 (v/v)) to give the desired compound, i.e., 3-ethylthio-5-t-butoxycarbonylaminopyridine-2-carboxylic acid ethyl ester (3.63 g, 56%).

Physical property: $^1$H-NMR (CDCl$_3$): 8.25 (d, 1H), 8.09 (d, 1H), 6.74 (s, 1H), 4.46 (dd, 2H), 2.97 (dd, 2H), 1.53 (s, 9H), 1.44 (t, 3H), 1.41 (t, 3H)

Production Example 5 of Intermediate (2)

Production Method of 5-Amino-3-ethylthiopyridine-2-carboxylic Acid Ethyl Ester

[Chem. 24]

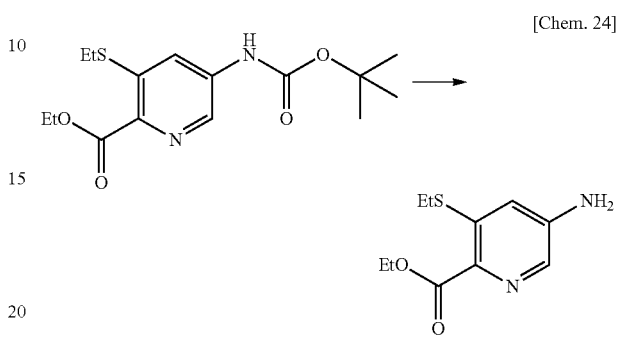

3-Ethylthio-5-t-butoxycarbonylaminopyridine-2-carboxylic acid ethyl ester (670 mg, 2.06 mmol) was dissolved in trifluoroacetic acid (30 mL), and the mixture was stirred at room temperature for 30 minutes. The reaction mixture was concentrated, and water, ethyl acetate and potassium carbonate were added to the residue. After ethyl acetate extraction was performed several times, the organic layer was dried over sodium sulfate and then concentrated. The residue was subjected to column chromatography (hexane-AcOEt=1:3 (v/v)) to give the desired compound, i.e., 5-amino-3-ethylthiopyridine-2-carboxylic acid ethyl ester (358 mg, 77%).

Physical property: $^1$H-NMR (CDCl$_3$): 7.89 (d, 1H), 6.80 (s, 1H), 4.43 (dd, 2H), 4.08 (s, 2H), 2.88 (dd, 2H), 1.56 (s, 9H), 1.42 (t, 3H), 1.40 (t, 3H)

Production Example 6 of Intermediate (2)

Production Method of 3-Ethylthio-5-iodopyridine-2-carboxylic Acid Ethyl Ester

[Chem. 25]

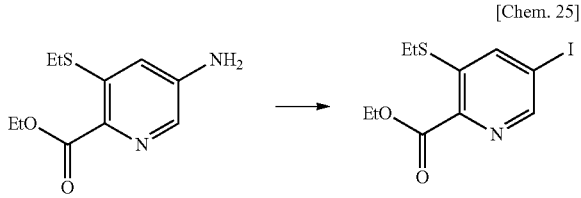

5-Amino-3-ethylthiopyridine-2-carboxylic acid ethyl ester (1 g, 4.44 mmol) was dissolved in acetonitrile (10 mL). To this, trifluoroacetic acid (500 mg, 1 Eq) and p-toluenesulfonic acid (2.6 g, 3 Eq) were added, and the mixture was cooled in a water bath of about 5° C. To the reaction mixture, an aqueous solution (10 mL) of potassium iodide (2.25 g, 3 Eq) and sodium nitrite (612 mg, 2 Eq) prepared in another vessel was added slowly. The mixture was stirred for 30 minutes, and then stirred at room temperature for 30 minutes. A "hypo" (sodium hyposulfite) solution was added to the reaction mixture, and ethyl acetate extraction was performed several times. The organic layer was dried and concentrated. The residue was subjected to column chromatography to give the desired compound, i.e., 3-ethylthio-5-iodopyridine-2-carboxylic acid ethyl ester (761 mg, 51%).

Physical property: $^1$H-NMR (CDCl$_3$): 8.61 (s, 1H), 7.95 (s, 1H), 4.45 (dd, 2H), 2.91 (dd, 2H), 1.43 (t, 3H), 1.39 (t, 3H)

Production Example 1 of Intermediate (2-b2

Production Method of
3-Ethylthio-5-hydroxymethylpyridine-2-carboxylic
Acid Ethyl Ester

[Chem. 26]

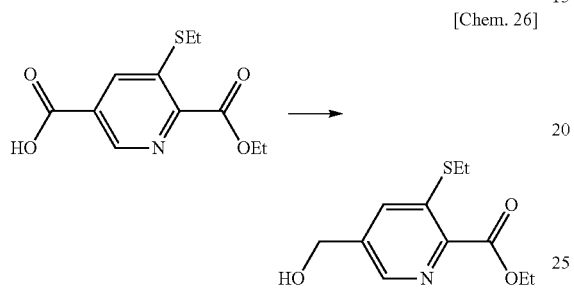

To a THF solution (100 mL) of 5-ethylthio-6-ethoxycarbonylpyridine-3-carboxylic acid (10 g), which compound was produced according to the production method described in the Production Example 4 of Intermediate (2) above, CDI (carbonyldiimidazole) (10 g) was added, and the mixture was stirred at room temperature for 2 hours. This THF solution was slowly added to a 100-mL aqueous solution of NaBH$_4$ (5.5 g) at 0° C., and the mixture was stirred at room temperature for 1 hour. After the completion of the reaction, a 4 M hydrochloric acid solution was added for adjustment of the pH to 2, and ethyl acetate extraction was performed. The organic layer was washed with a saturated aqueous sodium chloride solution, dried over anhydrous magnesium sulfate, and then concentrated in vacuo. The residue was purified by silica gel chromatography to give 3-ethylthio-5-hydroxymethylpyridine-2-carboxylic acid ethyl ester (6.4 g, 62%).

Production Example 2 of Intermediate (2-b2

Production Method of
3-Ethylthio-5-methoxymethoxypyridine-2-carboxylic
Acid Ethyl Ester

[Chem. 27]

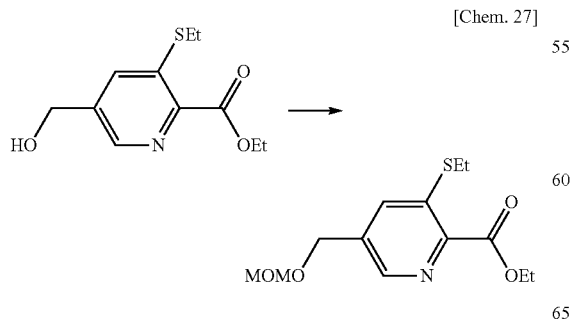

To a CHCl$_3$ Solution (50 mL) of 3-ethylthio-5-hydroxymethylpyridine-2-carboxylic acid ethyl ester (6.4 g), DIPEA (N,N-diisopropylethylamine) (13.6 mL) and methoxymethyl chloride (MOMCl) (6.0 mL) were added, and the mixture was stirred at room temperature for 1 hour. After the completion of the reaction, an aqueous ammonium chloride solution was added, and ethyl acetate extraction was performed. The organic layer was washed with a saturated aqueous sodium chloride solution, dried over anhydrous magnesium sulfate, and then concentrated in vacuo to give 3-ethylthio-5-methoxymethoxypyridine-2-carboxylic acid ethyl ester (7.1 g, 94%).

Production Example 1 of Intermediate (2-e4

Production Method of
3-Chloro-5-hydroxymethylpyridine-2-carboxylic
Acid Ethyl Ester

[Chem. 28]

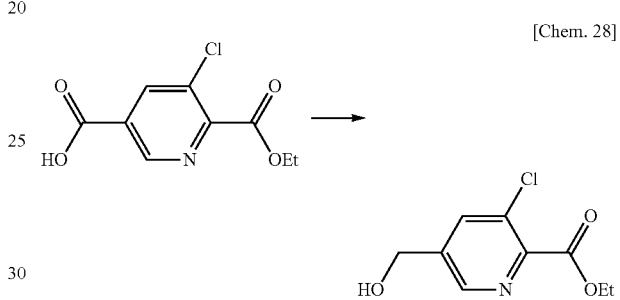

To a CHCl$_3$ solution (150 mL) of 5-chloro-6-ethoxycarbonylpyridine-3-carboxylic acid (8.3 g), which compound was produced according to the method of Production Example 1 of Intermediate (2), DMF (0.3 mL) and oxalyl chloride (4.7 mL) were successively added, and the mixture was stirred at room temperature for 1 hour. The reaction mixture was concentrated in vacuo. A CHCl$_3$ solution (50 mL) of the concentrated residue was slowly added to a water/CHCl$_3$ (1:3 (v/v)) solution (150 mL) of NaBH$_4$ (5.5 g) at 0° C., and the mixture was stirred at room temperature for 1 hour. After the completion of the reaction, a 4 M hydrochloric acid solution was added for adjustment of the pH to 2, and CHCl$_3$ extraction was performed. The organic layer was washed with a saturated aqueous sodium chloride solution, dried over anhydrous magnesium sulfate, and then concentrated in vacuo. The residue was purified by silica gel chromatography to give 3-chloro-5-hydroxymethylpyridine-2-carboxylic acid ethyl ester (4.9 g, 62%).

Production Example 2 of Intermediate (2-e4

Production Method of
3-Chloro-5-formylpyridine-2-carboxylic Acid Ethyl
Ester

[Chem. 29]

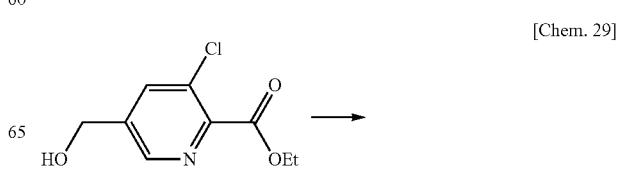

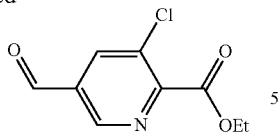

To a CHCl₃ solution (50 mL) of oxalyl chloride, dimethyl sulfoxide (8.0 mL) was slowly added dropwise at −78° C., and the reaction mixture was stirred for 10 minutes. To this, a CHCl₃ solution (15 mL×2) of 3-chloro-5-hydroxymethylpyridine-2-carboxylic acid ethyl ester (4.9 g) was added at −78° C., and the mixture was stirred for 15 minutes. To this, Et₃N (22 mL) was added at −78° C., and the mixture was stirred at 0° C. for 20 minutes. After the completion of the reaction, a saturated aqueous NH₄Cl solution was added, and ethyl acetate extraction was performed. The organic layer was washed with a saturated aqueous sodium chloride solution, dried over anhydrous magnesium sulfate, and dried in vacuo. The residue was purified by silica gel chromatography to give 3-chloro-5-formylpyridine-2-carboxylic acid ethyl ester (4.8 g, 99%).

Production Example 3 of Intermediate (2-e4

Production Method of 3-Chloro-5-(1,3-dioxan-2-yl)-2-pyridine-carboxylic Acid Ethyl Ester

[Chem. 30]

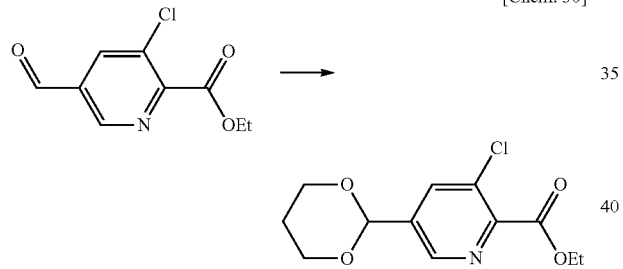

To a toluene solution (50 mL) of 3-chloro-5-formylpyridine-2-carboxylic acid ethyl ester (4.8 g), 1,3-propanediol (3.4 g) and CSA (10-camphorsulfonic acid) (0.5 g) were added, and the mixture was heated under reflux for 2 hours. After the completion of the reaction, the reaction mixture was concentrated in vacuo, and the residue was purified by silica gel chromatography to give 3-chloro-5-(1,3-dioxan-2-yl)-2-pyridine-carboxylic acid ethyl ester (4.9 g, 81%).

Production Example 4 of Intermediate (2-e4

Production Method of 3-Ethylthio-5-(1,3-dioxan-2-yl)-2-pyridine-carboxylic Acid Ethyl Ester

[Chem. 31]

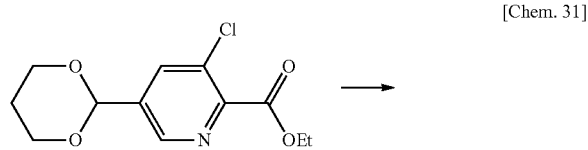

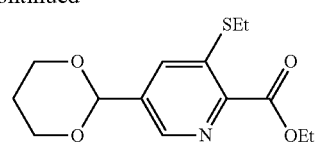

To a THF solution (40 mL) of 3-chloro-5-(1,3-dioxan-2-yl)-2-pyridine-carboxylic acid ethyl ester (4.9 g), NaH (1.5 g) and EtSH (1.7 mL) were added at 0° C., and the mixture was stirred at 50° C. for 2 hours. After the completion of the reaction, a saturated aqueous NH₄Cl solution was added, and ethyl acetate extraction was performed. The organic layer was washed with a saturated aqueous sodium chloride solution, dried over anhydrous magnesium sulfate, and dried in vacuo. The residue was purified by silica gel chromatography to give 3-ethylthio-5-(1,3-dioxan-2-yl)-2-pyridine-carboxylic acid ethyl ester (2.6 g, 49%).

Production Example 1 of Intermediate (3)

Production Method of 3-Methylamino-6-pentafluoroethyl Pyridazine

[Chem. 32]

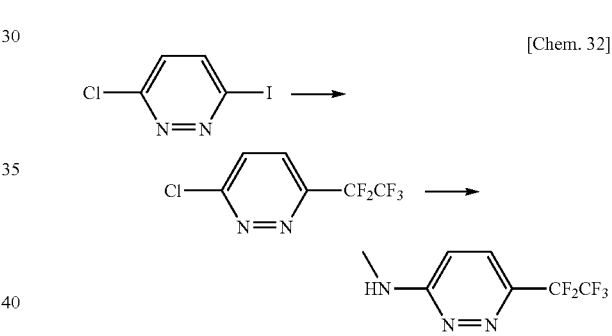

Under an argon atmosphere, 3-chloro-6-iodopyridazine (7.2 g) synthesized according to the method described in the previously-mentioned reference, copper iodide (2.86 g), 1,10-phenanthroline (2.7 g) and a solution (ca. 0.33 M, 80 mL) of a bisfluoro alkyl zinc reagent in NMP (N-methyl-2-pyrrolidone) prepared according to the method described in Program and Abstracts of the 94th Spring Annual Meeting of the Chemical Society of Japan (presentation No. 2B1-17, p. 1229) were mixed in a vessel with stirring at 90° C. for 40 minutes, and then allowed to cool down to room temperature. The resulting reaction mixture was slowly added dropwise to a mixture of THF (30 mL) and methylamine (30 mL of a 10 M solution of methylamine in methanol) in another vessel under ice cooling. The mixture was heated to room temperature and stirred for 1 hour. After addition of water and ethyl acetate, the mixture was stirred for 5 minutes and then filtered through Celite. The filtrate was extracted with ethyl acetate 3 times. The organic layer was dried over sodium sulfate and then concentrated. The residue was subjected to column chromatography to give the desired compound, i.e., 3-methylamino-6-pentafluoroethyl pyridazine (6.36 g).

Physical property: Melting point: 141 to 143° C.

Production Example 2 of Intermediate (3)

Production Method of 4-Bromo-3-methylamino-6-pentafluoroethyl Pyridazine

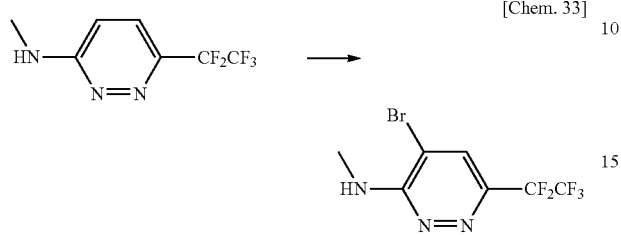

[Chem. 33]

To a solution of 3-methylamino-6-pentafluoroethyl pyridazine (6.05 g) in acetic acid (50 mL), 1,3-dibromo-5,5-dimethylhydantoin (8.4 g) was added, and the mixture was heated at 95° C. with stirring for 3 hours. The reaction mixture was concentrated, and water was added to the residue. This was neutralized with potassium carbonate, and ethyl acetate extraction was performed 3 times. The organic layer was dried over sodium sulfate and then concentrated. The residue was subjected to column chromatography to give the desired compound, i.e., 4-bromo-3-methylamino-6-pentafluoroethyl pyridazine (6.16 g, 76%).

Physical property: Melting point: 41 to 43° C.

Production Example 3 of Intermediate (3)

Production Method of 4-Amino-3-methylamino-6-pentafluoroethyl Pyridazine

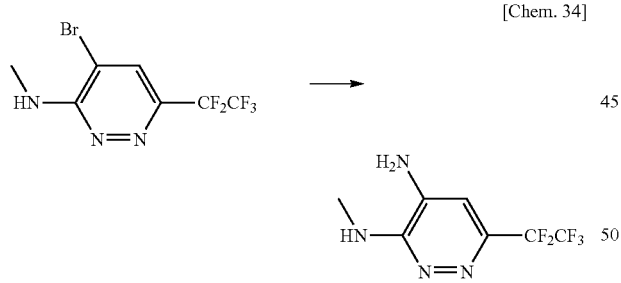

[Chem. 34]

An autoclave was charged successively with 4-bromo-3-methylamino-6-pentafluoroethyl pyridazine (6.16 g), copper (I) oxide (1.44 g), NMP (30 mL) and a 28% aqueous ammonia solution (30 mL), purged with argon, and then sealed. The mixture in the autoclave was heated at 80° C. with stirring for 3 hours and then allowed to cool down to room temperature. After addition of water and ethyl acetate, the mixture was stirred for 5 minutes and then filtered through Celite. The filtrate was extracted with ethyl acetate 3 times. The organic layer was dried over sodium sulfate and then concentrated. The residue was subjected to column chromatography to give the desired compound, i.e., 4-amino-3-methylamino-6-pentafluoroethyl pyridazine (3.39 g, 69%).

Physical property: $^1$H-NMR (CDCl$_3$): 6.75 (s, 1H), 5.18 (s, 1H), 4.59 (s, 2H), 2.85 (s, 3H)

Reference Example 1

Production Method of 2-(3-Ethylthio-5-iodopyridin-2-yl)-3-methyl-6-pentafluoroethyl-3H-imidazo[4,5-c]pyridazine

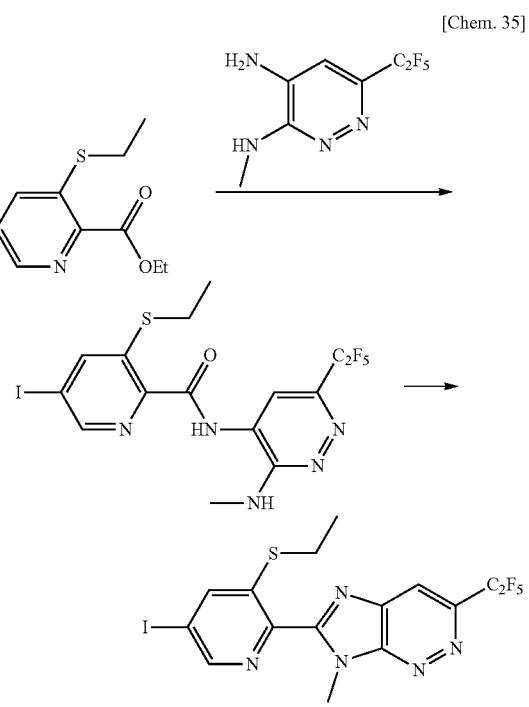

[Chem. 35]

To a tetrahydrofuran solution (240 mL) of 4-amino-3-methylamino-6-pentafluoroethyl pyridazine (17.9 g), sodium hydride (3.1 g) was added under ice cooling, and the mixture was stirred until no more bubbles formed. Next, a tetrahydrofuran solution (120 mL) of ethyl 3-ethylthio-5-iodo-2-pyridinecarboxylate (25 g) was added under ice cooling, and the mixture was allowed to come to room temperature and then stirred for 2 hours. A 0.5 M aqueous hydrochloric acid solution was added for adjustment of the pH to 3, and ethyl acetate extraction was performed. The organic layer was dried over anhydrous magnesium sulfate and then concentrated in vacuo to give 3-ethylthio-5-iodo-N-(3-methylamino-6-pentafluoroethylpyridazin-4-yl)-2-pyridine-carboxylic acid amide. This compound was directly used for the following reaction without purification.

To a toluene solution (300 mL) of 3-ethylthio-5-iodo-N-(3-methylamino-6-pentafluoroethylpyridazin-4-yl)-2-pyridine-carboxylic acid amide, acetic acid (40 mL) was added, and the mixture was heated under reflux for 6 hours. The reaction mixture was allowed to come to room temperature and then concentrated in vacuo. A saturated aqueous sodium bicarbonate solution was added to the residue, and ethyl acetate extraction was performed. The organic layer was dried over anhydrous magnesium sulfate and then concentrated in vacuo. A small amount of methyl t-butyl ether and hexane was added to the residue, and the resulting solid was collected by filtration.

As a result, 27 g of 2-(3-ethylthio-5-iodopyridin-2-yl)-3-methyl-6-pentafluoroethyl-3H-imidazo[4,5-c]pyridazine was obtained.

Yield: 71% Melting point: 127 to 128° C.

Reference Example 2

Production Method of 2-(3-Ethylsulfonyl-5-iodopyridin-2-yl)-3-methyl-6-pentafluoroethyl-3H-imidazo[4,5-c]pyridazine

[Chem. 36]

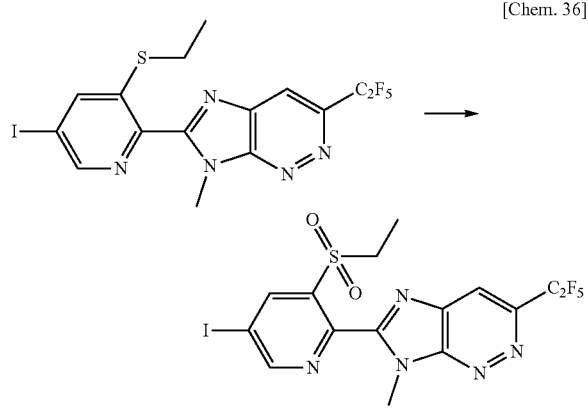

The imidazopyridazine compound (395 mg, 0.766 mmol) obtained in the previous step was dissolved in ethyl acetate (10 mL), m-chloroperoxybenzoic acid (450 mg, 2.2 Eq) was added to the solution, and the mixture was stirred at room temperature for 2 hours. To the reaction mixture, several drops of FAMSO (methyl(methylsulfinyl)methylsulfide) and triethylamine (1 mL) were added, and the mixture was concentrated. The residue was subjected to column chromatography to give the desired sulfone compound (406 mg, 97%).

Physical property: Melting point: 188 to 189° C.

Reference Example 3

Production Method of 2-(3-Ethylsulfonyl-5-vinylpyridin-2-yl)-3-methyl-6-pentafluoroethyl-3H-imidazo[4,5-c]pyridazine

[Chem. 37]

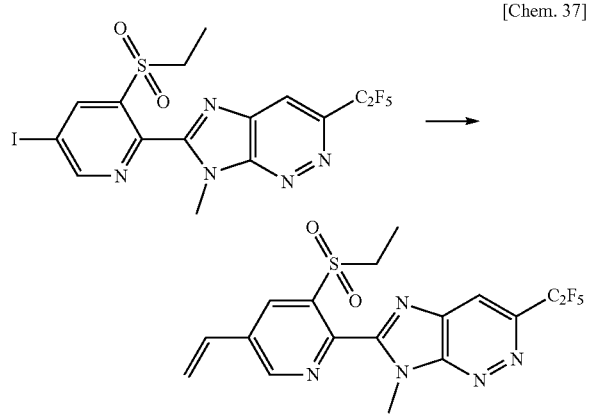

To a DME/H$_2$O (4:1 (v/v)) solution (4 mL) of 2-(3-ethylsulfonyl-5-iodopyridin-2-yl)-3-methyl-6-pentafluoroethyl-3H-imidazo[4,5-c]pyridazine (0.40 g, 0.73 mmol), potassium vinyltrifluoroborate (0.15 g, 1.1 mmol), a [(diphenylphosphino)ferrocene]dichloropalladium-dichloromethane complex (0.060 g, 0.073 mmol) and cesium carbonate (0.71 g, 2.2 Eq) were added, and the mixture was stirred at 80° C. for 1 hour. After the completion of the reaction, silica gel was added, and the mixture was concentrated in vacuo. The residue was subjected to silica gel column chromatography to give 2-(3-ethylsulfonyl-5-vinylpyridin-2-yl)-3-methyl-6-pentafluoroethyl-3H-imidazo[4,5-c]pyridazine.

Physical property: Melting point 188 to 190° C.

Reference Example 4

Production Method of 2-[3-Ethylsulfonyl-5-(1,2-dihydroxyethyl)pyridin-2-yl]-3-methyl-6-pentafluoroethyl-3H-imidazo[4,5-c]pyridazine

[Chem. 38]

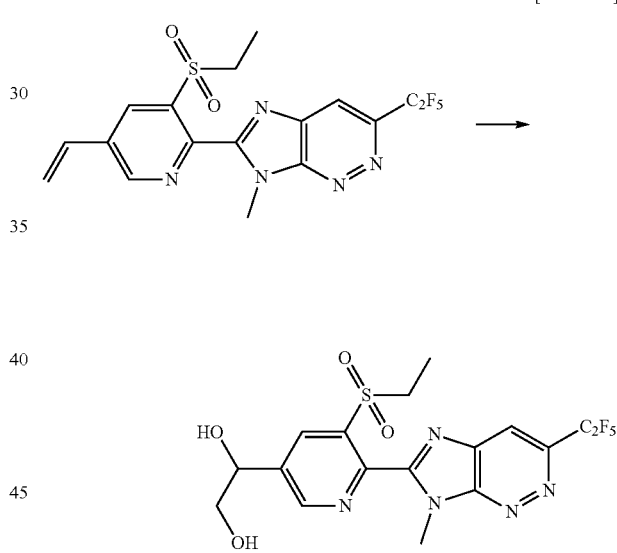

To a THF/water (2:1 (v/v)) solution (4 mL) of 2-(3-ethylsulfonyl-5-vinylpyridin-2-yl)-3-methyl-6-pentafluoroethyl-3H-imidazo[4,5-c]pyridazine, N-methylmorpholine oxide (0.51 g, 2.20 mmol, 50% aqueous solution) and osmium tetroxide (1.8 mL, 0.22 mmol, 0.039 M t-butanol solution) were added, and the mixture was stirred at room temperature overnight. To this, a saturated aqueous sodium carbonate solution was added, and AcOEt extraction was performed 3 times. The organic layer was washed with a saturated aqueous sodium chloride solution, dried over MgSO$_4$ and filtered, and the filtrate was concentrated in vacuo. The residue was purified by silica gel column chromatography to give 2-[3-ethylsulfonyl-5-(1,2-dihydroxyethyl)pyridin-2-yl]-3-methyl-6-pentafluoroethyl-3H-imidazo[4,5-c]pyridazine (0.31 g, 0.64 mmol, 88%).

Physical property: $^1$H-NMR (CDCl$_3$): 9.04 (d, 1H), 8.58 (d, 1H), 8.22 (s, 1H), 5.12 (brt, 1H), 4.06 (s, 3H), 4.00 (m, 1H), 3.75 (q, 2H), 3.82 (m, 1H), 1.36 (t, 3H)

Reference Example 5

Production Method of 2-(3-Ethylsulfonyl-5-formylpyridin-2-yl)-3-methyl-6-pentafluoroethyl-3H-imidazo[4,5-c]pyridazine

[Chem. 39]

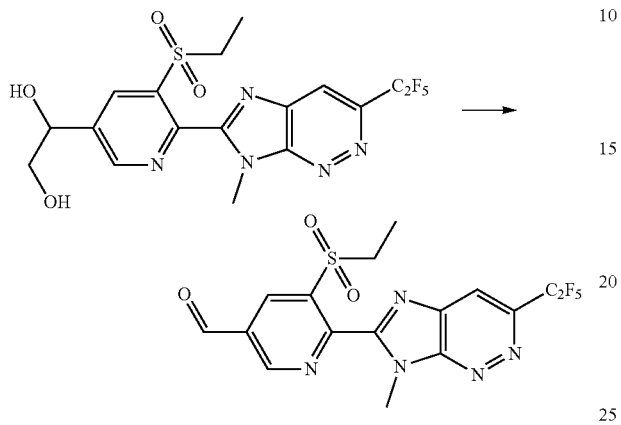

To a THF/water (2:1 (v/v)) solution (6 mL) of 2-[3-ethylsulfonyl-5-(1,2-dihydroxyethyl)pyridin-2-yl]-3-methyl-6-pentafluoroethyl-3H-imidazo[4,5-c]pyridazine (0.29 g, 0.60 mmol), sodium periodate (0.26 g, 1.2 mmol) was added, and the mixture was stirred at room temperature for 2 hours. After the completion of the reaction, AcOEt extraction was performed 3 times. The organic layer was washed with a saturated aqueous sodium chloride solution, dried over magnesium sulfate and filtered, and the filtrate was concentrated in vacuo. The residue was purified by silica gel column chromatography to give 2-(3-ethylsulfonyl-5-formylpyridin-2-yl)-3-methyl-6-pentafluoroethyl-3H-imidazo[4,5-c]pyridazine (0.25 g, 0.56 mmol, 92%).

Physical property: Melting point 238 to 239° C.

Production Example 1

Production Method of 2-(3-Ethylsulfonyl-5-hydroxyiminopyridin-2-yl)-3-methyl-6-pentafluoroethyl-3H-imidazo[4,5-c]pyridazine (Compound Number: 1-189

[Chem. 40]

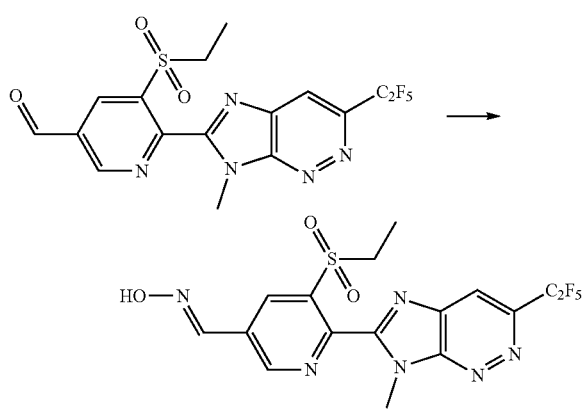

To an ethanol solution (1 mL) of 2-(3-ethylsulfonyl-5-formylpyridin-2-yl)-3-methyl-6-pentafluoroethyl-3H-imidazo[4,5-c]pyridazine (0.030 g, 0.067 mmol), hydroxylamine hydrochloride (0.0070 g, 0.10 mmol) and sodium acetate (0.0080 g, 0.10 mmol) were added, and the mixture was heated under reflux for 2 hours. The reaction mixture was concentrated in vacuo, and the residue was subjected to silica gel column chromatography to give 2-(3-ethylsulfonyl-5-hydroxyiminopyridin-2-yl)-3-methyl-6-pentafluoroethyl-3H-imidazo[4,5-c]pyridazine (0.028 g, 0.061 mmol, 92%).

Physical property: Melting point 240 to 242° C.

Production Example 2

Production Method of 2-(3-Ethylsulfonyl-5-(2,2,2-trifluoroethoxyimino)pyridin-2-yl)-3-methyl-6-pentafluoroethyl-3H-imidazo[4,5-c]pyridazine (Compound Number: 1-246

[Chem. 41]

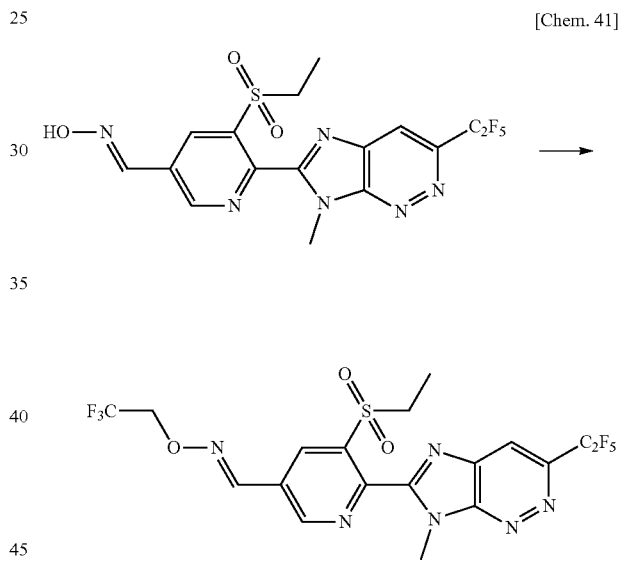

To an N,N-dimethylformamide solution (1 mL) of 2-(3-ethylsulfonyl-5-hydroxyiminopyridin-2-yl)-3-methyl-6-pentafluoroethyl-3H-imidazo[4,5-c]pyridazine (0.075 g), cesium carbonate (0.11 g) and trifluoromethanesulfonic acid 2,2,2-trifluoroethyl ester (75 mg) were added at 0° C., and the mixture was stirred at room temperature for 2 hours. After the completion of the reaction, an aqueous ammonium chloride solution was added, and ethyl acetate extraction was performed. The organic layer was dried over anhydrous magnesium sulfate and then concentrated in vacuo, and the residue was purified by silica gel column chromatography to give 2-(3-ethylsulfonyl-5-(2,2,2-trifluoroethoxyimino)pyridin-2-yl)-3-methyl-6-pentafluoroethyl-3H-imidazo[4,5-c]pyridazine (0.055 g, 63%).

Physical property: Melting point: 207 to 208° C.

Reference Example 6

Production Method of 2-(3-Ethylthio-5-iodopyridin-2-yl)-3-methyl-6-trifluoromethyl-3H-imidazo[4,5-b]pyridine

[Chem. 42]

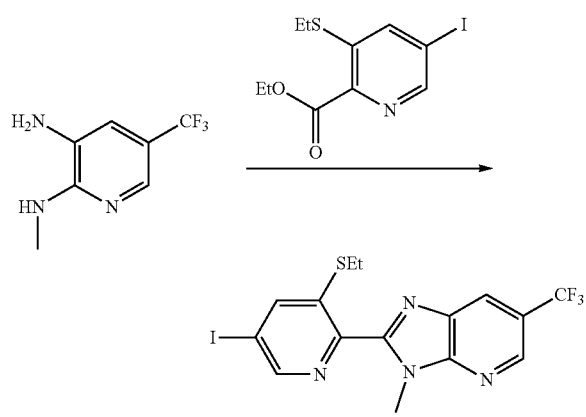

To a tetrahydrofuran solution (15 mL) of 3-amino-2-methylamino-5-trifluoromethylpyridine (0.71 g), sodium hydride (0.18 g) and a THF solution (5 mL) of ethyl 3-ethylthio-5-iodo-2-pyridinecarboxylate (1.25 g) were successively added under ice cooling. The mixture was allowed to come to room temperature and then stirred for 2 hours. After the completion of the reaction, a 1 M hydrochloric acid solution was added, and ethyl acetate extraction was performed. The organic layer was washed with a saturated aqueous sodium chloride solution and dried over anhydrous magnesium sulfate, and then the solvent was evaporated off. NMP (20 mL) and TsOH·H$_2$O (1.9 g) were added to the residue, and the mixture was stirred at 150° C. for 3 hours. After the completion of the reaction, a saturated aqueous NaHCO$_3$ solution was added, and ethyl acetate extraction was performed. The organic layer was washed with a saturated aqueous sodium chloride solution and dried over anhydrous magnesium sulfate, and then the solvent was evaporated off. The residue was purified by silica gel chromatography to give 2-(3-ethylthio-5-iodopyridin-2-yl)-3-methyl-6-trifluoromethyl-3H-imidazo[4,5-b]pyridine (1.52 g, 89%).

Reference Example 7

Production Method of 2-(3-Ethylthio-5-vinylpyridin-2-yl)-3-methyl-6-trifluoromethyl-3H-imidazo[4,5-b]pyridine

[Chem. 43]

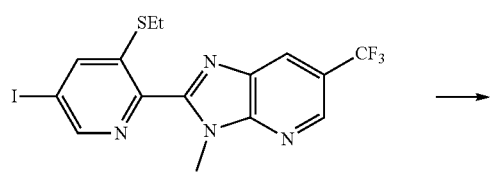

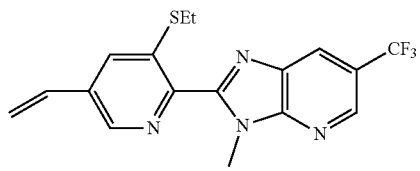

To a DME/H$_2$O (4:1 (v/v)) solution (20 mL) of 2-(3-ethylthio-5-iodopyridin-2-yl)-3-methyl-6-trifluoromethyl-3H-imidazo[4,5-b]pyridine (1.52 g), which compound was produced by the production method of the previous reference example, potassium vinyltrifluoroborate (0.44 g), PdCl$_2$ (dppf)-acetone (0.13 g) and Cs$_2$CO$_3$ (2.1 g) were added, and the mixture was heated under reflux for 2 hours. After the completion of the reaction, the reaction mixture was dried in vacuo, and the residue was purified by silica gel chromatography to give 2-(3-ethylthio-5-vinylpyridin-2-yl)-3-methyl-6-trifluoromethyl-3H-imidazo[4,5-b]pyridine (0.85 g, 71%). dppf stands for 1,1'-bis(diphenylphosphino)ferrocene.

Reference Example 8

Production Method of 2-(3-Ethylsulfonyl-5-formylpyridin-2-yl)-3-methyl-6-trifluoromethyl-3H-imidazo[4,5-b]pyridine

[Chem. 44]

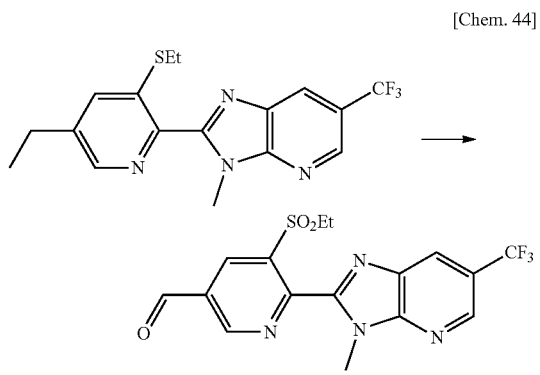

To a THF/aqueous pH 7 buffer (2:1 (v/v)) solution (20 mL) of 2-(3-ethylthio-5-vinylpyridin-2-yl)-3-methyl-6-trifluoromethyl-3H-imidazo[4,5-b]pyridine (0.85 g), which compound was produced by the production method of the previous reference example, NMO (N-methylmorpholine N-oxide) (1.64 g, 50% in H$_2$O) and OsO$_4$ (6.0 mL, 0.039 M in t-BuOH) were added, and the mixture was stirred at room temperature overnight. To this, NaIO$_4$ (1.5 g) was added, and the mixture was stirred at room temperature for 2 hours. After the completion of the reaction, a saturated Na$_2$S$_2$O$_3$ solution was added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(3-ethylsulfonyl-5-formylpyridin-2-yl)-3-methyl-6-trifluoromethyl-3H-imidazo[4,5-b]pyridine (0.54 g, 86%).

Production Example 3

Production Method of 2-(3-Ethylsulfonyl-5-(hydroxyimino)pyridin-2-yl)-3-methyl-6-trifluoromethyl-3H-imidazo[4,5-b]pyridine (Compound Number: 2-3

[Chem. 45]

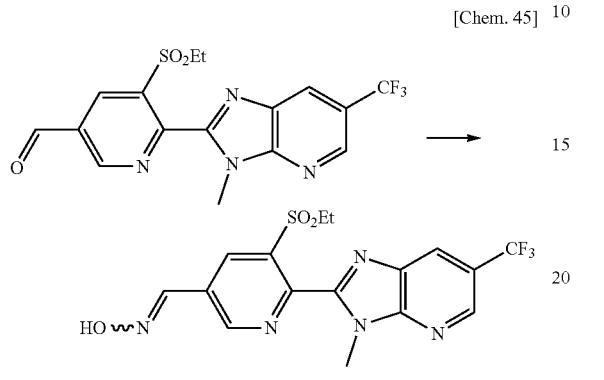

To an ethanol solution (10 mL) of 2-(3-ethylsulfonyl-5-formylpyridin-2-yl)-3-methyl-6-trifluoromethyl-3H-imidazo[4,5-b]pyridine (0.54 g), hydroxylamine hydrochloride (0.14 g) and sodium acetate (0.17 g) were added, and the mixture was heated under reflux for 4 hours. After the completion of the reaction, the reaction mixture was concentrated in vacuo, and the residue was purified by silica gel chromatography to give 2-(3-ethylsulfonyl-5-(hydroxylimino)pyridin-2-yl)-3-methyl-6-trifluoromethyl-3H-imidazo[4,5-b]pyridine (0.50 g, 89%).

Production Example 4

Production Method of 2-(3-Ethylsulfonyl-5-(2,2,2-trifluoroethoxyimino)pyridin-2-yl)-3-methyl-6-trifluoromethyl-3H-imidazo[4,5-b]pyridine (Compound Number: 2-33

[Chem. 46]

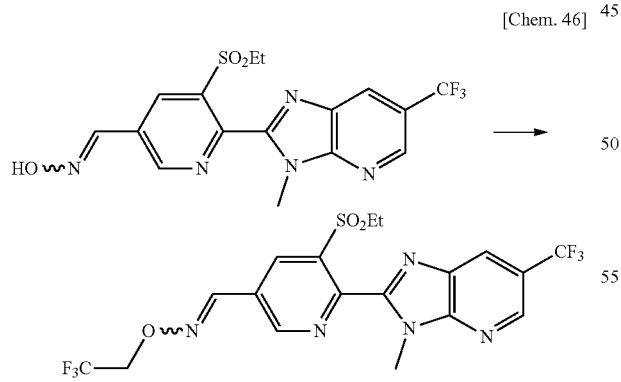

To a DMF solution (1 mL) of 2-(3-ethylsulfonyl-5-(hydroxylimino)pyridin-2-yl)-3-methyl-6-trifluoromethyl-3H-imidazo[4,5-b]pyridine (0.05 g), Cs₂CO₃ (0.06 g) and 2,2,2-trifluoroethyl trifluoromethanesulfonate (0.06 mg) were added, and the mixture was stirred at room temperature for 1 hour. After the completion of the reaction, an aqueous ammonium chloride solution was added, and ethyl acetate extraction was performed. The organic layer was dried over anhydrous magnesium sulfate and then concentrated in vacuo, and the residue was purified by silica gel column chromatography to give 2-(3-ethylsulfonyl-5-(2,2,2-trifluoroethoxyimino)pyridin-2-yl)-3-methyl-6-trifluoromethyl-3H-imidazo[4,5-b]pyridine (0.042 g, 71%).

Reference Example 9

Production Method of 2-(3,6-Dichloropyridin-2-yl)-3-methyl-6-trifluoromethyl-3H-imidazo[4,5-c]pyridazine

[Chem. 47]

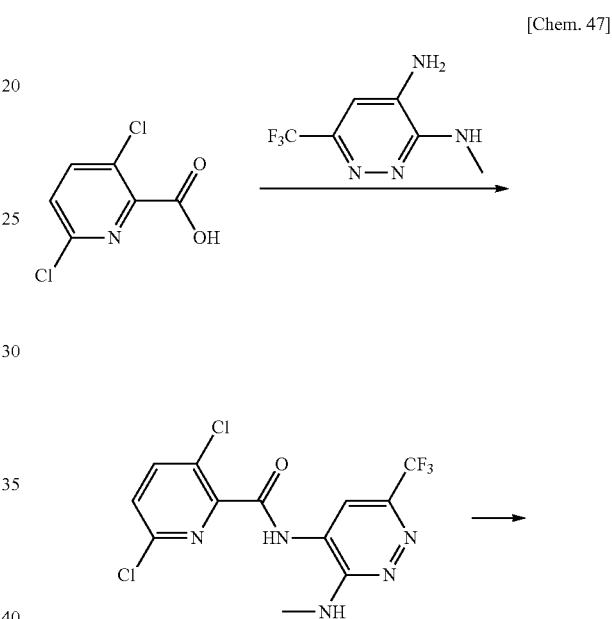

To a toluene solution (5 mL) of 3,6-dichloro-2-pyridinecarboxylic acid (1 g), DMF (0.02 mL) and SOCl₂ (1.0 mL) were added at 0° C., and the mixture was heated under reflux for 2 hours. After the completion of the reaction, the reaction mixture was concentrated in vacuo. A THF solution (5 mL) of the residue was added to a THF solution (5 mL) of 4-amino-3-methylamino-6-trifluoromethylpyridine (1.0 g) at 0° C., and the mixture was stirred at room temperature for 2 hours and then concentrated in vacuo. Acetic acid (10 mL) was added to the residue, and the mixture was heated with stirring for 2 hours. After the completion of the reaction, the reaction mixture was concentrated in vacuo, and the residue was purified by silica gel chromatography to give 2-(3,6-dichloropyridin-2-yl)-3-methyl-6-trifluoromethyl-3H-imidazo[4,5-c]pyridazine (3.2 g, 62%, two steps).

Reference Example 10

Production Method of 2-(3-Ethylthio-6-chloropyridin-2-yl)-3-methyl-6-trifluoromethyl-3H-imidazo[4,5-c]pyridazine

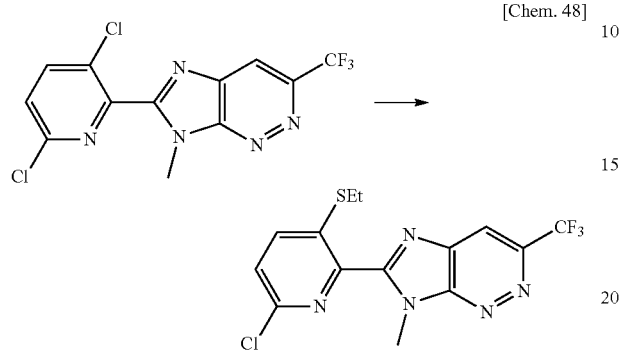

[Chem. 48]

To a THF solution (20 mL) of 2-(3,6-dichloropyridin-2-yl)-3-methyl-6-trifluoromethyl-3H-imidazo[4,5-c]pyridazine (1.1 g), NaH (0.2 g) and EtSH (0.24 mL) were added at 0° C., and the mixture was stirred at room temperature for 1 hour. After the completion of the reaction, a saturated aqueous $NH_4Cl$ solution was added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(3-ethylthio-6-chloropyridin-2-yl)-3-methyl-6-trifluoromethyl-3H-imidazo[4,5-c]pyridazine (0.82 g, 68%).

Reference Example 11

Production Method of 2-(3-Ethylsulfonyl-6-chloropyridin-2-yl)-3-methyl-6-trifluoromethyl-3H-imidazo[4,5-c]pyridazine

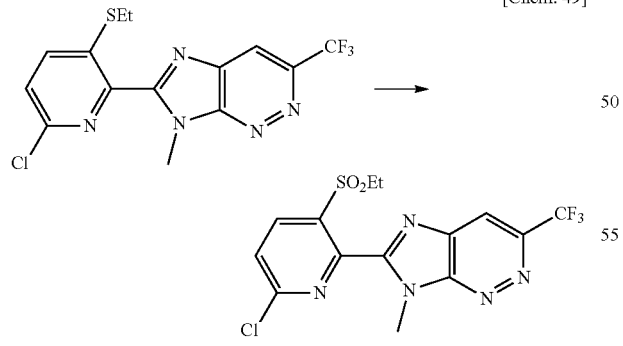

[Chem. 49]

To an ethyl acetate solution (20 mL) of 2-(3-ethylthio-6-chloropyridin-2-yl)-3-methyl-6-trifluoromethyl-3H-imidazo[4,5-c]pyridazine (0.82 g), m-chloroperoxybenzoic acid (1.13 g) was added at room temperature, and the mixture was stirred for 2 hours. After the completion of the reaction, a saturated aqueous sodium bicarbonate solution and a saturated aqueous sodium thiosulfate solution were added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(3-ethylsulfonyl-6-chloropyridin-2-yl)-3-methyl-6-trifluoromethyl-3H-imidazo[4,5-c]pyridazine (0.89 g, quantitative).

Reference Example 12

Production Method of 2-(3-Ethylsulfonyl-6-vinylpyridin-2-yl)-3-methyl-6-trifluoromethyl-3H-imidazo[4,5-c]pyridazine

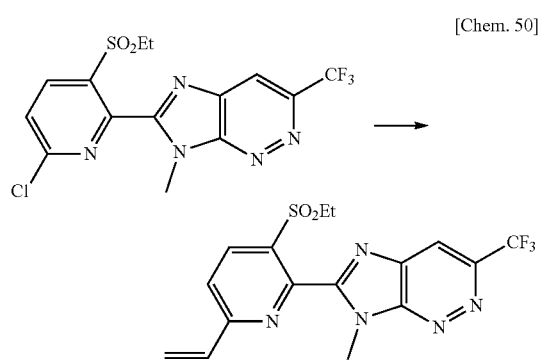

[Chem. 50]

To a $DME/H_2O$ (4:1) solution (10 mL) of 2-(3-ethylsulfonyl-6-chloropyridin-2-yl)-3-methyl-6-trifluoromethyl-3H-imidazo[4,5-c]pyridazine (0.92 g), potassium vinyltrifluoroborate (0.45 g), $PdCl_2$ (dppf)•acetone (0.17 g) and $Cs_2CO_3$ (1.5 g) were added, and the mixture was stirred at 80° C. for 1 hour. After the completion of the reaction, the reaction mixture was concentrated in vacuo, and the residue was purified by silica gel chromatography to give 2-(3-ethylsulfonyl-6-vinylpyridin-2-yl)-3-methyl-6-trifluoromethyl-3H-imidazo[4,5-c]pyridazine (0.59 g, 66%).

Reference Example 13

Production Method of 2-(3-Ethylsulfonyl-6-formylpyridin-2-yl)-3-methyl-6-trifluoromethyl-3H-imidazo[4,5-c]pyridazine

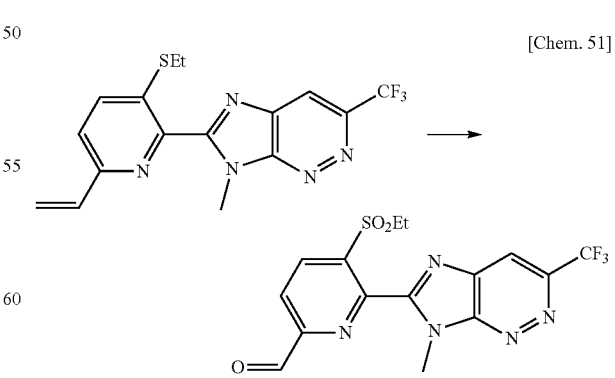

[Chem. 51]

To a THF/pH 7 phosphate buffer (2:1) solution (14 mL) of 2-(3-ethylsulfonyl-6-vinylpyridin-2-yl)-3-methyl-6-trifluoromethyl-3H-imidazo[4,5-c]pyridazine (0.59 g), NMO (1.04 g, 50% in H₂O) and OsO₄ (3.0 mL, 0.039 M in t-BuOH) were added, and the mixture was stirred at room temperature overnight. To this, NaIO₄ (0.38 g) was added, and the mixture was stirred at room temperature for 2 hours. After the completion of the reaction, a saturated Na₂S₂O₃ solution was added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(3-ethylsulfonyl-6-formylpyridin-2-yl)-3-methyl-6-trifluoromethyl-3H-imidazo[4,5-c]pyridazine (0.51 g, 86%).

Production Example 5

Production Method of 2-(3-Ethylsulfonyl-6-(hydroxyimino)pyridin-2-yl)-3-methyl-6-trifluoromethyl-3H-imidazo[4,5-c]pyridazine (Compound Number: 3-1)

[Chem. 52]

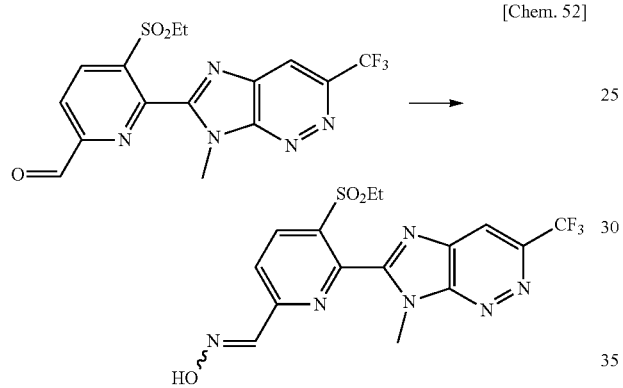

To an ethanol solution (5 mL) of 2-(3-ethylsulfonyl-6-formylpyridin-2-yl)-3-methyl-6-trifluoromethyl-3H-imidazo[4,5-c]pyridazine (0.51 g), hydroxylamine hydrochloride (0.13 g) and sodium acetate (0.26 g) were added, and the mixture was heated under reflux for 2 hours. After the completion of the reaction, the reaction mixture was concentrated in vacuo, and the residue was purified by silica gel chromatography to give 2-(3-ethylsulfonyl-6-(hydroxyimino)pyridin-2-yl)-3-methyl-6-trifluoromethyl-3H-imidazo[4,5-c]pyridazine (0.48 g, 91%).

Production Example 6

Production Method of 2-(3-Ethylsulfonyl-6-(2,2,2-trifluoroethoxyimino)pyridin-2-yl)-3-methyl-6-trifluoromethyl-3H-imidazo[4,5-c]pyridazine (Compound Number: 3-2)

[Chem. 53]

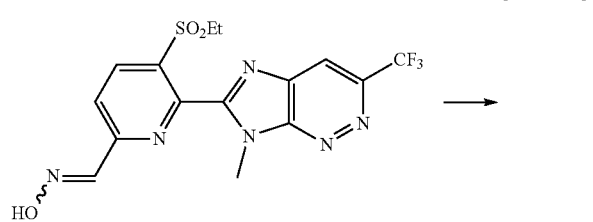

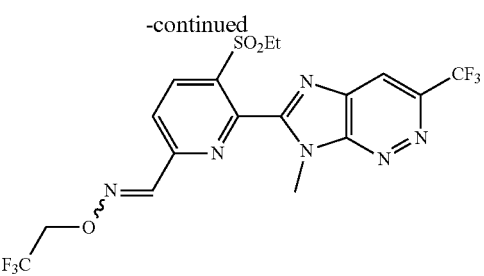

To a DMF solution (1 mL) of 2-(3-ethylsulfonyl-6-(hydroxyimino)pyridin-2-yl)-3-methyl-6-trifluoromethyl-3H-imidazo[4,5-c]pyridazine (0.1 g), Cs₂CO₃ (0.15 g) and 2,2,2-trifluoroethyl trifluoromethanesulfonate (0.11 mg) were added, and the mixture was stirred at room temperature for 1 hour. After the completion of the reaction, an aqueous ammonium chloride solution was added, and ethyl acetate extraction was performed. The organic layer was dried over anhydrous magnesium sulfate and then concentrated in vacuo, and the residue was purified by silica gel column chromatography to give 2-(3-ethylsulfonyl-6-(2,2,2-trifluoroethoxyimino)pyridin-2-yl)-3-methyl-6-trifluoromethyl-3H-imidazo[4,5-c]pyridazine (0.062 g, 68%).

Reference Example 14

Production Method of 3-Ethylthio-5-(1,3-dioxan-2-yl)-N-(2-hydroxy-5-(trifluoromethylthio)phenyl)-2-pyridine-carboxylic Acid Amide

[Chem. 54]

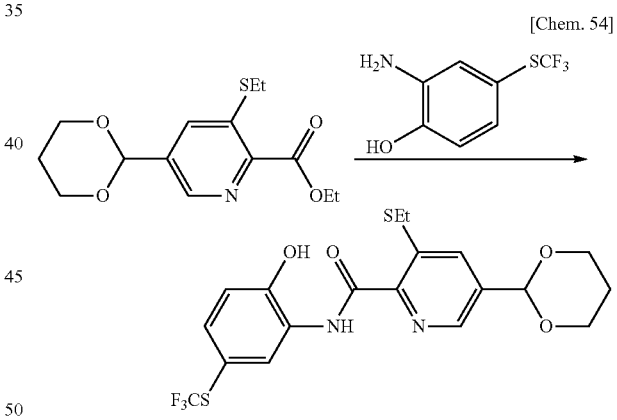

To a THF solution (10 mL) of 3-ethylthio-5-(1,3-dioxan-2-yl)-2-pyridine-carboxylic acid ethyl ester (0.60 g), which compound was produced by the Production Method of Intermediate (2-e4), NaH (0.32 g) and a THF solution (3 mL) of 2-amino-4-(trifluoromethylthio)phenol (0.79 g) were successively added at 0° C., and the mixture was stirred at 50° C. for 2 hours. After the completion of the reaction, a saturated aqueous NH₄Cl solution was added, and ethyl acetate extraction was performed. The organic layer was washed with a saturated aqueous sodium chloride solution, dried over anhydrous magnesium sulfate, and dried in vacuo. The residue was purified by silica gel chromatography to give 3-ethylthio-5-(1,3-dioxan-2-yl)-N-(2-hydroxy-5-(trifluoromethylthio)phenyl)-2-pyridine-carboxylic acid amide (0.73 g, 60%).

Reference Example 15

Production Method of 2-(5-(1,3-Dioxan-2-yl)-3-ethylthio-pyridin-2-yl)-5-(trifluoromethylthio)benzo[d]oxazole

[Chem. 55]

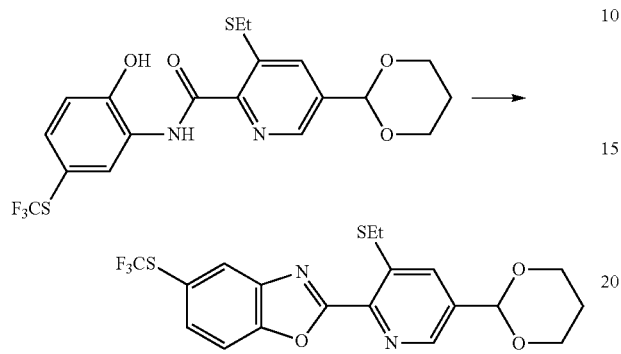

To a THF solution (5 mL) of 3-ethylthio-5-(1,3-dioxan-2-yl)-N-(2-hydroxy-5-(trifluoromethylthio)phenyl)-2-pyridine-carboxylic acid amide (0.73 g), PPh₃ (1.04 g) and bis(2-methoxyethyl) azodicarboxylate (0.93 g) were added, and the mixture was stirred at 60° C. for 1 hour. After the completion of the reaction, water was added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(5-(1,3-dioxan-2-yl)-3-ethylthio-pyridin-2-yl)-5-(trifluoromethylthio)benzo[d]oxazole (0.70 g, quantitative).

Reference Example 16

Production Method of 2-(5-(1,3-Dioxan-2-yl)-3-ethylsulfonyl-pyridin-2-yl)-5-(trifluoromethylthio)benzo[d]oxazole

[Chem. 56]

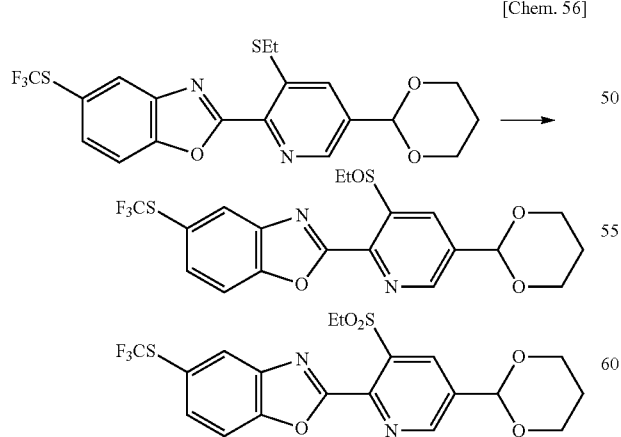

To an ethyl acetate solution (15 mL) of 2-(5-(1,3-dioxan-2-yl)-3-ethylthio-pyridin-2-yl)-5-(trifluoromethylthio)benzo[d]oxazole (0.68 g), m-chloroperoxybenzoic acid (0.74 g) was added at room temperature, and the mixture was stirred for 2 hours. After the completion of the reaction, a saturated aqueous sodium bicarbonate solution and a saturated aqueous sodium thiosulfate solution were added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(5-(1,3-dioxan-2-yl)-3-ethylsulfinyl-pyridin-2-yl)-5-(trifluoromethylthio)benzo[d]oxazole (0.31 g, 40%) and 2-(5-(1,3-dioxan-2-yl)-3-ethylsulfonyl-pyridin-2-yl)-5-(trifluoromethylthio)benzo[d]oxazole (0.40 g, 56%).

Production Example 7

Production Method of (E)-(5-ethylsulfonyl)-6-(trifluoromethylthio)benzo[d]oxazol-2-yl) nicotinaldehyde Oxime (Compound Number: 4-11

[Chem. 57]

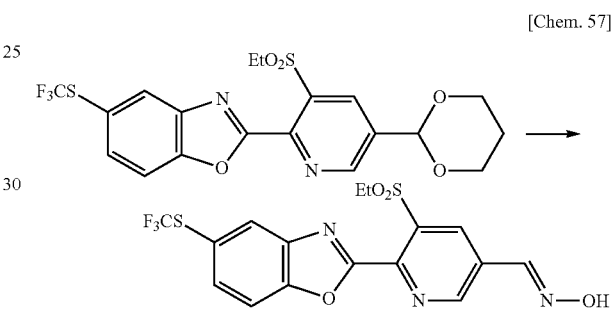

To a THF solution (20 mL) of 2-(5-(1,3-dioxan-2-yl)-3-ethylsulfonyl-pyridin-2-yl)-5-(trifluoromethylthio)benzo[d]oxazole (0.31 g), a 2 M HCl solution (10 mL) was added, and the mixture was stirred overnight. To the reaction mixture, AcOH (20 mL) was added, and the mixture was stirred at 80° C. for 1 hour. To this, hydroxylamine hydrochloride (0.15 g) was added, and the mixture was further stirred for 1 hour. After the completion of the reaction, the reaction mixture was concentrated in vacuo, and the residue was purified by silica gel chromatography to give 5-ethylsulfonyl-6-(trifluoromethylthio)benzo[d]oxazol-2-yl) nicotinaldehyde oxime (0.22 g, 78%).

Production Example 8

Production Method of (E)-(5-ethylsulfonyl)-6-(trifluoromethylthio)benzo[d]oxazol-2-yl)nicotinaldehyde O-(2,2,2-trifluoroethyl)oxime (Compound Number: 4-12

[Chem. 58]

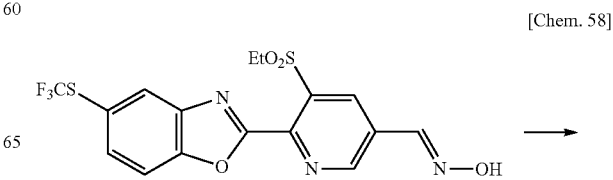

-continued

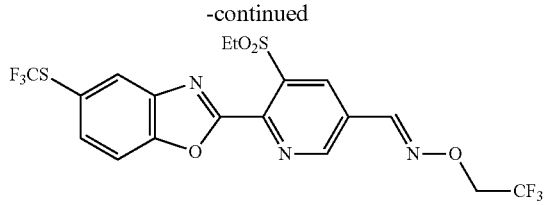

To a DMF solution (1 mL) of (E)-(5-ethylsulfonyl)-6-(trifluoromethylthio)benzo[d]oxazol-2-yl)nicotinaldehyde oxime (0.1 g), Cs$_2$CO$_3$ (0.15 g) and 2,2,2-trifluoroethyl trifluoromethanesulfonate (0.11 mg) were added, and the mixture was stirred at room temperature for 1 hour. After the completion of the reaction, an aqueous ammonium chloride solution was added, and ethyl acetate extraction was performed. The organic layer was dried over anhydrous magnesium sulfate and then concentrated in vacuo, and the residue was purified by silica gel column chromatography to give (E)-(5-ethylsulfonyl)-6-(trifluoromethylthio)benzo[d]oxazol-2-yl)nicotinaldehyde O-(2,2,2-trifluoroethyl)oxime (0.031 g, 32%).

Reference Example 17

Production Method of 3-Ethylthio-5-(methoxymethoxy)-N-(2-hydroxy-5-(trifluoromethylthio)phenyl)-2-pyridine-carboxylic Acid Amide

[Chem. 59]

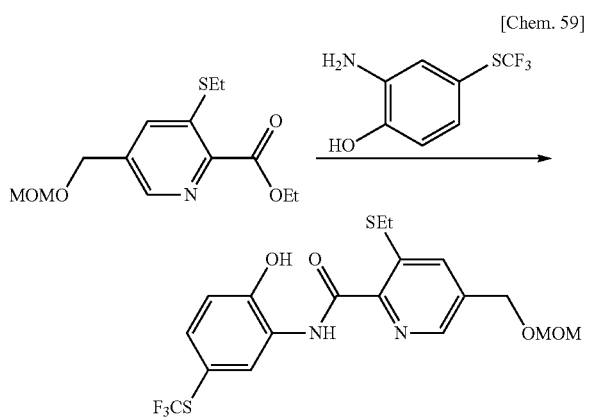

To a THF solution (10 mL) of 3-ethylthio-5-methoxymethyl-2-pyridinecarboxylic acid ethyl ester (0.64 g), which compound was produced by the Production Method of Intermediate (2-b2), NaH (0.36 g) and a THF solution (2 mL) of 2-amino-4-(trifluoromethylthio)phenol (0.4 g) were successively added at 0° C., and the mixture was stirred at 50° C. for 2 hours. After the completion of the reaction, a saturated aqueous NH$_4$Cl solution was added, and ethyl acetate extraction was performed. The organic layer was washed with a saturated aqueous sodium chloride solution, dried over anhydrous magnesium sulfate, and dried in vacuo. The residue was purified by silica gel chromatography to give 3-ethylthio-5-(methoxymethoxy)-N-(2-hydroxy-5-(trifluoromethylthio)phenyl)-2-pyridine-carboxylic acid amide (0.73 g, 60%).

Reference Example 18

Production Method of 2-(3-Ethylthio-5-(methoxymethoxy) pyridin-2-yl)-5-(trifluoromethylthio)benzo[d]oxazole

[Chem. 60]

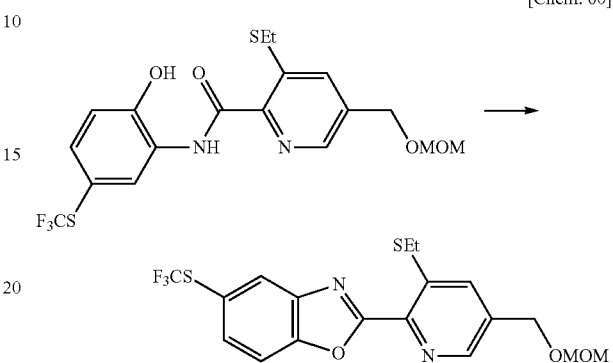

To a THF solution (5 mL) of 3-ethylthio-5-(methoxymethoxy)-N-(2-hydroxy-5-(trifluoromethylthio) phenyl)-2-pyridine-carboxylic acid amide (0.73 g), PPh$_3$ (1.04 g) and bis(2-methoxyethyl) azodicarboxylate (0.93 g) were added, and the mixture was stirred at 60° C. for 1 hour. After the completion of the reaction, H$_2$O was added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(3-ethylthio-5-(methoxymethoxy) pyridin-2-yl)-5-(trifluoro methylthio)benzo[d]oxazole (0.70 g, quantitative).

Reference Example 19

Production Method of 2-(5-Methoxymethoxy-3-ethylsulfonyl-pyridin-2-yl)-5-(trifluoromethylthio)benzo[d]oxazole

[Chem. 61]

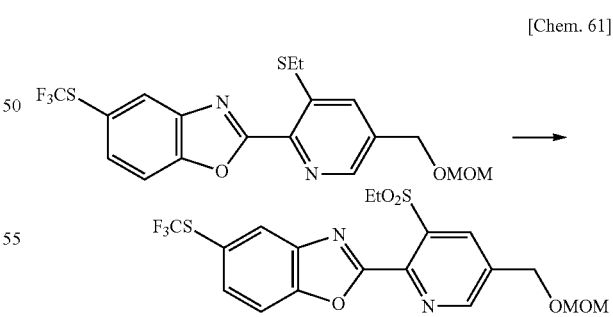

To an ethyl acetate solution (15 mL) of 2-(3-ethylthio-5-(methoxymethoxymethyl) pyridin-2-yl)-5-(trifluoromethylthio)benzo[d]oxazole (0.68 g), m-chloroperoxybenzoic acid (0.74 g) was added at room temperature, and the mixture was stirred for 2 hours. After the completion of the reaction, a saturated aqueous sodium bicarbonate solution and a saturated aqueous sodium thiosulfate solution were added, and ethyl acetate extraction was performed. The organic layer was washed with a saturated aqueous sodium chloride solution, dried over anhydrous magnesium sulfate, and dried in vacuo. The residue was purified by silica gel chromatography to give 2-(5-methoxymethoxy-3-ethylsulfonyl-pyridin-2-yl)-5-(trifluoromethylthio)benzo[d]oxazole (0.40 g, 60%).

Reference Example 20

Production Method of 2-(3-Ethylsulfonyl-5-(hydroxymethyl)pyridin-2-yl)-5-(trifluoromethylthio)benzo[d]oxazole

[Chem. 62]

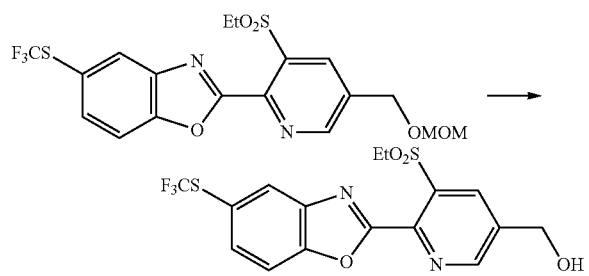

To a methanol solution (7 mL) of 2-(5-methoxymethoxy-3-ethylsulfonyl-pyridin-2-yl)-5-(trifluoromethylthio)benzo[d]oxazole (0.55 g), concentrated hydrochloric acid (2 mL) was added, and the mixture was stirred at room temperature overnight. After the completion of the reaction, the reaction mixture was dried in vacuo. A saturated aqueous sodium bicarbonate solution was added to the residue, and ethyl acetate extraction was performed. The organic layer was washed with a saturated aqueous sodium chloride solution, dried over anhydrous magnesium sulfate, and then concentrated in vacuo. The residue was purified by silica gel chromatography to give 2-(3-ethylsulfonyl-5-(hydroxymethyl)pyridin-2-yl)-5-(trifluoromethylthio)benzo[d]oxazole (0.34 g, 70%).

Reference Example 21

Production Method of (5-Ethylsulfonyl)-6-(trifluoromethylthio)benzo[d]oxazol-2-yl)nicotinaldehyde

[Chem. 63]

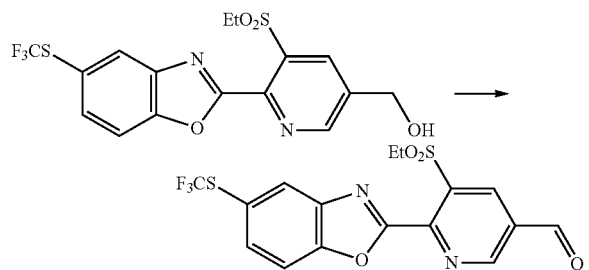

To a CHCl$_3$ solution (7 mL) of 2-(3-ethylsulfonyl-5-(hydroxymethyl)pyridin-2-yl)-5-(trifluoromethylthio)benzo[d]oxazole (0.34 g), BAIB ([bis(acetoxy)iodo]benzene) (0.32 g) and TEMPO (2,2,6,6-tetramethylpiperidine 1-oxyl free radical) (0.028 g) were added, and the mixture was stirred at room temperature overnight. After the completion of the reaction, a saturated aqueous sodium thiosulfate solution was added, and ethyl acetate extraction was performed. The organic layer was washed with a saturated aqueous sodium chloride solution, dried over anhydrous magnesium sulfate, and then concentrated in vacuo. The residue was purified by silica gel chromatography to give 5-ethylsulfonyl-6-(trifluoromethylthio)benzo[d]oxazol-2-yl) nicotinaldehyde (0.26 g, 75%).

(5-Ethylsulfonyl)-6-(trifluoromethylthio)benzo[d]oxazol-2-yl) nicotinaldehyde, which was produced by the above method, was converted to the compound of the present invention according to the production methods described in the Production Examples 7 and 8 above. That is, the compound represented by the following formula:

[Chem. 64]

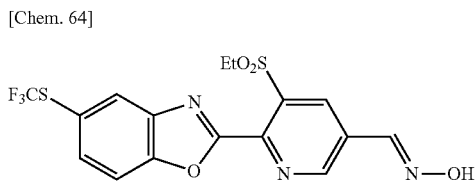

(E Isomer)

was first obtained, and from this compound, the compound represented by the following formula:

[Chem. 65]

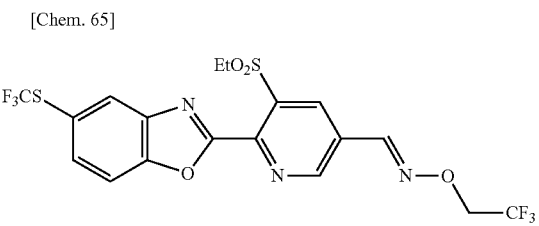

(E Isomer)

was obtained according to the method described in Production Example 8.

Hereinafter, formulation examples are shown, but the present invention is not limited thereto. In the formulation examples, the "part" means a part by weight.

Formulation Example 1

| | |
|---|---|
| Compound of the present invention | 10 parts |
| Xylene | 70 parts |
| N-methylpyrrolidone | 10 parts |
| Mixture of polyoxyethylene nonylphenyl ether and calcium alkylbenzene sulfonate (weight ratio 1:1) | 10 parts |

The above ingredients are uniformly mixed for dissolution to give an emulsifiable concentrate formulation.

Formulation Example 2

| Compound of the present invention | 3 parts |
|---|---|
| Clay powder | 82 parts |
| Diatomite powder | 15 parts |

The above ingredients are uniformly mixed and then pulverized to give a dust formulation.

Formulation Example 3

| Compound of the present invention | 5 parts |
|---|---|
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| Compound of the present invention | 20 parts |
|---|---|
| Kaolin and synthetic high-dispersion silicic acid | 75 parts |
| Mixture of polyoxyethylene nonylphenyl ether and calcium alkylbenzene sulfonate (weight ratio 1:1) | 5 parts |

The above ingredients are uniformly mixed and then pulverized to give a wettable powder formulation.

Hereinafter, test examples in connection with the present invention are shown, but the present invention is not limited thereto.

Test Example 1

Test of Control Effect on *Myzus persicae*

Chinese cabbage plants were planted in plastic pots (diameter: 8 cm, height: 8 cm), green peach aphids (*Myzus persicae*) were propagated on the plants, and the number of surviving green peach aphids in each pot was counted. The oxime group-containing condensed heterocyclic compounds represented by the general formula (1) of the present invention or salts thereof were separately dispersed in water and diluted to 500 ppm, and the agrochemical dispersions were applied to the foliage of the potted Chinese cabbage plants. After the plants were air-dried, the pots were kept in a greenhouse. At 6 days after the foliar application, the number of surviving green peach aphids on the Chinese cabbage plant in each pot was counted, the control rate was calculated according to the formula shown below, and the control effect was evaluated according to the criteria shown below.

$$\text{Control rate} = 100 - \{(T \times Ca)/(Ta \times C)\} \times 100 \quad \text{[Math. 1]}$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot Criteria
A: the control rate is 100%.
B: the control rate is 90 to 99%.
C: the control rate is 80 to 89%.
D: the control rate is 50 to 79%.

As a result, the compounds 1-3, 1-60, 1-72, 1-189, 1-192, 1-195, 1-198, 1-201, 1-204, 1-207, 1-210, 1-213, 1-216, 1-219, 1-222, 1-225, 1-228, 1-231, 1-234, 1-237, 1-240, 1-243, 1-246, 1-258, 1-306, 1-352, 1-353, 1-354, 2-3, 2-6, 2-9, 2-12, 2-15, 2-33, 2-39, 2-45, 2-235, 2-236, 2-237, 2-238, 2-239, 2-240, 2-241, 3-1, 3-2, 3-3, 3-4, 3-5, 3-11, 3-12, 3-13, 4-1, 4-2, 4-3, 4-11, 4-12, 4-13, 4-14, 4-15, 4-29, 4-30, 4-31, 4-32, 4-33, 4-34, 5-15, 5-16, 5-17, 5-18, 5-19 and 5-93 of the present invention showed the activity level evaluated as A.

Test Example 2

Insecticidal Test on *Laodelphax striatella*

The oxime group-containing condensed heterocyclic compounds represented by the general formula (1) of the present invention or salts thereof were separately dispersed in water and diluted to 500 ppm, and rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatella*, and then the glass test tubes were capped with cotton plugs. At 8 days after the inoculation, the numbers of surviving larvae and dead larvae were counted, the corrected mortality rate was calculated according to the formula shown below, and the insecticidal effect was evaluated according to the criteria of Test Example 1.

$$\text{Corrected mortality rate (\%)} = 100 \times (\text{Survival rate in a non-treatment plot} - \text{Survival rate in a treatment plot}) / \text{Survival rate in a non-treatment plot} \quad \text{[Math. 2]}$$

As a result, the compounds 1-3, 1-60, 1-72, 1-189, 1-192, 1-195, 1-198, 1-201, 1-204, 1-207, 1-210, 1-213, 1-216, 1-219, 1-222, 1-225, 1-228, 1-231, 1-234, 1-237, 1-240, 1-243, 1-246, 1-258, 1-306, 1-352, 1-353, 1-354, 2-3, 2-6, 2-9, 2-12, 2-15, 2-33, 2-39, 2-45, 2-235, 2-236, 2-237, 2-238, 2-239, 2-240, 2-241, 3-1, 3-2, 3-3, 3-4, 3-5, 3-11, 3-12, 3-13, 4-1, 4-2, 4-3, 4-11, 4-12, 4-13, 4-14, 4-15, 4-29, 4-30, 4-31, 4-32, 4-33, 4-34, 5-15, 5-16, 5-17, 5-18, 5-19 and 5-93 of the present invention showed the activity level evaluated as A.

Test Example 3

Insecticidal Test on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different kind of oxime group-containing condensed heterocyclic compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal effect was evaluated according to the criteria of Test Example 1. This test was conducted in triplicate using 10 adults of *Plutella xylostella* per plot.

Corrected mortality rate (%)=100×(Number of hatched larvae in a non-treatment plot−Number of hatched larvae in a treatment plot)/Number of hatched larvae in a non-treatment plot [Math. 3]

As a result, the compounds 1-3, 1-60, 1-72, 1-189, 1-192, 1-195, 1-198, 1-201, 1-204, 1-207, 1-210, 1-213, 1-216, 1-219, 1-222, 1-225, 1-228, 1-231, 1-234, 1-237, 1-240, 1-243, 1-246, 1-258, 1-306, 1-352, 1-353, 1-354, 2-3, 2-6, 2-9, 2-12, 2-15, 2-33, 2-39, 2-45, 2-235, 2-236, 2-237, 2-238, 2-239, 2-240, 2-241, 3-1, 3-2, 3-3, 3-4, 3-5, 3-11, 3-12, 3-13, 4-1, 4-2, 4-3, 4-11, 4-12, 4-13, 4-14, 4-15, 4-29, 4-30, 4-31, 4-32, 4-33, 4-34, 5-15, 5-16, 5-17, 5-18, 5-19 and 5-93 of the present invention showed the activity level evaluated as A.

INDUSTRIAL AVAILABILITY

The compound of the present invention is highly effective for the control of a wide range of agricultural and horticultural pests and thus is useful.

The invention claimed is:
1. A condensed heterocyclic compound represented by formula (1):

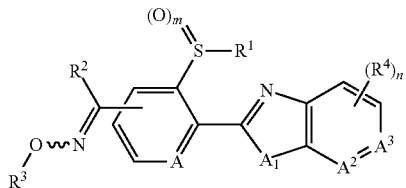

wherein
$R^1$ represents
(a1) a $(C_1-C_6)$ alkyl group;
(a2) a $(C_3-C_6)$ cycloalkyl group;
(a3) a $(C_2-C_6)$ alkenyl group; or
(a4) a $(C_2-C_6)$ alkynyl group,
$R^2$ represents
(b1) a hydrogen atom;
(b2) a $(C_1-C_6)$ alkyl group;
(b3) a $(C_3-C_6)$ cycloalkyl group;
(b4) a halo $(C_1-C_6)$ alkyl group;
(b5) an amino group;
(b6) a cyano group;
(b7) a $(C_1-C_6)$ alkoxycarbonyl group;
(b8) an aminocarbonyl group;
(b9) a mono-$(C_1-C_6)$ alkylaminocarbonyl group; or
(b10) a di-$(C_1-C_6)$ alkylaminocarbonyl group,
$R^3$ represents
(c1) a hydrogen atom;
(c2) a $(C_1-C_6)$ alkyl group;
(c3) a $(C_2-C_6)$ alkenyl group;
(c4) a $(C_2-C_6)$ alkynyl group;
(c5) a $(C_3-C_6)$ cycloalkyl group;
(c6) a $(C_3-C_6)$ cycloalkyl $(C_1-C_6)$ alkyl group;
(c7) a $(C_1-C_6)$ alkoxy $(C_1-C_6)$ alkyl group;
(c8) a halo $(C_1-C_6)$ alkyl group;
(c9) a halo $(C_2-C_6)$ alkenyl group;
(c10) a halo $(C_2-C_6)$ alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c13) a phenyl $(C_1-C_6)$ alkyl group;
(c14) a phenyl $(C_1-C_6)$ alkyl group having, on the ring, 1 to 5 substituting groups which may be the same or different and are selected from (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c15) a $(C_1-C_6)$ alkylcarbonyl group;
(c16) a $(C_3-C_6)$ cycloalkylcarbonyl group;
(c17) a cyanoalkyl group;
(c18) a $(C_1-C_6)$ alkylthio $(C_1-C_6)$ alkyl group;
(c19) a $(C_1-C_6)$ alkylsulfinyl $(C_1-C_6)$ alkyl group;
(c20) a $(C_1-C_6)$ alkylsulfonyl $(C_1-C_6)$ alkyl group;
(c21) a halo $(C_1-C_6)$ alkylthio $(C_1-C_6)$ alkyl group;
(c22) a halo $(C_1-C_6)$ alkylsulfinyl $(C_1-C_6)$ alkyl group; or
(c23) a halo $(C_1-C_6)$ alkylsulfonyl $(C_1-C_6)$ alkyl group,
$R^4$ represents
(d1) a halogen atom;
(d2) a cyano group;
(d3) a nitro group;
(d4) a $(C_1-C_6)$ alkyl group;
(d5) a $(C_1-C_6)$ alkoxy group;
(d6) a $(C_2-C_6)$ alkenyloxy group;
(d7) a $(C_2-C_6)$ alkynyloxy group;
(d8) a halo $(C_1-C_6)$ alkyl group;
(d9) a halo $(C_1-C_6)$ alkoxy group;
(d10) a halo $(C_2-C_6)$ alkenyloxy group;
(d11) a halo $(C_2-C_6)$ alkynyloxy group;
(d12) a $(C_1-C_6)$ alkylthio group;
(d13) a $(C_1-C_6)$ alkylsulfinyl group;
(d14) a $(C_1-C_6)$ alkylsulfonyl group;
(d15) a halo $(C_1-C_6)$ alkylthio group;
(d16) a halo $(C_1-C_6)$ alkylsulfinyl group; or
(d17) a halo $(C_1-C_6)$ alkylsulfonyl group,
A, $A^2$ and $A^3$ each represent CH or a nitrogen atom,
$A^1$ represents O, S or N—$R^5$ (wherein $R^5$ represents (e1) a $(C_1-C_6)$ alkyl group; (e2) a $(C_3-C_6)$ cycloalkyl group; (e3) a $(C_2-C_6)$ alkenyl group; or (e4) a $(C_2-C_6)$ alkynyl group),
m represents 0, 1 or 2, and
n represents 0, 1 or 2, or
a salt thereof.
2. The condensed heterocyclic compound according to claim 1 or a salt thereof, wherein the condensed heterocyclic compound is represented by formula (1A):

(1A)

wherein
$R^1$ represents (a1) a ($C_1$-$C_6$) alkyl group,
$R^2$ represents
(b1) a hydrogen atom; or
(b2) a ($C_1$-$C_6$) alkyl group,
$R^3$ represents
(c1) a hydrogen atom; or
(c8) a halo ($C_1$-$C_6$) alkyl group,
$R^4$ represents
(d8) a halo ($C_1$-$C_6$) alkyl group;
(d9) a halo ($C_1$-$C_6$) alkoxy group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
A represents a nitrogen atom,
$A^2$ and $A^3$ each represent CH or a nitrogen atom,
$A^1$ represents O or N—$R^5$ (wherein $R^5$ represents (e1) a ($C_1$-$C_6$) alkyl group),
m represents 0 or 2, and
n represents 1.

3. The condensed heterocyclic compound according to claim 2 or a salt thereof, wherein $A^1$ is O.

4. An agricultural and horticultural insecticide comprising the condensed heterocyclic compound according to claim 1 or a salt thereof as an active ingredient.

5. A method for using an agricultural and horticultural insecticide, the method comprising applying an effective amount of the condensed heterocyclic compound according to claim 1 or a salt thereof to plants or soil.

6. An animal ectoparasite control agent comprising an effective amount of the condensed heterocyclic compound according to claim 1 or a salt thereof as an active ingredient.

7. The condensed heterocyclic compound according to claim 1 or a salt thereof, wherein the condensed heterocyclic compound is represented by formula (1):

(1)

wherein
$R^1$ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
$R^2$ represents
(b1) a hydrogen atom;
(b2) a ($C_1$-$C_6$) alkyl group;
(b3) a ($C_3$-$C_6$) cycloalkyl group;
(b4) a halo ($C_1$-$C_6$) alkyl group; or
(b5) an amino group,
$R^3$ represents
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group;
(c14) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c15) a ($C_1$-$C_6$) alkylcarbonyl group; or
(c16) a ($C_3$-$C_6$) cycloalkylcarbonyl group,
$R^4$ represents
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
A, $A^2$ and $A^3$ each represent CH or a nitrogen atom,
$A^1$ represents O, S or N—$R^5$ (wherein $R^5$ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
m represents 0, 1 or 2, and
n represents 0, 1 or 2.

8. The condensed heterocyclic compound according to claim 7 or a salt thereof, wherein the condensed heterocyclic compound is represented by formula (1A):

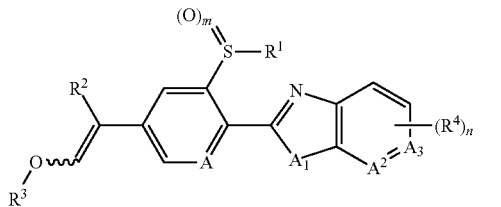

(1A)

wherein
R¹ represents
(a1) a $(C_1-C_6)$ alkyl group;
(a2) a $(C_3-C_6)$ cycloalkyl group;
(a3) a $(C_2-C_6)$ alkenyl group; or
(a4) a $(C_2-C_6)$ alkynyl group,
R² represents
(b1) a hydrogen atom;
(b2) a $(C_1-C_6)$ alkyl group;
(b3) a $(C_3-C_6)$ cycloalkyl group; or
(b5) an amino group,
R³ represents
(c1) a hydrogen atom;
(c2) a $(C_1-C_6)$ alkyl group;
(c3) a $(C_2-C_6)$ alkenyl group;
(c4) a $(C_2-C_6)$ alkynyl group;
(c5) a $(C_3-C_6)$ cycloalkyl group;
(c6) a $(C_3-C_6)$ cycloalkyl $(C_1-C_6)$ alkyl group;
(c7) a $(C_1-C_6)$ alkoxy $(C_1-C_6)$ alkyl group;
(c8) a halo $(C_1-C_6)$ alkyl group;
(c9) a halo $(C_2-C_6)$ alkenyl group;
(c10) a halo $(C_2-C_6)$ alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group;
(c13) a phenyl $(C_1-C_6)$ alkyl group; or
(c14) a phenyl $(C_1-C_6)$ alkyl group having, on the ring, 1 to 5 substituting groups which may be the same or different and are selected from (a) a halogen atom, (b) a cyano group, (c) a nitro group, (d) a formyl group, (e) a $(C_1-C_6)$ alkyl group, (f) a halo $(C_1-C_6)$ alkyl group, (g) a $(C_1-C_6)$ alkoxy group, (h) a halo $(C_1-C_6)$ alkoxy group, (i) a $(C_3-C_6)$ cycloalkyl $(C_1-C_6)$ alkoxy group, (j) a $(C_1-C_6)$ alkylthio group, (k) a halo $(C_1-C_6)$ alkylthio group, (l) a $(C_1-C_6)$ alkylsulfinyl group, (m) a halo $(C_1-C_6)$ alkylsulfinyl group, (n) a $(C_1-C_6)$ alkylsulfonyl group and (o) a halo $(C_1-C_6)$ alkylsulfonyl group,
R⁴ represents
(d1) a halogen atom;
(d2) a cyano group;
(d3) a nitro group;
(d4) a $(C_1-C_6)$ alkyl group;
(d5) a $(C_1-C_6)$ alkoxy group;
(d6) a $(C_2-C_6)$ alkenyloxy group;
(d7) a $(C_2-C_6)$ alkynyloxy group;
(d8) a halo $(C_1-C_6)$ alkyl group;
(d9) a halo $(C_1-C_6)$ alkoxy group;
(d10) a halo $(C_2-C_6)$ alkenyloxy group;
(d11) a halo $(C_2-C_6)$ alkynyloxy group;
(d12) a $(C_1-C_6)$ alkylthio group;
(d13) a $(C_1-C_6)$ alkylsulfinyl group;
(d14) a $(C_1-C_6)$ alkylsulfonyl group;
(d15) a halo $(C_1-C_6)$ alkylthio group;
(d16) a halo $(C_1-C_6)$ alkylsulfinyl group; or
(d17) a halo $(C_1-C_6)$ alkylsulfonyl group,
A, A² and A³ each represent CH or a nitrogen atom,
A¹ represents O, S or N—R⁵ (wherein R⁵ represents (e1) a $(C_1-C_6)$ alkyl group; (e2) a $(C_3-C_6)$ cycloalkyl group; (e3) a $(C_2-C_6)$ alkenyl group; or (e4) a $(C_2-C_6)$ alkynyl group),
m represents 0, 1 or 2, and
n represents 0, 1 or 2.

9. The condensed heterocyclic compound according to claim 8 or a salt thereof, wherein
R¹ represents (a1) a $(C_1-C_6)$ alkyl group,
R² represents
(b1) a hydrogen atom; or
(b2) a $(C_1-C_6)$ alkyl group,
R³ represents
(c1) a hydrogen atom;
(c2) a $(C_1-C_6)$ alkyl group;
(c3) a $(C_2-C_6)$ alkenyl group;
(c7) a $(C_1-C_6)$ alkoxy $(C_1-C_6)$ alkyl group;
(c11) a phenyl group; or
(c13) a phenyl $(C_1-C_6)$ alkyl group,
R⁴ represents
(d8) a halo $(C_1-C_6)$ alkyl group; or
(d15) a halo $(C_1-C_6)$ alkylthio group,
A, A² and A³ each represent a nitrogen atom,
A¹ represents N—R⁵ (wherein R⁵ represents (e1) a $(C_1-C_6)$ alkyl group),
m represents 0, 1 or 2, and
n represents 1.

10. The condensed heterocyclic compound according to claim 8 or a salt thereof, wherein
R¹ represents (a1) a $(C_1-C_6)$ alkyl group,
R² represents
(b1) a hydrogen atom; or
(b2) a $(C_1-C_6)$ alkyl group,
R³ represents
(c1) a hydrogen atom;
(c2) a $(C_1-C_6)$ alkyl group;
(c3) a $(C_2-C_6)$ alkenyl group;
(c7) a $(C_1-C_6)$ alkoxy $(C_1-C_6)$ alkyl group;
(c11) a phenyl group; or
(c13) a phenyl $(C_1-C_6)$ alkyl group,
R⁴ represents (d8) a halo $(C_1-C_6)$ alkyl group,
A, A² and A³ each represent a nitrogen atom,
A¹ represents N—R⁵ (wherein R⁵ represents (e1) a $(C_1-C_6)$ alkyl group),
m represents 2, and
n represents 1.

11. The condensed heterocyclic compound according to claim 7 or a salt thereof, wherein the condensed heterocyclic compound is represented by formula (1B):

(1B)

$$\begin{array}{c}\text{(O)}_m\\ \overset{\|}{S}-R^1\end{array}\quad\begin{array}{c}(R^4)_n\\ \diagdown\end{array}$$

[Structure with substituents R¹, R², R³, R⁴, and ring atoms A, A¹, A², A³]

wherein
R¹ represents
(a1) a ($C_1$-$C_6$) alkyl group;
(a2) a ($C_3$-$C_6$) cycloalkyl group;
(a3) a ($C_2$-$C_6$) alkenyl group; or
(a4) a ($C_2$-$C_6$) alkynyl group,
R² represents
(b1) a hydrogen atom;
(b2) a ($C_1$-$C_6$) alkyl group;
(b3) a ($C_3$-$C_6$) cycloalkyl group; or
(b5) an amino group,
R³ represents
(c1) a hydrogen atom;
(c2) a ($C_1$-$C_6$) alkyl group;
(c3) a ($C_2$-$C_6$) alkenyl group;
(c4) a ($C_2$-$C_6$) alkynyl group;
(c5) a ($C_3$-$C_6$) cycloalkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a halo ($C_1$-$C_6$) alkyl group;
(c9) a halo ($C_2$-$C_6$) alkenyl group;
(c10) a halo ($C_2$-$C_6$) alkynyl group;
(c11) a phenyl group;
(c12) a phenyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(c13) a phenyl ($C_1$-$C_6$) alkyl group; or
(c14) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group,
R⁴ represents
(d1) a halogen atom;
(d2) a cyano group;
(d3) a nitro group;
(d4) a ($C_1$-$C_6$) alkyl group;
(d5) a ($C_1$-$C_6$) alkoxy group;
(d6) a ($C_2$-$C_6$) alkenyloxy group;
(d7) a ($C_2$-$C_6$) alkynyloxy group;
(d8) a halo ($C_1$-$C_6$) alkyl group;
(d9) a halo ($C_1$-$C_6$) alkoxy group;
(d10) a halo ($C_2$-$C_6$) alkenyloxy group;
(d11) a halo ($C_2$-$C_6$) alkynyloxy group;
(d12) a ($C_1$-$C_6$) alkylthio group;
(d13) a ($C_1$-$C_6$) alkylsulfinyl group;
(d14) a ($C_1$-$C_6$) alkylsulfonyl group;
(d15) a halo ($C_1$-$C_6$) alkylthio group;
(d16) a halo ($C_1$-$C_6$) alkylsulfinyl group; or
(d17) a halo ($C_1$-$C_6$) alkylsulfonyl group,
A, A² and A³ each represent CH or a nitrogen atom,
A¹ represents O, S or N—R⁵ (wherein R⁵ represents (e1) a ($C_1$-$C_6$) alkyl group; (e2) a ($C_3$-$C_6$) cycloalkyl group; (e3) a ($C_2$-$C_6$) alkenyl group; or (e4) a ($C_2$-$C_6$) alkynyl group),
m represents 0, 1 or 2, and
n represents 0, 1 or 21.

12. The condensed heterocyclic compound according to claim 11 or a salt thereof, wherein
R¹ represents (a1) a ($C_1$-$C_6$) alkyl group,
R² represents
(b1) a hydrogen atom; or
(b2) a ($C_1$-$C_6$) alkyl group,
R³ represents
(c1) a hydrogen atom;
(c2) a ($C_1$-$C_6$) alkyl group;
(c3) a ($C_2$-$C_6$) alkenyl group;
(c7) a ($C_1$-$C_6$) alkoxy ($C_1$-$C_6$) alkyl group;
(c11) a phenyl group; or
(c13) a phenyl ($C_1$-$C_6$) alkyl group,
R⁴ represents
(d8) a halo ($C_1$-$C_6$) alkyl group; or
(d15) a halo ($C_1$-$C_6$) alkylthio group,
A, A² and A³ each represent a nitrogen atom,
A¹ represents N—R⁵ (wherein R⁵ represents (e1) a ($C_1$-$C_6$) alkyl group),
m represents 0, 1 or 2, and
n represents 1.

13. The condensed heterocyclic compound according to claim 11 or a salt thereof, wherein
R¹ represents (a1) a ($C_1$-$C_6$) alkyl group,
R² represents
(b1) a hydrogen atom; or
(b2) a ($C_1$-$C_6$) alkyl group,
R³ represents
(c1) a hydrogen atom;
(c2) a ($C_1$-$C_6$) alkyl group;
(c3) a ($C_2$-$C_6$) alkenyl group;
(c7) a ($C_1$-$C_6$) alkoxy ($C_1$-$C_6$) alkyl group;
(c11) a phenyl group; or
(c13) a phenyl ($C_1$-$C_6$) alkyl group,
R⁴ represents (d8) a halo ($C_1$-$C_6$) alkyl group,
A, A² and A³ each represent a nitrogen atom,
A¹ represents N—R⁵ (wherein R⁵ represents (e1) a ($C_1$-$C_6$) alkyl group),
m represents 2, and
n represents 1.

14. An agricultural and horticultural insecticide comprising the condensed heterocyclic compound according to claim 7 or a salt thereof as an active ingredient.

15. A method for using an agricultural and horticultural insecticide, the method comprising applying an effective amount of the condensed heterocyclic compound according to claim 7 or a salt thereof to plants or soil.

16. An animal ectoparasite control agent comprising an effective amount of the condensed heterocyclic compound according to claim 7 or a salt thereof as an active ingredient.

\* \* \* \* \*